United States Patent
Raitano et al.

(10) Patent No.: US 7,217,799 B2
(45) Date of Patent: May 15, 2007

(54) ANTIBODIES THAT RECOGNIZE THE 85P1B3 PROTEIN USEFUL IN TREATMENT AND DETECTION OF CANCER

(75) Inventors: Arthur B. Raitano, Los Angeles, CA (US); Mary Faris, Los Angeles, CA (US); Rene S. Hubert, Los Angeles, CA (US); Daniel E. Afar, Brisbane, CA (US); Wangmao Ge, Los Angeles, CA (US); Pia M. Challita-Eid, Encino, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 09/942,052

(22) Filed: Aug. 28, 2001

(65) Prior Publication Data

US 2003/0170626 A1    Sep. 11, 2003

Related U.S. Application Data

(60) Provisional application No. 60/228,432, filed on Aug. 28, 2000.

(51) Int. Cl.
| | |
|---|---|
| C07K 16/00 | (2006.01) |
| C12P 21/08 | (2006.01) |
| A61K 39/395 | (2006.01) |
| C12P 21/04 | (2006.01) |
| C12N 15/02 | (2006.01) |
| C12N 5/06 | (2006.01) |
| C07H 21/04 | (2006.01) |

(52) U.S. Cl. ............... 530/387.9; 530/387.3; 530/388.1; 530/388.8; 530/391.7; 424/133.1; 424/139.1; 424/155.1; 424/181.1

(58) Field of Classification Search ............ 424/130.1, 424/133.1, 135.1, 141.1, 155.1, 181.1, 139.1; 530/387.1, 387.3, 388.1, 388.8, 391.3, 391.7, 530/387.9
See application file for complete search history.

(56) References Cited

U.S. PATENT DOCUMENTS 5,530,101 A * 6/1996 Queen et al.
6,261,791 B1 * 7/2001 Reiter et al.

FOREIGN PATENT DOCUMENTS

| WO | WO9845436 A2 | 10/1998 |
|---|---|---|
| WO | WO200153312 A1 | 7/2001 |
| WO | WO200157182 A2 | 8/2001 |
| WO | WO200210198 A2 | 2/2002 |
| WO | WO200210449 A2 | 2/2002 |
| WO | WO200218578 A2 | 3/2002 |

OTHER PUBLICATIONS

Reiger et al. Glossary of Genetics and Cytogenetics, Classical and Molecular, 4th Ed., Springer-Verlay, Berlin, 1976.*
Fu et al. EMBO Journal, 1996, vol. 15, pp. 4392-4401.*
Powell et al. Pharmacogenetics, 1998, vol. 8, pp. 411-421.*
Vallejo et al. Biochimie, 2000, vol. 82, pp. 1129-1133.*
Jang et al. Clinical and Experimental Metastasis, 1997, vol. 15, pp. 469-483.*
Coleman P. M. Research in Immunology. 145: 33-36, 1994.*
Pennica et al. Proc. Natl. Acad. Sci. USA 95:14717-14722, 1998.*
Konopka et al. Proc. Natl. Acad. Sci. 83:4049-4052, 1986.*
Haynes et al. Electrophoresis 19:1862-1871, 1998.*
Lewin B. Genes VI, CH. 29, pp. 847-848, 1997.*
Gokman-Polar et al. Cancer Research, 61:1375-1381, 2001.*
Reiger et al. Glossary of Genetics and Cytogenetics, Classical and Molecular, 4th Ed., Springer-Verlay, Berlin, pp. 17-18, 1976.*
Burgess et al. Journal of Cell Biology, vol. 111:2129-2138, Nov. 1990.*
Lazar et al. Molecular and Cellular Biology, 8(3):1247-1252, Mar. 1988.*
Schwartz et al. Proc Natl Acad Sci USA, 84:6408-6411, 1987.*
Lederman et al. Molecular Immunology 28:1171-1181, 1991.*
Li et al. Proc. Natl. Acad. Sci. USA 77:3211-3214, 1980.*
Coleman P. M. Research in Immunology, 145:33-36, 1994.*
Williams et al. Molecular Microbiology 27(1):171-186, 1998.*
Campbell A. M. Monoclonal Antibody Technology, Elsevier Science Publishers, NY, chapter 1, pp. 1-32, 1986.*
Chang et al., Cancer Research (1997) 57:4075-4081.
Database EMBL Sequence Library [Online] Accession No. AF025441, Jan. 31, 1998.
Gulukota et al., Journal of Molecular Biology (1997) 267:1258-1267.
Takeuchi et al., Urological Research (2000) 28:82-85.

* cited by examiner

*Primary Examiner*—Sheel J. Huff
*Assistant Examiner*—David J. Blanchard
(74) *Attorney, Agent, or Firm*—Morrison & Foerster LLP

(57) ABSTRACT

A novel gene (designated 85P1B3) and its encoded protein are described. While 85P1B3 exhibits tissue specific expression in normal adult tissue, it is aberrantly expressed in multiple cancers including set forth in Table 1. Consequently, 85P1B3 provides a diagnostic and/or therapeutic target for cancers. The 85P1B3 gene or fragment thereof, or its encoded protein or a fragment thereof, can be used to elicit an immune response.

8 Claims, 24 Drawing Sheets

Fig. 1

85P1B3 SSH sequence and GenBank homology to OIP5

```
GATCAGAGGACACATGGGACTCTGCATCTTAATTCCTAAATTTACAGTCAAAGACATTTTCAGAGATAAGTATTAT
GAATTCAATAAGAATCTAAAGTAAGTTCTTAAGGCAAATAGCTATAAAAGAGAAGAATCCTTAGTCTCTCATCTTC
TAAAAACAGCTTCACAAATAATTTGGAAAATCAGCCTAAAGGTAAATAGAAACTGCATTTCCCCTCCATTCTTGAA
GCCAATCTTTTTCAAGAAATGACTAAGCAGCACCTGTTGTTGAAGACAGCAATAAAGCCTGAACCTGACACTCAAG
CTTTGGTACAGGATC
```

```
gb|AF025441.1|AF025441    Homo sapiens Opa-interacting protein...    632   e-179
gb|AF158642.1|AF158642    Homo sapiens metalloproteinase-disin...     42   0.12
gb|AC005075.2|AC005075    Homo sapiens clone RG219E16, complet...     42   0.12
emb|AL096773.6|HS1000E10  Human DNA sequence from clone 1000...       40   0.48
```

>gb|AF025441.1|AF025441 Homo sapiens Opa-interacting protein OIP5 mRNA,
partial cds
          Length = 1197

Score =  632 bits (319), Expect = e-179
 Identities = 319/319 (100%)
 Strand = Plus / Minus

```
Query:    1   gatcagaggacacatgggactctgcatcttaattcctaaatttacagtcaaagacatttt   60
              ||||||||||||||||||||||||||||||||||||||||||||||||||||||||||||
Sbjct: 1013   gatcagaggacacatgggactctgcatcttaattcctaaatttacagtcaaagacatttt   954

Query:   61   cagagataagtattatgaattcaataagaatctaaagtaagttcttaaggcaaatagcta   120
              ||||||||||||||||||||||||||||||||||||||||||||||||||||||||||||
Sbjct:  953   cagagataagtattatgaattcaataagaatctaaagtaagttcttaaggcaaatagcta   894

Query:  121   taaaagagaagaatccttagtctctcatcttctaaaaacagcttcacaaataatttggaa   180
              ||||||||||||||||||||||||||||||||||||||||||||||||||||||||||||
Sbjct:  893   taaaagagaagaatccttagtctctcatcttctaaaaacagcttcacaaataatttggaa   834

Query:  181   aatcagcctaaaggtaaatagaaactgcatttcccctccattcttgaagccaatctttt   240
              ||||||||||||||||||||||||||||||||||||||||||||||||||||||||||||
Sbjct:  833   aatcagcctaaaggtaaatagaaactgcatttcccctccattcttgaagccaatctttt   774

Query:  241   caagaaatgactaagcagcacctgttgttgaagacagcaataaagcctgaacctgacact   300
              ||||||||||||||||||||||||||||||||||||||||||||||||||||||||||||
Sbjct:  773   caagaaatgactaagcagcacctgttgttgaagacagcaataaagcctgaacctgacact   714

Query:  301   caagctttggtacaggatc   319
              |||||||||||||||||||
Sbjct:  713   caagctttggtacaggatc   695
```

Fig. 2-A
cDNA Sequence and ORF of 85P1B3/OIP5 clone A

```
             9              18              27              36              45              54
5' GGC TGC GGG AAG ATG GCG GCT CAG CCG CTG CGG CAT CGC TCA CGT TGT GCA ACG
   --- --- --- --- --- --- --- --- --- --- --- --- --- --- --- --- --- ---
               M   A   A   Q   P   L   R   H   R   S   R   C   A   T 63              72              81              90              99             108
   CCG CCC CGG GGG GAC TTT TGT GGT GGC ACT GAG AGG GCG ATT GAC CAA GCT TCT
   --- --- --- --- --- --- --- --- --- --- --- --- --- --- --- --- --- ---
    P   P  |R   G   D|  F   C   G   G   T   E   R   A   I   D   Q   A   S 117             126             135             144             153             162
   TTT ACG ACC TCC ATG GAG TGG GAT ACG CAG GTG GTG AAG GGG TCC TCG CCG CTC
   --- --- --- --- --- --- --- --- --- --- --- --- --- --- --- --- --- ---
    F   T   T   S   M   E   W   D   T   Q   V   V   K   G   S   S   P   L 171             180             189             198             207             216
   GGC CCC GCA GGG CTG GGG GCT GAG GAG CCA GCC GCC GGC CCG CAG CTG CCG TCT
   --- --- --- --- --- --- --- --- --- --- --- --- --- --- --- --- --- ---
    G   P   A   G   L   G   A   E   E   P   A   A   G   P   Q   L   P   S 225             234             243             252             261             270
   TGG CTG CAG CCT GAG AGG TGC GCT GTG TTC CAG TGC GCA CAG TGT CAC GCA GTG
   --- --- --- --- --- --- --- --- --- --- --- --- --- --- --- --- --- ---
    W   L   Q   P   E   R   C   A   V   F   Q   C   A   Q   C   H   A   V 279             288             297             306             315             324
   CTC GCC GAC TCG GTG CAC CTC GCC TGG GAC CTG TCG CGG TCC CTC GGG GCC GTG
   --- --- --- --- --- --- --- --- --- --- --- --- --- --- --- --- --- ---
    L   A   D   S   V   H   L   A   W   D   L   S   R   S   L   G   A   V 333             342             351             360             369             378
   GTC TTC TCC AGA GTT ACA AAT AAC GTC GTT TTG GAA GCG CCC TTC CTA GTT GGC
   --- --- --- --- --- --- --- --- --- --- --- --- --- --- --- --- --- ---
    V   F   S   R   V   T   N   N   V   V   L   E   A   P   F   L   V   G 387             396             405             414             423             432
   ATT GAA GGT TCA CTC AAA GGC AGT ACT TAC AAC CTT TTA TTC TGT GGT TCT TGT
   --- --- --- --- --- --- --- --- --- --- --- --- --- --- --- --- --- ---
    I   E   G   S   L   K   G   S   T   Y   N   L   L   F   C   G   S   C 441             450             459             468             477             486
   GGG ATT CCC GTT GGT TTC CAT CTG TAT TCT ACC CAT GCT GCC CTG GCT GCC TTG
   --- --- --- --- --- --- --- --- --- --- --- --- --- --- --- --- --- ---
    G   I   P   V   G   F   H   L   Y   S   T   H   A   A   L   A   A   L 495             504             513             522             531             540
   AGA GGT CAC TTC TGC CTT TCC AGT GAC AAA ATG GTG TGC TAT CTC TTA AAA ACA
   --- --- --- --- --- --- --- --- --- --- --- --- --- --- --- --- --- ---
    R   G   H   F   C   L   S   S   D   K   M   V   C   Y   L   L   K   T 549             558             567             576             585             594
   AAA GCC ATA GTA AAT GCA TCA GAG ATG GAT ATT CAA AAT GTT CCT CTA TCA GAA
   --- --- --- --- --- --- --- --- --- --- --- --- --- --- --- --- --- ---
    K   A   I   V   N   A   S   E   M   D   I   Q   N   V   P   L   S   E 603             612             621             630             639             648
   AAG ATT GCA GAG CTG AAA GAG AAG ATA GTG CTA ACG CAC AAT CGC TTA AAA TCA
   --- --- --- --- --- --- --- --- --- --- --- --- --- --- --- --- --- ---
    K   I   A   E   L   K   E   K   I   V   L   T   H   N   R   L   K   S
             657             666             675             684             693             702
   CTA ATG AAG ATT CTG AGT GAA GTG ACT CCT GAC CAG TCC AAG CCA GAA AAC TGA
   --- --- --- --- --- --- --- --- --- --- --- --- --- --- --- --- --- ---
    L   M   K   I   L   S   E   V   T   P   D   Q   S   K   P   E   N   *
             711             720             729             738             747             756
```

Fig. 2-B

```
TCC TGT ACC AAA GCT TGA GTG TCA GGT TCA GGC TTT ATT GCT GTC TTC AAC AAC
            765         774         783         792         801         810
AGG TGC TGC TTA GTC ATT TCT TGA AAA AGA TTG GCT TCA AGA ATG GAG GGG AAA
            819         828         837         846         855         864
TGC AGT TTC TAT TTA CCT TTA GGC TGA TTT TCC AAA TTA TTT GTG AAG CTG TTT
            873         882         891         900         909         918
TTA GAA GAT GAG AGA CTA AGG ATT CTT CTC TTT TAT AGC TAT TTG CCT TAA GAA
            927         936         945         954         963         972
CTT ACT TTA GAT TCT TAT TGA ATT CAT AAT ACT TAT CTC TGA AAA TGT CTT TGA
            981         990         999        1008        1017        1026
CTG TAA ATT TAG GAA TTA AGA TGC AGA GTC CCA TGT GTC CTC TGA TCT AAA GTT
           1035        1044        1053        1062        1071        1080
GCA TGG TTG GTC TGA AAA TAG AGT TGG GCT TAA TGT TGA CTT CTA TTA CTC CTG
           1089        1098        1107        1116        1125        1134
CAT GGA GCA GTT GTT ATG AAT ACT AAT ACA TCA CTT TTT AAC TTC TGT AAA ATA
           1143        1152        1161        1170        1179        1188
CAG ATC ATA ATA TTC TAT AGG TAA TGT TTA ATA AAT TGC CTG AAT AAT AAA AAA
           1197        1206        1215        1224        1233        1242
AAA AAA AAA AAA AAA AAA AAA AAA AAA AAA AAA AAA AAA AAA AAA AAA AAA AAA
           1251        1260
AAA AAA AAA AAA AAA AAA AA 3'
```

Fig. 3

85P1B3/OIP5 protein sequence.

```
  1 MAAQPLRHRS RCATPPRGDF CGGTERAIDQ ASFTTSMEWD TQVVKGSSPL GPAGLGAEEP
 61 AAGPQLPSWL QPERCAVFQC AQCHAVLADS VHLAWDLSRS LGAVVFSRVT NNVVLEAPFL
121 VGIEGSLKGS TYNLLFCGSC GIPVGFHLYS THAALAALRG HFCLSSDKMV CYLLKTKAIV
181 NASEMDIQNV PLSEKIAELK EKIVLTHNRL KSLMKILSEV TPDQSKPEN*
```

Fig. 4

Alignment of 85P1B3 with OIP5.

>gi|2815610|gb|AAC39561.1| (AF025441) Opa-interacting protein OIP5 [Homo sapiens]
     Length = 231

Score = 462 bits (1189), Expect = e-130
Identities = 229/229 (100%), Positives = 229/229 (100%)

```
85P1B3:  1   MAAQPLRHRSRCATPPRGDFCGGTERAIDQASFTTSMEWDTQVVKGSSPLGPAGLGAEEP   60
             MAAQPLRHRSRCATPPRGDFCGGTERAIDQASFTTSMEWDTQVVKGSSPLGPAGLGAEEP
OIP5:    3   MAAQPLRHRSRCATPPRGDFCGGTERAIDQASFTTSMEWDTQVVKGSSPLGPAGLGAEEP   62

85P1B3:  61  AAGPQLPSWLQPERCAVFQCAQCHAVLADSVHLAWDLSRSLGAVVFSRVTNNVVLEAPFL  120
             AAGPQLPSWLQPERCAVFQCAQCHAVLADSVHLAWDLSRSLGAVVFSRVTNNVVLEAPFL
OIP5:    63  AAGPQLPSWLQPERCAVFQCAQCHAVLADSVHLAWDLSRSLGAVVFSRVTNNVVLEAPFL  122

85P1B3: 121  VGIEGSLKGSTYNLLFCGSCGIPVGFHLYSTHAALAALRGHFCLSSDKMVCYLLKTKAIV  180
             VGIEGSLKGSTYNLLFCGSCGIPVGFHLYSTHAALAALRGHFCLSSDKMVCYLLKTKAIV
OIP5:   123  VGIEGSLKGSTYNLLFCGSCGIPVGFHLYSTHAALAALRGHFCLSSDKMVCYLLKTKAIV  182

85P1B3: 181  NASEMDIQNVPLSEKIAELKEKIVLTHNRLKSLMKILSEVTPDQSKPEN  229
             NASEMDIQNVPLSEKIAELKEKIVLTHNRLKSLMKILSEVTPDQSKPEN
OIP5:   183  NASEMDIQNVPLSEKIAELKEKIVLTHNRLKSLMKILSEVTPDQSKPEN  231
```

Fig. 5: 85P1B3 Hydrophilicity Profile
(Hopp T.P., Woods K.R., 1981. Proc. Natl. Acad. Sci. U.S.A. 78:3824-3828)
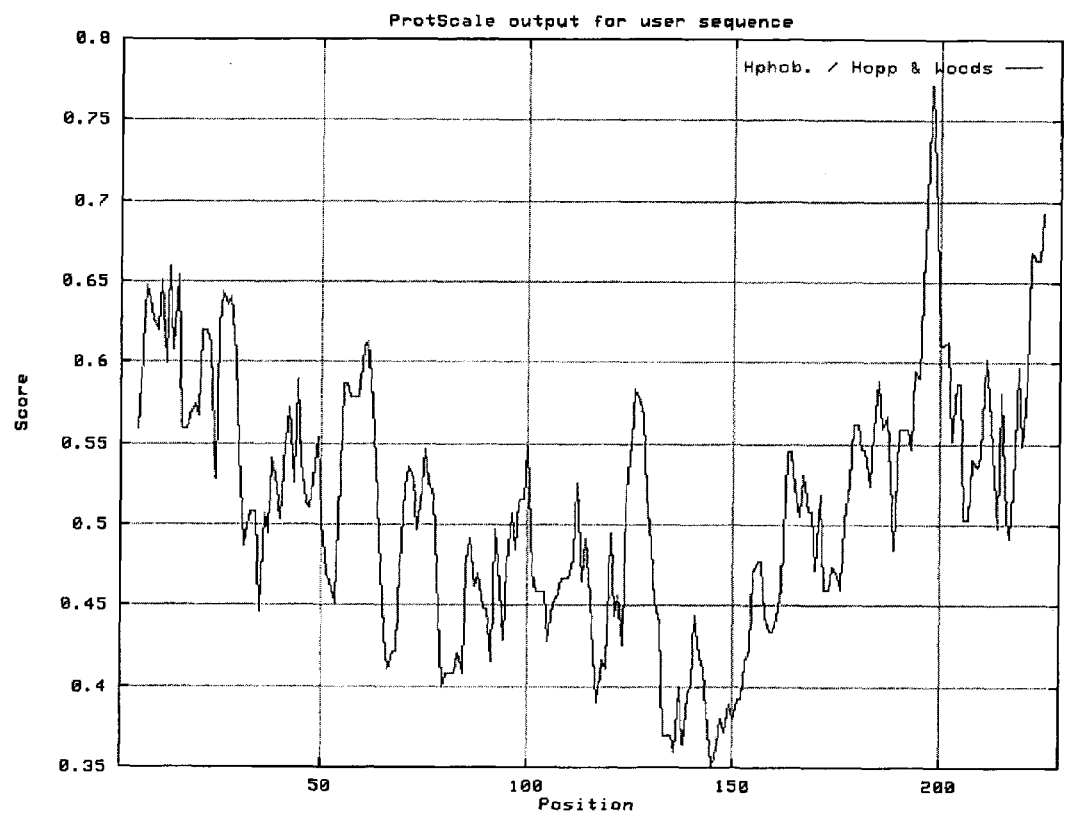

Fig. 6: 85P1B3 Hydropathicity Profile
(Kyte J., Doolittle R.F., 1982. J. Mol. Biol. 157:105-132)
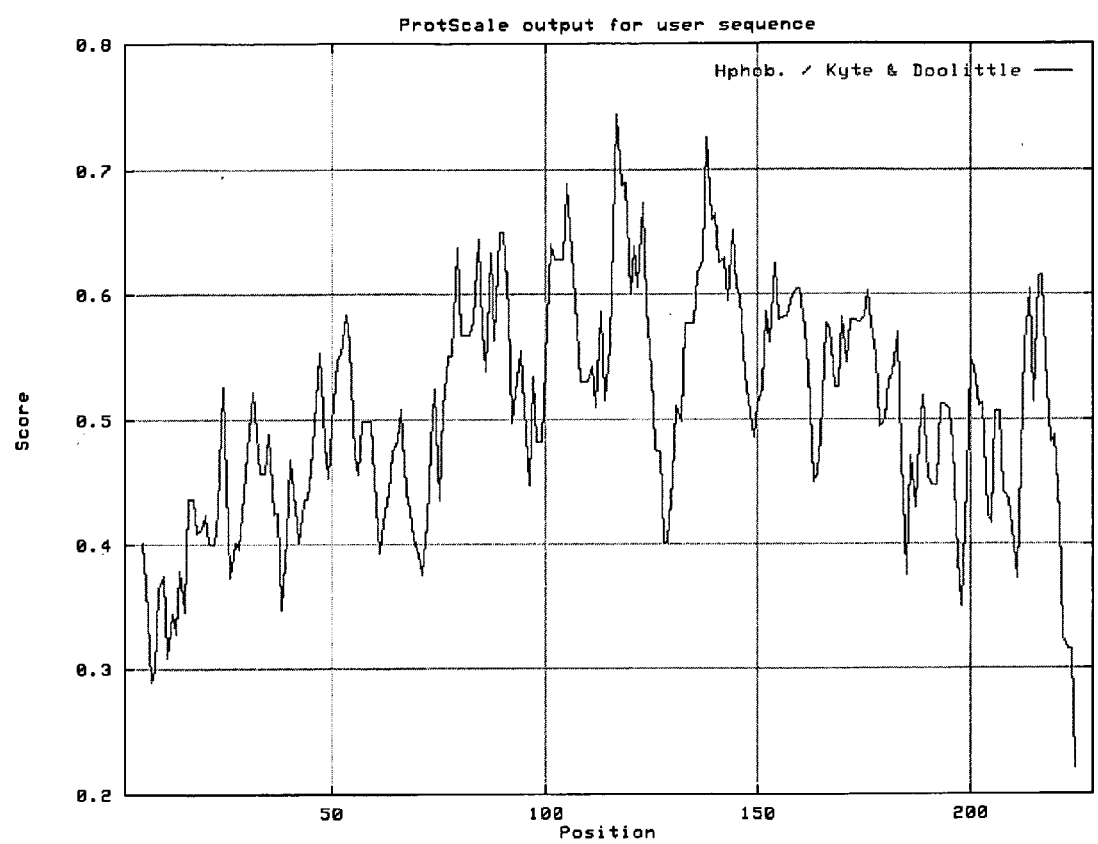

Fig. 7: 85P1B3 % Accessible Residues Profile
(Janin J., 1979. Nature 277:491-492)
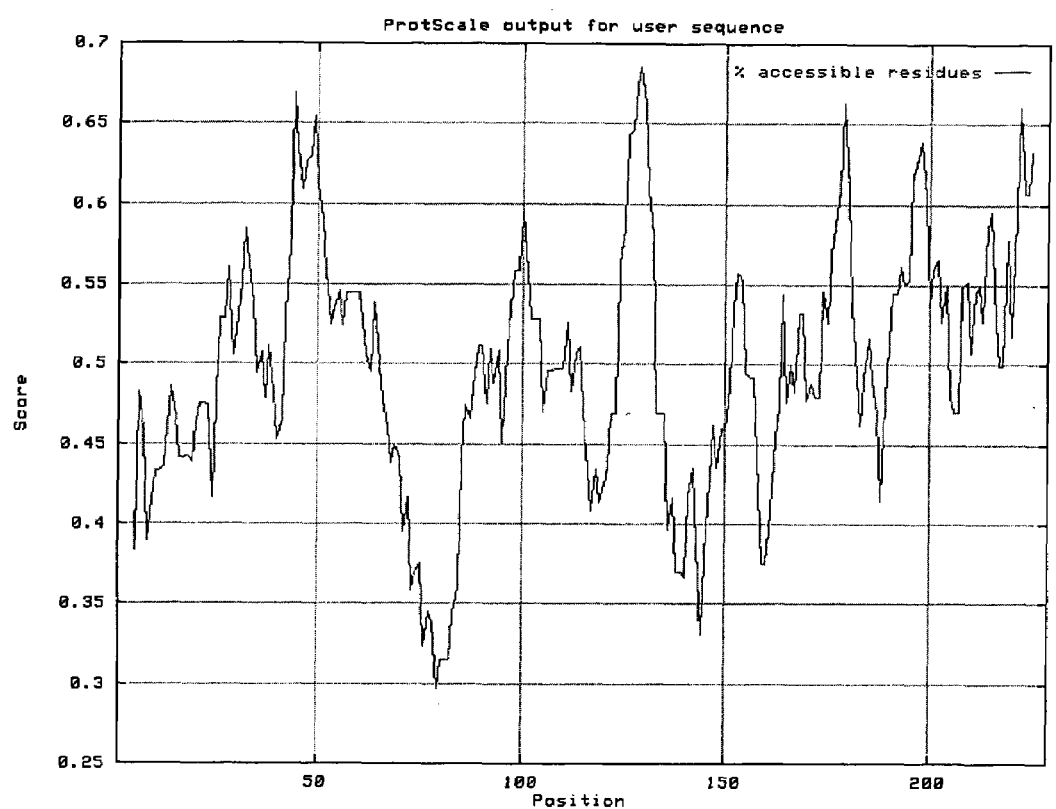

Fig. 8: 85P1B3 Average Flexibility Profile
(Bhaskaran R., Ponnuswamy P.K., 1988. Int. J. Pept. Protein Res. 32:242-255)
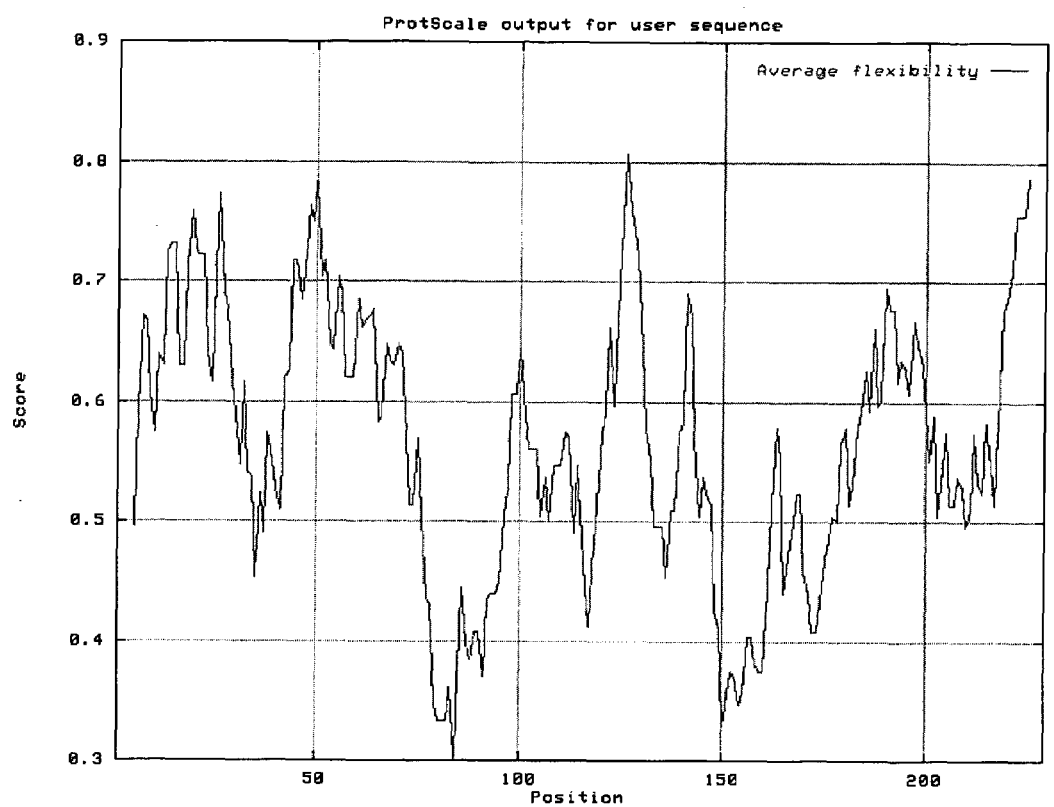

Fig. 9: 85P1B3 Beta-turn Profile
(Deleage, G., Roux B. 1987. Protein Engineering 1:289-294)
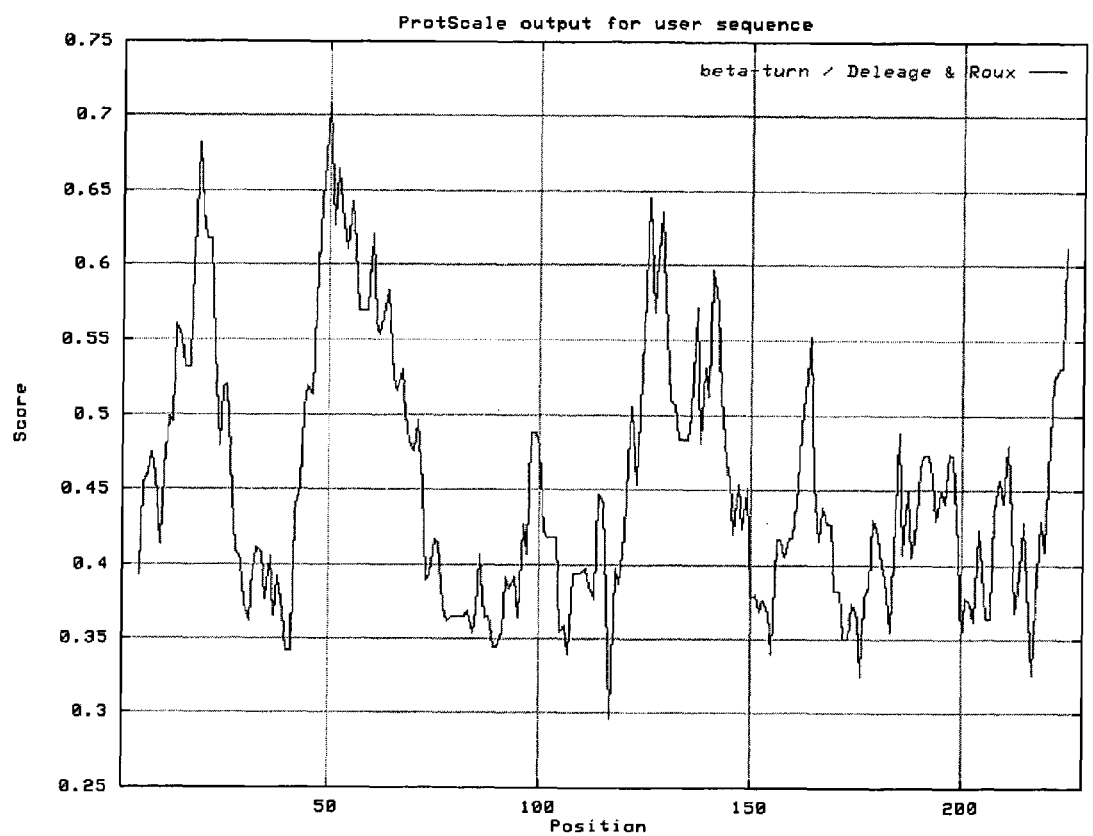

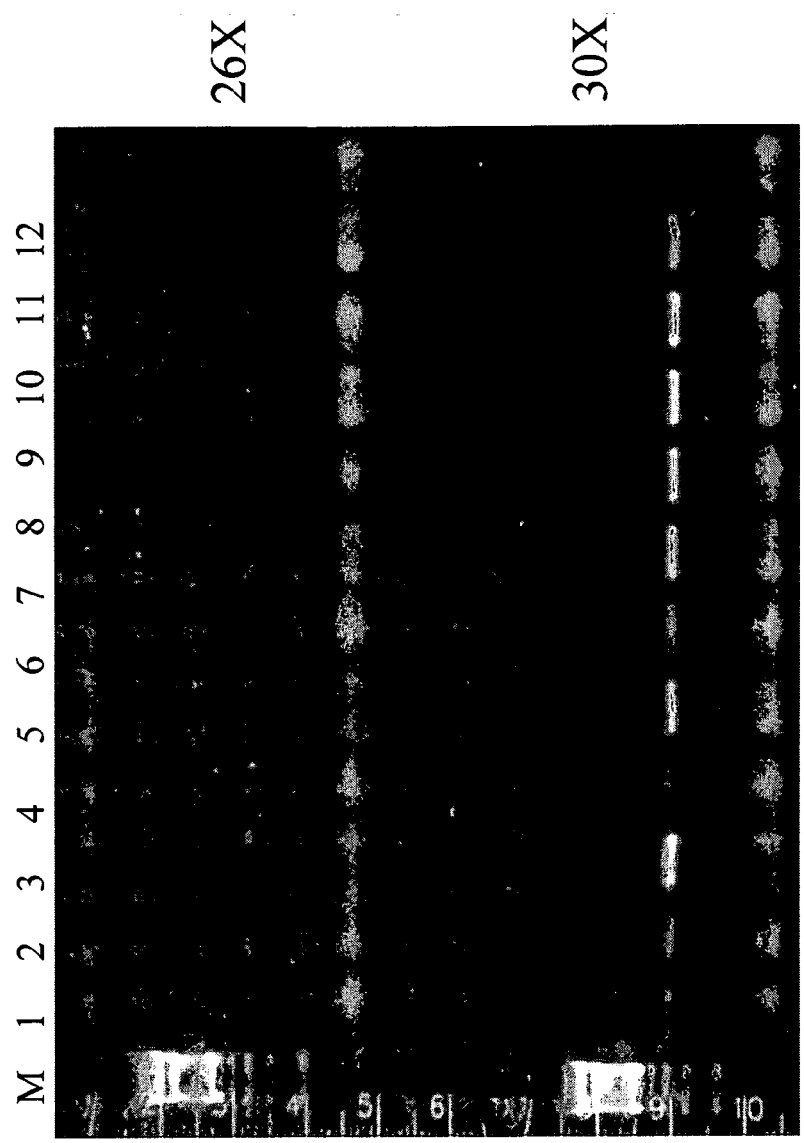
Fig. 10: RT-PCR Analysis of 85P1B3 Expression
1) Vital Pool 1
2) Vital Pool 2
3) Xenograft Pool
4) Prostate Cancer Pool
5) Bladder Cancer Pool
6) Kidney Cancer Pool
7) Colon Cancer Pool
8) Lung Cancer Pool
9) Ovary Cancer Pool
10) Breast Cancer Pool
11) Metastasis Pool
12) H2O

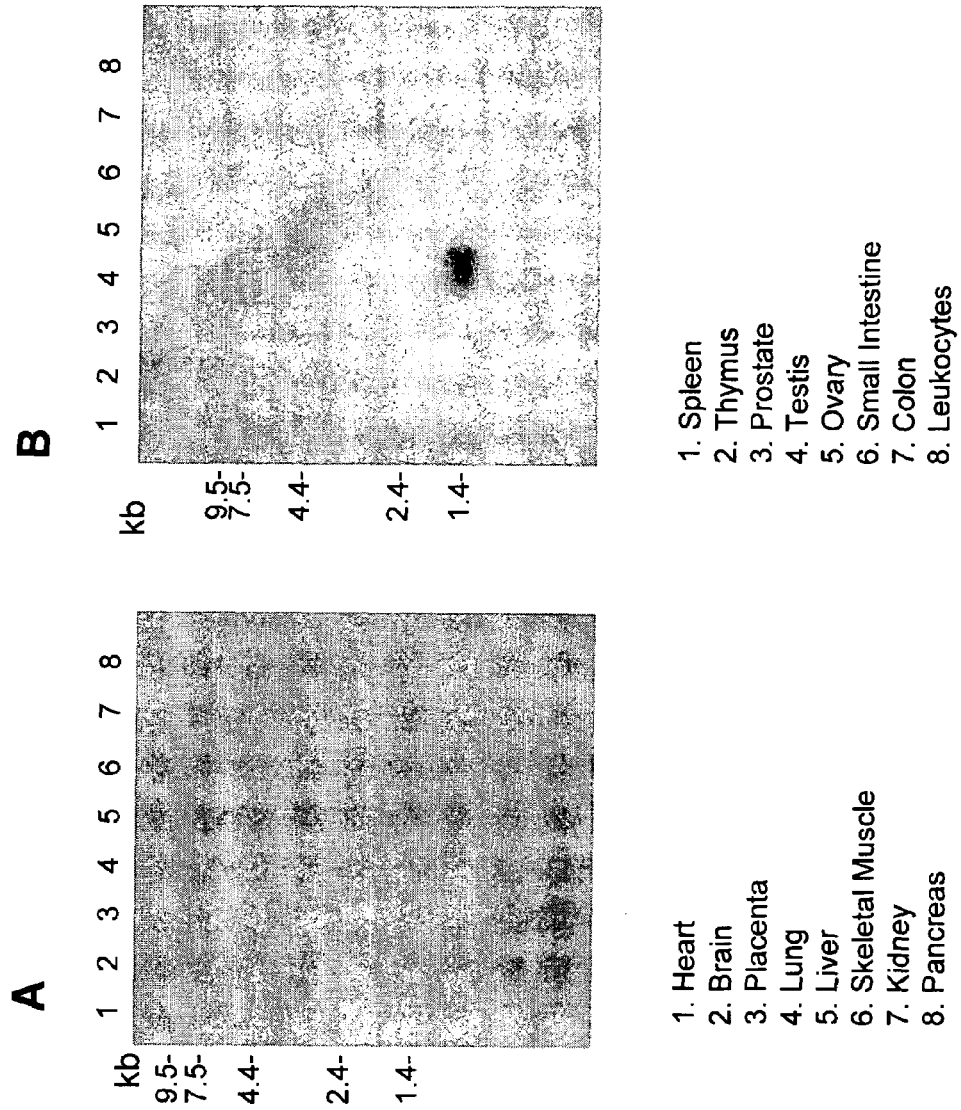
Fig. 11: Expression of 85P1B3 in Normal Human Tissues

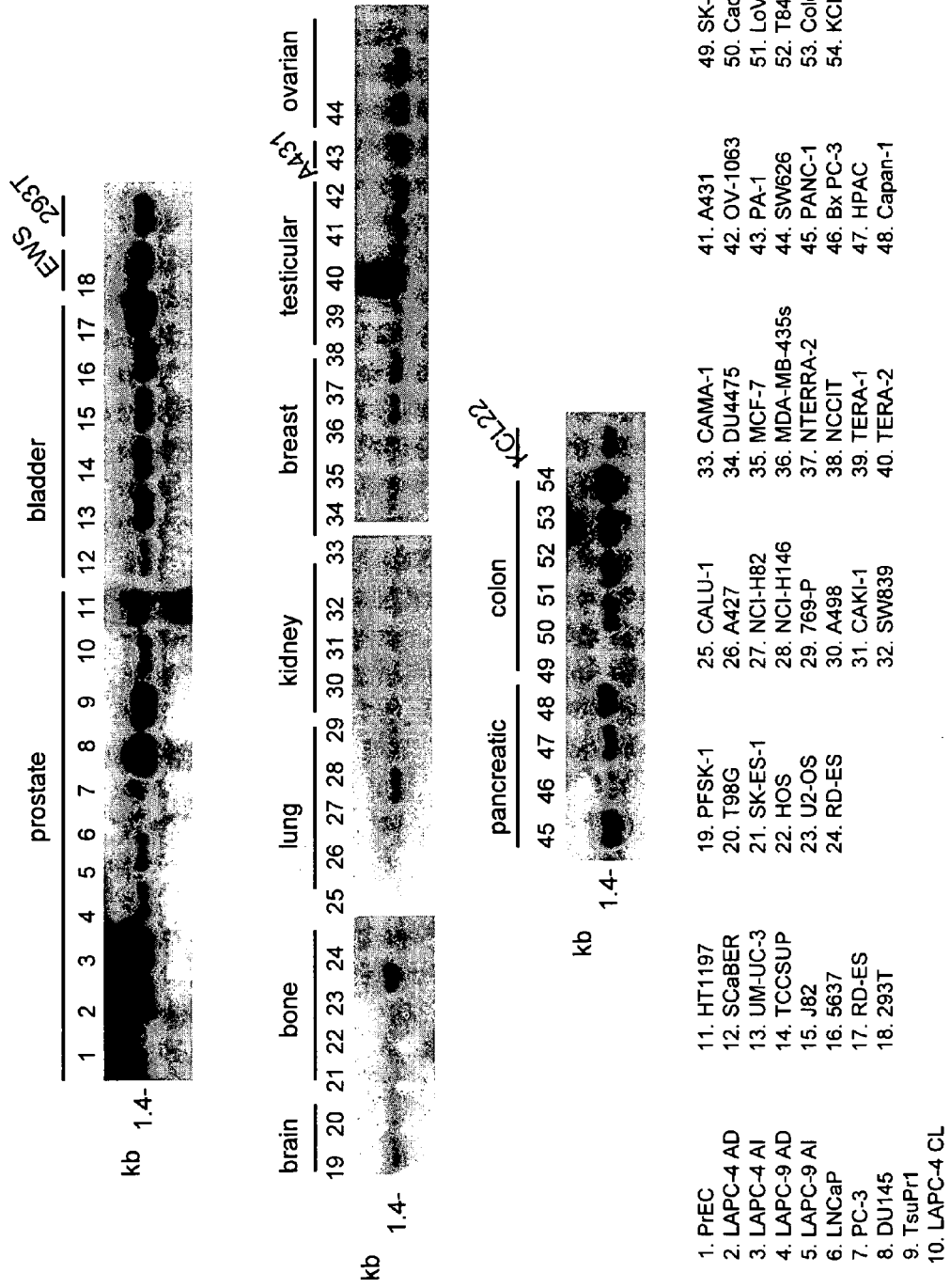
Fig. 12: Expression of 85P1B3 in Human Cancer Cell lines

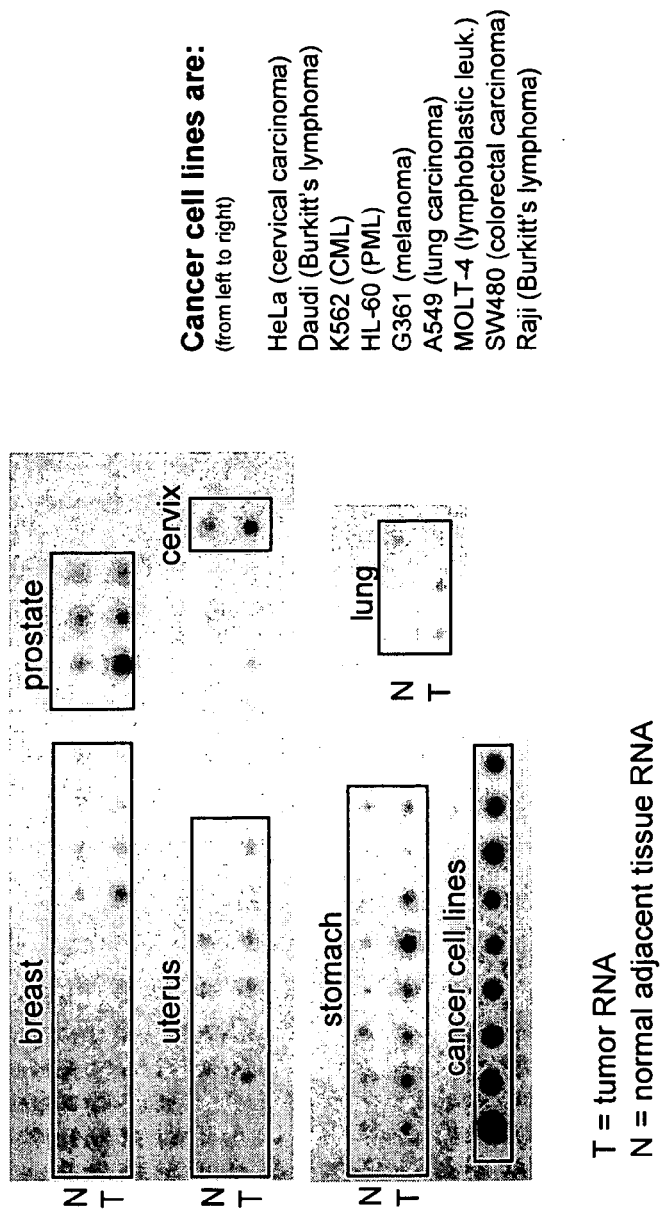
Fig. 13: Expression of 85P1B3 in Patient Cancer Specimens and Cancer Cell Lines

Fig. 14: Expression of 85P1B3 in Colon Cancer Patient Specimens
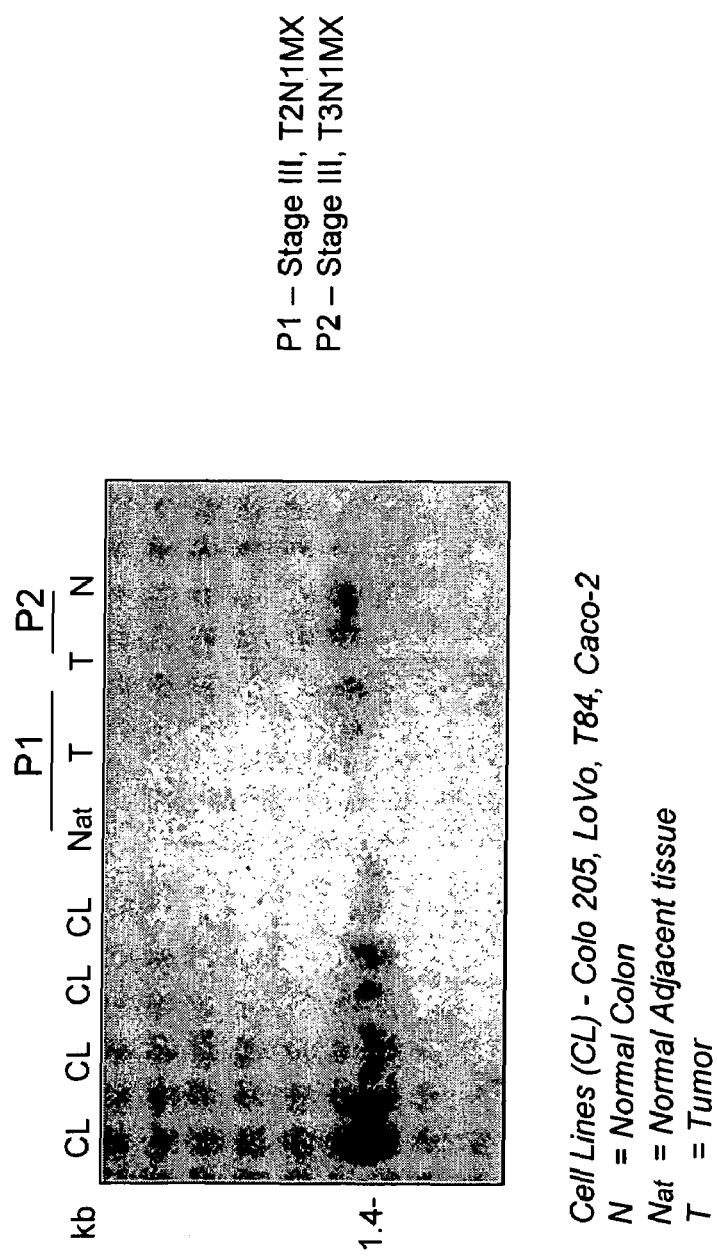

Fig. 15: Expression of 85P1B3 in Bladder Cancer Patient Specimens
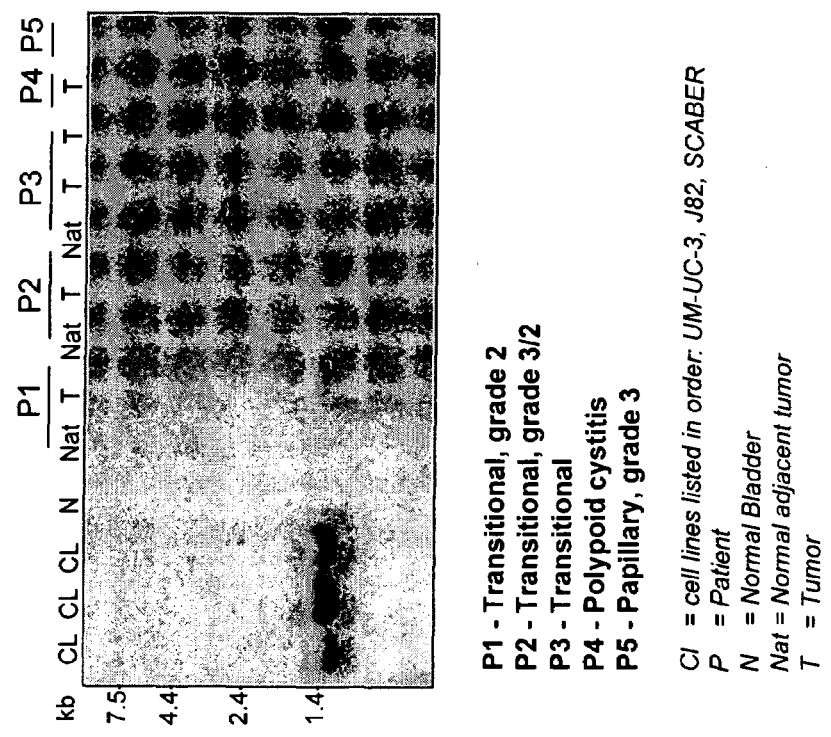

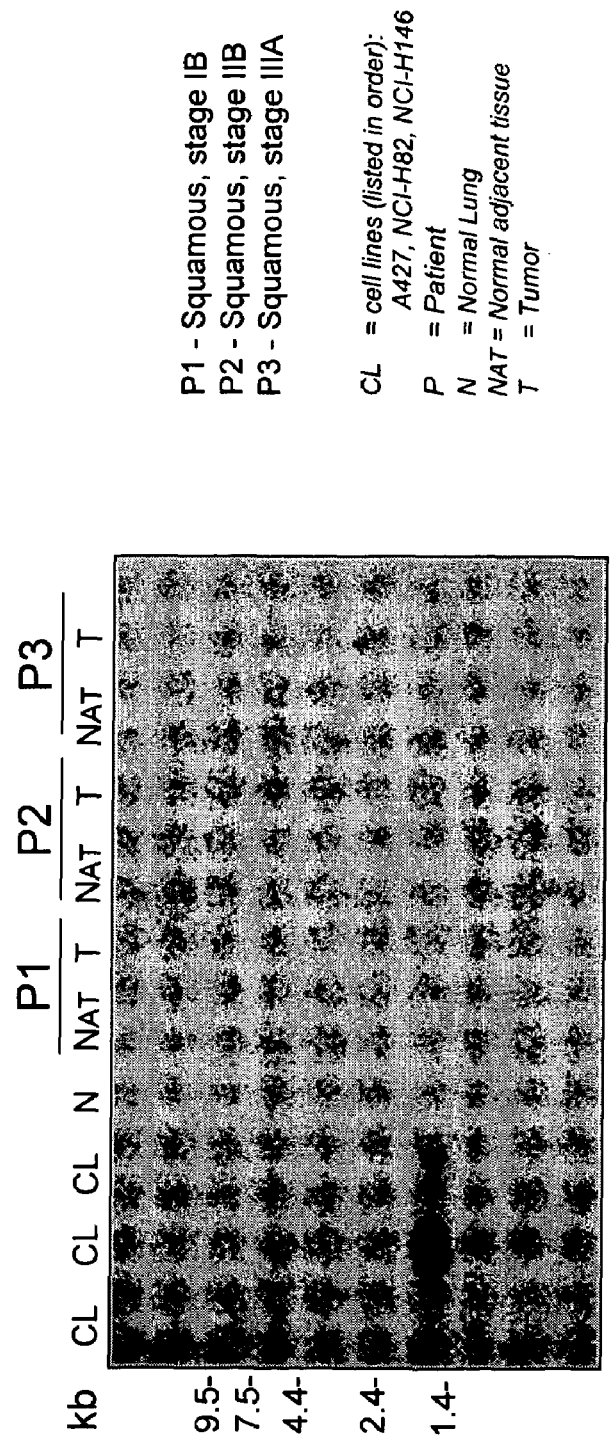
Fig. 16: Expression of 85P1B3 in Lung Cancer Patient Specimens

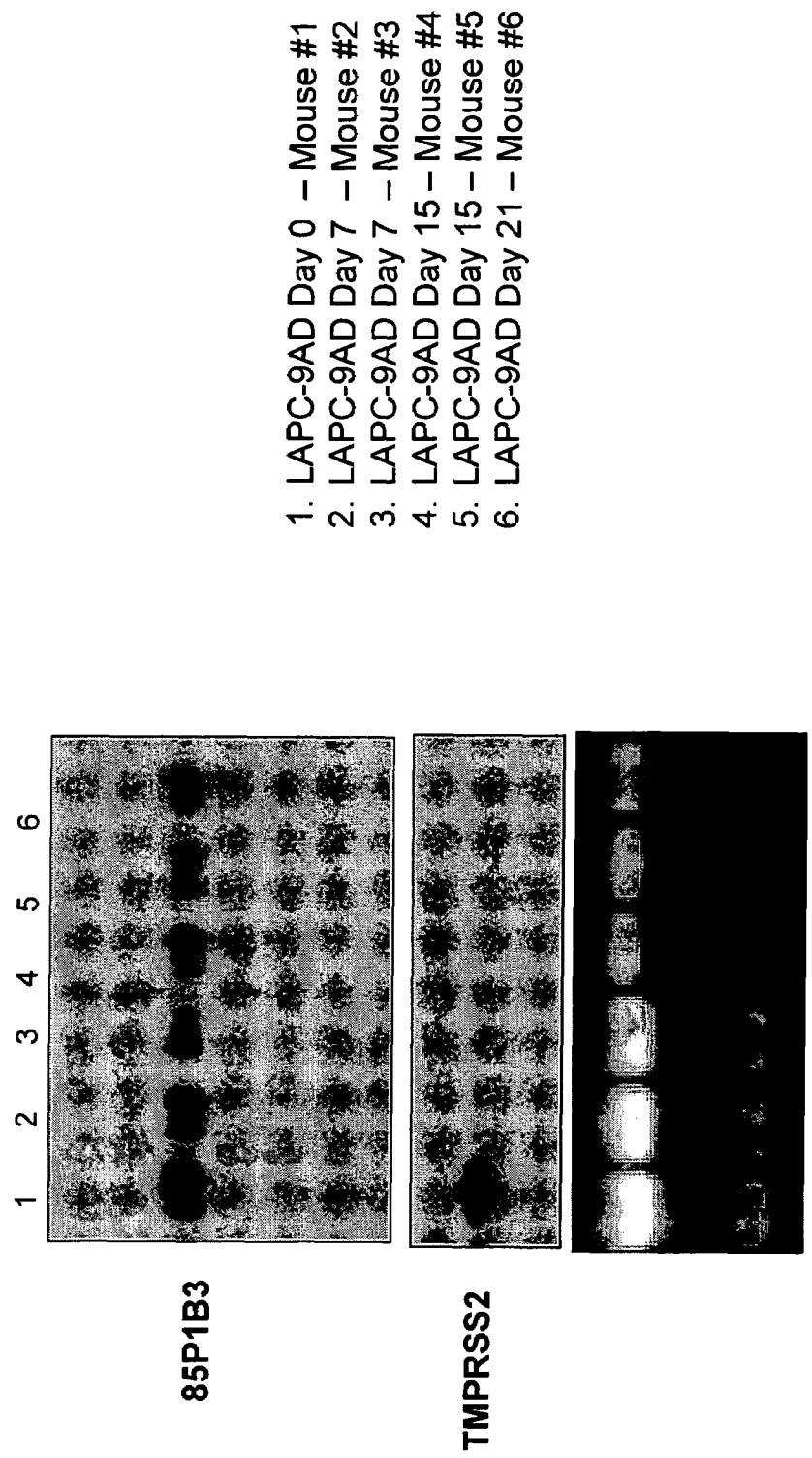
Fig. 17: Expression of 85P1B3 in Prostate Cancer Xenografts Following Castration

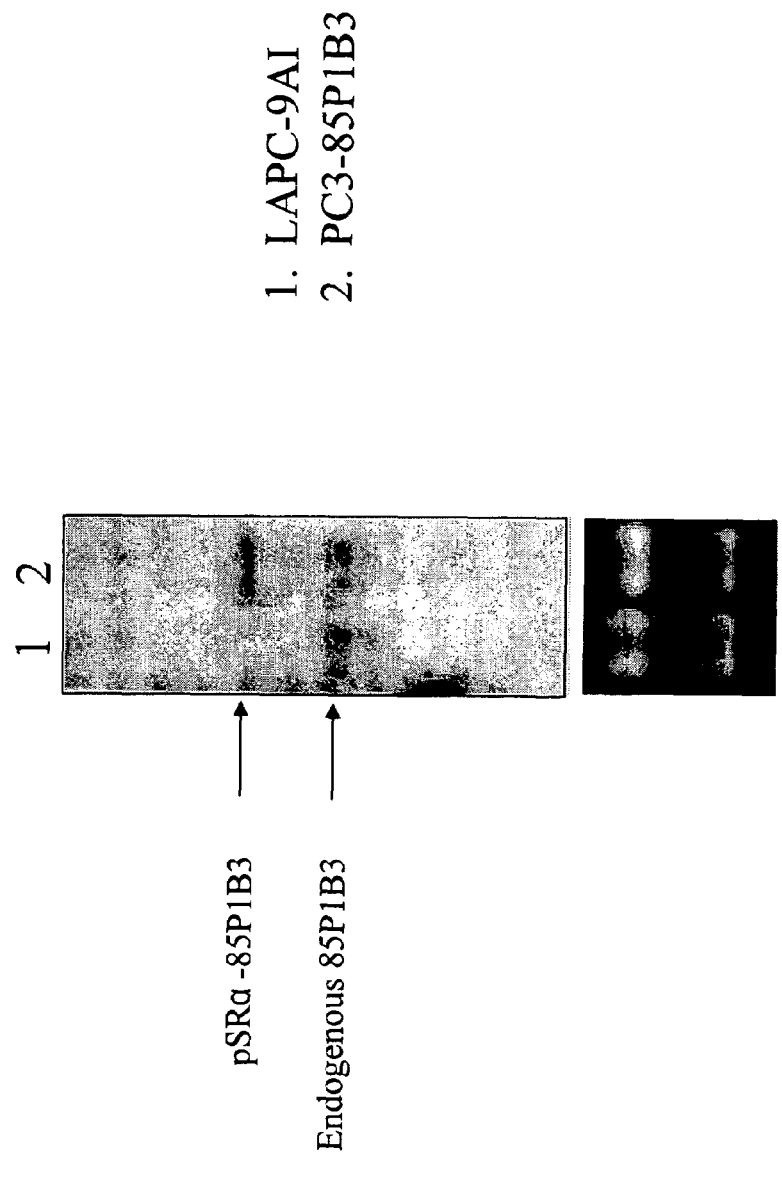
Fig. 18: Expression of 85P1B3 in PC3 Cells Following Retroviral-Mediated Gene Delivery

Fig. 21A

```
        10        20        30        40        50        60        70
         |         |         |         |         |         |         |
MAAQPLRHRSRCATPPRGDFCGGTERAIDQASFTTSMEWDTQVVKGSSPLGPAGLGAEEPAAGPQLPSWL
cccccccccccccccccccccccccccchhhccccccccccceeecccccccccccccccccccccccc
QPERCAVFQCAQCHAVIADSVHLAWDLSRSLGAVVFSRVTNNVLEAPFLVGIEGSLKGSTYNLLFCGSC
chhhhhhhhhhhhhhhhhhhhhhhhhhhhccceeeeeeccccceeeeeeccccccccccceeeeecccc
GIPVGFHLYSTHAALAALRGHFCLSSDKMVCYLLKTKAIVNASEMDIQNVPLSEKIAELKEKIVLTHNRL
cccchhhhhhhhhhhhhhhcccccccchhhhhhhhhhceeeccccccccchhhhhhhhhhhhhhhhhhh
KSLMKILSEVTPDQSKPEN
hhhhhhehccccccccccc
``` c: random coil (49.34%)
e: extended strand (13.97%)
h: alpha helix (36.68%)

ANTIBODIES THAT RECOGNIZE THE 85P1B3 PROTEIN USEFUL IN TREATMENT AND DETECTION OF CANCER

This application claims the benefit of U.S. provisional patent application Ser. No. 60/228,432, filed Aug. 28, 2000, the entire contents of which are hereby incorporated herein by reference.

SUBMISSION ON COMPACT DISC

The contents of the following submission on compact discs are incorporated herein by reference in its entirety: A compact disc copy of the Sequence Listing (COPY 1) (file name: 5115820028.txt, date recorded: Feb. 13, 2003, size: 216 KB); a duplicate compact disc copy of the Sequence Listing (COPY 2) (file name: 5115820028.txt, date recorded: Feb. 13, 2003, size: 216 KB); a computer readable form copy of the Sequence Listing (CRF COPY) (file name: 5115820028.txt, date recorded: Feb. 13, 2003, size: 216 KB).

FIELD OF THE INVENTION

The invention described herein relates to a novel gene and its encoded protein, termed 85P1B3, and to diagnostic and therapeutic methods and compositions useful in the management of various cancers that express 85P1B3.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 September 2 (9): 1445–51), STEAP (Hubert, et al., Proc Natl Acad Sci USA. 1999 Dec. 7; 96(25): 14523–8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and 8 per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992–1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992–1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992–1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCFS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992–1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to a novel gene, designated 85P1B3, that is over-expressed in multiple cancers listed in Table 1. Northern blot expression analysis of 85P1B3 gene expression in normal tissues shows a restricted expression pattern in adult tissues. The nucleotide (FIG. 2) and amino acid (FIG. 2, and FIG. 3) sequences of 85P1B3 are provided. The tissue-related profile of 85P1B3 in normal adult tissues, combined with the over-expression observed in prostate and other tumors, shows that 85P1B3 is aberrantly over-expressed in at least some cancers, and thus serves as a useful diagnostic and/or therapeutic target for cancers of the tissues such as those listed in Table 1.

The invention provides polynucleotides corresponding or complementary to all or part of the 85P1B3 genes, mRNAs, and/or coding sequences, preferably in isolated form, including polynucleotides encoding 85P1B3-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 85P1B3-related protein, as well as the peptides/proteins themselves; DNA, RNA, DNA/RNA hybrids, and related molecules, polynucleotides or oligonucleotides complementary or having at least a 90% homology to the 85P1B3 genes or mRNA sequences or parts thereof, and polynucleotides or oligonucleotides that hybridize to the 85P1B3 genes, mRNAs, or to 85P1B3-encoding polynucleotides. Also provided are means for isolating cDNAs and the genes encoding 85P1B3. Recombinant DNA molecules containing 85P1B3 polynucleotides, cells transformed or transduced with such molecules, and host-vector systems for the expression of 85P1B3 gene products are also provided. The invention further provides antibodies that bind to 85P1B3 proteins and polypeptide fragments thereof, including polyclonal and monoclonal antibodies, murine and other mammalian antibodies, chimeric antibodies, humanized and fully human antibodies, and antibodies labeled with a detectable marker.

The invention further provides methods for detecting the presence and status of 85P1B3 polynucleotides and proteins in various biological samples, as well as methods for identifying cells that express 85P1B3. A typical embodiment of this invention provides methods for monitoring 85P1B3 gene products in a tissue or hematology sample having or suspected of having some form of growth dysregulation such as cancer.

The invention further provides various immunogenic or therapeutic compositions and strategies for treating cancers that express 85P1B3 such as prostate cancers, including therapies aimed at inhibiting the transcription, translation, processing or function of 85P1B3 as well as cancer vaccines.

BRIEF DESCRIPTION OF THE FIGURES

FIG. 1. 85P1B3 SSH sequence. The 85P1B3 SSH sequence contains 259 bp. (SEQ ID. NO.: 724) and it's alignment with a fragment of the *Homo sapiens* Opa-interacting protein OIP5 (SEQ ID NO: 725) cDNA.

FIG. 2. The cDNA (SEQ ID. NO.:727) and amino acid sequence (SEQ ID. NO.:728) of 85P1B3. The start methionine is underlined. The open reading frame extends from nucleic acid 13 to 702 including the stop codon.

FIG. 3. Amino acid sequence of 85P1B3 (SEQ ID. NO.:728). The 85P1B3 protein has 229 amino acids.

FIG. 4. Sequence alignment of 85P1B3 (SEQ ID NO: 728) with GenBank accession number AAC39561.1 (AF025441), Opa-interacting protein OIP5 (SEQ ID. NO.: 731).

FIG. 5. Hydrophilicity amino acid profile of 85P1B3 determined by computer algorithm sequence analysis using the method of Hopp and Woods (Hopp T. P., Woods K. R., 1981. Proc. Natl. Acad. Sci. U.S.A. 78:3824–3828) accessed on the Protscale website through the ExPasy molecular biology server.

FIG. 6. Hydropathicity amino acid profile of 85P1B3 determined by computer algorithm sequence analysis using the method of Kyte and Doolittle (Kyte J., Doolittle R. F., 1982. J. Mol. Biol. 157:105–132) accessed on the ProtScale website through the ExPasy molecular biology server.

FIG. 7. Percent accessible residues amino acid profile of 85P1B3 determined by computer algorithm sequence analysis using the method of Janin (Janin J., 1979 Nature 277: 491–492) accessed on the ProtScale website through the ExPasy molecular biology server.

FIG. 8. Average flexibility amino acid profile of 85P1B3 determined by computer algorithm sequence analysis using the method of Bhaskaran and Ponnuswamy (Bhaskaran R., and Ponnuswamy P. K., 1988. Int. J. Pept. Protein Res. 32:242–255) accessed on the ProtScale website through the ExPasy molecular biology server.

FIG. 9. Beta-turn amino acid profile of 85P1B3 determined by computer algorithm sequence analysis using the method of Deleage and Roux (Deleage, G., Roux B. 1987 Protein Engineering 1:289–294) accessed on the ProtScale website through the ExPasy molecular biology server.

FIG. 10. RT-PCR analysis of 85P1B3 expression. First strand cDNA was prepared from vital pool 1 (VP1: liver, lung and kidney), vital pool 2 (VP2, pancreas, spleen and stomach), prostate xenograft pool (LAPC-4AD, LAPC-4AI, LAPC-9AD, LAPC-9AI), prostate cancer pool, bladder cancer pool, kidney cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 85P1B3, was performed at 26 and 30 cycles of amplification.

FIG. 11. Expression of 85P1B3 in normal human tissues. Two multiple tissue northern blots (Clontech) with 2 µg of mRNA/lane, were probed with the 85P1B3 SSH sequence. Size standards in kilobases (kb) are indicated on the side. The results show exclusive expression of an approximately 1.4 kb 85P1B3 transcript in testis but not in any other normal tissues.

FIG. 12. Expression of 85P1B3 in human cancer cell lines. RNA was extracted from a panel of human cancer cell lines. Northern blots with 10 µg of total RNA/lane were probed with the 85P1B3 SSH sequence. Size standards in kilobases (kb) are indicated on the side.

FIG. 13. Expression of 85P1B3 in human patient cancer specimens and cancer cell lines. Expression of 85P1B3 was assayed in a panel of human cancers (T) and their respective matched normal tissues (N) on RNA dot blots. 85P1B3 expression was detected in the cancers of the breast, prostate, uterus, cervix, stomach and lung. 85P1B3 was also found to be highly expressed in all human cancer cell lines tested.

FIG. 14. Expression of 85P1B3 in colon cancer patient specimens. RNA was extracted from colon cancer cell lines (CL), normal colon (N), colon tumors (T) and their normal adjacent tissues (Nat) derived from colon cancer patients. Northern blots with 10 µg of total RNA/lane were probed with the 85P1B3 SSH sequence. Size standards in kilobases (kb) are indicated on the side. Results show expression of 85P1B3 in 2 colon tumor specimens but not in the corresponding normal adjacent tissue. Expression is also seen in all 4 colon cancer cell lines (Colo 205, LoVo, T84, Caco-2). P1—Stage III, T2N1MX; P2—Stage III, T3N1MX.

FIG. 15. Expression of 85P1B3 in bladder cancer patient specimens. RNA was extracted from bladder cancer cell lines (CL), normal bladder (N), bladder tumors (T) and their normal adjacent tissue (Nat) derived from bladder cancer patients. Northern blot with 10 µg of total RNA/lane were probed with the 85P1B3 SSH sequence. Size standards in kilobases (kb) are indicated on the side. Results show expression of 85P1B3 in 3 of 5 bladder tumor specimens. Expression is also seen in all three bladder cancer cell lines, UM-UC-3, J82, and SCABER.

FIG. 16. Expression of 85P1B3 in lung cancer patient specimens. RNA was extracted from lung cancer cell lines (CL), normal lung (N), lung tumors (T) and their normal adjacent tissue (NAT) derived from lung cancer patients. Northern blot with 10 µg of total RNA/lane was probed with the 85P1B3 SSH sequence. Size standards in kilobases (kb) are indicated on the side. Results show expression of 85P1B3 in three lung tumor specimens. Expression is also seen in all lung cancer cell lines.

FIG. 17. Expression of 85P1B3 in Prostate Cancer Xenografts Following Castration. Male mice were injected with LAPC-9AD tumor cells. When tumor reached a palpable size (0.3–0.5 cm in diameter), mice were castrated and tumors harvested at different time points following castration. RNA was isolated from the xenograft tissues. Northern blots with 10 µg of total RNA/lane were probed with the 85P1B3 SSH fragment. Size standards in kilobases (kb) are indicated on the side. Results show expression of 85P1B3 is maintained following castration. A picture of the ethidium-bromide staining of the RNA gel is also presented. Hybridization of the same northern blot with the androgen-dependent gene TMPRSS2 confirms the quality of the androgen deprivation following castration.

FIG. 18. Expression of 85P1B3 in PC3 Cells Following Retroviral-Mediated Gene Delivery. PC3 cells were transduced with the pSRα retroviral vector encoding the 85P1B3 gene. Following selection with neomycin, the cells were expanded and RNA was extracted. Northern blot with 10 µg of total RNA/lane was probed with the 85P1B3 SSH sequence. Size standards in kilobases (kb) are indicated on the side. Results show expression of the 85P1B3 transcript driven from the retroviral LTR, which migrates slower than the endogenous 1.4 kb 85P1B3 transcript. LAPC-9A1 shows only expression of the endogenous 85P1B3, but not the pSRα transcript.

DETAILED DESCRIPTION OF THE INVENTION

Figure 19:
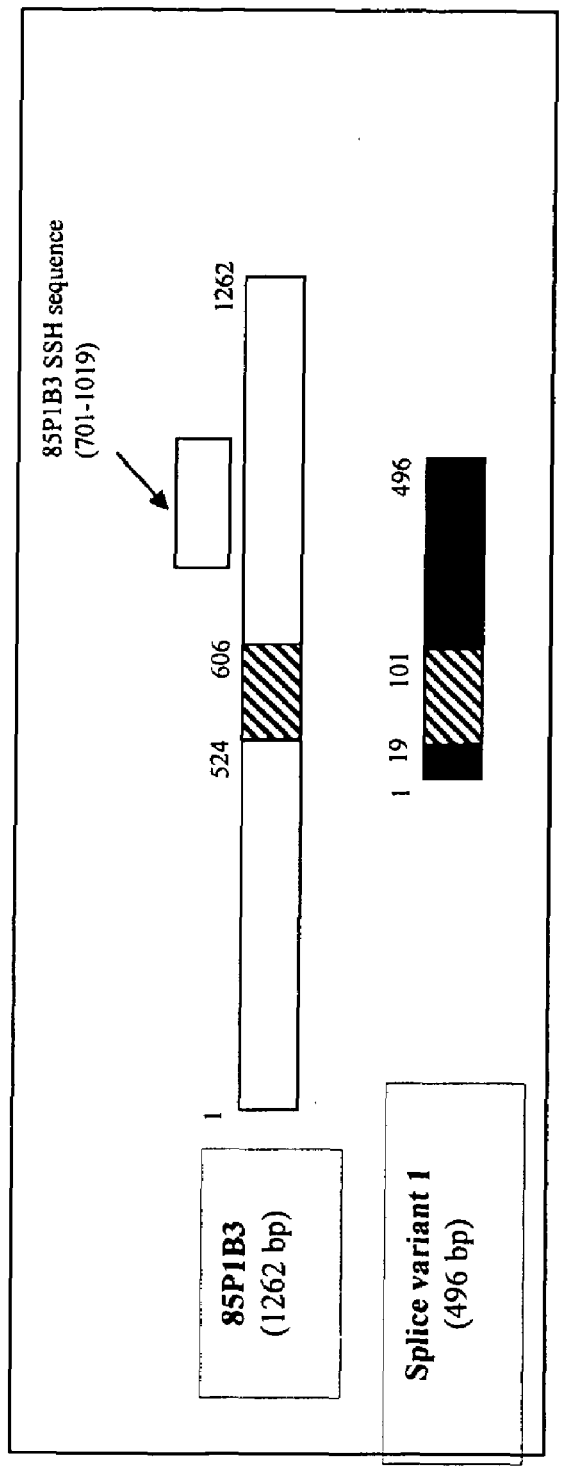
FIG. 19. Schematic diagram of the alignment of 85P1B3 with its splice variant. The region of homology between 85P1B3 and its splice variant 1 is marked with a hatched box. Regions specific for 85P1B3 are marked in white boxes, and the ones specific for the splice variant 1 as black boxes. The SSH sequence of 85P1B3 is also indicated by a white box.

Outline of Sections
I.) Definitions
II.) 85P1B3 Polynucleotides
    II.A.) Uses of 85P1B3 Polynucleotides
        II.A.1.) Monitoring of Genetic Abnormalities
        II.A.2.) Antisense Embodiments
        II.A.3.) Primers and Primer Pairs
        II.A.4.) Isolation of 85P1B3-Encoding Nucleic Acid Molecules
        II.A.5.) Recombinant Nucleic Acid Molecules and Host-Vector Systems
III.) 85P1B3-related Proteins
    III.A.) Motif-bearing Protein Embodiments
    III.B.) Expression of 85P1B3-related Proteins
    III.C.) Modifications of 85P1B3-related Proteins
    III.D.) Uses of 85P1B3-related Proteins
IV.) 85P1B3 Antibodies
V.) 85P1B3 Cellular Immune Responses
VI.) 85P1B3 Transgenic Animals
VII.) Methods for the Detection of 85P1B3
VIII.) Methods for Monitoring the Status of 85P1B3-related Genes and Their Products IX.) Identification of Molecules That Interact With 85P1B3

X.) Therapeutic Methods and Compositions

X.A.) Anti-Cancer Vaccines

X.B.) 85P1B3 as a Target for Antibody-Based Therapy

X.C.) 85P1B3 as a Target for Cellular Immune Responses

X.C.1. Minigene Vaccines

X.C.2. Combinations of CTL Peptides with Helper Peptides

X.C.3. Combinations of CTL Peptides with T Cell Priming Agents

X.C.4. Vaccine Compositions Comprising DC Pulsed with CTL and/or HTL Peptides

X.D.) Adoptive Immunotherapy

X.E.) Administration of Vaccines for Therapeutic or Prophylactic Purposes

XI.) Diagnostic and Prognostic Embodiments of 85P1B3.

XII.) Inhibition of 85P1B3 Protein Function

XII.A.) Inhibition of 85P1B3 With Intracellular Antibodies

XII.B.) Inhibition of 85P1B3 with Recombinant Proteins

XII.C.) Inhibition of 85P1B3 Transcription or Translation

XII.D.) General Considerations for Therapeutic Strategies

XIII.) KITS

I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage $C_1$–$C_2$ disease under the Whitmore-Jewett system, and stage T3–T4 and N+disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 85P1B3 (either by removing the underlying glycosylation site or by deleting the glycosylation by chemical and/or enzymatic means), and/or adding one or more glycosylation sites that are not present in the native sequence 85P1B3. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 85P1B3-related protein). For example an analog of the 85P1B3 protein can be specifically bound by an antibody or T cell that specifically binds to 85P1B3.

The term "antibody" is used in the broadest sense. Therefore an "antibody" can be naturally occurring or man-made such as monoclonal antibodies produced by conventional hybridoma technology. Anti-85P1B3 antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-85P1B3 antibodies and clones thereof (including agonist, antagonist and neutralizing antibodies) and anti-85P1B3 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

The term "cytotoxic agent" refers to a substance that inhibits or prevents the function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, TAXOL™, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, 8$^{TH}$ ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/ 100 µg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 85P1B3 gene or that encode polypeptides other than 85P1B3 gene product or fragments thereof. A skilled artisan can readily employ nucleic acid isolation procedures to obtain an isolated 85P1B3 polynucleotide. A protein is said to be "isolated," for example, when physical, mechanical or chemical methods are employed to remove the 85P1B3 protein from cellular constituents that are normally associated with the protein. A skilled artisan can readily employ standard purification methods to obtain an isolated 85P1B3 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of an 85P1B3-related protein, refers to any pattern of amino acids forming part of the primary sequence of a protein, that is associated with a particular function (e.g. protein—protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) (as shown for example in SEQ ID NO: 702) can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. In another embodiment, for example, the primary anchor residues of a peptide that will bind an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

A "recombinant" DNA or RNA molecule is a DNA or RNA molecule that has been subjected to molecular manipulation in vitro.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1–150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 85P1B3 protein shown in FIG. 2 or FIG. 3). An analog is an example of a variant protein.

The 85P1B3-related proteins of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 85P1B3 proteins or fragments thereof, as well as fusion proteins of a 85P1B3 protein and a heterologous polypeptide are also included. Such 85P1B3 proteins are collectively referred to as the 85P1B3-related proteins, the proteins of the invention, or 85P1B3. The term "85P1B3-related protein" refers to a polypeptide fragment or an 85P1B3 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100 or more than 100 amino acids.

II.) 85P1B3 Polynucleotides

One aspect of the invention provides polynucleotides corresponding or complementary to all or part of an 85P1B3 gene, mRNA, and/or coding sequence, preferably in isolated form, including polynucleotides encoding an 85P1B3-related protein and fragments thereof, DNA, RNA, DNA/RNA hybrid, and related molecules, polynucleotides or oligonucleotides complementary to an 85P1B3 gene or mRNA sequence or a part thereof, and polynucleotides or oligonucleotides that hybridize to an 85P1B3 gene, mRNA, or to an 85P1B3 encoding polynucleotide (collectively, "85P1B3 polynucleotides"). In all instances when referred to in this section, T can also be U in FIG. 2.

Embodiments of a 85P1B3 polynucleotide include: a 85P1B3 polynucleotide having the sequence shown in FIG. 2, the nucleotide sequence of 85P1B3 as shown in FIG. 2, wherein T is 1; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 85P1B3 nucleotides comprise, without limitation:

(a) a polynucleotide comprising or consisting of the sequence as shown in FIG. 2 (SEQ ID NO.: 727), wherein T can also be U;
(b) a polynucleotide comprising or consisting of the sequence as shown in FIG. 2 (SEQ ID NO.: 727), from nucleotide residue number 13 through nucleotide residue number 699, wherein T can also be U;
(c) a polynucleotide that encodes a 85P1B3-related protein whose sequence is encoded by cDNA contained in a plasmid deposited with American Type Culture Collection.
(d) a polynucleotide that encodes an 85P1B3-related protein that is at least 90% homologous to the entire amino acid sequence shown in SEQ ID NO.:728;
(e) a polynucleotide that encodes an 85P1B3-related protein that is at least identical to the entire amino acid sequence shown in SEQ ID NO: 728;
(f) a polynucleotide that encodes at least one peptide set forth in Tables V–XVIII;
(g) a polynucleotide that encodes a peptide region of at least 5 amino acids FIG. 3 in any whole number increment up to 229 that includes an amino acid position having a value greater than 0.5 in the Hydrophilicity profile of FIG. 5;
(h) a polynucleotide that encodes a peptide region of at least 5 amino acids of FIG. 3 in any whole number increment up to 229 that includes an amino acid position having a value less than 0.5 in the Hydropathicity profile of FIG. 6;
(i) a polynucleotide that encodes a peptide region of at least 5 amino acids of FIG. 3 in any whole number increment up to 229 that includes an amino acid position having a value greater than 0.5 in the Percent Accessible Residues profile of FIG. 7;
(j) a polynucleotide that encodes a peptide region of at least 5 amino acids of FIG. 3 in any whole number increment up to 229 that includes an amino acid position having a value greater than 0.5 in the Average Flexibility profile on FIG. 8;
(k) a polynucleotide that encodes a peptide region of at least 5 amino acids of FIG. 3 in any whole number increment up to 229 that includes an amino acid position having a value greater than 0.5 in the Beta-turn profile of FIG. 9;
(l) a polynucleotide that is fully complementary to a polynucleotide of any one of (a)–(k);
(m) a polynucleotide that selectively hybridizes under stringent conditions to a polynucleotide of (a)–(l); and
(n) a polynucleotide of any of (a)–(m) or peptide of (o) (see immediately below) together with a pharmaceutical excipient and/or in a human unit dose form.

Regarding item (n) immediately above, examples of embodiments of 85P1B3 polypeptides comprise, without limitation:

(o) a peptide that is encoded by any of (a)–(k).

As used herein, a range is understood to specifically disclose all whole unit positions thereof.

Typical embodiments of the invention disclosed herein include 85P1B3 polynucleotides that encode specific portions of the 85P1B3 mRNA sequence (and those which are complementary to such sequences) such as those that encode the protein and fragments thereof, for example of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, or 229 contiguous amino acids.

For example, representative embodiments of the invention disclosed herein include: polynucleotides and their encoded peptides themselves encoding about amino acid 1 to about amino acid 10 of the 85P1B3 protein shown in FIG. 2 or FIG. 3, polynucleotides encoding about amino acid 10 to about amino acid 20 of the 85P1B3 protein shown in FIG. 2, or FIG. 3, polynucleotides encoding about amino acid 20 to about amino acid 30 of the 85P1B3 protein shown in FIG. 2 or FIG. 3, polynucleotides encoding about amino acid 30 to about amino acid 40 of the 85P1B3 protein shown in FIG. 2 or FIG. 3, polynucleotides encoding about amino acid 40 to about amino acid 50 of the 85P1B3 protein shown in FIG. 2 or FIG. 3, polynucleotides encoding about amino acid 50 to about amino acid 60 of the 85P1B3 protein shown in FIG. 2 or FIG. 3, polynucleotides encoding about amino acid 60 to about amino acid 70 of the 85P1B3 protein shown in FIG. 2 or FIG. 3, polynucleotides encoding about amino acid 70 to about amino acid 80 of the 85P1B3 protein shown in FIG. 2 or FIG. 3, polynucleotides encoding about amino acid 80 to about amino acid 90 of the 85P1B3 protein shown in FIG. 2 or FIG. 3, polynucleotides encoding about amino acid 90 to about amino acid 100 of the 85P1B3 protein shown in FIG. 2 or FIG. 3, in increments of about 10 amino acids, ending at the carboxyl terminal amino acid set forth in FIG. 2 or FIG. 3. Accordingly polynucleotides encoding portions of the amino acid sequence (of about 10 amino acids), of amino acids 100 through the carboxyl terminal amino acid of the 85P1B3 protein are embodiments of the invention. Wherein it is understood that each particular amino acid position discloses that position plus or minus five amino acid residues.

Polynucleotides encoding relatively long portions of the 85P1B3 protein are also within the scope of the invention. For example, polynucleotides encoding from about amino acid 1 (or 20 or 30 or 40 etc.) to about amino acid 20, (or 30, or 40 or 50 etc.) of the 85P1B3 protein shown in FIG. 2 or FIG. 3 can be generated by a variety of techniques well known in the art. These polynucleotide fragments can include any portion of the 85P1B3 sequence as shown in FIG. 2 or FIG. 3.

Additional illustrative embodiments of the invention disclosed herein include 85P1B3 polynucleotide fragments encoding one or more of the biological motifs contained within the 85P1B3 protein sequence, including one or more of the motif-bearing subsequences of the 85P1B3 protein set forth in Tables V–XVIII. In another embodiment, typical polynucleotide fragments of the invention encode one or more of the regions of 85P1B3 that exhibit homology to a known molecule. In another embodiment of the invention, typical polynucleotide fragments can encode one or more of the 85P1B3 N-glycosylation sites, cAMP and cGMP-dependent protein kinase phosphorylation sites, casein kinase II phosphorylation sites or N-myristoylation site and amidation sites.

II.A.) Uses of 85P1B3 Polynucleotides

II.A.1.) Monitoring of Genetic Abnormalities

The polynucleotides of the preceding paragraphs have a number of different specific uses. The human 85P1B3 gene maps to the chromosomal location set forth in Example 3. For example, because the 85P1B3 gene maps to this chromosome, polynucleotides that encode different regions of the 85P1B3 protein are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(34): 81–83 (1998); Johansson et al., Blood 86(10): 3905–3914 (1995) and Finger et al., P.N.A.S. 85(23): 9158–9162 (1988)). Thus, polynucleotides encoding specific regions of the 85P1B3 protein provide new tools that can be used to delineate, with greater precision than previously possible, cytogenetic abnormalities in the chromosomal region that encodes 85P1B3 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055–1057 (1994)).

Furthermore, as 85P1B3 was shown to be highly expressed in prostate and other cancers, 85P1B3 polynucleotides are used in methods assessing the status of 85P1B3 gene products in normal versus cancerous tissues. Typically, polynucleotides that encode specific regions of the 85P1B3 protein are used to assess the presence of perturbations (such as deletions, insertions, point mutations, or alterations resulting in a loss of an antigen etc.) in specific regions of the 85P1B3 gene, such as such regions containing one or more motifs. Exemplary assays include both RT-PCR assays as well as single-strand conformation polymorphism (SSCP) analysis (see, e.g., Marrogi et al., J. Cutan. Pathol. 26(8): 369–378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 85P1B3. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 85P1B3 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 85P1B3. See for example, Jack Cohen, Oligodeoxynucleotides, Antisense Inhibitors of Gene Expression, CRC Press, 1989; and Synthesis 1:1–5 (1988). The 85P1B3 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See Iyer, R. P. et al, J. Org. Chem. 55:4693–4698 (1990); and Iyer, R. P. et al., J. Am. Chem. Soc. 112:1253–1254 (1990). Additional 85P1B3 antisense oligonucleotides of the present invention include morpholino antisense oligonucleotides known in the art (see, e.g., Partridge et al., 1996, Antisense & Nucleic Acid Drug Development 6: 169–175).

The 85P1B3 antisense oligonucleotides of the present invention typically can be RNA or DNA that is complementary to and stably hybridizes with the first 100 5' codons or last 100 3' codons of the 85P1B3 genomic sequence or the corresponding mRNA. Absolute complementarity is not required, although high degrees of complementarity are preferred. Use of an oligonucleotide complementary to this region allows for the selective hybridization to 85P1B3 mRNA and not to mRNA specifying other regulatory subunits of protein kinase. In one embodiment, 85P1B3 antisense oligonucleotides of the present invention are 15 to 30-mer fragments of the antisense DNA molecule that have a sequence that hybridizes to 85P1B3 mRNA. Optionally, 85P1B3 antisense oligonucleotide is a 30-mer oligonucleotide that is complementary to a region in the first 10 5' codons or last 10 3' codons of 85P1B3. Alternatively, the antisense molecules are modified to employ ribozymes in the inhibition of 85P1B3 expression, see, e.g., L. A. Couture & D. T. Stinchcomb; *Trends Genet* 12: 510–515 (1996).

II.A.3.) Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 85P1B3 polynucleotide in a sample and as a means for detecting a cell expressing a 85P1B3 protein.

Examples of such probes include polypeptides comprising all or part of the human 85P1B3 cDNA sequence shown in FIG. 2. Examples of primer pairs capable of specifically amplifying 85P1B3 mRNAs are also described in the Examples. As will be understood by the skilled artisan, a great many different primers and probes can be prepared based on the sequences provided herein and used effectively to amplify and/or detect a 85P1B3 mRNA.

The 85P1B3 polynucleotides of the invention are useful for a variety of purposes, including but not limited to their use as probes and primers for the amplification and/or detection of the 85P1B3 gene(s), mRNA(s), or fragments thereof; as reagents for the diagnosis and/or prognosis of prostate cancer and other cancers; as coding sequences capable of directing the expression of 85P1B3 polypeptides; as tools for modulating or inhibiting the expression of the 85P1B3 gene(s) and/or translation of the 85P1B3 transcript(s); and as therapeutic agents.

The present invention includes the use of any probe as described herein to identify and isolate a 85P1B3 or 85P1B3 related nucleic acid sequence from a naturally occurring source, such as humans or other mammals, as well as the isolated nucleic acid sequence per se, which would comprise all or most of the sequences found in the probe used.

II.A.4.) Isolation of 85P1B3-Encoding Nucleic Acid Molecules

The 85P1B3 cDNA sequences described herein enable the isolation of other polynucleotides encoding 85P1B3 gene product(s), as well as the isolation of polynucleotides encoding 85P1B3 gene product homologs, alternatively spliced isoforms, allelic variants, and mutant forms of the 85P1B3 gene product as well as polynucleotides that encode analogs of 85P1B3-related proteins. Various molecular cloning methods that can be employed to isolate full length cDNAs encoding an 85P1B3 gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 85P1B3 gene cDNAs can be identified by probing with a labeled 85P1B3 cDNA or a fragment thereof. For example, in one embodiment, the 85P1B3 cDNA (FIG. 2) or a portion thereof can be synthesized and used as a probe to retrieve overlapping and full-length cDNAs corresponding to a 85P1B3 gene. The 85P1B3 gene itself can be isolated by screening genomic DNA libraries, bacterial artificial chromosome libraries (BACs), yeast artificial chromosome libraries (YACs), and the like, with 85P1B3 DNA probes or primers.

II.A.5.) Recombinant Nucleic Acid Molecules and Host-Vector Systems

The invention also provides recombinant DNA or RNA molecules containing an 85P1B3 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al, 1989, supra).

The invention further provides a host-vector system comprising a recombinant DNA molecule containing a 85P1B3 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 85P1B3 or a fragment, analog or homolog thereof can be used to generate 85P1B3 proteins or fragments thereof using any number of host-vector systems routinely used and widely known in the art.

A wide range of host-vector systems suitable for the expression of 85P1B3 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 85P1B3 can be expressed in several prostate cancer and non-prostate cell lines, including for example 293, 293T, rat-1, NIH 3T3 and TsuPr1. The host-vector systems of the invention are useful for the production of a 85P1B3 protein or fragment thereof. Such host-vector systems can be employed to study the functional properties of 85P1B3 and 85P1B3 mutations or analogs.

Recombinant human 85P1B3 protein or an analog or homolog or fragment thereof can be produced by mammalian cells transfected with a construct encoding a 85P1B3-related nucleotide. For example, 293T cells can be transfected with an expression plasmid encoding 85P1B3 or fragment, analog or homolog thereof, the 85P1B3 or related protein is expressed in the 293T cells, and the recombinant 85P1B3 protein is isolated using standard purification methods (e.g., affinity purification using anti-85P1B3 antibodies). In another embodiment, a 85P1B3 coding sequence is subcloned into the retroviral vector pSRαMSVtkneo and used to infect various mammalian cell lines, such as NIH 3T3, TsuPr1, 293 and rat-1 in order to establish 85P1B3 expressing cell lines. Various other expression systems well known in the art can also be employed. Expression constructs encoding a leader peptide joined in frame to the 85P1B3 coding sequence can be used for the generation of a secreted form of recombinant 85P1B3 protein.

As discussed herein, redundancy in the genetic code permits variation in 85P1B3 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.,* 9:5073–5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662–2666, (1995) and Kozak NAR 15(20): 8125–8148 (1987)).

III.) 85P1B3-Related Proteins

Another aspect of the present invention provides 85P1B3-related proteins. Specific embodiments of 85P1B3 proteins comprise a polypeptide having all or part of the amino acid sequence of human 85P1B3 as shown in FIG. 2 or FIG. 3. Alternatively, embodiments of 85P1B3 proteins comprise variant, homolog or analog polypeptides that have alterations in the amino acid sequence of 85P1B3 shown in FIG. 2 or FIG. 3.

In general, naturally occurring allelic variants of human 85P1B3 share a high degree of structural identity and homology (e.g., 90% or more homology). Typically, allelic variants of the 85P1B3 protein contain conservative amino acid substitutions within the 85P1B3 sequences described herein or contain a substitution of an amino acid from a corresponding position in a homologue of 85P1B3. One class of 85P1B3 allelic variants are proteins that share a high degree of homology with at least a small region of a particular 85P1B3 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13–15 "Biochemistry" $2^{nd}$ ED. Lubert Stryer ed (Stanford University); Henikoff et al., PNAS 1992 Vol 89 10915–10919; Lei et al., J Biol Chem 1995 May 19; 270(20):118826).

Embodiments of the invention disclosed herein include a wide variety of art-accepted variants or analogs of 85P1B3 proteins such as polypeptides having amino acid insertions, deletions and substitutions. 85P1B3 variants can be made using methods known in the art such as site-directed mutagenesis, alanine scanning, and PCR mutagenesis. Site-directed mutagenesis (Carter et al., *Nucl. Acids Res.*, 3:4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA*, 317:415 (1986)) or other known techniques can be performed on the cloned DNA to produce the 85P1B3 variant DNA.

Scanning amino acid analysis can also be employed to identify one or more amino acids along a contiguous sequence that is involved in a specific biological activity such as a protein—protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 85P1B3 variants, analogs or homologs, have the distinguishing attribute of having at least one epitope that is "cross reactive" with a 85P1B3 protein having the amino acid sequence of SEQ ID NO: 703. As used in this sentence, "cross reactive" means that an antibody or T cell that specifically binds to an 85P1B3 variant also specifically binds to the 85P1B3 protein having the amino acid sequence of SEQ ID NO: 703. A polypeptide ceases to be a variant of the protein shown in SEQ ID NO: 703 when it no longer contains any epitope capable of being recognized by an antibody or T cell that specifically binds to the 85P1B3 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165(12): 6949–6955; Hebbes et al., Mol Immunol (1989) 26(9):865–73; Schwartz et al., J Immunol (1985) 135(4):2598–608.

Another class of 85P1B3-related protein variants share 70%, 75%, 80%, 85% or 90% or more similarity with the amino acid sequence of SEQ ID NO: 703 or a fragment thereof. Another specific class of 85P1B3 protein variants or analogs comprise one or more of the 85P1B3 biological motifs described herein or presently known in the art. Thus, encompassed by the present invention are analogs of 85P1B3 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of the 85P1B3 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of the 85P1B3 protein shown in FIG. 2 or FIG. 3.

Moreover, representative embodiments of the invention disclosed herein include polypeptides consisting of about amino acid 1 to about amino acid 10 of the 85P1B3 protein shown in FIG. 2 or FIG. 3, polypeptides consisting of about amino acid 10 to about amino acid 20 of the 85P1B3 protein shown in FIG. 2 or FIG. 3, polypeptides consisting of about amino acid 20 to about amino acid 30 of the 85P1B3 protein shown in FIG. 2 or FIG. 3, polypeptides consisting of about amino acid 30 to about amino acid 40 of the 85P1B3 protein shown in FIG. 2 or FIG. 3, polypeptides consisting of about amino acid 40 to about amino acid 50 of the 85P1B3 protein shown in FIG. 2 or FIG. 3, polypeptides consisting of about amino acid 50 to about amino acid 60 of the 85P1B3 protein shown in FIG. 2 or FIG. 3, polypeptides consisting of about amino acid 60 to about amino acid 70 of the 85P1B3 protein shown in FIG. 2 or FIG. 3, polypeptides consisting of about amino acid 70 to about amino acid 80 of the 85P1B3 protein shown in FIG. 2 or FIG. 3, polypeptides consisting of about amino acid 80 to about amino acid 90 of the 85P1B3 protein shown in FIG. 2 or FIG. 3, polypeptides consisting of about amino acid 90 to about amino acid 100 of the 85P1B3 protein shown in FIG. 2 or FIG. 3, etc. throughout the entirety of the 85P1B3 amino acid sequence. Moreover, polypeptides consisting of about amino acid 1 (or 20 or 30 or 40 etc.) to about amino acid 20, (or 130, or 140 or 150 etc.) of the 85P1B3 protein shown in FIG. 2 or FIG. 3 are embodiments of the invention. It is to be appreciated that the starting and stopping positions in this paragraph refer to the specified position as well as that position plus or minus 5 residues.

85P1B3-related proteins are generated using standard peptide synthesis technology or using chemical cleavage methods well known in the art. Alternatively, recombinant methods can be used to generate nucleic acid molecules that encode a 85P1B3-related protein. In one embodiment, nucleic acid molecules provide a means to generate defined fragments of the 85P1B3 protein (or variants, homologs or analogs thereof).

III.A.) Motif-Bearing Protein Embodiments

Additional illustrative embodiments of the invention disclosed herein include 85P1B3 polypeptides comprising the amino acid residues of one or more of the biological motifs contained within the 85P1B3 polypeptide sequence set forth in FIG. 2 or FIG. 3. Various motifs are known in the art, and a protein can be evaluated for the presence of such motifs by a number of publicly available Internet sites (see, e.g., Epimatrix™ and Epimer™, Brown University, and BIMAS).

Motif bearing subsequences of the 85P1B3 protein are set forth and identified in Table XIX.

Table XX sets forth several frequently occurring motifs based on pfam searches. The columns of Table XX list (1) motif name abbreviation. (2) percent identity found amongst the different member of the motif family, (3) motif name or description and (4) most common function; location information is included if the motif is relevant for location.

Polypeptides comprising one or more of the 85P1B3 motifs discussed above are useful in elucidating the specific characteristics of a malignant phenotype in view of the observation that the 85P1B3 motifs discussed above are associated with growth dysregulation and because 85P1B3 is overexpressed in certain cancers (See, e.g., Table 1). Casein kinase II, cAMP and camp-dependent protein kinase, and Protein Kinase C, for example, are enzymes known to be associated with the development of the malignant phenotype (see e.g. Chen et al., Lab Invest., 78(2): 165–174 (1998); Gaiddon et al., Endocrinology 136(10): 4331–4338 (1995); Hall et al., Nucleic Acids Research 24(6): 1119–1126 (1996); Peterziel et al., Oncogene 18(46): 6322–6329 (1999) and O'Brian, Oncol. Rep. 5(2): 305–309 (1998)). Moreover, both glycosylation and myristoylation are protein modifications also associated with cancer and cancer progression (see e.g. Dennis et al., Biochem. Biophys. Acta 1473(1):21–34 (1999); Raju et al., Exp. Cell Res. 235(1): 145–154 (1997)). Amidation is another protein modification also associated with cancer and cancer progression (see e.g. Treston et al., J. Natl. Cancer Inst. Monogr. (13): 169–175 (1992)).

In another embodiment, proteins of the invention comprise one or more of the immunoreactive epitopes identified in accordance with art-accepted methods, such as the peptides set forth in Tables V–XVIII. CTL epitopes can be determined using specific algorithms to identify peptides within an 85P1B3 protein that are capable of optimally binding to specified HLA alleles (e.g., Table IV; Epimatrix™ and Epimer™, Brown University and BIMAS.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, one can substitute out a deleterious residue in favor of any other residue, such as a preferred residue as defined in Table IV; substitute a less-preferred residue with a preferred residue as defined in Table IV; or substitute an originally-occurring preferred residue with another preferred residue as defined in Table IV. Substitutions can occur at primary anchor positions or at other positions in a peptide; see, e.g., Table IV.

A variety of references reflect the art regarding the identification and generation of epitopes in a protein of interest as well as analogs thereof. See, for example, WO 9733602 to Chesnut et al.; Sette, Immunogenetics 1999 50(34): 201–212; Sette et al., J. Immunol. 2001 166(2): 1389–1397; Sidney et al., Hum. Immunol. 1997 58(1): 12–20; Kondo et al., Immunogenetics 1997 45(4): 249–258; Sidney et al., J. Immunol. 1996 157(8): 3480–90; and Falk et al., Nature 351: 290–6 (1991); Hunt et al., Science 255:1261–3 (1992); Parker et al., J. Immunol. 149:3580–7 (1992); Parker et al., J. Immunol. 152:163–75 (1994)); Kast et al., 1994 152(8): 3904–12; Borras-Cuesta et al., Hum. Immunol. 2000 61(3): 266–278; Alexander et al., J. Immunol. 2000 164(3); 164(3): 1625–1633; Alexander et al., PMID: 7895164, UI: 95202582; O'Sullivan et al., J. Immunol. 1991 147(8): 2663–2669; Alexander et al., Immunity 1994 1(9): 751–761 and Alexander et al., Immunol. Res. 1998 18(2): 79–92.

Related embodiments of the inventions include polypeptides comprising combinations of the different motifs set forth in Table XIX, and/or, one or more of the predicted CTL epitopes of Table V through Table XVIII, and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

85P1B3-related proteins are embodied in many forms, preferably in isolated form. A purified 85P1B3 protein molecule will be substantially free of other proteins or molecules that impair the binding of 85P1B3 to antibody, T cell or other ligand. The nature and degree of isolation and purification will depend on the intended use. Embodiments of a 85P1B3-related proteins include purified 85P1B3-related proteins and functional, soluble 85P1B3-related proteins. In one embodiment, a functional, soluble 85P1B3 protein or fragment thereof retains the ability to be bound by antibody, T cell or other ligand.

The invention also provides 85P1B3 proteins comprising biologically active fragments of the 85P1B3 amino acid sequence shown in FIG. 2 or FIG. 3. Such proteins exhibit properties of the 85P1B3 protein, such as the ability to elicit the generation of antibodies that specifically bind an epitope associated with the 85P1B3 protein; to be bound by such antibodies; to elicit the activation of HTL or CTL; and/or, to be recognized by HTL or CTL.

85P1B3-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments that contain such structures are particularly useful in generating subunit-specific anti-85P1B3 antibodies, or T cells or in identifying cellular factors that bind to 85P1B3.

CTL epitopes can be determined using specific algorithms to identify peptides within an 85P1B3 protein that are capable of optimally binding to specified HLA alleles (e.g., by using the SYFPEITHI site at World Wide Web URL syfpeithi.bmi-heidelberg.com/; the listings in Table IV(A)–(E); Epimatrix™ and Epimer™, Brown University and BIMAS). Illustrating this, peptide epitopes from 85P1B3 that are presented in the context of human MHC class I molecules HLA-A1, A2, A3, A11, A24, B7 and B35 were predicted (Tables V–XVIII). Specifically, the complete amino acid sequence of the 85P1B3 protein was entered into the HLA Peptide Motif Search algorithm found in the Bioinformatics and Molecular Analysis Section (BIMAS) web site listed above. The HLA peptide motif search algorithm was developed by Dr. Ken Parker based on binding of specific peptide sequences in the groove of HLA Class I molecules, in particular HLA-A2 (see, e.g., Falk et al., Nature 351: 290–6 (1991); Hunt et al., Science 255:1261–3 (1992); Parker et al., J. Immunol. 149:3580–7 (1992); Parker et al., J. Immunol. 152:163–75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L) or methionine (M) at position 2 and a valine (V) or leucine (L) at the C-terminus (see, e.g., Parker et al., J. Immunol. 149:3580–7 (1992)). Selected results of 85P1B3 predicted binding peptides are shown in Tables V–XVIII herein. In Tables V–XVIII, the top 50 ranking candidates, 9-mers and 10-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73–8 (1997) and Peshwa et al., Prostate 36:129–38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/) are to be "applied" to the 85P1B3 protein. As used in this context "applied" means that the 85P1B3 protein is evaluated, e.g., visually or by computer-based patterns finding methods, as appreciated by those of skill in the relevant art. Every subsequence of the 85P1B3 of 8, 9, 10, or 11 amino acid residues that bears an HLA Class I motif, or a subsequence of 9 or more amino acid residues that bear an HLA Class I motif are within the scope of the invention.

III.B.) Expression of 85P1B3-Related Proteins

In an embodiment described in the examples that follow, 85P1B3 can be conveniently expressed in cells (such as 293T cells) transfected with a commercially available expression vector such as a CMV-driven expression vector encoding 85P1B3 with a C-terminal 6×His (SEQ ID NO: 709) and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 85P1B3 protein in transfected cells. The secreted HIS-tagged 85P1B3 in the culture media can be purified, e.g., using a nickel column using standard techniques.

III.C.) Modifications of 85P1B3-Related Proteins

Modifications of 85P1B3-related proteins such as covalent modifications are included within the scope of this invention. One type of covalent modification includes reacting targeted amino acid residues of a 85P1B3 polypeptide with an organic derivatizing agent that is capable of reacting with selected side chains or the N- or C-terminal residues of the 85P1B3. Another type of covalent modification of the 85P1B3 polypeptide included within the scope of this invention comprises altering the native glycosylation pattern of a protein of the invention. Another type of covalent modification of 85P1B3 comprises linking the 85P1B3 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 85P1B3-related proteins of the present invention can also be modified to form a chimeric molecule comprising 85P1B3 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of the 85P1B3 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 85P1B3. A chimeric molecule can comprise a fusion of a 85P1B3-related protein with a polyhistidine epitope tag, which provides an epitope to which immobilized nickel can selectively bind, with cytokines or with growth factors. The epitope tag is generally placed at the amino- or carboxyl-terminus of the 85P1B3. In an alternative embodiment, the chimeric molecule can comprise a fusion of a 85P1B3-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 85P1B3 polypeptide in place of at least one variable region within an Ig molecule. In a preferred embodiment, the immunoglobulin fusion includes the hinge, CH2 and CH3, or the hinge, CH1, CH2 and CH3 regions of an IgG1 molecule. For the production of immunoglobulin fusions see, e.g., U.S. Pat. No. 5,428,130 issued Jun. 27, 1995.

III.D.) Uses of 85P1B3-Related Proteins

The proteins of the invention have a number of different specific uses. As 85P1B3 is highly expressed in prostate and other cancers, 85P1B3-related proteins are used in methods that assess the status of 85P1B3 gene products in normal versus cancerous tissues, thereby elucidating the malignant phenotype. Typically, polypeptides from specific regions of the 85P1B3 protein are used to assess the presence of perturbations (such as deletions, insertions, point mutations etc.) in those regions (such as regions containing one or more motifs). Exemplary assays utilize antibodies or T cells targeting 85P1B3-related proteins comprising the amino acid residues of one or more of the biological motifs contained within the 85P1B3 polypeptide sequence in order to evaluate the characteristics of this region in normal versus cancerous tissues or to elicit an immune response to the epitope. Alternatively, 85P1B3-related proteins that contain the amino acid residues of one or more of the biological motifs in the 85P1B3 protein are used to screen for factors that interact with that region of 85P1B3.

85P1B3 protein fragments/subsequences are particularly useful in generating and characterizing domain-specific antibodies (e.g., antibodies recognizing an extracellular or intracellular epitope of an 85P1B3 protein), for identifying agents or cellular factors that bind to 85P1B3 or a particular structural domain thereof, and in various therapeutic and diagnostic contexts, including but not limited to diagnostic assays, cancer vaccines and methods of preparing such vaccines.

Proteins encoded by the 85P1B3 genes, or by analogs, homologs or fragments thereof, have a variety of uses, including but not limited to generating antibodies and in methods for identifying ligands and other agents and cellular constituents that bind to an 85P1B3 gene product. Antibodies raised against an 85P1B3 protein or fragment thereof are useful in diagnostic and prognostic assays, and imaging methodologies in the management of human cancers characterized by expression of 85P1B3 protein, such as those listed in Table 1. Such antibodies can be expressed intracellularly and used in methods of treating patients with such cancers. 85P1B3-related nucleic acids or proteins are also used in generating HTL or CTL responses.

Various immunological assays useful for the detection of 85P1B3 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 85P1B3-expressing cells (e.g., in radioscintigraphic imaging methods). 85P1B3 proteins are also particularly useful in generating cancer vaccines, as further described herein.

IV.) 85P1B3 Antibodies

Another aspect of the invention provides antibodies that bind to 85P1B3-related proteins. Preferred antibodies specifically bind to a 85P1B3-related protein and do not bind (or bind weakly) to peptides or proteins that are not 85P1B3-related proteins. For example, antibodies bind 85P1B3 can bind 85P1B3-related proteins such as the homologs or analogs thereof.

85P1B3 antibodies of the invention are particularly useful in prostate cancer diagnostic and prognostic assays, and imaging methodologies. Similarly, such antibodies are useful in the treatment, diagnosis, and/or prognosis of other cancers, to the extent 85P1B3 is also expressed or overexpressed in these other cancers. Moreover, intracellularly expressed antibodies (e.g., single chain antibodies) are therapeutically useful in treating cancers in which the expression of 85P1B3 is involved, such as advanced or metastatic prostate cancers.

The invention also provides various immunological assays useful for the detection and quantification of 85P1B3 and mutant 85P1B3-related proteins. Such assays can comprise one or more 85P1B3 antibodies capable of recognizing and binding a 85P1B3-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 85P1B3 are also provided by the invention, including but not limited to radioscintigraphic imaging methods using labeled 85P1B3 antibodies. Such assays are clinically useful in the detection, monitoring, and prognosis of 85P1B3 expressing cancers such as prostate cancer.

85P1B3 antibodies are also used in methods for purifying a 85P1B3-related protein and for isolating 85P1B3 homologues and related molecules. For example, a method of purifying a 85P1B3-related protein comprises incubating an 85P1B3 antibody, which has been coupled to a solid matrix, with a lysate or other solution containing a 85P1B3-related protein under conditions that permit the 85P1B3 antibody to bind to the 85P1B3-related protein; washing the solid matrix to eliminate impurities; and eluting the 85P1B3-related protein from the coupled antibody. Other uses of the 85P1B3 antibodies of the invention include generating anti-idiotypic antibodies that mimic the 85P1B3 protein.

Various methods for the preparation of antibodies are well known in the art. For example, antibodies can be prepared by immunizing a suitable mammalian host using a 85P1B3-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 85P1B3 can also be used, such as a 85P1B3 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 85P1B3-related protein is synthesized and used as an immunogen.

In addition, naked DNA immunization techniques known in the art are used (with or without purified 85P1B3-related protein or 85P1B3 expressing cells) to generate an immune response to the encoded immunogen (for review, see Donnelly et al., 1997, Ann. Rev. Immunol. 15: 617–648).

The amino acid sequence of 85P1B3 as shown in FIG. 2 or FIG. 3 can be analyzed to select specific regions of the 85P1B3 protein for generating antibodies. For example, hydrophobicity and hydrophilicity analyses of the 85P1B3 amino acid sequence are used to identify hydrophilic regions in the 85P1B3 structure. Regions of the 85P1B3 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Thus, each region identified by any of these programs or methods is within the scope of the present invention. Methods for the generation of 85P1B3 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 85P1B3 immunogen is often conducted by injection over a suitable time period and with use of a suitable adjuvant, as is understood in the art. During the immunization schedule, titers of antibodies can be taken to determine adequacy of antibody formation.

85P1B3 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 85P1B3-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of the 85P1B3 protein can also be produced in the context of chimeric or complementarity determining region (CDR) grafted antibodies of multiple species origin. Humanized or human 85P1B3 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522–525; Riechmann et al., 1988, Nature 332: 323–327; Verhoeyen et al., 1988, Science 239: 1534–1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535–539). Fully human 85P1B3 monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45–64 (1993); Burton and Barbas, Human Antibodies from combinatorial libraries. Id., pp 65–82). Fully human 85P1B3 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607–614; U.S. Pat. No. 6,162,963 issued 19 Dec. 2000; U.S. Pat. No. 6,150,584 issued 12 Nov. 2000; and, U.S. Pat. No. 6,114,598 issued 5 Sep. 2000). This method avoids the in vitro manipulation required with phage display technology and efficiently produces high affinity authentic human antibodies.

Reactivity of 85P1B3 antibodies with an 85P1B3-related protein can be established by a number of well known means, including Western blot, immunoprecipitation, ELISA, and FACS analyses using, as appropriate, 85P1B3-related proteins, 85P1B3-expressing cells or extracts thereof A 85P1B3 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 85P1B3 epitopes are generated using methods generally known in the art. Homodimeric antibodies can also be generated by cross-linking techniques known in the art (e.g., Wolff et al., Cancer Res. 53: 2560–2565).

V.) 85P1B3 Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., Cell 47:1071, 1986; Babbitt, B. P. et al., Nature 317:359, 1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., J. Immunol. 160:3363, 1998; Rammensee, et al., Immunogenetics 41:178, 1995; Rammensee et al., SYFPEITHI, access via World Wide Web at URL syfpeithi.bmi-heidelberg.com/; Sette, A. and Sidney, J. Curr. Opin. Immunol. 10:478, 1998; Engelhard, V. H., Curr. Opin. Immunol. 6:13, 1994; Sette, A. and Grey, H. M., Curr. Opin. Immunol. 4:79, 1992; Sinigaglia, F. and Hammer, J. Curr. Biol. 6:52, 1994; Ruppert et al., Cell 74:929–937, 1993; Kondo et al., J. Immunol. 155:4307–4312, 1995; Sidney et al., J. Immunol. 157:3480–3490, 1996; Sidney et al, Human Immunol. 45:79–93, 1996; Sette, A. and Sidney, J. Immunogenetics 1999 November; 50(3–4):201–12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al., Immunity 4:203, 1996; Fremont et al., Immunity 8:305, 1998; Stern et al., Structure 2:245, 1994; Jones, E. Y. Curr. Opin. Immunol. 9:75, 1997; Brown, J. H. et al., Nature 364:33, 1993; Guo, H. C. et al., Proc. Natl. Acad. Sci. USA 90:8053, 1993; Guo, H. C. et al., Nature 360:364, 1992; Silver, M. L. et al., Nature 360:367, 1992; Matsumura, M. et al., Science 257:927, 1992; Madden et al., Cell 70:1035, 1992; Fremont, D. H. et al., Science 257:919, 1992; Saper, M. A., Bjorkman, P. J. and Wiley, D. C., J. Mol. Biol. 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1–2 weeks in the presence of test peptide plus antigen presenting cells (APC) to allow activation of "memory" T cells, as compared to "naive" T cells. At the end of the culture period, T cell activity is detected using assays including 5 ICr release involving peptide-sensitized targets, T cell proliferation, or lymphokine release.

VI.) 85P1B3 Transgenic Animals

Nucleic acids that encode a 85P1B3-related protein can also be used to generate either transgenic animals or "knock out" animals which, in turn, are useful in the development and screening of therapeutically useful reagents. In accordance with established techniques, cDNA encoding 85P1B3 can be used to clone genomic DNA that encodes 85P1B3. The cloned genomic sequences can then be used to generate transgenic animals containing cells that express DNA that encode 85P1B3. Methods for generating transgenic animals, particularly animals such as mice or rats, have become conventional in the art and are described, for example, in U.S. Pat. No. 4,736,866 issued 12 Apr. 1988, and U.S. Pat. No. 4,870,009 issued 26 Sep. 1989. Typically, particular cells would be targeted for 85P1B3 transgene incorporation with tissue-specific enhancers.

Transgenic animals that include a copy of a transgene encoding 85P1B3 can be used to examine the effect of increased expression of DNA that encodes 85P1B3. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 85P1B3 can be used to construct a 85P1B3 "knock out" animal that has a defective or altered gene encoding 85P1B3 as a result of homologous recombination between the endogenous gene encoding 85P1B3 and altered genomic DNA encoding 85P1B3 introduced into an embryonic cell of the animal. For example, cDNA that encodes 85P1B3 can be used to clone genomic DNA encoding 85P1B3 in accordance with established techniques. A portion of the genomic DNA encoding 85P1B3 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell,* 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al. *Cell,* 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113–152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of the 85P1B3 polypeptide.

VII.) Methods for the Detection of 85P1B3

Another aspect of the present invention relates to methods for detecting 85P1B3 polynucleotides and 85P1B3-related proteins, as well as methods for identifying a cell that expresses 85P1B3. The expression profile of 85P1B3 makes it a diagnostic marker for metastasized disease. Accordingly, the status of 85P1B3 gene products provides information useful for predicting a variety of factors including susceptibility to advanced stage disease, rate of progression, and/or tumor aggressiveness. As discussed in detail herein, the status of 85P1B3 gene products in patient samples can be analyzed by a variety protocols that are well known in the art including immunohistochemical analysis, the variety of Northern blotting techniques including in situ hybridization, RT-PCR analysis (for example on laser capture microdissected samples), Western blot analysis and tissue array analysis.

More particularly, the invention provides assays for the detection of 85P1B3 polynucleotides in a biological sample, such as serum, bone, prostate, and other tissues, urine, semen, cell preparations, and the like. Detectable 85P1B3 polynucleotides include, for example, a 85P1B3 gene or fragment thereof, 85P1B3 mRNA, alternative splice variant 85P1B3 mRNAs, and recombinant DNA or RNA molecules that contain a 85P1B3 polynucleotide. A number of methods for amplifying and/or detecting the presence of 85P1B3 polynucleotides are well known in the art and can be employed in the practice of this aspect of the invention.

In one embodiment, a method for detecting an 85P1B3 mRNA in a biological sample comprises producing cDNA from the sample by reverse transcription using at least one primer; amplifying the cDNA so produced using an 85P1B3 polynucleotides as sense and antisense primers to amplify 85P1B3 cDNAs therein; and detecting the presence of the amplified 85P1B3 cDNA. Optionally, the sequence of the amplified 85P1B3 cDNA can be determined.

In another embodiment, a method of detecting a 85P1B3 gene in a biological sample comprises first isolating genomic DNA from the sample; amplifying the isolated genomic DNA using 85P1B3 polynucleotides as sense and antisense primers; and detecting the presence of the amplified 85P1B3 gene. Any number of appropriate sense and antisense probe combinations can be designed from the nucleotide sequence provided for the 85P1B3 (FIG. 2) and used for this purpose.

The invention also provides assays for detecting the presence of an 85P1B3 protein in a tissue or other biological sample such as serum, semen, bone, prostate, urine, cell preparations, and the like. Methods for detecting a 85P1B3-related protein are also well known and include, for example, immunoprecipitation, immunohistochemical analysis, Western blot analysis, molecular binding assays, ELISA, ELIFA and the like. For example, a method of detecting the presence of a 85P1B3-related protein in a biological sample comprises first contacting the sample with a 85P1B3 antibody, a 85P1B3-reactive fragment thereof, or a recombinant protein containing an antigen binding region of a 85P1B3 antibody; and then detecting the binding of 85P1B3-related protein in the sample.

Methods for identifying a cell that expresses 85P1B3 are also within the scope of the invention. In one embodiment, an assay for identifying a cell that expresses a 85P1B3 gene comprises detecting the presence of 85P1B3 mRNA in the cell. Methods for the detection of particular mRNAs in cells are well known and include, for example, hybridization assays using complementary DNA probes (such as in situ hybridization using labeled 85P1B3 riboprobes, Northern blot and related techniques) and various nucleic acid amplification assays (such as RT-PCR using complementary primers specific for 85P1B3, and other amplification type detection methods, such as, for example, branched DNA, SISBA, TMA and the like). Alternatively, an assay for identifying a cell that expresses a 85P1B3 gene comprises detecting the presence of 85P1B3-related protein in the cell or secreted by the cell. Various methods for the detection of proteins are well known in the art and are employed for the detection of 85P1B3-related proteins and cells that express 85P1B3-related proteins.

85P1B3 expression analysis is also useful as a tool for identifying and evaluating agents that modulate 85P1B3 gene expression. For example, 85P1B3 expression is significantly upregulated in prostate cancer, and is expressed in cancers of the tissues listed in Table 1. Identification of a molecule or biological agent that inhibits 85P1B3 expression or over-expression in cancer cells is of therapeutic value. For example, such an agent can be identified by using a screen that quantifies 85P1B3 expression by RT-PCR, nucleic acid hybridization or antibody binding.

VIII.) Methods for Monitoring the Status of 85P1B3-Related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437–438 (1997) and Isaacs et al., Cancer Surv. 23: 19–32 (1995)). In this context, examining a biological sample for evidence of dysregulated cell growth (such as aberrant 85P1B3 expression in cancers) allows for early detection of such aberrant physiology, before a pathologic state such as cancer has progressed to a stage that therapeutic options are more limited and or the prognosis is worse. In such examinations, the status of 85P1B3 in a biological sample of interest can be compared, for example, to the status of 85P1B3 in a corresponding normal sample (e.g. a sample from that individual or alternatively another individual that is not affected by a pathology). An alteration in the status of 85P1B3 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2):306–14 and U.S. Pat. No. 5,837,501) to compare 85P1B3 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 85P1B3 expressing cells) as well as the level, and biological activity of expressed gene products (such as 85P1B3 mRNA, polynucleotides and polypeptides). Typically, an alteration in the status of 85P1B3 comprises a change in the location of 85P1B3 and/or 85P1B3 expressing cells and/or an increase in 85P1B3 mRNA and/or protein expression.

85P1B3 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of the 85P1B3 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 85P1B3 in a biological sample is evaluated by various methods utilized by skilled artisans including, but not limited to genomic Southern analysis (to examine, for example perturbations in the 85P1B3 gene), Northern analysis and/or PCR analysis of 85P1B3 mRNA (to examine, for example alterations in the polynucleotide sequences or expression levels of 85P1B3 mRNAs), and, Western and/or immunohistochemical analysis (to examine, for example alterations in polypeptide sequences, alterations in polypeptide localization within a sample, alterations in expression levels of 85P1B3 proteins and/or associations of 85P1B3 proteins with polypeptide binding partners). Detectable 85P1B3 polynucleotides include, for example, a 85P1B3 gene or fragment thereof, 85P1B3 mRNA, alternative splice variants, 85P1B3 mRNAs, and recombinant DNA or RNA molecules containing a 85P1B3 polynucleotide.

The expression profile of 85P1B3 makes it a diagnostic marker for local and/or metastasized disease, and provides information on the growth or oncogenic potential of a biological sample. In particular, the status of 85P1B3 provides information useful for predicting susceptibility to particular disease stages, progression, and/or tumor aggressiveness. The invention provides methods and assays for determining 85P1B3 status and diagnosing cancers that express 85P1B3, such as cancers of the tissues listed in Table 1. For example, because 85P1B3 mRNA is so highly expressed in prostate and other cancers relative to normal prostate tissue, assays that evaluate the levels of 85P1B3 mRNA transcripts or proteins in a biological sample can be used to diagnose a disease associated with 85P1B3 dysregulation, and can provide prognostic information useful in defining appropriate therapeutic options.

The expression status of 85P1B3 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 85P1B3 in biological samples such as those from individuals suffering from, or suspected of suffering from a pathology characterized by dysregulated cellular growth, such as cancer.

As described above, the status of 85P1B3 in a biological sample can be examined by a number of well-known procedures in the art. For example, the status of 85P1B3 in a biological sample taken from a specific location in the body can be examined by evaluating the sample for the presence or absence of 85P1B3 expressing cells (e.g. those that express 85P1B3 mRNAs or proteins). This examination can provide evidence of dysregulated cellular growth, for example, when 85P1B3-expressing cells are found in a biological sample that does not normally contain such cells (such as a lymph node), because such alterations in the status of 85P1B3 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315–317 (2000); Su et al., Semin. Surg. Oncol. 18(1):17–28 (2000) and Freeman et al., J Urol 1995 µg 154(2 Pt 1):474–8).

In one aspect, the invention provides methods for monitoring 85P1B3 gene products by determining the status of 85P1B3 gene products expressed by cells from an individual suspected of having a disease associated with dysregulated cell growth (such as hyperplasia or cancer) and then comparing the status so determined to the status of 85P1B3 gene products in a corresponding normal sample. The presence of aberrant 85P1B3 gene products in the test sample relative to the normal sample provides an indication of the presence of dysregulated cell growth within the cells of the individual.

In another aspect, the invention provides assays useful in determining the presence of cancer in an individual, comprising detecting a significant increase in 85P1B3 mRNA or protein expression in a test cell or tissue sample relative to expression levels in the corresponding normal cell or tissue. The presence of 85P1B3 mRNA can, for example, be evaluated in tissue samples including but not limited to those listed in Table 1. The presence of significant 85P1B3 expression in any of these tissues is useful to indicate the emergence, presence and/or severity of a cancer, since the corresponding normal tissues do not express 85P1B3 mRNA or express it at lower levels.

In a related embodiment, 85P1B3 status is determined at the protein level rather than at the nucleic acid level. For example, such a method comprises determining the level of 85P1B3 protein expressed by cells in a test tissue sample and comparing the level so determined to the level of 85P1B3 expressed in a corresponding normal sample. In one embodiment, the presence of 85P1B3 protein is evaluated, for example, using immunohistochemical methods. 85P1B3 antibodies or binding partners capable of detecting 85P1B3 protein expression are used in a variety of assay formats well known in the art for this purpose.

In a further embodiment, one can evaluate the status of 85P1B3 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369–378). For example, a mutation in the sequence of 85P1B3 may be indicative of the presence or promotion of a tumor. Such assays therefore have diagnostic and predictive value where a mutation in 85P1B3 indicates a potential loss of function or increase in tumor growth.

A wide variety of assays for observing perturbations in nucleotide and amino acid sequences are well known in the art. For example, the size and structure of nucleic acid or amino acid sequences of 85P1B3 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. No. 5,382,510 issued 7 Sep. 1999, and U.S. Pat. No. 5,952,170 issued 17 Jan. 1995).

Additionally, one can examine the methylation status of the 85P1B3 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985–1992 (1999)). In addition, this alteration is present in at least 70% of cases of high-grade prostatic intraepithelial neoplasia (PIN) (Brooks et al, Cancer Epidemiol. Biomarkers Prev., 1998, 7:531–536). In another example, expression of the LAGE-1 tumor specific gene (which is not expressed in normal prostate but is expressed in 25–50% of prostate cancers) is induced by deoxy-azacytidine in lymphoblastoid cells, suggesting that tumoral expression is due to demethylation (Lethe et al., Int. J. Cancer 76(6): 903–908 (1998)). A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil)

followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 85P1B3. Gene amplification is measured in a sample directly, for example, by conventional Southern blotting or Northern blotting to quantitate the transcription of mRNA (Thomas, 1980, Proc. Natl. Acad. Sci. USA, 77:5201–5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 85P1B3 expression. The presence of RT-PCR amplifiable 85P1B3 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373–384; Ghossein et al., 1995, J. Clin. Oncol. 13:1195–2000; Heston et al., 1995, Clin. Chem. 41:1687–1688).

A further aspect of the invention is an assessment of the susceptibility that an individual has for developing cancer. In one embodiment, a method for predicting susceptibility to cancer comprises detecting 85P1B3 mRNA or 85P1B3 protein in a tissue sample, its presence indicating susceptibility to cancer, wherein the degree of 85P1B3 mRNA expression correlates to the degree of susceptibility. In a specific embodiment, the presence of 85P1B3 in prostate or other tissue is examined, with the presence of 85P1B3 in the sample providing an indication of prostate cancer susceptibility (or the emergence or existence of a prostate tumor). Similarly, one can evaluate the integrity 85P1B3 nucleotide and amino acid sequences in a biological sample, in order to identify perturbations in the structure of these molecules such as insertions, deletions, substitutions and the like. The presence of one or more perturbations in 85P1B3 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 85P1B3 mRNA or 85P1B3 protein expressed by tumor cells, comparing the level so determined to the level of 85P1B3 mRNA or 85P1B3 protein expressed in a corresponding normal tissue taken from the same individual or a normal tissue reference sample, wherein the degree of 85P1B3 mRNA or 85P1B3 protein expression in the tumor sample relative to the normal sample indicates the degree of aggressiveness. In a specific embodiment, aggressiveness of a tumor is evaluated by determining the extent to which 85P1B3 is expressed in the tumor cells, with higher expression levels indicating more aggressive tumors. Another embodiment is the evaluation of the integrity of 85P1B3 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 85P1B3 mRNA or 85P1B3 protein expressed by cells in a sample of the tumor, comparing the level so determined to the level of 85P1B3 mRNA or 85P1B3 protein expressed in an equivalent tissue sample taken from the same individual at a different time, wherein the degree of 85P1B3 mRNA or 85P1B3 protein expression in the tumor sample over time provides information on the progression of the cancer. In a specific embodiment, the progression of a cancer is evaluated by determining 85P1B3 expression in the tumor cells over time, where increased expression over time indicates a progression of the cancer. Also, one can evaluate the integrity 85P1B3 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 85P1B3 gene and 85P1B3 gene products (or perturbations in 85P1B3 gene and 85P1B3 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74–88; Epstein, 1995, Hum. Pathol. 26(2):223–9; Thorson et al., 1998, Mod. Pathol. 11(6):543–51; Baisden et al., 1999, Am. J. Surg. Pathol. 23(8):918–24). Methods for observing a coincidence between the expression of 85P1B3 gene and 85P1B3 gene products (or perturbations in 85P1B3 gene and 85P1B3 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 85P1B3 gene and 85P1B3 gene products (or perturbations in 85P1B3 gene and 85P1B3 gene products) and another factor associated with malignancy entails detecting the overexpression of 85P1B3 mRNA or protein in a tissue sample, detecting the overexpression of PSA mRNA or protein in a tissue sample (or PSCA or PSM expression), and observing a coincidence of 85P1B3 mRNA or protein and PSA mRNA or protein overexpression (or PSCA or PSM expression). In a specific embodiment, the expression of 85P1B3 and PSA mRNA in prostate tissue is examined, where the coincidence of 85P1B3 and PSA mRNA overexpression in the sample indicates the existence of prostate cancer, prostate cancer susceptibility or the emergence or status of a prostate tumor.

Methods for detecting and quantifying the expression of 85P1B3 mRNA or protein are described herein, and standard nucleic acid and protein detection and quantification technologies are well known in the art. Standard methods for the detection and quantification of 85P1B3 mRNA include in situ hybridization using labeled 85P1B3 riboprobes, Northern blot and related techniques using 85P1B3 polynucleotide probes, RT-PCR analysis using primers specific for 85P1B3, and other amplification type detection methods, such as, for example, branched DNA, SISBA, TMA and the like. In a specific embodiment, semi-quantitative RT-PCR is used to detect and quantify 85P1B3 mRNA expression. Any number of primers capable of amplifying 85P1B3 can be used for this purpose, including but not limited to the various primer sets specifically described herein. In a specific embodiment, polyclonal or monoclonal antibodies specifically reactive with the wild-type 85P1B3 protein can be used in an immunohistochemical assay of biopsied tissue.

IX.) Identification of Molecules that Interact with 85P1B3

The 85P1B3 protein and nucleic acid sequences disclosed herein allow a skilled artisan to identify proteins, small molecules and other agents that interact with 85P1B3, as well as pathways activated by 85P1B3 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein—protein interactions in vivo through reconstitution of a eukaryotic transcriptional activator, see, e.g., U.S. Pat. No. 5,955,280 issued 21 Sep. 1999, U.S. Pat. No. 5,925,523 issued 20 Jul. 1999, U.S. Pat. No. 5,846,722 issued 8 Dec. 1998 and U.S. Pat. No. 6,004,746 issued 21 Dec. 1999. Algorithms are also available in the art for genome-based predictions of protein function (see, e.g., Marcotte, et al., Nature 402: 4 November 1999, 83–86).

Alternatively one can screen peptide libraries to identify molecules that interact with 85P1B3 protein sequences. In such methods, peptides that bind to 85P1B3 are identified by screening libraries that encode a random or controlled collection of amino acids. Peptides encoded by the libraries are expressed as fusion proteins of bacteriophage coat proteins, the bacteriophage particles are then screened against the 85P1B3 protein.

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 85P1B3 protein sequences are disclosed for example in U.S. Pat. No. 5,723,286 issued 3 Mar. 1998 and U.S. Pat. No. 5,733,731 issued 31 Mar. 1998.

Alternatively, cell lines that express 85P1B3 are used to identify protein—protein interactions mediated by 85P1B3. Such interactions can be examined using immunoprecipitation techniques (see, e.g., Hamilton B J, et al. Biochem. Biophys. Res. Commun. 1999, 261:646–51). 85P1B3 protein can be immunoprecipitated from 85P1B3-expressing cell lines using anti-85P1B3 antibodies. Alternatively, antibodies against His-tag can be used in a cell line engineered to express fusions of 85P1B3 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 85P1B3 can be identified through related embodiments of such screening assays. For example, small molecules can be identified that interfere with protein function, including molecules that interfere with 85P1B3's ability to mediate phosphorylation and de-phosphorylation, interaction with DNA or RNA molecules as an indication of regulation of cell cycles, second messenger signaling or tumorigenesis. Similarly, small molecules that modulate 85P1B3-related ion channel, protein pump, or cell communication functions are identified and used to treat patients that have a cancer that expresses 85P1B3 (see, e.g., Hille, B., Ionic Channels of Excitable Membranes $2^{nd}$ Ed., Sinauer Assoc., Sunderland, Mass., 1992). Moreover, ligands that regulate 85P1B3 function can be identified based on their ability to bind 85P1B3 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 85P1B3 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators which activate or inhibit 85P1B3.

An embodiment of this invention comprises a method of screening for a molecule that interacts with an 85P1B3 amino acid sequence shown in FIG. 2 or FIG. 3, comprising the steps of contacting a population of molecules with the 85P1B3 amino acid sequence, allowing the population of molecules and the 85P1B3 amino acid sequence to interact under conditions that facilitate an interaction, determining the presence of a molecule that interacts with the 85P1B3 amino acid sequence, and then separating molecules that do not interact with the 85P1B3 amino acid sequence from molecules that do. In a specific embodiment, the method further comprises purifying, characterizing and identifying a molecule that interacts with the 85P1B3 amino acid sequence. The identified molecule can be used to modulate a function performed by 85P1B3. In a preferred embodiment, the 85P1B3 amino acid sequence is contacted with a library of peptides.

X.) Therapeutic Methods and Compositions

The identification of 85P1B3 as a protein that is normally expressed in a restricted set of tissues, but which is also expressed in prostate and other cancers, opens a number of therapeutic approaches to the treatment of such cancers. As contemplated herein, 85P1B3 functions as a transcription factor involved in activating tumor-promoting genes or repressing genes that block tumorigenesis.

Accordingly, therapeutic approaches that inhibit the activity of the 85P1B3 protein are useful for patients suffering from a cancer that expresses 85P1B3. These therapeutic approaches generally fall into two classes. One class comprises various methods for inhibiting the binding or association of the 85P1B3 protein with its binding partner or with other proteins. Another class comprises a variety of methods for inhibiting the transcription of the 85P1B3 gene or translation of 85P1B3 mRNA.

X.A.) Anti-Cancer Vaccines

The invention provides cancer vaccines comprising a 85P1B3-related protein or 85P1B3-related nucleic acid. In view of the expression of 85P1B3, cancer vaccines prevent and/or treat 85P1B3-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231–237; Fong et al., 1997, J. Immunol. 159:3113–3117).

Such methods can be readily practiced by employing a 85P1B3-related protein, or an 85P1B3-encoding nucleic acid molecule and recombinant vectors capable of expressing and presenting the 85P1B3 immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 February 31(1): 66–78; Maruyama et al., Cancer Immunol Immunother 2000 June 49(3): 123–32) Briefly, such methods of generating an immune response (e.g. humoral and/or cell-mediated) in a mammal, comprise the steps of: exposing the mammal's immune system to an immunoreactive epitope (e.g. an epitope present in the 85P1B3 protein shown in SEQ ID NO: 703 or analog or homolog thereof) so that the mammal generates an immune response that is specific for that epitope (e.g. generates antibodies that specifically recognize that epitope). In a preferred method, the 85P1B3 immunogen contains a biological motif, see e.g., Tables V–XVIII, or a peptide of a size range from 85P1B3 indicated in FIG. 5, FIG. 6, FIG. 7, FIG. 8, and FIG. 9.

The entire 85P1B3 protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287–294, 1991: Alonso et al., *Vaccine* 12:299–306, 1994; Jones et al., *Vaccine* 13:675–681, 1995), peptide compositions contained in immune stimulating complexes (ISCOMS) (see, e.g., Takahashi et al., *Nature* 344:873–875, 1990; Hu et al., *Clin Exp Immunol.* 113:235–243, 1998), multiple antigen peptide systems (MAPs) (see e.g., Tam, J. P., *Proc. Natl. Acad. Sci. U.S.A.* 85:5409–5413, 1988; Tam, J. P., *J. Immunol. Methods* 196:17–32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al, *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259: 1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 85P1B3-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 85P1B3 protein that bind corresponding HLA alleles (see e.g., Table IV; Epimer™ and Epimatrix™, Brown University and, BIMAS, and SYFPEITHI). In a preferred embodiment, the 85P1B3 immunogen contains one or more amino acid sequences identified using techniques well known in the art, such as the sequences shown in Tables V–XVIII or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. the 85P1B3 protein) so that an immune response is generated. A typical embodiment consists of a method for generating an immune response to 85P1B3 in a host, by contacting the host with a sufficient amount of at least one 85P1B3 B cell or cytotoxic T-cell epitope or analog thereof; and at least one periodic interval thereafter re-contacting the host with the 85P1B3 B cell or cytotoxic T-cell epitope or analog thereof. A specific embodiment consists of a method of generating an immune response against a 85P1B3-related protein or a man-made multiepitopic peptide comprising: administering 85P1B3 immunogen (e.g. the 85P1B3 protein or a peptide fragment thereof, an 85P1B3 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625–1633; Alexander et al., Immunity 1994 1(9): 751–761 and Alexander et al., Immunol. Res. 1998 18(2): 79–92). An alternative method comprises generating an immune response in an individual against a 85P1B3 immunogen by: administering in vivo to muscle or skin of the individual's body a DNA molecule that comprises a DNA sequence that encodes an 85P1B3 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 85P1B3. Constructs comprising DNA encoding a 85P1B3-related protein/immunogen and appropriate regulatory sequences can be injected directly into muscle or skin of an individual, such that the cells of the muscle or skin take-up the construct and express the encoded 85P1B3 protein/immunogen. Alternatively, a vaccine comprises a 85P1B3-related protein. Expression of the 85P1B3-related protein immunogen results in the generation of prophylactic or therapeutic humoral and cellular immunity against cells that bear 85P1B3 protein. Various prophylactic and therapeutic genetic immunization techniques known in the art can be used. Nucleic acid-based delivery is described, for instance, in Wolff et. al., Science 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658–663; Tsang et al. *J. Natl. Cancer Inst.* 87:982–990 (1995)). Non-viral delivery systems can also be employed by introducing naked DNA encoding a 85P1B3-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456–460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 85P1B3-related nucleic acid molecule. In one embodiment, the full-length human 85P1B3 cDNA is employed. In another embodiment, 85P1B3 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 85P1B3 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65–69; Murphy et al., 1996, Prostate 29:371–380). Thus, dendritic cells can be used to present 85P1B3 peptides to T cells in the context of MHC class I or II molecules. In one embodiment, autologous dendritic cells are pulsed with 85P1B3 peptides capable of binding to MHC class I and/or class II molecules. In another embodiment, dendritic cells are pulsed with the complete 85P1B3 protein. Yet another embodiment involves engineering the overexpression of the 85P1B3 gene in dendritic cells using various implementing vectors known in the art, such as adenovirus (Arthur et al., 1997, Cancer Gene Ther. 4:17–25), retrovirus (Henderson et al., 1996, Cancer Res. 56:3763–3770), lentivirus, adeno-associated virus, DNA transfection (Ribas et al., 1997, Cancer Res. 57:2865–2869), or tumor-derived RNA transfection (Ashley et al., 1997, J. Exp. Med. 186:1177–1182). Cells that express 85P1B3 can also be engineered to express immune modulators, such as GM-CSF, and used as immunizing agents.

X. B.) 85P1B3 as a Target for Antibody-Based Therapy

85P1B3 is an attractive target for antibody-based therapeutic strategies. A number of antibody strategies are known in the art for targeting both extracellular and intracellular molecules (see, e.g., complement and ADCC mediated killing as well as the use of intrabodies). Because 85P1B3 is expressed by cancer cells of various lineages relative to corresponding normal cells, systemic administration of 85P1B3-immunoreactive compositions are prepared that exhibit excellent sensitivity without toxic, non-specific and/or non-target effects caused by binding of the immunoreactive composition to non-target organs and tissues. Antibodies specifically reactive with domains of 85P1B3 are useful to treat 85P1B3-expressing cancers systemically, either as conjugates with a toxin or therapeutic agent, or as naked antibodies capable of inhibiting cell proliferation or function.

85P1B3 antibodies can be introduced into a patient such that the antibody binds to 85P1B3 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 85P1B3, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of the 85P1B3 sequence shown in FIG. 2 or FIG. 3. In addition, skilled artisans understand that it is routine to conjugate antibodies to cytotoxic agents (see, e.g., Slevers et al. *Blood* 93:11 3678–3684 (Jun. 1, 1999)). When cytotoxic and/or therapeutic agents are delivered directly to cells, such as by conjugating them to antibodies specific for a molecule expressed by that cell (e.g. 85P1B3), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-85P1B3 antibody) that binds to a marker (e.g. 85P1B3) expressed, accessible to binding or localized on the cell surfaces. A typical embodiment is a method of delivering a cytotoxic and/or therapeutic agent to a cell expressing 85P1B3, comprising conjugating the cytotoxic agent to an antibody that immunospecifically binds to a 85P1B3 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-85P1B3 antibodies can be done in accordance with various approaches that have been successfully employed in the treatment of other types of cancer, including but not limited to colon cancer (Arlen et al., 1998, Crit. Rev. Immunol. 18:133–138), multiple myeloma (Ozaki et al., 1997, Blood 90:3179–3186, Tsunenari et al., 1997, Blood 90:2437–2444), gastric cancer (Kasprzyk et al., 1992, Cancer Res. 52:2771–2776), B-cell lymphoma (Funakoshi et al., 1996, J. Immunother. Emphasis Tumor Immunol. 19:93–101), leukemia (Zhong et al., 1996, Leuk. Res. 20:581–589), colorectal cancer (Moun et al., 1994, Cancer Res. 54:6160–6166; Velders et al., 1995, Cancer Res. 55:4398–4403), and breast cancer (Shepard et al., 1991, J. Clin. Immunol. 11:117–127). Some therapeutic approaches involve conjugation of naked antibody to a toxin, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). To treat prostate cancer, for example, 85P1B3 antibodies can be administered in conjunction with radiation, chemotherapy or hormone ablation.

Although 85P1B3 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 85P1B3 expression, preferably using immunohistochemical assessments of tumor tissue, quantitative 85P1B3 imaging, or other techniques that reliably indicate the presence and degree of 85P1B3 expression. Immunohistochemical analysis of tumor biopsies or surgical specimens is preferred for this purpose. Methods for immunohistochemical analysis of tumor tissues are well known in the art.

Anti-85P1B3 monoclonal antibodies that treat prostate and other cancers include those that initiate a potent immune response against the tumor or those that are directly cytotoxic. In this regard, anti-85P1B3 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-85P1B3 mAbs that exert a direct biological effect on tumor growth are useful to treat cancers that express 85P1B3. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-85P1B3 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 85P1B3 antigen with high affinity but exhibit low or no antigenicity in the patient.

Therapeutic methods of the invention contemplate the administration of single anti-85P1B3 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-85P1B3 mAbs can be administered concomitantly with other therapeutic modalities, including but not limited to various chemotherapeutic agents, androgen-blockers, immune modulators (e.g., IL-2, GM-CSF), surgery or radiation. The anti-85P1B3 mAbs are administered in their "naked" or unconjugated form, or can have a therapeutic agent(s) conjugated to them.

Anti-85P1B3 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-85P1B3 antibody preparation, via an acceptable route of administration such as intravenous injection (IV), typically at a dose in the range of about 0.1 to about 10 mg/kg body weight. In general, doses in the range of 10–500 mg mAb per week are effective and well tolerated.

Based on clinical experience with the Herceptin mAb in the treatment of metastatic breast cancer, an initial loading dose of approximately 4 mg/kg patient body weight IV, followed by weekly doses of about 2 mg/kg IV of the anti-85P1B3 mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 85P1B3 expression in the patient, the extent of circulating shed 85P1B3 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 85P1B3 in a given sample (e.g. the levels of circulating 85P1B3 antigen and/or 85P1B3 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-85P1B3 antibodies can also be used in anti-cancer therapy as a vaccine for inducing an immune response to cells expressing a 85P1B3-related protein. In particular, the generation of anti-idiotypic antibodies is well known in the art; this methodology can readily be adapted to generate anti-idiotypic anti-85P1B3 antibodies that mimic an epitope on a 85P1B3-related protein (see, for example, Wagner et al., 1997, Hybridoma 16: 3340; Foon et al., 1995, J. Clin. Invest. 96:334–342: Herlyn et al., 1996, Cancer Immunol. Immunother. 43:65–76). Such an anti-idiotypic antibody can be used in cancer vaccine strategies.

X.C.) 85P1B3 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-5-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis *J. Immunol.* 165:539–547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 85P1B3 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3–4 epitopes that come from at least one tumor associated antigen (TAA). For HLA Class II a similar rationale is employed; again 34 epitopes are selected from at least one TAA (see, e.g., Rosenberg et al., *Science* 278: 1447–1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915–3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 85P1B3, the PADRE® universal helper T cell epitope (or multiple HTL epitopes from 85P1B3), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30–100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis.

Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al, *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830–843 (QYIKAN-SKFIGITE; SEQ ID NO: 710), *Plasmodium falciparum* circumsporozoite (CS) protein at positions 378–398 (DIEK-KIAKMEKASSVFNVVNS; SEQ ID NO: 711), and *Streptococcus* 18 kD protein at positions 116–131 (GAVDSILG-GVATYGAA; SEQ ID NO: 712). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO: 713), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinly-seryl-serine ($P_3CSS$) can be used to prime virus specific CTL when covalently attached to an appropriate peptide (see, e.g., Deres, et al. Nature 342:561, 1989). Peptides of the invention can be coupled to $P_3CSS$, for example, and the lipopeptide administered to an individual to specifically prime an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 85P1B3. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 85P1B3.

X.D. Adoptive Immunotherapy

Antigenic 85P1B3-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7–28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 85P1B3. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 85P1B3. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 85P1B3-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 85P1B3, a vaccine comprising 85P1B3-specific CTL may be more efficacious in killing tumor cells in patient with advanced disease than alternative embodiments.

It is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for a human typically range from about 500 μg to about 50,000 μg per 70 kilogram patient. Boosting dosages of between about 1.0 μg to about 50,000 μg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 μg and the higher value is about 10,000; 20,000; 30,000; or 50,000 μg. Dosage values for a human typically range from about 500 μg to about 50,000 μg per 70 kilogram patient. This is followed by boosting dosages of between about 1.0 μg to about 50,000 μg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, $17^{th}$ Edition, A. Gennaro, Editor, Mack Publishing Co., Easton, Pa., 1985). For example a peptide dose for initial immunization can be from about 1 to about 50,000 μg, generally 100–5,000 μg, for a 70 kg patient. For example, for nucleic acids an initial immunization may be performed using an expression vector in the form of naked nucleic acid administered IM (or SC or ID) in the amounts of 0.5–5 mg at multiple sites. The nucleic acid (0.1 to 1000 μg) can also be administered using a gene gun. Following an incubation period of 34 weeks, a booster dose is then administered. The booster can be recombinant fowlpox virus administered at a dose of $5–10^7$ to $5\times10^9$ pfu. For antibodies, a reatment generally involves repeated administration of the anti-85P1B3 antibody preparation, via an acceptable route of administration such as intravenous injection (IV), typically at a dose in the range of about 0.1 to about 10 mg/kg body weight. In general, doses in the range of 10–500 mg mAb per week are effective and well tolerated. Moreover, an initial loading dose of approximately 4 mg/kg patient body weight IV, followed by weekly doses of about 2 mg/kg IV of the anti-85P1B3 mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 85P1B3 expression in the patient, the extent of circulating shed 85P1B3 antigen, the desired steady-state concentration level, frequency of treatment, and the influence of chemotherapeutic or other agents used in combination with the treatment method of the invention, as well as the health status of a particular patient.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 80, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, immunogenic peptides are preferably supplied in finely divided form along with a surfactant and propellant. Typical percentages of peptides are about 0.01%–20% by weight, preferably about 1%–10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%–20% by weight of the composition, preferably about 0.25–5%. The balance of the composition is ordinarily propellant. A carrier can also be included, as desired, as with, e.g., lecithin for intranasal delivery.

XI.) Diagnostic and Prognostic Embodiments of 85P1B3.

As disclosed herein, 85P1B3 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in Example 4).

85P1B3 can be analogized to a prostate associated antigen PSA, the archetypal marker that has been used by medical practitioners for years to identify and monitor the presence of prostate cancer (see, e.g., Merrill et al., J. Urol. 163(2): 503–5120 (2000); Polascik et al., J. Urol. August; 162(2): 293–306 (1999) and Fortier et al., J. Nat. Cancer Inst. 91(19): 1635–1640 (1999)). A variety of other diagnostic markers are also used in similar contexts including p53 and K-ras (see, e.g., Tulchinsky et al., Int J Mol Med 1999 July 4(1):99–102 and Minimoto et al., Cancer Detect Prev 2000; 24(1):1–12). Therefore, this disclosure of the 85P1B3 polynucleotides and polypeptides (as well as the 85P1B3 polynucleotide probes and anti-85P1B3 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 85P1B3 polynucleotides, polypeptides, reactive T cells and antibodies are analogous to those methods from well-established diagnostic assays which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567–74 (1994)) and primers (for example in PCR analysis, see, e.g., Okegawa et al., J. Urol. 163(4): 1189–1190 (2000)) to observe the presence and/or the level of PSA mRNAs in methods of monitoring PSA overexpression or the metastasis of prostate cancers, the 85P1B3 polynucleotides described herein can be utilized in the same way to detect 85P1B3 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560–3 (2000)) or the metastasis of prostate cells (see, e.g., Alanen et al., Pathol. Res. Pract. 192(3):233–7 (1996)), the 85P1B3 polypeptides described herein can be utilized to generate antibodies for use in detecting 85P1B3 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 85P1B3 polynucleotides and/or polypeptides can be used to provide evidence of metastasis. For example, when a biological sample from tissue that does not normally contain 85P1B3-expressing cells (lymph node) is found to contain 85P1B3-expressing cells such as the 85P1B3 expression seen in LAPC-4 and LAPC9, xenografts isolated from lymph node and bone metastasis, respectively, this finding is indicative of metastasis.

Alternatively 85P1B3 polynucleotides and/or polypeptides can be used to provide evidence of cancer, for example, when cells in a biological sample that do not normally express 85P1B3 or express 85P1B3 at a different level are found to express 85P1B3 or have an increased expression of 85P1B3 (see, e.g., the 85P1B3 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 85P1B3) such as PSA, PSCA etc. (see, e.g., Alanen et al., Pathol. Res. Pract. 192(3): 233–237 (1996)).

Just as PSA polynucleotide fragments and polynucleotide variants are employed by skilled artisans for use in methods of monitoring PSA, 85P1B3 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472–476, 478–480 (1998); Robertson et al., Methods Mol. Biol. 98:121–154 (1998)). An additional illustration of the use of such fragments is provided in Example 4, where a 85P1B3 polynucleotide fragment is used as a probe to show the expression of 85P1B3 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November–December 11(6):407–13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g. the 85P1B3 polynucleotide shown in SEQ ID NO: 701) under conditions of high stringency.

Furthermore, PSA polypeptides which contain an epitope that can be recognized by an antibody or T cell that specifically binds to that epitope are used in methods of monitoring PSA. 85P1B3 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 85P1B3 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. the 85P1B3 polypeptide shown in SEQ ID NO: 703).

As shown herein, the 85P1B3 polynucleotides and polypeptides (as well as the 85P1B3 polynucleotide probes and anti-85P1B3 antibodies or T cells used to identify the presence of these molecules) exhibit specific properties that make them useful in diagnosing cancers such as those listed in Table 1. Diagnostic assays that measure the presence of 85P1B3 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g. Alanen et al., Pathol. Res. Pract. 192(3): 233–237 (1996)), and consequently, materials such as 85P1B3 polynucleotides and polypeptides (as well as the 85P1B3 polynucleotide probes and anti-85P1B3 antibodies used to identify the presence of these molecules) must be employed to confirm metastases of prostatic origin.

Finally, in addition to their use in diagnostic assays, the 85P1B3 polynucleotides disclosed herein have a number of other utilities such as their use in the identification of oncogenetic associated chromosomal abnormalities in the chromosomal region to which the 85P1B3 gene maps (see Example 3 below). Moreover, in addition to their use in diagnostic assays, the 85P1B3-related proteins and polynucleotides disclosed herein have other utilities such as their use in the forensic analysis of tissues of unknown origin (see, e.g., Takahama K Forensic Sci Int 1996 Jun. 28; 80(1–2): 63–9).

Additionally, 85P1B3-related proteins or polynucleotides of the invention can be used to treat a pathologic condition characterized by the over-expression of 85P1B3. For example, the amino acid or nucleic acid sequence of FIG. 2 or FIG. 3, or fragments of either, can be used to generate an immune response to the 85P1B3 antigen. Antibodies or other molecules that react with 85P1B3 can be used to modulate the function of this molecule, and thereby provide a therapeutic benefit.

XII.) Inhibition of 85P1B3 Protein Function

The invention includes various methods and compositions for inhibiting the binding of 85P1B3 to its binding partner or its association with other protein(s) as well as methods for inhibiting 85P1B3 function.

XII.A.) Inhibition of 85P1B3 with Intracellular Antibodies

In one approach, a recombinant vector that encodes single chain antibodies that specifically bind to 85P1B3 are introduced into 85P1B3 expressing cells via gene transfer technologies. Accordingly, the encoded single chain anti-85P1B3 antibody is expressed intracellularly, binds to 85P1B3 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL (SEQ ID NO: 708) amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 85P1B3 in the nucleus, thereby preventing its activity within the nucleus. Nuclear targeting signals are engineered into such 85P1B3 intrabodies in order to achieve the desired targeting. Such 85P1B3 intrabodies are designed to bind specifically to a particular 85P1B3 domain. In another embodiment, cytosolic intrabodies that specifically bind to the 85P1B3 protein are used to prevent 85P1B3 from gaining access to the nucleus, thereby preventing it from exerting any biological activity within the nucleus (e.g., preventing 85P1B3 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 85P1B3 with Recombinant Proteins

In another approach, recombinant molecules bind to 85P1B3 and thereby inhibit 85P1B3 function. For example, these recombinant molecules prevent or inhibit 85P1B3 from accessing/binding to its binding partner(s) or associating with other protein(s). Such recombinant molecules can, for example, contain the reactive part(s) of a 85P1B3 specific antibody molecule. In a particular embodiment, the 85P1B3 binding domain of a 85P1B3 binding partner is engineered into a dimeric fusion protein, whereby the fusion protein comprises two 85P1B3 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 85P1B3, whereby the dimeric fusion protein specifically binds to 85P1B3 and blocks 85P1B3 interaction with a binding partner. Such dimeric fusion proteins are further combined into multimeric proteins using known antibody linking technologies.

XII.C.) Inhibition of 85P1B3 Transcription or Translation

The present invention also comprises various methods and compositions for inhibiting the transcription of the 85P1B3 gene. Similarly, the invention also provides methods and compositions for inhibiting the translation of 85P1B3 mRNA into protein.

In one approach, a method of inhibiting the transcription of the 85P1B3 gene comprises contacting the 85P1B3 gene with a 85P1B3 antisense polynucleotide. In another approach, a method of inhibiting 85P1B3 mRNA translation comprises contacting the 85P1B3 mRNA with an antisense polynucleotide. In another approach, a 85P1B3 specific ribozyme is used to cleave the 85P1B3 message, thereby inhibiting translation. Such antisense and ribozyme based methods can also be directed to the regulatory regions of the 85P1B3 gene, such as the 85P1B3 promoter and/or enhancer elements. Similarly, proteins capable of inhibiting a 85P1B3 gene transcription factor are used to inhibit 85P1B3 mRNA transcription. The various polynucleotides and compositions useful in the aforementioned methods have been described above. The use of antisense and ribozyme molecules to inhibit transcription and translation is well known in the art.

Other factors that inhibit the transcription of 85P1B3 by interfering with 85P1B3 transcriptional activation are also useful to treat cancers expressing 85P1B3. Similarly, factors that interfere with 85P1B3 processing are useful to treat cancers that express 85P1B3. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 85P1B3 (i.e., antisense, ribozyme, polynucleotides encoding intrabodies and other 85P1B3 inhibitory molecules). A number of gene therapy approaches are known in the art. Recombinant vectors encoding 85P1B3 antisense polynucleotides, ribozymes, factors capable of interfering with 85P1B3 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 85P1B3 to a binding partner, etc.

In vivo, the effect of a 85P1B3 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402–408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a 85P1B3-related protein or a 85P1B3 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequence of FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

EXAMPLES

Various aspects of the invention are further described and illustrated by way of the several examples that follow, none of which are intended to limit the scope of the invention.

Example 1

SSH-Generated Isolation of a cDNA Fragment of the 85P1B3 Gene

To isolate genes that are involved in the progression of androgen dependent (AD) prostate cancer to androgen independent (AI) cancer, we conducted an experiment with the LAPC-4 AD xenograft in male SCID mice. Mice that harbored LAPC-4 AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually the tumors develop an AI phenotype and start growing again in the castrated males. Tumors were harvested at different time points after castration to identify genes that are turned on or off during the transition to androgen independence.

The gene 85P1B3 was derived from an LAPC-4 AD (3 days post-castration) minus LAPC-4 AD subtraction. The SSH DNA sequence of 319 bp (FIG. 1) is a fragment of the Opa-Interacting Protein 5 gene (OIP-5).

Materials and Methods

LAPC Xenografts and Human Tissues:

LAPC xenografts were obtained from Dr. Charles Sawyers (UCLA) and generated as described (Klein et al, 1997, Nature Med. 3: 402–408; Craft et al., 1999, Cancer Res. 59: 5030–5036). Androgen dependent and independent LAPC-4

AD and AI xenografts were grown in male SCID mice and were passaged as small tissue chunks in recipient males. LAPC-4 AI xenografts were derived from LAPC-4 AD tumors, respectively. To generate the AI xenografts, male mice bearing AD tumors were castrated and maintained for 2–3 months. After the tumors re-grew, the tumors were harvested and passaged in castrated males or in female SCID mice.

Cell Lines:

Human cell lines (e.g., HeLa) were obtained from the ATCC and were maintained in DMEM with 5% fetal calf serum.

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

post-castration) was used as the source of the "tester" cDNA. Double stranded cDNAs corresponding to tester and driver cDNAs were synthesized from 2 μg of poly(A)$^+$ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Driver cDNA was generated by combining in a 1:1 ratio Dpn II digested cDNA from the relevant xenograft source (see above) with a mix of digested cDNAs derived from the human cell lines HeLa, 293, A431, Colo205, and mouse liver.

Tester cDNA was generated by diluting 1 μl of Dpn II digested cDNA from the relevant xenograft source (see above) (400 ng) in 5 μl of water. The diluted cDNA (2 μl,

```
Oligonucleotides:
The following HPLC purified oligonucleotides were used.

DPNCDN (cDNA synthesis primer):
5'TTTTGATCAAGCTT₃₀3'                              (SEQ ID NO: 714)

Adaptor 1:
5'CTAATACGACTCACTATAGGGCTCGAGCGGCCGCCCGGGCAG3'    (SEQ ID NO: 715)
3'GGCCCGTCCTAG5'                                  (SEQ ID NO: 716)

Adaptor 2:
5'GTAATACGACTCACTATAGGGCAGCGTGGTCGCGGCCGAG3'      (SEQ ID NO: 717)
3'CGGCTCCTAG5'                                    (SEQ ID NO: 718)

PCR primer 1:
5'CTAATACGACTCACTATAGGGC3'                        (SEQ ID NO: 719)

Nested primer (NP)1:
5'TCGAGCGGCCGCCCGGGCAGGA3'                        (SEQ ID NO: 720)

Nested primer (NP)2:
5'AGCGTGGTCGCGGCCGAGGA3'                          (SEQ ID NO: 721)
```

Suppression Subtractive Hybridization:

Suppression Subtractive Hybridization (SSH) was used to identify cDNAs corresponding to genes that may be differentially expressed in prostate cancer. The SSH reaction utilized cDNA from two LAPC-4 AD xenografts. Specifically, to isolate genes that are involved in the progression of androgen dependent (AD) prostate cancer to androgen independent (AI) cancer, an experiment was conducted with the LAPC-4 AD xenograft in male SCID mice. Mice that harbored LAPC-4 AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually the tumors develop an AI phenotype and start growing again in the castrated males. Tumors were harvested at different time points after castration to identify genes that are turned on or off during the transition to androgen independence.

The gene 85P1B3 was derived from an LAPC-4 AD (3 days post-castration) minus LAPC-4 AD subtraction. The SSH DNA sequence (FIG. 1) was identified.

The cDNA derived from an LAPC-4 AD tumor (grown in intact male mouse) was used as the source of the "driver" cDNA, while the cDNA from the LAPC-4 AD tumor (3 days 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10–12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NC1-CGAP databases.

RT-PCR Expression Analysis:

First strand cDNAs can be generated from 1 µg of mRNA with oligo (dT) 12–18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'atatcgc-cgcgctcgtcgtcgacaa3' (SEQ ID NO: 722) and 5'agccacacg-cagctcattgtagaagg 3' (SEQ ID NO: 723) to amplify β-actin. First strand cDNA (5 µl) were amplified in a total volume of 50 µl containing 0.4 µM primers, 0.2 µM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 b.p. β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 85P1B3 gene, 5 µl of normalized first strand cDNA were analyzed by PCR using 26, and 30 cycles of amplification. Semi-quantitative expression analysis can be achieved by comparing the PCR products at cycle numbers that give light band intensities.

A typical RT-PCR expression analysis is shown in FIG. 10. RT-PCR expression analysis was performed on first strand cDNAs generated using pools of tissues from multiple samples. The cDNAs were shown to be normalized using beta-actin PCR. Strong expression of 85P1B3 was observed in xenograft pool, bladder cancer pool, kidney cancer pool, colon cancer pool, lung cancer pool, breast cancer pool, ovary cancer pool, and cancer metastasis pool. Lower levels of expression were observed in VP1, VP2, and prostate cancer pool.

Example 2

Full Length Cloning of 85P1B3

To isolate genes that are involved in the progression of androgen dependent (AD) prostate cancer to androgen independent (AI) cancer, an experiment was conducted with the LAPC-4 AD xenograft in male SCID mice. Mice that harbored LAPC-4 AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually the tumors develop an AI phenotype and start growing again in the castrated males. Tumors were harvested at different time points after castration to identify genes that are turned on or off during the transition to androgen independence.

The gene 85P1B3 was derived from an LAPC-4 AD (3 days post-castration minus LAPC-4 AD) (no castration) subtraction. The SSH DNA sequence (FIG. 1) was designated 85P1B3. cDNA clone 85P1B3-clone A (FIG. 2) was identified by screening a human testis library (Display Target, Pangene) using the 85P1B3 SSH DNA sequence. The cDNA (clone A) of 1,262 bp revealed an ORF encoding 229 amino acids (FIG. 2 and FIG. 3). The nucleotide and protein sequence of 85P1B3 corresponds to the OIP-5 gene (FIG. 4). The 85P1B3 protein is predicted to be cytoplasmic using the PSORT program (URL psort.nibb.ac.jp:8800/form.html).

Example 3

Chromosomal Localization

Chromosomal localization can implicate genes in disease pathogenesis. Several chromosome mapping approaches are available in the art, including fluorescent in situ hybridization (FISH), human/hamster radiation hybrid (RH) panels (Walter et al., 1994; Nature Genetics 7:22; Research Genetics, Huntsville Ala.), human-rodent somatic cell hybrid panels such as is available from the Coriell Institute (Camden, N.J.), and genomic viewers utilizing BLAST homologies to sequenced and mapped genomic clones (NCBI, Bethesda, Md.). 85P1B3 maps to chromosome 15q14, using 85P1B3 sequence and the NCBI BLAST tool The chromosomal localization of 85P1B3 was also determined using the GeneBridge4 Human/Hamster radiation hybrid (RH) panel (Walter et al., 1994; Nature Genetics 7:22)(Research Genetics, Huntsville Ala.).

The following PCR primers were used:

```
                                       (SEQ ID NO:732)
85P1B3.1    5' catgggactctgcatcttaattcc 3'

(SEQ ID NO:733)
85P1B3.2    5' caggttcaggctttattgctgtct 3'
```

The resulting 85P1B3 mapping vector for the 93 radiation hybrid panel DNAs (100100010101000101000000000001010000001210110000101110010000101110001001010110010110110101), the 85P1B3 gene was localized to chromosome 15q13.2- q14.

Of note, chromosome 15q13.2- q14 is a region implicated in cancers (Tomlinson et al., Gastroenterology 1999 April; 116(4):789–95).

Example 4

Expression Analysis of 85P1B3 in Normal Tissues and Patient Specimens

Analysis of 85P1B3 by RT-PCR is shown in FIG. 10. Strong expression of 85P1B3 is observed in xenograft pool, bladder cancer pool, kidney cancer pool, colon cancer pool, lung cancer pool, breast cancer pool, ovary cancer pool, and cancer metastasis pool. Lower levels of expression are observed in VP1, VP2, and prostate cancer pool.

Extensive Northern blot analysis of 85P1B3 in 16 human normal tissues demonstrated that 85P1B3 expression is reminiscent of a cancer-testis gene (FIG. 11). A 1.4 kb transcript was detected in testis but not in any other normal tissues. 85P1B3 expression was also shown in prostate cancer xenografts and in all cancer cell lines tested, such as in the cancers of the prostate (LAPC 4AD, LAPC 4AI, LAPC 9AD, LAPC 9AI, LNCaP, PC-3, DU145, Tsu-Prl and LAPC-4 CL), bladder (HT1197, SCaBER, UM-UC-3, TCCSUP, J82, 5637), 293T cell line, Ewing's sarcoma (EWS), brain (PFSK-1, T98G), bone (SK-ES-1, HOS, U-2 OS, RD-ES), lung (CALU-1, A427, NCI-H82, NCI-H146), kidney (769-P, A498, CAKI-1, SW839), breast (CAMA-1, DU4475, MCF-7, MDA-MB-435s), testicular (NTERRA-2, NCC1T, TERA-1, TERA-2), ovarian (OV-1063, PA-1, SW 626), pancreas (PANC-1, Bx PC-3, HPAC, Capan-1), colon (Caco-2, LoVo, T84, Colo205), and cervical (A431) (FIG. 12). These results indicate that 85P1B3 is a testis-specific gene that is upregulated in multiple cancers.

Expression of 85P1B3 was assayed in a panel of human patient tumors (T) and their respective matched normal tissues (N) on RNA dot blots (FIG. 13). 85P1B3 expression was seen in the cancers of the breast, prostate, uterus, ovary, cervix, stomach and lung. The expression detected in normal adjacent tissues (isolated from diseased tissues) but not in normal tissues (isolated from healthy donors) may indicate that these tissues are not fully normal and that 85P1B3 may be expressed in early stage tumors. 85P1B3 was also found to be highly expressed in all human cancer cell lines tested, HeLa (cervical carcinoma), Daudi (Burkitt's lymphoma), K562 (CML), HL-60 (PML), G361 (melanoma), A549 (lung carcinoma), MOLT4 (lymphoblastic leukemia), SW480 (colorectal carcinoma), and Raji (Burkitt's lymphoma).

Northern blot analysis on individual patient tumor specimens showed expression of 85P1B3 in two colon tumor tissues tested, and in the colon cancer cell lines Colo 205, LoVo, T84 and Caco-2, but not in normal colon (FIG. 14).

Expression of 85P1B3 was also detected in the tumors of 4 out of 5 bladder cancer patients, and in all three bladder cancer cell lines tested, but not in normal bladder (FIG. 15).

In lung cancer samples, 85P1B3 expression was observed in three lung tumor specimens, all three lung cancer cell lines tested, but not in normal lung (FIG. 16).

In order to assay for androgen regulation of 85P1B3 expression, LAPC-9AD tumor cells were injected in male mice (FIG. 17). When tumors reached a palpable size (0.3–0.5 cm in diameter), mice were castrated and tumors harvested at different time points. RNA was isolated from the xenograft tissues and Northern blots with 10 μg of total RNA/lane were probed with the 85P1B3 SSH fragment. Results showed that expression of 85P1B3 is not affected by androgen deprivation, and therefore, is not androgen-regulated.

The restricted expression of 85P1B3 in normal tissues and the expression detected in bladder cancer, kidney cancer, colon cancer, lung cancer, prostate cancer, ovarian cancer, and breast cancer indicate that 85P1B3 is a therapeutic and/or prophylactic target and a prognostic and/or diagnostic marker for human cancers.

Example 5

Production of Recombinant 85P1B3 in Prokaryotic Systems

To express recombinant 85P1B3 in prokaryotic cells, the full or partial length 85P1B3 cDNA sequences can be cloned into any one of a variety of expression vectors known in the art. One or more of the following regions of 85P1B3 are expressed in these constructs, amino acids 1 to 229; or any 8, 9, 10, 11, 12, 13, 14, 15, 16, 17, 18, 19, 20, 21, 22, 23, 24, 25, 26, 27, 28, 29, 30 or more contiguous amino acids from 85P1B3, variants, or analogs thereof.

A. In vitro Transcription and Translation Constructs:

pCRII: To generate 85P1B3 sense and anti-sense RNA probes for RNA in situ investigations, pCRII constructs (Invitrogen, Carlsbad Calif.) are generated encoding either all or fragments of the 85P1B3 cDNA. The pCRII vector has Sp6 and T7 promoters flanking the insert to drive the transcription of 85P1B3 RNA for use as probes in RNA in situ hybridization experiments. These probes are used to analyze the cell and tissue expression of 85P1B3 at the RNA level. Transcribed 85P1B3 RNA representing the cDNA amino acid coding region of the 85P1B3 gene is used in in vitro translation systems such as the TnT™ Coupled Reticulolysate System (Promega, Corp., Madison, Wis.) to synthesize 85P1B3 protein.

B. Bacterial Constructs:

pGEX Constructs: To generate recombinant 85P1B3 proteins in bacteria that are fused to the Glutathione S-transferase (GST) protein, all or parts of the 85P1B3 cDNA protein coding sequence are fused to the GST gene by cloning into pGEX-6P-1 or any other GST-fusion vector of the pGEX family (Amersham Pharmacia Biotech, Piscataway, N.J.). These constructs allow controlled expression of recombinant 85P1B3 protein sequences with GST fused at the amino-terminus and a six histidine epitope (6×His) (SEQ ID NO: 709) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag (SEQ ID NO: 709) is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 85P1B3-related protein. The ampicillin resistance gene and pBR322 origin permits selection and maintenance of the pGEX plasmids in *E. coli*.

Figure 20:
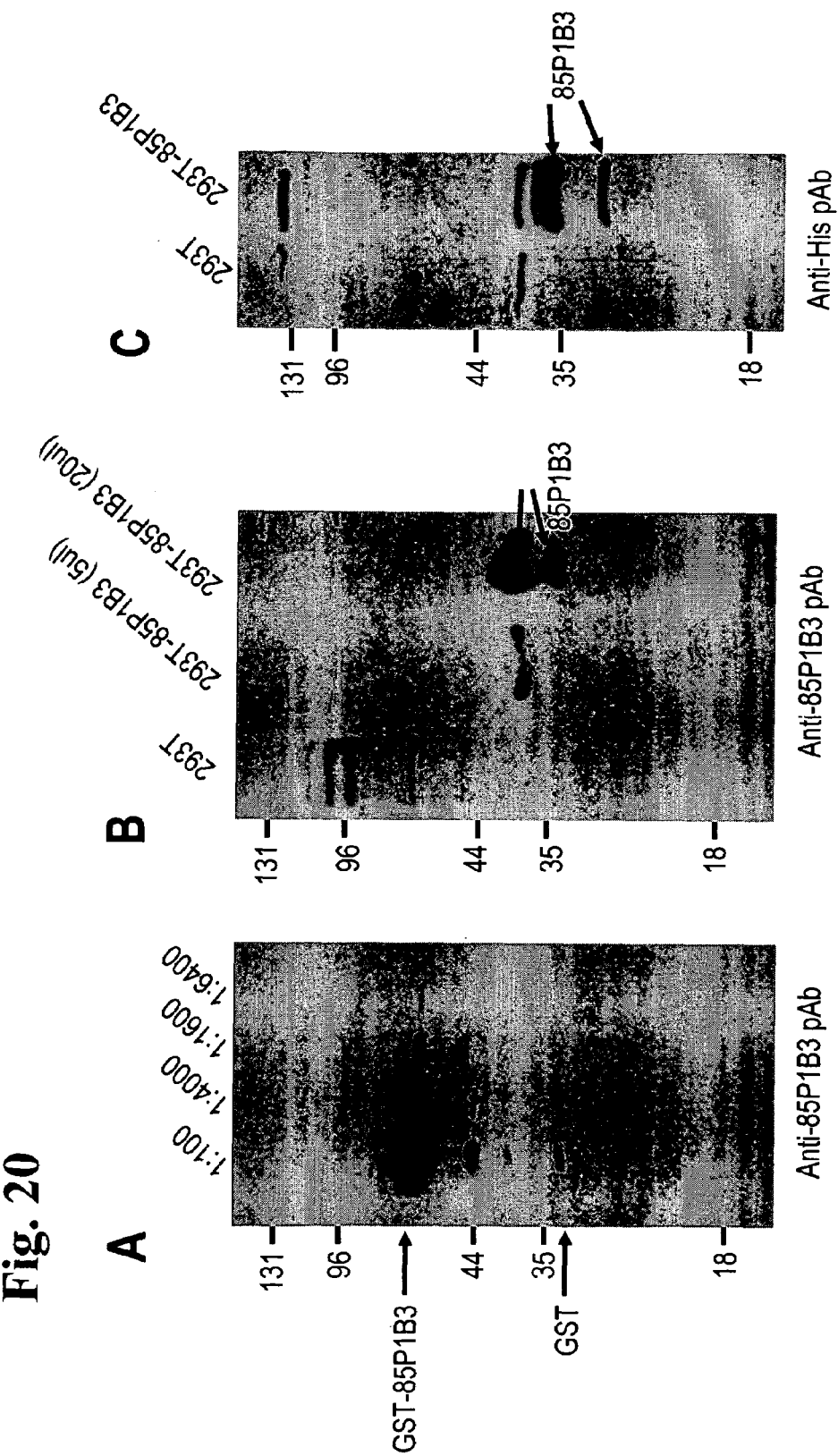
FIG. 20. Western analysis of 85P1B3 expression with an anti-85P1B3 polyclonal antibody. Panel A. Detection of GST-85P1B3 with anti-GST-85P1B3 rabbit serum. 200 ng of GST-85P1B3 (amino acids 1–229) and 200 ng of GST alone were separated by SDS-PAGE and transferred to nitrocellulose. The blot was then incubated with indicated dilutions of anti-85P1B3 serum. Immunoreactive bands were detected by incubation with anti-rabbit IgG HPP-secondary antibody and visualized by enhanced chemiluminescence and exposure to autoradiography film. Shown with arrows is detection of the GST-85P1B3 protein and minimal detection of GST alone. Panel B. 293T cells were transiently transfected with either empty pCDNA 3.1 vector or pCDNA 3.1 carrying the 85P1B3 cDNA. Lysates of the cells were separated by SDS-PAGE and subjected to Western analysis as performed for the data in Panel A, with 2 µg/ml of purified anti-85P1B3 polyclonal antibody. Panel C. Western analysis was carried out as for the data in Panel B, but using an anti-His polyclonal antibody (Santa Cruz Biotechnology, Santa Cruz, Calif.). Arrows indicate the immunoreactive bands corresponding to His-tagged 85P1B3 protein.

In one embodiment, a GST-fusion protein encoding the full length 85P1B3 protein sequence (amino acids 1–229) was constructed and purified from induced bacteria. This preparation was then used as immunogen to generate a rabbit anti-85P1B3 polyclonal antibody (see the section entitled "Generation of 85P1B3 Polyclonal Antibodies". As can be seen in FIG. 20A, the pAb strongly recognizes the original GST-fusion immunogen as well as 85P1B3 protein expressed in 293T cells (FIG. 20B and FIG. 20C).

pMAL Constructs: To generate, in bacteria, recombinant 85P1B3 proteins that are fused to maltose-binding protein (MBP), all or parts of the 85P1B3 cDNA protein coding sequence are fused to the MBP gene by cloning into the pMAL-c2X and pMAL-p2X vectors (New England Biolabs, Beverly, Mass.). These constructs allow controlled expression of recombinant 85P1B3 protein sequences with MBP fused at the amino-terminus and a 6xHis epitope tag at the carboxyl-terminus. The MBP and 6xHis tags (SEQ ID NO: 709) permit purification of the recombinant protein from induced bacteria with the appropriate affinity matrix and allow recognition of the fusion protein with anti-MBP and anti-His antibodies. The 6xHis epitope tag (SEQ ID NO: 709) is generated by adding 6 histidine codons to the 3' cloning primer. A Factor Xa recognition site permits cleavage of the pMAL tag from 85P1B3. The pMAL-c2X and pMAL-p2X vectors are optimized to express the recombinant protein in the cytoplasm or periplasm respectively. Periplasm expression enhances folding of proteins with disulfide bonds.

pET Constructs: To express 85P1B3 in bacterial cells, all or parts of the 85P1B3 cDNA protein coding sequence are cloned into the pET family of vectors (Novagen, Madison, Wis.). These vectors allow tightly controlled expression of recombinant 85P1B3 protein in bacteria with and without fusion to proteins that enhance solubility, such as NusA and thioredoxin (Trx), and epitope tags, such as 6xHis (SEQ ID NO: 709) and S-Tag™ that aid purification and detection of the recombinant protein. For example, constructs are made utilizing pET NusA fusion system 43.1 such that regions of the 85P1B3 protein are expressed as amino-terminal fusions to NusA.

C. Yeast Constructs:

pESC Constructs: To express 85P1B3 in the yeast species *Saccharomyces cerevisiae* for generation of recombinant protein and functional studies, all or parts of the 85P1B3 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein—protein interactions of 85P1B3. In addition, expression in yeast yields similar post-translational modifications, such as glycosylations and phosphorylations, that are found when expressed in eukaryotic cells.

pESP Constructs: To express 85P1B3 in the yeast species *Saccharomyces pombe*, all or parts of the 85P1B3 cDNA protein coding sequence are cloned into the pESP family of vectors. These vectors allow controlled high level of expression of a 85P1B3 protein sequence that is fused at either the amino terminus or at the carboxyl terminus to GST which aids purification of the recombinant protein. A Flag™ epitope tag allows detection of the recombinant protein with anti-Flag™ antibody.

Example 6

Production of Recombinant 85P1B3 in Eukaryotic Systems

A. Mammalian Constructs:

To express recombinant 85P1B3 in eukaryotic cells, the full or partial length 85P1B3 cDNA sequences can be cloned into any one of a variety of expression vectors known in the art. One or more of the following regions of 85P1B3 are expressed in these constructs, amino acids 1 to 229; or any 8, 9, 10, 11, 12, 13, 14, 15, 16, 17, 18, 19, 20, 21, 22, 23, 24, 25, 26, 27, 28, 29, 30 or more contiguous amino acids from 85P1B3, variants, or analogs thereof.

The constructs can be transfected into any one of a wide variety of mammalian cells such as 293T cells. Transfected 293T cell lysates can be probed with the anti-85P1B3 polyclonal serum, described herein.

pcDNA4/HisMax Constructs: To express 85P1B3 in mammalian cells, the 85P1B3 ORF, or portions thereof, of 85P1B3 are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6xHis) (SEQ ID NO: 709) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/MycHis Constructs: To express 85P1B3 in mammalian cells, the 85P1B3 ORF, or portions thereof, of 85P1B3 with a consensus Kozak translation initiation site are cloned into pcDNA3.1/MycHis Version A (Invitrogen, Carlsbad, Calif.). Protein expression is driven from the cytomegalovirus (CMV) promoter. The recombinant proteins have the myc epitope and 6xHis epitope (SEQ ID NO: 709) fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli*.

pcDNA3.1/CT-GFP-TOPO Construct: To express 85P1B3 in mammalian cells and to allow detection of the recombinant proteins using fluorescence, the 85P1B3 ORF, or portions thereof, of 85P1B3 with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E. coli*. Additional constructs with an amino-terminal GFP fusion are made in pcDNA3.1NT-GFP-TOPO spanning the entire length of the 85P1B3 proteins.

PAPtag: The 85P1B3 ORF, or portions thereof of 85P1B3 are cloned into pAPtag-5 (GenHunter Corp. Nashville, Tenn.). This construct generates an alkaline phosphatase fusion at the carboxyl-terminus of the 85P1B3 proteins while fusing the IgGK signal sequence to the amino-terminus. Constructs are also generated in which alkaline phosphatase with an amino-terminal IgGK signal sequence is fused to the amino-terminus of 85P1B3 proteins. The resulting recombinant 85P1B3 proteins are optimized for secretion into the media of transfected mammalian cells and can be used to identify proteins such as ligands or receptors that interact with the 85P1B3 proteins. Protein expression is driven from the CMV promoter and the recombinant proteins also contain myc and 6×His (SEQ ID NO: 709) epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

ptag5: The 85P1B3 ORF, or portions thereof, of 85P1B3 was cloned into pTag-5. This vector is similar to pAPtag but without the alkaline phosphatase fusion. This construct generated 85P1B3 protein with an amino-terminal IgGK signal sequence and myc and 6×His epitope (SEQ ID NO: 709) tags at the carboxyl-terminus that facilitate detection and affinity purification. The resulting recombinant 85P1B3 protein was optimized for secretion into the media of transfected mammalian cells, and was used as immunogen or ligand to identify proteins such as ligands or receptors that interact with the 85P1B3 proteins. Protein expression is driven from the CMV promoter. The Zeocin resistance gene present in the vector allows for selection of mammalian cells expressing the protein, and the ampicillin resistance gene permits selection of the plasmid in E. coli.

PsecFc: The 85P1B3 ORF, or portions thereof, of 85P1B3 are also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 85P1B3 proteins, while fusing the IgGK signal sequence to N-terminus. 85P1B3 fusions utilizing the murine IgG1 Fc region are also used. The resulting recombinant 85P1B3 proteins are optimized for secretion into the media of transfected mammalian cells, and can be used as immunogens or to identify proteins such as ligands or receptors that interact with the 85P1B3 protein. Protein expression is driven from the CMV promoter. The hygromycin resistance gene present in the vector allows for selection of mammalian cells that express the recombinant protein, and the ampicillin resistance gene permits selection of the plasmid in E. coli.

pSRα Constructs: To generate mammalian cell lines that express 85P1B3, or portions thereof, constitutively, the ORF of 85P1B3 was cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus was used to infect a variety of mammalian cell lines, resulting in the integration of the cloned gene, 85P1B3, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in E. coli. FIG. 18 shows expression of 85P1B3 using the pSRα retroviral vector in the prostate cancer cell line PC3. The retroviral vectors can thereafter be used for infection and generation of various cell lines using, for example, SCaBER, NIH 3T3, TsuPr1, 293 or rat-1 cells.

Additional pSRα constructs are made that fuse an epitope tag such as the FLAG™ tag to the carboxyl-terminus of 85P1B3 sequences to allow detection using anti-Flag antibodies. For example, the FLAG™ sequence 5' gat tac aag gat gac gac gat aag 3' (SEQ ID NO: 734) is added to cloning primer at the 3' end of the ORF. Additional pSRα constructs are made to produce both amino-terminal and carboxyl-terminal GFP and myc/6×His (SEQ ID NO: 709) fusion proteins of the full-length 85P1B3 proteins.

Additional Viral Vectors: Additional constructs are made for viral-mediated delivery and expression of 85P1B3. High virus titer leading to high level expression of 85P1B3 is achieved in viral delivery systems such as adenoviral vectors and herpes amplicon vectors. The 85P1B3 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 85P1B3 coding sequences or fragments thereof are cloned into the HSV-1 vector (Imgenex) to generate herpes viral vectors. The viral vectors are thereafter used for infection of various cell lines such as SCaBER, NIH 3T3, 293 or rat-1 cells.

Regulated Expression Systems: To control expression of 85P1B3 in mammalian cells, coding sequences of 85P1B3, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 85P1B3. These vectors are thereafter used to control expression of 85P1B3 in various cell lines such as SCaBER, NIH 3T3, 293 or rat-1 cells.

B. Baculovirus Expression Systems

To generate recombinant 85P1B3 proteins in a baculovirus expression system, 85P1B3 ORF, or portions thereof, are cloned into the baculovirus transfer vector pBlueBac 4.5 (Invitrogen), which provides a His-tag at the N-terminus. Specifically, pBlueBac-85P1B3 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 85P1B3 protein is then generated by infection of HighFive insect cells (Invitrogen) with purified baculovirus. Recombinant 85P1B3 protein can be detected using anti-85P1B3 or anti-His-tag antibody. 85P1B3 protein can be purified and used in various cell-based assays or as immunogen to generate polyclonal and monoclonal antibodies specific for 85P1B3.

Example 7

Antigenicity Profiles and Secondary Structure

FIG. 5, FIG. 6, FIG. 7, FIG. 8, and FIG. 9 depict graphically five amino acid profiles of the 85P1B3 amino acid sequence, each assessment available by accessing the ProtScale website on the ExPasy molecular biology server.

These profiles: FIG. 5, Hydrophilicity, (Hopp T. P., Woods K. R., 1981. Proc. Natl. Acad. Sci. U.S.A. 78:3824–3828); FIG. 6, Hydropathicity, (Kyte J., Doolittle R. F., 1982. J. Mol. Biol. 157:105–132); FIG. 7, Percentage Accessible Residues (Janin J., 1979 Nature 277:491–492); FIG. 8, Average Flexibility, (Bhaskaran R., and Ponnuswamy P. K., 1988. Int. J. Pept. Protein Res. 32:242–255); FIG. 9, Beta-turn (Deleage, G., Roux B. 1987 Protein Engineering 1:289–294); and optionally others available in the art, such as on the ProtScale website, were used to identify antigenic regions of the 85P1B3 protein. Each of the above amino acid profiles of 85P1B3 were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 85P1B3 protein indicated, e.g., by the profiles set forth in FIG. 5, FIG. 6, FIG. 7, FIG. 8, and/or FIG. 9 are used to prepare immunogens, either peptides or nucleic acids that encode them, to generate therapeutic and diagnostic anti-85P1B3 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 85P1B3 protein. In particular, peptide immunogens of the invention can comprise, a peptide region of at least 5 amino acids of FIG. 2 in any whole number increment up to 229 that includes an amino acid position having a value greater than 0.5 in the Hydrophilicity profile of FIG. 5; a peptide region of at least 5 amino acids of FIG. 2 in any whole number increment up to 229 that includes an amino acid position having a value less than 0.5 in the Hydropathicity profile of FIG. 6; a peptide region of at least 5 amino acids of FIG. 2 in any whole number increment up to 229 that includes an amino acid position having a value greater than 0.5 in the Percent Accessible Residues profile of FIG. 7; a peptide region of at least 5 amino acids of FIG. 2 in any whole number increment up to 229 that includes an amino acid position having a value greater than 0.5 in the Average Flexibility profile on FIG. 8; and, a peptide region of at least 5 amino acids of FIG. 2 in any whole number increment up to 229 that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 85P1B3, namely the predicted presence and location of alpha helices, extended strands, and random coils, is predicted from the primary amino acid sequence using the HNN—Hierarchical Neural Network method (Guermeur, 1997), accessed from the ExPasy molecular biology server. The analysis indicates that 85P1B3 is composed of 36.8% alpha helix, 13.97% extended strand, and 49.34% random coil (FIG. 21A).

Figure 21B:
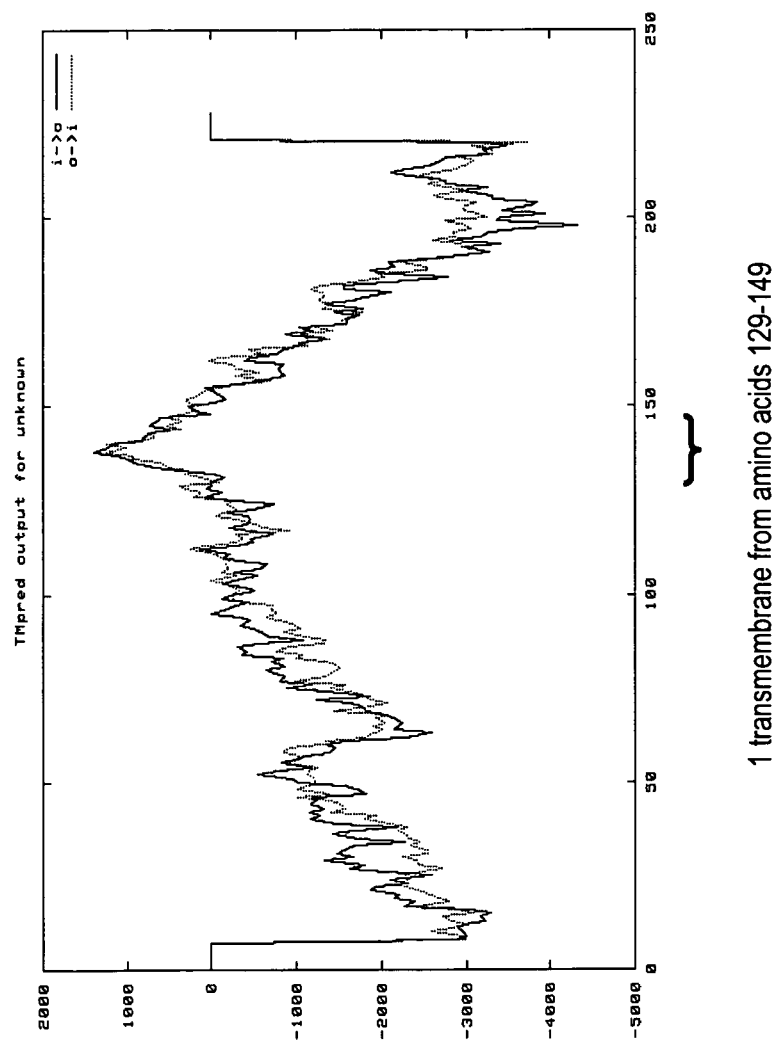
FIG. 21. Secondary structure and transmembrane prediction for 85P1B3. Panel A. The secondary structure of 85P1B3 protein was predicted using the HNN—Hierarchical Neural Network method (Guermeur, 1997), accessed from the ExPasy molecular biology server. This method indicates the presence and location of alpha helices (h), extended strands (e), and random coils (c) from the primary protein sequence. The percent of the protein in a given secondary structure is also given. Panel B. Schematic representation of the probability of existence of transmembrane regions of 85P1B3 based on the TMpred algorithm of Hofmann and Stoffel which utilizes TMBASE (K. Hofmann, W. Stoffel. TMBASE-A database of membrane spanning protein segments Biol. Chem. Hoppe-Seyler 374:166, 1993). Stretches of amino acids approximately 17–33 amino acids in length with a value greater than 0 are potential transmembrane helices. This program indicates the presence of one helix in 85P1B3. Panel C. Schematic representation of the probability of the existence of transmembrane regions and the extracellular and intracellular orientation of 85P1B3 based on the algorithm of Sonnhammer, von Heijne, and Krogh (Erik, L. L., et al., A hidden Markov model for predicting transmembrane helices in protein sequences. In Proc. of Sixth Int. Conf. on Intelligent Systems for Molecular Biology, p 175–182 Ed J. Glasgow, et al., Menlo Park, Calif.: AAAI Press, 1998). This program indicates 85P1B3 to be an intracellular protein without transmembrane domains. These transmembrane prediction results are also summarized in Table XXV.
Figure 21C:
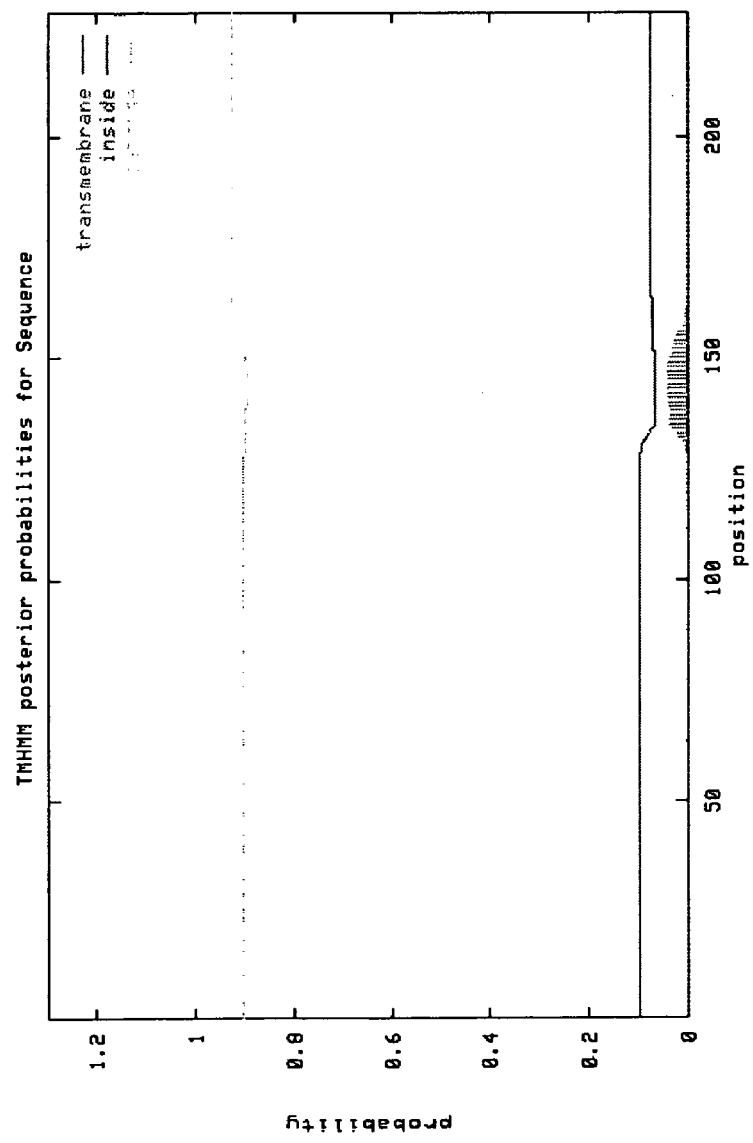

Analysis for the potential presence of transmembrane domains in 85P1B3 was carried out using a variety of transmembrane prediction algorithms accessed from the ExPasy molecular biology server. A potential transmembrane domain composed of amino acids 129–149 is predicted by the TMpred program (FIG. 21B). HMMTop predicts a transmembrane region from amino acids 134–158. The SOSUI and TMHMM (FIG. 21C) programs predict that 85P1B3 is a soluble protein without transmembrane domains. The results of the transmembrane predictions are summarized in Table XXV.

Example 8

Generation of 85P1B3 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 85P1B3 protein, computer algorithms are employed in design of immunogens that, based on amino acid sequence analysis contain characteristics of being antigenic and available for recognition by the immune system of the immunized host (see the Example entitled "Antigenicity Profiles"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 85P1B3).

For example, 85P1B3 recombinant bacterial fusion proteins or peptides encoding hydrophilic, flexible, beta-turn regions of the 85P1B3 sequence, such as amino acids 1–77 and 190–229 are used as antigens to generate polyclonal antibodies in New Zealand White rabbits. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 190–206 of 85P1B3 is conjugated to KLH and used to immunize the rabbit. Alternatively the immunizing agent may include all or portions of the 85P1B3 protein, analogs or fusion proteins thereof. For example, the 85P1B3 amino acid sequence can be fused using recombinant DNA techniques to any one of a variety of fusion protein partners that are well known in the art, such as glutathione-S-transferase (GST) and HIS tagged fusion proteins. Such fusion proteins are purified from induced bacteria using the appropriate affinity matrix.

In one embodiment, a GST-fusion protein encoding the full length 85P1B3 protein sequence was produced and purified and used as immunogen (see the section entitled "Production of 85P1B3 in Prokaryotic Systems"). Shorter sequences are also fused to GST in order to direct antibody to specific regions of the protein such as amino acids 1–77 to generate amino-terminal specific antibodies. Other recombinant bacterial fusion proteins that may be employed include maltose binding protein, LacZ, thioredoxin, NusA, or an immunoglobulin constant region (see the section entitled "Production of 85P1B3 in Prokaryotic Systems" and Current Protocols In Molecular Biology, Volume 2, Unit 16, Frederick M. Ausubul et al. eds., 1995; Linsley, P. S., Brady, W., Umes, M., Grosmaire, L., Damle, N., and Ledbetter, L. (1991) J. Exp. Med. 174, 561–566).

In addition to bacterial derived fusion proteins, mammalian expressed protein antigens are also used. These antigens are expressed from mammalian expression vectors such as the Tag5 and Fc-fusion vectors (see the section entitled "Production of Recombinant 85P1B3 in Eukaryotic Systems"), and retain post-translational modifications such as glycosylations found in native protein. In one embodiment, a predicted antigenic region of 85P1B3, amino acids 190–229, is cloned into the Tag5 mammalian secretion vector. The recombinant protein is purified by metal chelate chromatography from tissue culture supernatants of 293T cells stably expressing the recombinant vector. The purified Tag5 85P1B3 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 µg, typically 100–200 µg, of fusion protein or peptide conjugated to KLH mixed in complete Freund's adjuvant (CFA). Rabbits are then injected subcutaneously every two weeks with up to 200 µg, typically 100–200 µg, of the immunogen in incomplete Freund's adjuvant (IFA). Test bleeds are taken approximately 7–10 days following each immunization and used to monitor the titer of the antiserum by ELISA.

To test reactivity and specificity of immune serum, such as the rabbit serum raised from immunization with GST-85P1B3 full length fusion protein, the full-length 85P1B3 cDNA was cloned into pCDNA 3.1 myc-his expression vector (Invitrogen, see the Example entitled "Production of Recombinant 85P1B3 in Eukaryotic Systems"). After transfection of the constructs into 293T cells, cell lysates were probed with the anti-85P1B3 serum and with anti-His antibody (Santa Cruz Biotechnologies, Santa Cruz, Calif.) to determine specific reactivity to denatured 85P1B3 protein using the Western blot technique. As can be seen in FIG. 20B, the anti-85P1B3 pAb specifically recognized 85P1B3 protein expressed in 293T cells that is the same molecular weight as that detected by the anti-His Ab (FIG. 20C). Recognition of native protein by the antiserum is determined by immunoprecipitation and flow cytometric analyses of 293T and other recombinant 85P1B3-expressing cells. In addition, specificity of the antiserum is tested by Western blot, immunoprecipitation, fluorescent microscopy, and flow cytometric techniques using cells that endogenously express 85P1B3.

To purify the anti-serum derived from the GST-85P1B3 immunized rabbit, the serum was passed over an affinity column composed of GST to remove anti-GST reactive antibodies. The serum was then further purified by protein G affinity chromatography to isolate the IgG fraction. Serum from rabbits immunized with other fusion proteins, such as MBP fusion proteins, are purified by depletion of antibodies reactive to MBP, or other fusion partner sequence, by passage over an affinity column containing the fusion partner either alone or in the context of an irrelevant fusion protein. Sera from His-tagged protein and peptide immunized rabbits as well as fusion partner depleted sera are further purified by passage over an affinity column composed of the original protein immunogen or free peptide coupled to Affigel matrix (BioRad).

Example 9

Generation of 85P1B3 Monoclonal Antibodies (mAbs)

In one embodiment, therapeutic mAbs to 85P1B3 comprise those that react with epitopes of the protein that would disrupt or modulate the biological function of 85P1B3, for example those that would disrupt its interaction with ligands or proteins that mediate or are involved in its biological activity. Therapeutic mAbs also comprise those which specifically bind epitopes of 85P1B3 exposed on the cell surface and thus are useful in targeting mAb-toxin conjugates. Immunogens for generation of such mAbs include those designed to encode or contain the entire 85P1B3 protein or regions of the 85P1B3 protein predicted to be antigenic from computer analysis of the amino acid sequence (see, e.g., FIG. 5, FIG. 6, FIG. 7, FIG. 8, or FIG. 9, and the Example entitled "Antigenicity Profiles").

Immunogens include peptides, recombinant bacterial proteins, and mammalian expressed Tag 5 proteins and human and murine IgG FC fusion proteins. To generate mAbs to 85P1B3, mice are first immunized intraperitoneally (IP) with, typically, 10–50 µg of protein immunogen mixed in complete Freund's adjuvant. Mice are then subsequently immunized IP every 2–4 weeks with, typically, 10–50 µg of antigen mixed in incomplete Freund's adjuvant. Alternatively, MPL-TDM adjuvant is used in immunizations. In addition, a DNA-based immunization protocol is employed in which a mammalian expression vector encoding 85P1B3 sequence is used to immunize mice by direct injection of the plasmid DNA. For example, either pCDNA 3.1 encoding the full length 85P1B3 cDNA, amino acids 1–77, or 190–229 of 85P1B3 (predicted to be antigenic from sequence analysis, see, e.g., FIG. 5, FIG. 6, FIG. 7, FIG. 8 or FIG. 9) fused at the amino-terminus to an IgK leader sequence and at the carboxyl-terminus to the coding sequence of murine or human IgG Fc region, is used. This protocol is used alone and in combination with protein immunogens. Test bleeds are taken 7–10 days following immunization to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment for generating 85P1B3 monoclonal antibodies, a glutathione-S-transferase (GST) fusion protein encoding the full length 85P1B3 protein is expressed and purified. A cleavage fragment encoding 85P1B3 specific amino acids is then used as immunogen in which GST is removed by site-specific proteolysis. Balb C mice are initially immunized intraperitoneally with 25 µg of the 85P1B3 cleavage protein mixed in complete Freund's adjuvant. Mice are subsequently immunized every two weeks with 25 µg of 85P1B3 cleavage protein mixed in incomplete Freund's adjuvant for a total of three immunizations. The titer of serum from immunized mice is determined by ELISA using the full length GST-fusion protein and the cleaved immunogen. Reactivity and specificity of serum to full length 85P1B3 protein is monitored by Western blotting, immunoprecipitation and flow cytometry using 293T cells transfected with an expression vector encoding the 85P1B3 cDNA. Other recombinant 85P1B3-expressing cells (see e.g., the Example entitled "Production of 85P1B3 in Eukaryotic Systems") or cells endogenously expressing 85P1B3 are also used. Mice showing the strongest reactivity are rested and given a final injection of 85P1B3 cleavage protein in PBS and then sacrificed four days later. The spleens of the sacrificed mice are harvested and fused to SPO/2 myeloma cells using standard procedures (Harlow and Lane, 1988). Supernatants from growth wells following HAT selection are screened by ELISA, Western blot, immunoprecipitation, fluorescent microscopy, and flow cytometry to identify 85P1B3 specific antibody-producing clones.

The binding affinity of a 85P1B3 monoclonal antibody is determined using standard technologies. Affinity measurements quantify the strength of antibody to epitope binding and are used to help define which 85P1B3 monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 10

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1–10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10–20% of the total radioactivity. All subsequent inhibition and direct binding assays are performed using these HLA concentrations.

Since under these conditions [label]<[HLA] and $IC_{50}$>[HLA], the measured $IC_{50}$ values are reasonable approximations of the true $K_D$ values. Peptide inhibitors are typically tested at concentrations ranging from 120 μg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides.

Example 11

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" and Tables V–XVIII employ the protein sequence data from the gene product of 85P1B3 set forth in FIGS. 2 and 3.

Computer searches for epitopes bearing HLA Class I or Class II supermotifs or motifs are performed as follows. All translated 85P1B3 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or ΔG) of peptide-HLA molecule interactions can be approximated as a linear polynomial function of the type:

$$"\Delta G" = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide.

The method of derivation of specific algorithm coefficients has been described in Gulukota et al., *J. Mol. Biol.* 267:1258–126, 1997; (see also Sidney et al., *Human Immunol.* 45:79–93, 1996; and Southwood et al., *J. Immunol.* 160:3363–3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-Reactive Peptides

Complete protein sequences from 85P1B3 are scanned utilizing motif identification software, to identify 8-, 9- 10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-Bearing Epitopes

The 85P1B3 protein sequence scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of $\leq 500$ nM, often $\leq 200$ nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 85P1B3 protein is also analyzed for the presence of 8-, 9- 10-, or 11-mer peptides with the HLA-B7-supermotif Corresponding peptides are synthesized and tested for binding to HLA-B*0702, the molecule encoded by the most common B7-supertype allele (i.e., the prototype B7 supertype allele). Peptides binding B*0702 with $IC_{50}$ of $\leq 500$ nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the 85P1B3 protein can also be performed to identify HLA-A1- and A24-motif-containing sequences.

High affinity and/or cross-reactive binding epitopes that bear other motif and/or supermotifs are identified using analogous methodology.

Example 12

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The .221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 µg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M-450) and the detacha-bead® reagent. Typically about $200-250 \times 10^6$ PBMC are processed to obtain $24 \times 10^6$ CD8+ T-cells (enough for a 48-well plate culture). Briefly, the PBMCs are thawed in RPMI with 30 µg/ml DNAse, washed once with PBS containing 1% human AB serum and resuspended in PBS/1% AB serum at a concentration of $20 \times 10^6$ cells/ml. The magnetic beads are washed 3 times with PBS/AB serum, added to the cells (140 µl beads/$20 \times 10^6$ cells) and incubated for 1 hour at 4° C. with continuous mixing. The beads and cells are washed 4× with PBS/AB serum to remove the nonadherent cells and resuspended at $100 \times 10^6$ cells/ml (based on the original cell number) in PBS/AB serum containing 100 µl/ml detacha-bead® reagent and 30 µg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5–7 minutes, washed once with PBS with 1% BSA, counted and pulsed with 40 µg/ml of peptide at a cell concentration of $1-2 \times 10^6$/ml in the presence of 3 µg/ml $\beta_2$-microglobulin for 4 hours at 20° C. The DC are then irradiated (4,200 rads), washed 1 time with medium and counted again.

Setting up induction cultures: 0.25 ml cytokine-generated DC (at $1 \times 10^5$ cells/ml) are co-cultured with 0.25 ml of CD8+ T-cells (at $2 \times 10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at $5 \times 10^6$ cells/ml and irradiated at ~4200 rads. The PBMCs are plated at $2 \times 10^6$ in 0.5 ml complete medium per well and incubated for 2 hours at 37° C. The plates are washed twice with RPMI by tapping the plate gently to remove the nonadherent cells and the adherent cells pulsed with 10 µg/ml of peptide in the presence of 3 µg/ml $\beta_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2–3 days later at 50 IU/ml (Tsai et al., *Critical Reviews in Immunology* 18(1–2):65–75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labelled with 200 μCi of $^{51}$Cr sodium chromate (Dupont, Wilmington, Del.) for 1 hour at 37° C. Labelled target cells are resuspended at $10^6$ per ml and diluted 1:10 with K562 cells at a concentration of $3.3\times10^6$/ml (an NK-sensitive erythroblastoma cell line used to reduce non-specific lysis). Target cells (100 μl) and effectors (10011) are plated in 96 well round-bottom plates and incubated for 5 hours at 37° C. At that time, 100 μl of supernatant are collected from each well and percent lysis is determined according to the formula:

[(cpm of the test sample–cpm of the spontaneous $^{51}$Cr release sample)/(cpm of the maximal $^{51}$Cr release sample–cpm of the spontaneous $^{51}$Cr release sample)]×100.

Maximum and spontaneous release are determined by incubating the labelled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In situ Measurement of Human IFNγ Production as an Indicator of Peptide-Specific and Endogenous Recognition Immulon 2 plates are coated with mouse anti-human IFNγ monoclonal antibody (4 μg/ml 0.1M NaHCO$_3$, pH8.2) overnight at 4° C. The plates are washed with Ca$^{2+}$, Mg$^{2+}$-free PBS/0.05% Tween 20 and blocked with PBS/10% FCS for two hours, after which the CTLs (100 μl/well) and targets (100 μl/well) are added to each well, leaving empty wells for the standards and blanks (which received media only). The target cells, either peptide-pulsed or endogenous targets, are used at a concentration of $1\times10^6$ cells/ml. The plates are incubated for 48 hours at 37° C. with 5% CO$_2$.

Recombinant human IFN-gamma is added to the standard wells starting at 400 pg or 1200 pg/100 microliter/well and the plate incubated for two hours at 37° C. The plates are washed and 100 μl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5–15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, $5\times10^4$ CD8+ cells are added to a T25 flask containing the following: $1\times10^6$ irradiated (4,200 rad) PBMC (autologous or allogeneic) per ml, $2\times10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 μM 2-mercaptoethanol, L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds $1\times10^6$/ml and the cultures are assayed between days 13 and 15 at E:T ratios of 30, 10, 3 and 1:1 in the $^{51}$Cr release assay or at $1\times10^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and $5\times10^4$ CD8$^+$ cells are added to a T25 flask containing the following: $1\times10^6$ autologous PBMC per ml which have been peptide-pulsed with 10 μg/ml peptide for two hours at 37° C. and irradiated (4,200 rad); $2\times10^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 85P1B3. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 13

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analogued to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 500 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate <500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480–3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analogued peptides are additionally tested for the ability to stimulate a recall response using PBMC from patients with 85P1B3-expressing tumors.

Other Analoging Strategies

Another form of peptide analoguing, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and 1. Chen, John Wiley & Sons, England, 1999).

Thus, by the use of single amino acid substitutions, the binding properties and/or cross-reactivity of peptide ligands for HLA supertype molecules can be modulated.

Example 14

Identification and Confirmation of 85P1B3-derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 85P1B3-derived, HLA class II HTL epitopes, the 85P1B3 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160: 3363–3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 85P1B3-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 85P1B3-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 85P1B3 antigens are analyzed for sequences carrying one of the two DR3-specific binding motifs reported by Geluk et al. (*J. Immunol.* 152:5742–5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR3 binding.

Example 15

Immunogenicity of 85P1B3-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 85P1B3-expressing tumors.

Example 16

Calculation of Phenotypic Frequencies of HLA-supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1−(SQRT(1−af)) (see, e.g., Sidney et al., *Human Immunol.* 45:79–93, 1996). To obtain overall phenotypic frequencies, cumulative gene frequencies are calculated, and the cumulative antigen frequencies derived by the use of the inverse formula [$af=1-(1-Cgf)^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%. An analagous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 17

CTL Recognition of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes. are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with 85P1B3 expression vectors.

The results demonstrate that CTL lines obtained from animals primed with peptide epitope recognize endogenously synthesized 85P1B3 antigen. The choice of transgenic mouse model to be used for such an analysis depends upon the epitope(s) that are being evaluated. In addition to HLA-A*0201/K$^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 18

Activity Of CTL-HTL Conjugated Epitopes in Transgenic Mice

This example illustrates the induction of CTLs and HTLs in transgenic mice, by use of a 85P1B3-derived CTL and HTL peptide vaccine compositions. The vaccine composition used herein comprise peptides to be administered to a patient with a 85P1B3-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol.* 159:4753–4761, 1997). For example, A2/K$^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/K$^b$ chimeric gene (e.g., Vitiello et al., *J. Exp. Med.* 173:1007, 1991)

In vitro CTL activation: One week after priming, spleen cells (30×10$^6$ cells/flask) are co-cultured at 37° C. with syngeneic, irradiated (3000 rads), peptide coated lymphoblasts (10×10$^6$ cells/flask) in 10 ml of culture medium/T25 flask. After six days, effector cells are harvested and assayed for cytotoxic activity.

Assay for cytotoxic activity: Target cells (1.0 to 1.5×10$^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, 10$^4$ $^{51}$Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release–spontaneous release)/(maximum release–spontaneous release). To facilitate comparison between separate CTL assays run under the same conditions, % $^{51}$Cr release data is expressed as lytic units/10$^6$ cells. One lytic unit is arbitrarily defined as the number of effector cells required to achieve 30% lysis of 10,000 target cells in a six hour $^{51}$Cr release assay. To obtain specific lytic units/10$^6$, the lytic units/10$^6$ obtained in the absence of peptide is subtracted from the lytic units/10$^6$ obtained in the presence of peptide. For example, if 30% $^{51}$Cr release is obtained at the effector (E): target (T) ratio of 50:1 (i.e., 5×10$^5$ effector cells for 10,000 targets) in the absence of peptide and 5:1 (i.e., 5×10$^4$ effector cells for 10,000 targets) in the presence of peptide, the specific lytic units would be: [(1/50,000)–(1/500,000)]×10$^6$=18 LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity". Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 19

Selection of CTL and HTL Epitopes for Inclusion in an 85P1B3-specific Vaccine This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 85P1B3 clearance. The number of epitopes used depends on observations of patients who spontaneously clear 85P1B3. For example, if it has been observed that patients who spontaneously clear 85P1B3 generate an immune response to at least three (3) from 85P1B3 antigen, then three or four (34) epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site, at URL bimas.dcrt.nih.gov.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 85P1B3, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 85P1B3.

Example 20

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 85P1B3, are selected such that multiple supermotifs/motifs are represented to ensure broad population coverage. Similarly, HLA class II epitopes are selected from 85P1B3 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 μg of each of two oligonucleotides are annealed and extended: In an example using eight oligonucleotides, i.e., four pairs of primers, oligonucleotides 1+2, 3+4, 5+6, and 7+8 are combined in 100 μl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 μg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 21

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683–692, 1996; Demotz et al., *Nature* 342:682–684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567–576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751–761, 1994.

For example, to confirm the capacity of a DNA minigene construct containing at least one HLA-A2 supermotif peptide to induce CTLs in vivo, HLA-A2.1/K$^b$ transgenic mice, for example, are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-A$^b$-restricted mice, for example, are immunized intramuscularly with 100 μg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. *Immunity* 1:751–761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299–S309, 1998) or recombinant vaccinia, for example, expressing a minigene or DNA encoding the complete protein of interest (see, e.g., Hanke et al., *Vaccine* 16:439–445, 1998; Sedegah et al., *Proc. Natl. Acad. Sci USA* 95:7648–53, 1998; Hanke and McMichael, *Immunol. Letters* 66:177–181, 1999; and Robinson et al., *Nature Med.* 5:526–34, 1999).

For example, the efficacy of the DNA minigene used in a prime boost protocol is initially evaluated in transgenic mice. In this example, A2.1/K$^b$ transgenic mice are immunized IM with 100 μg of a DNA minigene encoding the immunogenic peptides including at least one HLA-A2 supermotif-bearing peptide. After an incubation period (ranging from 3–9 weeks), the mice are boosted IP with 10$^7$ pfu/mouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol

Example 22

Peptide Composition for Prophylactic Uses

Vaccine compositions of the present invention can be used to prevent 85P1B3 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 85P1B3-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 μg, generally 100–5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 85P1B3-associated disease.

Alternatively, a composition typically comprising transfecting agents is used for the administration of a nucleic acid-based vaccine in accordance with methodologies known in the art and disclosed herein.

Example 23

Polyepitopic Vaccine Compositions Derived from Native 85P1B3 Sequences

A native 85P1B3 polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes is selected; it can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 85P1B3 antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (excluding an analoged embodiment) directs the immune response to multiple peptide sequences that are actually present in native 85P1B3, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 24

Polyepitopic Vaccine Compositions From Multiple Antigens

The 85P1B3 peptide epitopes of the present invention are used in conjunction with epitopes from other target tumor-associated antigens, to create a vaccine composition that is useful for the prevention or treatment of cancer that expresses 85P1B3 and such other antigens. For example, a vaccine composition can be provided as a single polypeptide that incorporates multiple epitopes from 85P1B3 as well as tumor-associated antigens that are often expressed with a target cancer associated with 85P1B3 expression, or can be administered as a composition comprising a cocktail of one or more discrete epitopes. Alternatively, the vaccine can be administered as a minigene construct or as dendritic cells which have been loaded with the peptide epitopes in vitro.

Example 25

Use of Peptides to Evaluate an Immune Response

Peptides of the invention may be used to analyze an immune response for the presence of specific antibodies, CTL or HTL directed to 85P1B3. Such an analysis can be performed in a manner described by Ogg et al., *Science* 279:2103–2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 85P1B3 HLA-A*0201-specific CTL frequencies from HLA A*0201-positive individuals at different stages of disease or following immunization comprising an 85P1B3 peptide containing an A*0201 motif Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tri-color analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 85P1B3 epitope, and thus the status of exposure to 85P1B3, or exposure to a vaccine that elicits a protective or therapeutic response.

Example 26

Use of Peptide Epitopes to Evaluate Recall Responses

The peptide epitopes of the invention are used as reagents to evaluate T cell responses, such as acute or recall responses, in patients. Such an analysis may be performed on patients who have recovered from 85P1B3-associated disease or who have been vaccinated with an 85P1B3 vaccine.

For example, the class I restricted CTL response of persons who have been vaccinated may be analyzed. The vaccine may be any 85P1B3 vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co. St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128–140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 ul of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with non-diseased control subjects as previously described (Rehermann, et al., Nature Med. 2:1104, 1108, 1996; Rehermann et al., J. Clin. Invest. 97:1655–1665, 1996; and Rehermann et al. J. Clin. Invest. 98:1432–1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. J. Virol. 66:2670–2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 µM, and labeled with 100 µCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20–50:1 on day 14. Percent cytotoxicity is determined from the formula: 100×[(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 85P1B3 or an 85P1B3 vaccine.

Similarly, Class II restricted HTL responses may also be analyzed. Purified PBMC are cultured in a 96-well flat bottom plate at a density of $1.5 \times 10^5$ cells/well and are stimulated with 10 µg/ml synthetic peptide of the invention, whole 85P1B3 antigen. or PHA. Cells are routinely plated in replicates of 4–6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 27

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 28

Phase II Trials in Patients Expressing 85P1B3

Phase II trials are performed to study the effect of administering the CTL-HTL peptide compositions to patients having cancer that expresses 85P1B3. The main objectives of the trial are to determine an effective dose and regimen for inducing CTLs in cancer patients that express 85P1B3, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21–65 and represent diverse ethnic backgrounds. All of them have a tumor that expresses 85P1B3.

Clinical manifestations or antigen-specific T-cell responses are monitored to assess the effects of administering the peptide compositions. The vaccine composition is found to be both safe and efficacious in the treatment of 85P1B3-associated disease.

Example 29

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of 'Minigene' Multi-Epitope DNA Plasmids" in the form of naked nucleic acid administered IM (or SC or ID) in the amounts of 0.5–5 mg at multiple sites. The nucleic acid (0.1 to 1000 µg) can also be administered using a gene gun. Following an incubation period of 34 weeks, a booster dose is then administered. The booster can be recombinant fowlpox virus administered at a dose of $5-10^7$ to $5\times10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 85P1B3 is generated.

Example 30

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 85P1B3 protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although $2-50\times10^6$ DC per patient are typically administered, larger number of DC, such as $10^7$ or $10^8$ can also be provided. Such cell populations typically contain between 50–90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5\times10^6$ DC, then the patient will be injected with a total of $2.5\times10^8$ peptide-loaded PBMC. The percent DC mobilized by an agent such as Progenipoietin™ is typically estimated to be between 2–10%, but can vary as appreciated by one of skill in the art.

Ex vivo Activation of CTL/HTL Responses

Alternatively, ex vivo CTL or HTL responses to 85P1B3 antigens can be induced by incubating, in tissue culture, the patient's, or genetically compatible, CTL or HTL precursor cells together with a source of APC, such as DC, and immunogenic peptides. After an appropriate incubation time (typically about 7–28 days), in which the precursor cells are activated and expanded into effector cells, the cells are infused into the patient, where they will destroy (CTL) or facilitate destruction (HTL) of their specific target cells, i.e., tumor cells.

Example 31

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 85P1B3. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 85P1B3 to isolate peptides corresponding to 85P1B3 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 32

Complementary Polynucleotides

Sequences complementary to the 85P1B3-encoding sequences, or any parts thereof, are used to detect, decrease, or inhibit expression of naturally occurring 85P1B3. Although use of oligonucleotides comprising from about 15 to 30 base pairs is described, essentially the same procedure is used with smaller or with larger sequence fragments. Appropriate oligonucleotides are designed using. e.g., OLIGO 4.06 software (National Biosciences) and the coding sequence of 85P1B3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the 85P1B3-encoding transcript.

Example 33

Purification of Naturally-occurring or Recombinant 85P1B3 Using 85P1B3 Specific Antibodies Naturally occurring or recombinant 85P1B3 is substantially purified by immunoaffinity chromatography using antibodies specific for 85P1B3. An immunoaffinity column is constructed by covalently coupling anti-85P1B3 antibody to an activated chromatographic resin, such as CNBr-activated SEPHAROSE (Amersham Pharmacia Biotech). After the coupling, the resin is blocked and washed according to the manufacturer's instructions.

Media containing 85P1B3 are passed over the immunoaffinity column, and the column is washed under conditions that allow the preferential absorbance of 85P1B3 (e.g., high ionic strength buffers in the presence of detergent). The column is eluted under conditions that disrupt antibody/85P1B3 binding (e.g., a buffer of pH 2 to pH 3, or a high concentration of a chaotrope, such as urea or thiocyanate ion), and GCR.P is collected.

Example 34

Identification of Molecules Which Interact with 85P1B3

85P1B3, or biologically active fragments thereof, are labeled with 121 1 Bolton-Hunter reagent.

(See, e.g., Bolton et al. (1973) Biochem. J. 133:529.) Candidate molecules previously arrayed in the wells of a multi-well plate are incubated with the labeled 85P1B3, washed, and any wells with labeled 85P1B3 complex are assayed. Data obtained using different concentrations of 85P1B3 are used to calculate values for the number, affinity, and association of 85P1B3 with the candidate molecules. Throughout this application, various website data content, publications, applications and patents are referenced. (Websites are referenced by their Uniform Resource Locator, or URL, addresses on the World Wide Web.) The disclosures of each of these items of information are hereby incorporated by reference herein in their entireties.

Example 35

In Vivo Assay for 85P1B3 Tumor Growth Promotion

The effect of the 85P1B3 protein on tumor cell growth can be confirmed in vivo by gene overexpression in a variety of cancer cells, including prostate, kidney and bladder. For example, SCID mice can be injected SQ on each flank with $1 \times 10^6$ prostate, kidney or bladder cancer cells (such as PC3, LNCaP, SCaBER, UM-UC-3, HT1376, RT4, T24, Caki, A-498 and SW839 cells) containing tkNeo empty vector or 85P1B3.

At least two strategies may be used: (1) Constitutive 85P1B3 expression under regulation of a promoter such as a constitutive promoter obtained from the genomes of viruses such as polyoma virus, fowlpox virus (UK 2,211,504 published 5 Jul. 1989), adenovirus (such as Adenoviris 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems. (2) Regulated expression under control of an inducible vector system, such as ecdysone, tet, etc., can be used provided such promoters are compatible with the host cell systems. Tumor volume is then monitored at the appearance of palpable tumors and is followed over time to validate that 85P1B3-expressing cells grow at a faster rate and that tumors produced by 85P1B3-expressing cells demonstrate characteristics of altered aggressiveness (e.g. enhanced metastasis, vascularization, reduced responsiveness to chemotherapeutic drugs). Additionally, mice can be implanted with the same cells orthotopically in the prostate, bladder or kidney to determine if 85P1B3 has an effect on local growth in the prostate, bladder or kidney or on the ability of the cells to metastasize, specifically to lungs or lymph nodes (Fu, X., et al., Int. J. Cancer, 1991. 49: p. 938–939; Chang, S., et al., Anticancer Res., 1997. 17: p. 3239–3242; Peralta, E. A., et al., J. Urol., 1999. 162: p. 1806–1811).

Furthermore, this assay is useful to confirm the 85P1B3 inhibitory effect of candidate therapeutic compositions, such as for example, 85P1B3 antibodies or intrabodies, and 85P1B3 antisense molecules or ribozymes.

Example 36

85P1B3 Monoclonal Antibody-Mediated Inhibition of Tumors In Vivo

The significant expression of 85P1B3 in cancer tissues, together with its restricted expression in normal tissues, makes 85P1B3 an excellent target for antibody therapy. In cases where the monoclonal antibody target is a cell surface protein, antibodies have been shown to be efficacious at inhibiting tumor growth (See, e.g., (Saffran, D., et al., PNAS 10:1073–1078). In cases where the target is not on the cell surface, such as PSA and PAP in prostate cancer, antibodies have also been shown to recognize and inhibit growth of cells expressing those proteins (Saffran, D. C., et al., Cancer and Metastasis Reviews, 1999. 18: p. 437–449). As with any cellular protein with a restricted expression profile, 85P1B3 is a target for T cell-based immunotherapy.

Accordingly, the therapeutic efficacy of anti-85P1B3 mAbs in human colon, kidney, bladder and prostate cancer mouse models is modeled in 85P1B3-expressing kidney, bladder or prostate cancer xenografts or cancer cell lines, such as those described in the Example entitled "In Vivo Assay for 85P1B3 Tumor Growth Promotion", that have been engineered to express 85P1B3.

Antibody efficacy on tumor growth and metastasis formation is confirmed, e.g., in a mouse orthotopic in the prostate, colon, bladder or kidney cancer xenograft model. The antibodies can be unconjugated, or can be conjugated to a therapeutic modality, as appreciated in the art. It is confirmed that anti-85P1B3 mAbs inhibit formation of 85P1B3-expressing kidney, bladder and prostate tumors. Anti-85P1B3 mAbs also retard the growth of established orthotopic tumors and prolong survival of tumor-bearing mice. These results indicate the utility of anti-85P1B3 mAbs in the treatment of local and advanced stages of cancer. (See, e.g., Saffran, D., et al., PNAS 10:1073–1078.)

Administration of anti-85P1B3 mAbs retard established orthotopic tumor growth and inhibit metastasis to distant sites, resulting in a significant prolongation in the survival of tumor-bearing mice. These studies indicate that 85P1B3 is an attractive target for immunotherapy and demonstrate the therapeutic potential of anti-85P1B3 mAbs for the treatment of local and metastatic kidney, colon, bladder and prostate cancer.

This example demonstrates that unconjugated 85P1B3 monoclonal antibodies effectively to inhibit the growth of human bladder tumors grown in SCID mice; accordingly a combination of such efficacious monoclonal antibodies is also effective.

Example 37

Induction of a Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 38

Splice Variants of 85P1B3

Splice variants are also called alternative transcripts. When a gene is transcribed from genomic DNA, the initial RNA is generally spliced to produce functional mRNA, which has only exons and is used for translation into an amino acid sequence. Accordingly, a given gene can have zero to many alternatively spliced mRNA products. Alternative transcripts each have a unique exon makeup, and can have different coding and/or non-coding (5' or 3' end) portions, from the original transcript. Alternative transcripts can code for similar proteins with the same or a similar function or may encode proteins with different functions, and may be expressed in the same tissue at the same time, or at different tissue at different times, proteins encoded by alternative transcripts can have similar or different cellular or extracellular localizations, e.g., be secreted.

Splice variants are identified by a variety of art-accepted methods. For example, splice variants are identified by use of EST data. First, all human ESTs were grouped into clusters which show direct or indirect identity with each other. Second, ESTs in the same cluster were further grouped into sub-clusters and assembled into a consensus sequence. The starting gene is compared to the consensus sequence(s). Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs are available in the art that identify splice variants based on genomic sequences. Genomic-based variant identification programs include FgenesH (A. Salamov and V. Solovyev, "Ab initio gene finding in *Drosophila* genomic DNA," Genome Research. 2000 April; 10(4):516–22); Grail and GenScan. For a general discussion of spice variant identification protocols see, e.g., Southan C., "A genomic perspective on human proteases," FEBS Lett. 2001 Jun. 8; 498(2–3):214–8; de Souza S J, et al., "Identification of human chromosome 22 transcribed sequences with ORF expressed sequence tags," Proc. Natl Acad Sci USA. 2000 Nov. 7; 97(23):12690–3.

For variants identified by the EST-based method, Table XXI shows the nucleotide sequences of the splice variants. Figure Table XXII shows the alignment of the splice variant with the 85P1B3 nucleic acid sequence. Table XXIII displays the single longest alignment of an amino acid sequence encoded by a splice variant, out of all six potential reading frames with 85P1B3. Thus, for each splice variant, a variant's reading frame that encodes the longest single contiguous peptide homology between 85P1B3 and the variant is the proper reading frame orientation for the variant. Due to the possibility of sequencing errors in EST or genomic data, other peptides in the relevant reading frame orientation (5' to 3' or 3' to 5') can also be encoded by the variant. Table XXIV lays out all three frame shifted amino acid translations of the splice variant for the identified reading frame orientation.

For variants identified by any one of the genomic sequence-based methods, Table XXI shows the nucleotide sequences of the splice variant. Figure Table XXII shows the alignment of the splice variant with the 85P1B3 nucleic acid sequence. Table XXIII displays the alignment of amino acid sequence of the predicted transcripts with 85P1B3. The genomic-based computer programs predict a transcript from genomic sequence, and not only predict exons but also set open reading frame as the first forward open reading frame. The predicted transcript does not contain 5' or 3' untranslated region (UTR). It starts with ATG and ends with a stop codon, TAG, TGA or TAA. In case the transcript is predicted on the reverse strand of the genomic sequence, the sequence of the transcript is reverse-complemented to the genomic sequence of the exons. Thus, the genomic-based programs provide the correct transcript sequence, with 5' to 3' orientation and +1 as the open reading frame. However, due to the possibility of inaccurate prediction of exons or the possibility of sequencing errors in genomic data, other peptides in other forward open reading frame can also be encoded by the variant. Table XXIV lays out all amino acid translations of the splice variant in each of the three forward reading frames.

To further confirm the parameters of a splice variant, a variety of techniques are available in the art, such as proteomic validation, PCR-based validation, and 5' RACE validation, etc. (see e.g., Proteomic Validation: Brennan S O, Fellowes A P, George P M.; "Albumin banks peninsula: a new termination variant characterised by electrospray mass spectrometry." Biochim Biophys Acta. 1999 μg. 17; 1433 (1–2):321–6; Ferranti P, et al., "Differential splicing of pre-messenger RNA produces multiple forms of mature caprine alpha(s1)-casein." Eur J. Biochem. 1997 Oct. 1; 249(1):1–7; PCR-based Validation: Wellmann S, et al., "Specific reverse transcription-PCR quantification of vascular endothelial growth factor (VEGF) splice variants by LightCycler technology." Clin Chem. 2001 April; 47(4): 654–60; Jia H P, et al., Discovery of new human beta-defensins using a genomics-based approach," Gene. 2001 Jan. 24; 263(1–2):211–8; PCR-based and 5' RACE Validation: Brigle K E, et al., "Organization of the murine reduced folate carrier gene and identification of variant splice forms," Biochim Biophys Acta. 1997 μg. 7; 1353(2): 191–8.

It is known in the art that genomic regions are upregulated in cancers. When the genomic region to which 85P1B3 maps is upregulated in a particular cancer, the splice variants of 85P1B3 are upregulated as well. Disclosed herein is that 85P1B3 has a particular expression profile. Splice variants of 85P1B3 that are structurally and/or functionally similar to 85P1B3 share this expression pattern, thus serving as tumor-associated markers/antigens.

Using the EST assembly approach, we identified one splice variants designated splice variant 1.

TABLE XXIA

Nucleotide sequence of splice variant 1. (SEQ ID NO: 701)

```
  1 TTTTTTTTTT CCTATCTAGC TATCTCTTAA AAACAAAAGC CATAGTAAAT GCATCAGAGA

61 TGGATATTCA AAATGTTCCT CTATCAGAAA AGATTGCAGA GGTAAAATTT CATGATGGTT

121 GTATGCTTTT TTAAAATACA GACAACTCTT GATAACTTCT ACCAATGAAC TTGGGCATGA

181 TGAAATGGCA TGATGCTCAA TAATCCTTTT TACTTGATTT GACCTTCCCT ATTGAATTTG

241 TAATGAAAAA CAAAATACTA AAACCACACT GTAAGGTATA GTTCAGGAAG AAAGGAAAAG

301 CTGCTCAACT GCTGCACTCC TGCATTCTCC TTTGTGCTGG GAATGGATAT CATCATCTTG

361 CCATAGAGGT GTCTTCTTTG CAAATACCTT GTAATTGCTC AACTGTCTCA GACATAAGAG

421 TGATGAAACA GTTATTAAGA ATTCCTGGCC GGGCGTGGTG GCTCACGCCT GTAATCCCAG

481 CACTTTGGCC TCGTGC
```

TABLE XXIIA

Nucleotide sequence alignment of 85P1B3 with splice variant 1.

Score = 160 bits (83), Expect = 3e-36
Identities = 83/83 (100%)
Strand = Plus/Plus

```
85P1B3:   524
          gctatctcttaaaaacaaaagccatagtaaatgcatcagagatggatattcaaaatgttc   583
          ||||||||||||||||||||||||||||||||||||||||||||||||||||||||||||
          gctatctcttaaaaacaaaagccatagtaaatgcatcagagatggatattcaaaatgttc    78
Vrnt 1:    19

85P1B3:   584    ctctatcagaaaagattgcagag  606  (SEQ ID NO: 702)
                 |||||||||||||||||||||||
Vrnt 1:    79    ctctatcagaaaagattgcagag  101  (SEQ ID NO: 703)
```

TABLE XXIIIA

Amino acid sequence alignment of 85P1B3 and splice variant 1.

Score = 64.8 bits (135), Expect = 2e-08
Identities = 28/29 (96%)
Frame = +1/+3

```
85P1B3:   526   YLLKTKAIVNASEMDIQNVPLSEKIAELK   612
                YLLKTKAIVNASEMDIQNVPLSEKIAE+K
                (SEQ ID NO:704)
Vrnt 1:    21   YLLKTKAIVNASEMDIQNVPLSEKIAEVK   107
                (SEQ ID NO:707)
```

TABLE XXIVA

Peptide sequences from the translation of the nucleotide sequence of splice variant 1.

| Open reading frame | Amino acid sequences |
| --- | --- |
| Frame 1 (SEQ ID NO:705) | FFFSYLAIS*KQKP**MHQRWIFKMFLYQKRLQR*NFMMVVCFFKIQTTLDNFYQ*TWG* *NGMMLNNPFYLI*PSLLNL**KTKY*NHTVRYSSGRKEKLLNCCTPAFSFVLGMDIIIL P*RCLLCKYLVIAQLSQT*E**NSY*EFLAGRGGSRL*SQHFGLV |
| Frame 2 (SEQ ID NO:706) | FFFPI*LSLKNKSHSKCIRDGYSKCSSIRKDCRGKIS*WLYAFLKYRQLLITSTNELGDD EMA*CSIILFT*FDLPY*ICNEKQNTKTTL*GIVQEERKSCSTAALLHSPLCWEWISSSC HRGVFFANTL*LLNCLRHKSDETVIKNSWPGVVAHACNPSTLASC |
| Frame 3 (SEQ ID NO:707) | FFFLSSYLLKTKAIVNASEMDIQNVPLSEKIAEVKFHDGCMLF*NTDNS**LLPMNLGMM KWHDAQ*SFLLDLTFPIEFVMKNKILKPHCKV*FRKKGKAAQLLHSCILLCAGNGYHHLA IEVSSLQIPCNCSTVSDIRVMKQLLRIPGRAWWLTPVIPALWPR |

Note:
Frame 3 gives the longest subsequence that is identical with 85P1B3 amino acid sequence. In this Table each (*)indicates the product of a single codon, i.e., a single unknown amino acid or a stop codon.

Example 39

Expression Analysis of 85P1B3 Splice Variants in Normal Tissues and Patient Tumor Specimens Expression of 85P1B3 described in Example 4 was performed using the 85P1B3 SSH sequence as a probe. This nucleic acid sequence spans region 701–1019 of the 85P1B3 gene, a region absent in the 85P1B3 splice variant 1 (FIG. 19). Therefore, the Northern blots described in FIG. 11, FIG. 12, FIG. 13, FIG. 14, FIG. 15, FIG. 16, FIG. 17, and FIG. 18 detected the transcript of 85P1B3 but not of splice variant 1.

A probe comprising region of homology between 85P1B3 and its splice variant 1 is generated (Probe 1). This region spans nucleotide positions 524–606 of 85P1B3 and 19–101 of splice variant 1. Normal tissue northern blots and patient cancer northern blots are probed with probe 1. The results have two bands, and show expression of the 1.2 kb transcript of 85P1B3 and the transcript of its splice variant 1.

In another study, a probe comprising a region present in the ORF of the splice variant but not in the ORF of 85P1B3 is generated (Probe 2). This region spans nucleotide positions 102496 of the splice variant 1. Normal tissue northern blots and patient cancer Northern blots are probed with probe 2. The results have single bands, and show expression of splice variant 1 but not the transcript of 85P1B3.

When 85P1B3 splice variant 1 is expressed in patient cancer specimens, and shows restricted expression in normal tissues, 85P1B3 splice variant 1 is a suitable cancer target for cancer diagnosis and therapy.

Example 40

Splice Variant Protein Characteristics

The present variant protein is understood to be partial, and thus to comprise domains of the full protein. Amino acids 7–35 of the 85P1B3 variant 1 protein align with amino acids 172–200 of 85P1B3 with 96% identity, while the remaining downstream amino acids diverge from the 85P1B3. This pattern of high homology to one section of the parent protein coupled to a high divergence from the remaining portions of the parent protein form the hallmark of a splice variant.

Protein blast analysis of variant 1 shows that the 85P1B3 variant is homologous to OIP5, a human protein known to be involved in adhesion and invasion of epithelial cells (Brooks G F et al, Mol Microbiol. 1991, 5:3063; Weel J F et al, J Exp Med. 1991, 173:1395), with 96% identity over 28 amino acids. Analysis by pFam or prosite failed to identify any motifs. However motif homology was observed to Glyoxalase 1 at aa 114–153 of the variant protein. Glyoxalase is a glutathione-mediating detoxifying enzyme, that protects cells from advanced glycation endproducts (AGEs) (Thornalley P J. Chem Biol Interact. 1998, 111: 137). Glyoxalase is highly expressed in breast cancer cells (Rulli A et al, Breast Cancer Res Treat. 2001, 66:67).

Regarding localization, the 85P1B3 variant localizes to the cytoplasm (cytoplasmic 60.9% PSORT II) or the mitochondria (mitochondrial 0.519, PSORT).

Based on bioinformatic analysis (TMPred, Sosui) the 85P1B3 variant does not appear to contain transmembrane domains, but forms a soluble intracellular protein. Due to its homology to OIP5 and Glyoxalase 1, 85P1B3 is involved in the adhesion and invasion of epithelial cells, and has a cancer-related expression pattern.

Example 41

Homology Comparison of 85P1B3 to Known Sequences

The 85P1B3 protein of FIG. 3 has 229 amino acids with calculated molecular weight of 24.69 kDa, and pI of 7.02. 85P1B3 is predicted to be a mitochondrial (60.9%) or cytoplasmic (21.7) protein.

85P1B3 shows best homology to human Opa interacting protein 5 (gi 2815610) sharing 100% identity with that protein. Opacity associated proteins (Opa) were identified in Neisseria gonorrhoeae as outer membrane proteins that are involved in mediating the adhesion of Neisseria to mammalian cells and the invasion of human epithelial cells (Brooks G F et al, Mol Microbiol. 1991, 5:3063; Weel I F et al, J Exp Med. 1991, 173:1395). OPA proteins bind to membrane proteins, such as CD66 and carcinoembryonic antigen related cellular molecule (CEACAM), on the surface of human epithelial and mononuclear cells, thereby facilitating entry of Neisseria into mammalian host cells (Muenzner P et al, J. Biol. Chem. 2001, 276:24331; Chen T et al, J. Exp. Med. 1997, 185:1557). In order to delineate the role of Opa in adherence and invasion of human cells, Williams et al used a two yeast hybrid system to identify Opa interacting proteins (Williams J M et al, Mol. Microbiol. 1998, 27:171). Screening a human cDNA library for Opa interacting partners, they identified Opa interacting protein 5 or OIP5. OIP5 is an intracellular, cytoplasmic protein with homology to thyroid hormone receptor interacting protein-6 (TRIP6) (Williams J M & Rest R F. Ann N Y Acad. Sci. 1996, 797:288). TRIP6 is an intracellular signaling molecule that relays information to the nucleus thereby regulating gene expression (Zhao M et al, Gene Expr. 1999, 207; Wang Y et al, Gene. 1999, 234:403).

This information indicates that 85P1B3 can play a role in the adhesion and invasion of epithelial cells into adjacent tissues and basement membranes, and regulate transcription by transmitting cell surface signals to the nucleus.

Accordingly, when 85P1B3 functions as a regulator of cell adhesion and invasion, or as a modulator of transcription involved in activating genes associated with tumorigenesis or in blocking expression of genes that repress tumorigenesis, 85P1B3 is used for therapeutic, diagnostic, prognostic and/or preventative purposes.

Example 42

Identification and Confirmation of Potential Signal Transduction Pathways

Many mammalian proteins have been reported to interact with signaling molecules and to participate in regulating signaling pathways. (J. Neurochem. 2001; 76:217–223). In particular, OPA has been reported to associate with a phosphatase and surface receptors (Hauck C et al, Infect. Immun. 1999, 67:5490; Muenzner P et al, J. Biol. Chem. 2001, 276:24331). Using immunoprecipitation and Western blotting techniques, proteins are identified that associate with 85P1B3 and mediate signaling events. Several pathways known to play a role in cancer biology can be regulated by 85P1B3, including phospholipid pathways such as P13K, AKT, etc, adhesion and migration pathways, including FAK, Rho, Rac-1, etc, as well as mitogenic/survival cascades such as ERK, p38, etc (Cell Growth Differ. 2000, 11:279; J Biol. Chem. 1999, 274:801; Oncogene. 2000, 19:3003, J. Cell Biol. 1997, 138:913.).

Using, e.g., Western blotting techniques the ability of 85P1B3 to regulate these pathways is confirmed. Cells expressing or lacking 85P1B3 are either left untreated or stimulated with cytokines, androgen and anti-integrin antibodies. Cell lysates are analyzed using anti-phospho-specific antibodies (Cell Signaling, Santa Cruz Biotechnology) in order to detect phosphorylation and regulation of ERK, p38, AKT, P13K, PLC and other signaling molecules. When 85P1B3 plays a role in the regulation of signaling pathways, whether individually or communally, it is used as a target for diagnostic, prognostic, preventative and/or therapeutic purposes.

To confirm that 85P1B3 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 85P1B3 are mapped and used for the identification and validation of therapeutic targets. When 85P1B3 is involved in cell signaling, it is used as target for diagnostic, prognostic, preventative and/or therapeutic purposes.

Example 43

Involvement in Tumor Progression

The 85P1B3 gene can contribute to the growth of cancer cells. The role of 85P1B3 in tumor growth is confirmed in a variety of primary and transfected cell lines including prostate, colon, bladder and kidney cell lines, as well as NIH 3T3 cells engineered to stably express 85P1B3. Parental cells lacking 85P1B3 and cells expressing 85P1B3 are evaluated for cell growth using a well-documented proliferation assay (Fraser S P, Grimes J A, Djamgoz M B. Prostate. 2000; 44:61, Johnson D E, Ochieng 1, Evans S L. Anticancer Drugs. 1996, 7:288).

To confirm the role of 85P1B3 in the transformation process, its effect in colony forming assays is investigated. Parental NIH3T3 cells lacking 85P1B3 are compared to NHI-3T3 cells expressing 85P1B3 using a soft agar assay under stringent and more permissive conditions (Song Z. et al. Cancer Res. 2000; 60:6730).

To confirm the role of 85P1B3 in invasion and metastasis of cancer cells, a well-established assay is used, e.g., a Transwell Insert System assay (Becton Dickinson) (Cancer Res. 1999; 59:6010). Control cells, including prostate, colon, bladder and kidney cell lines lacking 85P1B3 are compared to cells expressing 85P1B3. Cells are loaded with the fluorescent dye, calcein, and plated in the top well of the Transwell insert coated with a basement membrane analog. Invasion is determined by fluorescence of cells in the lower chamber relative to the fluorescence of the entire cell population.

85P1B3 can also play a role in cell cycle and apoptosis. Parental cells and cells expressing 85P1B3 are compared for differences in cell cycle regulation using a well-established BrdU assay (Abdel-Malek Z A. J Cell Physiol. 1988, 136:247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 85P1B3, including normal and tumor prostate, colon and lung cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death by 85P1B3 can play a critical role in regulating tumor progression and tumor load.

When 85P1B3 plays a role in cell growth, transformation, invasion or apoptosis, it is used as a target for diagnostic, prognostic, preventative and/or therapeutic purposes.

Example 44

Involvement in Angiogenesis

Angiogenesis or new capillary blood vessel formation is necessary for tumor growth (Hanahan D, Folkman J. Cell. 1996, 86:353; Folkman J. Endocrinology. 1998 139:441). Several assays have been developed to measure angiogenesis in vitro and in vivo, such as the tissue culture assays endothelial cell tube formation and endothelial cell proliferation. Using these assays as well as in vitro neo-vascularization, the role of 85P1B3 in angiogenesis, enhancement or inhibition, is confirmed.

For example, endothelial cells engineered to express 85P1B3 are evaluated using tube formation and proliferation assays. The effect of 85P1B3 is also confirmed in animal models in vivo. For example, cells either expressing or lacking 85P1B3 are implanted subcutaneously in immunocompromised mice. Endothelial cell migration and angiogenesis are evaluated 5–15 days later using immunohistochemistry techniques. When 85P1B3 affects angiogenesis, it is used as a target for diagnostic, prognostic, preventative and/or therapeutic purposes.

Example 45

Regulation of Transcription

The cytoplasmic localization of 85P1B3 and its similarity to TRIP5 support the use in accordance with the present invention of 85P1B3 as a modulator of the transcriptional regulation of eukaryotic genes. Regulation of gene expression is confirmed, e.g., by studying gene expression in cells expressing or lacking 85P1B3. For this purpose, two types of experiments are performed.

In the first set of experiments, RNA from parental and 85P1B3-expressing cells are extracted and hybridized to commercially available gene arrays (Clontech) (Smid-Koopman E et al. Br J Cancer. 2000. 83:246). Resting cells as well as cells treated with FBS or androgen are compared. Differentially expressed genes are identified in accordance with procedures known in the art. The differentially expressed genes are then mapped to biological pathways (Chen K et al. Thyroid. 2001. 11:41.).

In the second set of experiments, specific transcriptional pathway activation is evaluated using commercially available (Stratagene) luciferase reporter constructs including: NFkB-luc, SRE-luc, ELKI-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

When 85P1B3 plays a role in gene regulation, it is used as a target for diagnostic, prognostic, preventative and/or therapeutic purposes.

Example 46

Involvement in Cell Adhesion

Cell adhesion plays a critical role in tissue colonization and metastasis. 85P1B3 can participate in cellular organization, and as a consequence cell adhesion and motility. This is supported by the presence of an RGD motif in the N-terminal portion of 85P1B3 (see Table XIX). To confirm that 85P1B3 regulates cell adhesion, control cells lacking 85P1B3 are compared to cells expressing 85P1B3, using techniques previously described (see, e.g., Haier et al, Br. J. Cancer. 1999, 80:1867; Lehr and Pienta, J. Natl. Cancer Inst. 1998, 90:118). Briefly, in one embodiment, cells labeled with a fluorescent indicator, such as calcein, are incubated on tissue culture wells coated with media alone or with matrix proteins. Adherent cells are detected by fluorimetric analysis and percent adhesion is calculated. In another embodiment, cells lacking or expressing 85P1B3 are analyzed for their ability to mediate cell—cell adhesion using similar experimental techniques as described above. Both of these experimental systems are used to identify proteins, antibodies and/or small molecules that modulate cell adhesion to extracellular matrix and cell—cell interaction. Since cell adhesion plays a critical role in tumor growth, progression, and, colonization, when 85P1B3 is involved in these processes it serves as a diagnostic, prognostic, preventative and/or therapeutic modality.

Example 47

Protein—Protein Association

Two proteins with homology to 85P1B3, namely OIP5 and TRIP6, have been shown to interact with other proteins, thereby regulating signal transduction, gene transcription, and cell adhesion. Using immunoprecipitation techniques as well as two yeast hybrid systems, proteins are identified that associate with 85P1B3. Immunoprecipitates from cells expressing 85P1B3 and cells lacking 85P1B3 are compared for specific protein—protein associations.

Studies are performed to confirm the extent of association of 85P1B with effector molecules, such as receptors, adaptor proteins and SH2-containing proteins. Studies comparing 85P1B3 positive and 85P1B3 negative cells as well as studies comparing unstimulated/resting cells and cells treated with epithelial cell activators, such as cytokines, growth factors, androgen and anti-integrin Ab reveal unique interactions.

In addition, protein—protein interactions are confirmed using two yeast hybrid methodology (Curr Opin Chem Biol. 1999, 3:64). A vector carrying a library of proteins fused to the activation domain of a transcription factor is introduced into yeast expressing a 85P1B3-DNA-binding domain fusion protein and a reporter construct. Protein-protein interaction is detected by colorimetric reporter activity. Specific association with effector molecules and transcription factors directs one of skill to the mode of action of 85P1B3, and thus identifies therapeutic, prognostic, preventative and/or diagnostic targets for cancer. This and similar assays are also used to identify and screen for small molecules that interact with 85P1B3.

When 85P1B3 associates with proteins or small molecules it is used as a target for diagnostic, prognostic, preventative and/or therapeutic purposes.

Throughout this application, various website data content, publications, patent applications and patents are referenced. The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues that Express 85P1B3 When Malignant

Prostate
Bladder
Kidney
Colon
Lung
Ovary
Breast
Stomach
Uterus
Cervix

TABLE II

AMINO ACID ABBREVIATIONS

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

AMINO ACID SUBSTITUTION MATRIX

Adapted from the GCG Software 9.0 BLOSUM62 amino acid substitution matrix (block substitution matrix). The higher the value, the more likely a substitution is found in related, natural proteins.
(See URL www.ikp.unibe.ch/manual/blosum62.html)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|   | 9 | −3 | −4 | −2 | −3 | −3 | −1 | −3 | −1 | −1 | −3 | −3 | −3 | −3 | −1 | −1 | −1 | −2 | −2 | C |
|   |   | 6 | 2 | −3 | −1 | −1 | −3 | −1 | −4 | −3 | 1 | −1 | 0 | −2 | 0 | −1 | −3 | −4 | −3 | D |
|   |   |   | 5 | −3 | −2 | 0 | −3 | 1 | −3 | −2 | 0 | −1 | 2 | 0 | 0 | −1 | −2 | −3 | −2 | E |
|   |   |   |   | 6 | −3 | −1 | 0 | −3 | 0 | 0 | −3 | −4 | −3 | −3 | −2 | −2 | −1 | 1 | 3 | F |
|   |   |   |   |   | 6 | −2 | −4 | −2 | −4 | −3 | 0 | −2 | −2 | −2 | 0 | −2 | −3 | −2 | −3 | G |

TABLE III-continued

AMINO ACID SUBSTITUTION MATRIX

Adapted from the GCG Software 9.0 BLOSUM62 amino acid substitution matrix (block substitution matrix). The higher the value, the more likely a substitution is found in related, natural proteins.
(See URL www.ikp.unibe.ch/manual/blosum62.html)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| | | | | | | 8 | −3 | −1 | −3 | −2 | 1 | −2 | 0 | 0 | −1 | −2 | −3 | −2 | 2 | H |
| | | | | | | | 4 | −3 | 2 | 1 | −3 | −3 | −3 | −3 | −2 | −1 | 3 | −3 | −1 | I |
| | | | | | | | | 5 | −2 | −1 | 0 | −1 | 1 | 2 | 0 | −1 | −2 | −3 | −2 | K |
| | | | | | | | | | 4 | 2 | −3 | −3 | −2 | −2 | −2 | −1 | 1 | −2 | −1 | L |
| | | | | | | | | | | 5 | −2 | −2 | 0 | −1 | −1 | −1 | 1 | −1 | −1 | M |
| | | | | | | | | | | | 6 | −2 | 0 | 0 | 1 | 0 | −3 | −4 | −2 | N |
| | | | | | | | | | | | | 7 | −1 | −2 | −1 | −1 | −2 | −4 | −3 | P |
| | | | | | | | | | | | | | 5 | 1 | 0 | −1 | −2 | −2 | −1 | Q |
| | | | | | | | | | | | | | | 5 | −1 | −1 | −3 | −3 | −2 | R |
| | | | | | | | | | | | | | | | 4 | 1 | −2 | −3 | −2 | S |
| | | | | | | | | | | | | | | | | 5 | 0 | −2 | −2 | T |
| | | | | | | | | | | | | | | | | | 4 | −3 | −1 | V |
| | | | | | | | | | | | | | | | | | | 11 | 2 | W |
| | | | | | | | | | | | | | | | | | | | 7 | Y |

TABLE IV A

| SUPERMOTIFS | POSITION 2 (Primary Anchor) | POSITION 3 (Primary Anchor) | POSITION C Terminus (Primary Anchor) |
|---|---|---|---|
| A1 | TI*LVMS* (SEQ ID NO:748) | | FWY |
| A2 | LIVM*ATQ* (SEQ ID NO:749) | | IV*MATL* (SEQ ID NO:750) |
| A3 | VSMA*TLI* (SEQ ID NO:751) | | RK |
| A24 | YF*WIVLMT* (SEQ ID NO:752) | | FI*YWLM* (SEQ ID NO:753) |
| B7 | P | | VILF*MWYA* (SEQ ID NO:754) |
| B27 | RHK | | FYL*WMIVA* (SEQ ID NO:755) |
| B44 | E*D* | | FWYLIMVA (SEQ ID NO:756) |
| B58 | ATS | | FWY*LIVMA* (SEQ ID NO:757) |
| B62 | QL*IVMP* (SEQ ID NO:758) | | FWYMIVLA (SEQ ID NO:759) |
| MOTIFS | | | |
| A1 | TSM | | Y |
| A1 | DE*AS* (SEQ ID NO:806) | | Y |
| A2.1 | LM*VQIAT* (SEQ ID NO:760) | | V*LIMAT* (SEQ ID NO:761) |
| A3 | LMVISATF*CGD* (SEQ ID NO:762) | | KYR*HFA* (SEQ ID NO:763) |
| A11 | VTMLISAGN*CDF* (SEQ ID NO:764) | | KR*YH* (SEQ ID NO:765) |
| A24 | YFW*M* (SEQ ID NO:766) | | FLIW (SEQ ID NO:767) |
| A*3101 | MVT*ALIS* (SEQ ID NO:768) | | R*K* |
| A*3301 | MVALF*IST* (SEQ ID NO:769) | | RK |
| A*6801 | AVT*MSLI* (SEQ ID NO:770) | | RK |
| B*0702 | P | | LMF*WYAIV* (SEQ ID NO:771) |
| B*3501 | P | | LMFWY*IVA* (SEQ ID NO:772) |
| B51 | P | | LIVF*WYAM* (SEQ ID NO:773) |

TABLE IV A-continued

| SUPERMOTIFS | POSITION 2 (Primary Anchor) | POSITION 3 (Primary Anchor) | POSITION C Terminus (Primary Anchor) |
|---|---|---|---|
| B*5301 | P | | IMFWY_ALV_ (SEQ ID NO:774) |
| B*5401 | P | | ATIV_LMFWY_ (SEQ ID NO:748) |

Bolded residues are preferred, italicized residues are less preferred: A peptide is considered motif-bearing if it has primary anchors at each primary anchor position for a motif or supermotif as specified in the above table.

TABLE IV (B)

HLA CLASS II SUPERMOTIF

| 1 | 6 | 9 |
|---|---|---|
| W, F, Y, V, .I, L | A, V, I, L, P, C, S, T | A, V, I, L, C, S, T, M, Y |

TABLE IV C

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY_LIVW_ (SEQ ID NO:776) | M | T | | I | VST_CPALIM_ (SEQ ID NO:777) | MH | | MH |
| | deleterious | | | | W | | | R | | WDE |
| DR1 | preferred | MF_LIVWY_ (SEQ ID NO:778) | | | PAMQ (SEQ ID NO:779) | | VMAT_SPLIC_ (SEQ ID NO:780) | M | | AVM |
| | deleterious | | C | CH | FD | CWD | | GDE | D | |
| DR7 | preferred | MF_LIVWY_ (SEQ ID NO:781) | M | W | A | | IVMSA_CTPL_ (SEQ ID NO:782) | M | | IV |
| | deleterious | | C | | G | | | GRD | N | G |

| DR3 | MOTIFS | 1° anchor 1 | 2 | 3 | 1° anchor 4 | 5 | 1° anchor 6 |
|---|---|---|---|---|---|---|---|
| motif a preferred | | LIVMFY (SEQ ID NO:783) | | | D | | |
| motif b preferred | | LIVMFAY (SEQ ID NO:784) | | | DNQEST (SEQ ID NO:785) | | KRH |
| DR Supermotif | | MF_LIVWY_ (SEQ ID NO:786) | | | | | VMSTA_CPLI_ (SEQ ID NO:787) |

Italicized residues indicate less preferred or "tolerated" residues.

TABLE IV (D)

| SUPER MOTIFS | POSITION | | | | | | | | |
|---|---|---|---|---|---|---|---|---|---|
| | 1 | 2 | 3 | 4 | 5 | 6 | 7 | 8 | C-terminus |
| A1 | | 1° Anchor <u>TILVM</u> (SEQ ID NO:788) | | | | | | | 1° Anchor <u>FWY</u> |
| A2 | | 1° Anchor <u>LIVMATQ</u> (SEQ ID NO:789) | | | | | | | 1° Anchor <u>LIVMAT</u> (SEQ ID NO:790) |

TABLE IV (D)-continued

| SUPER MOTIFS | | 1 | 2 | 3 | 4 | 5 | 6 | 7 | 8 | C-terminus |
|---|---|---|---|---|---|---|---|---|---|---|
| A3 | preferred | | 1° Anchor<br>VSMATLI<br>(SEQ ID NO:791) | YFW (4/5) | | | YFW (3/5) | YFW (4/5) | P (4/5) | 1° Anchor<br>RK |
| | deleterious | DE (3/5);<br>P (5/5) | | DE (4/5) | | | | | | |
| A24 | | | 1° Anchor<br>YFWIVLMT<br>(SEQ ID NO:792) | | | | | | | 1° Anchor<br>FIYWLM<br>(SEQ ID NO:793) |
| B7 | preferred | FWY (5/5),<br>LIVM (3/5)<br>(SEQ ID NO:794) | 1° Anchor<br>P | FWY (4/5) | | | | | FWY (3/5) | 1° Anchor<br>VILFMWYA<br>(SEQ ID NO:795) |
| | deleterious | DE (3/5);<br>P(5/5);<br>G(4/5);<br>A(3/5);<br>QN(3/5) | | | | DE (3/5) | G (4/5) | QN (4/5) | DE (4/5) | |
| B27 | | | | 1° Anchor<br>RHK | | | | | | 1° Anchor<br>FYLWMIVA<br>(SEQ ID NO:796) |
| B44 | | | | 1° Anchor<br>ED | | | | | | 1° Anchor<br>FWYLIMVA<br>(SEQ ID NO:797) |
| B58 | | | | 1° Anchor<br>ATS | | | | | | 1° Anchor<br>FWYLIVMA<br>(SEQ ID NO:798) |
| B62 | | | | 1° Anchor<br>QLIVMP<br>(SEQ ID NO:799) | | | | | | 1° Anchor<br>FWYMIVLA<br>(SEQ ID NO:800) |

TABLE IV E

| POSITION: | 1 | 2 | 3 | 4 | 5 | 6 | 7 | 8 | 9 or C-terminus | 9 C-terminus |
|---|---|---|---|---|---|---|---|---|---|---|
| A1 9-mer | preferred | GFYW (SEQ ID NO:801) | 1° Anchor STM | DEA | YFW | | P | DEQN (SEQ ID NO:802) | YFW | 1° Anchor Y |
| | deleterious | DE | | RHKLIVMP (SEQ ID NO:803) | A | G | A | | | |
| A1 9-mer | preferred | GRHK (SEQ ID NO:804) | ASTCLIVM (SEQ ID NO:805) | 1° Anchor DEAS (SEQ ID NO:806) | GSTC (SEQ ID NO:807) | | ASTC (SEQ ID NO:808) | LIVM (SEQ ID NO:809) | DE | 1° Anchor Y |
| | deleterious | A | RHKDEPYFW (SEQ ID NO:810) | | DE | PQN | RHK | PG | GP | |
| A1 10-mer | preferred | YFW | 1° Anchor STM | DEAQN (SEQ ID NO:811) | A | YFWQN (SEQ ID NO:812) | | PASTC (SEQ ID NO:813) | GDE | P |
| | deleterious | GP | | RHKGLIVM (SEQ ID NO:814) | DE | RHK | QNA | RHKYFW (SEQ ID NO:815) | RHK | A |
| A1 10-mer | preferred | YFW | STCLIVM (SEQ ID NO:816) | 1° Anchor DEAS (SEQ ID NO:817) | A | YFW | | PG | G | YFW |
| | deleterious | RHK | RHKDEPYFW (SEQ ID NO:818) | | | P | G | | PRHK (SEQ ID NO:819) | QN |
| A2.1 9-mer | preferred | YFW | 1° Anchor LMIVQAT (SEQ ID NO:820) | YFW | STC | YFW | A | A | P | 1° Anchor VLIMAT (SEQ ID NO:821) |
| | deleterious | DEP | | DERKH (SEQ ID NO:822) | | | RKH | DERKH (SEQ ID NO:823) | | |

TABLE IV E-continued

| POSITION: | 1 | 2 | 3 | 4 | 5 | 6 | 7 | 8 | or C-terminus | 9 C-terminus |
|---|---|---|---|---|---|---|---|---|---|---|
| A2.1 10-mer | preferred | AYFW | 1° Anchor LMIVQAT (SEQ ID NO:824) | LVIM (SEQ ID NO:825) | G | | G | | FYWL VIM (SEQ ID NO:826) | 1° Anchor VLIMAT (SEQ ID NO:827) |
| | deleterious | DEP | | DE | RKHA (SEQ ID NO:828) | P | | RKH | DERKLH (SEQ ID NO:829) | RKH |
| A3 | preferred | RHK | 1° Anchor LMVISATFCGD (SEQ ID NO:830) | YFW | PRHKK YFW (SEQ ID NO:831) | A | YFW | | P | 1° Anchor KYRHFA (SEQ ID NO:832) |
| | deleterious | DEP | | DE | | | | | | |
| A11 | preferred | A | 1° Anchor VTLMISAGNCDF (SEQ ID NO:833) | YFW | YFW | A | YFW | YFW | P | 1° Anchor KRYH (SEQ ID NO:834) |
| | deleterious | DEP | | | | | | A | G | |
| A24 9-mer | preferred | YFWRHK (SEQ ID NO:835) | 1° Anchor YFWM (SEQ ID NO:836) | | STC | | | YFW | YFW | 1° Anchor FLIW (SEQ ID NO:837) |
| | deleterious | DEG | | DE | G | QNP | DERHK (SEQ ID NO:838) | G | AQN | |
| A24 10-mer | preferred | | 1° Anchor YFWM (SEQ ID NO:839) | | P | YFWP (SEQ ID NO:840) | | P | | 1° Anchor FLIW (SEQ ID NO:841) |
| | deleterious | | | GDE | QN | RHK | DE | A | QN | |
| A3101 | preferred | RHK | 1° Anchor MVTALIS (SEQ ID NO:842) | YFW | P | | YFW | YFW | AP | 1° Anchor RK |
| | deleterious | DEP | | DE | | ADE | DE | DE | DE | DEA |

TABLE IV E-continued

| POSITION: | 1 | 2 | 3 | 4 | 5 | 6 | 7 | 8 | or C-terminus | 9 C-terminus |
|---|---|---|---|---|---|---|---|---|---|---|
| A3301 | preferred | | 1° Anchor MVALFIST (SEQ ID NO:843) | YFW | | | | AYFW (SEQ ID NO:844) | | 1° Anchor RK |
| | deleterious | GP | | | | | | | | |
| A6801 | preferred | YFWSTC (SEQ ID NO:845) | 1° Anchor AVTMSLI (SEQ ID NO:846) | | | YFWLIVM (SEQ ID NO:847) | | YFW | P | 1° Anchor RK |
| | deleterious | GP | | DE | | | | | A | |
| B0702 | preferred | RHKFWY (SEQ ID NO:848) | 1° Anchor P | DEG | | RHK | | RHK | PA | 1° Anchor LMFWYAIV (SEQ ID NO:849) |
| | deleterious | DEQNP (SEQ ID NO:850) | | RHK | DE | RHK | RHK | QN | DE | |
| B3501 | preferred | FWYLIVM (SEQ ID NO:851) | 1° Anchor P | DEP | | DE | GDE | | | 1° Anchor LMFWYIVA (SEQ ID NO:852) |
| | deleterious | AGP | | FWY | | | FWY | | | |
| B51 | preferred | LIVMFWY (SEQ ID NO:856) | 1° Anchor P | FWY | STC | FWY | G | G | FWY | 1° Anchor LIVFWYAM (SEQ ID NO:853) |
| | deleterious | AGPDERH KSTC (SEQ ID NO:854) | | | | DE | G | DEQN (SEQ ID NO:855) | GDE | |
| B5301 | preferred | LIVMFWY (SEQ ID NO:856) | 1° Anchor P | FWY | STC | FWY | | LIVMFWY (SEQ ID NO:857) | FWY | 1° Anchor IMFWYALV (SEQ ID NO:858) |

TABLE IV E-continued

| POSITION: | 1 | 2 | 3 | 4 | 5 | 6 | 7 | 8 | 9 or C-terminus | C-terminus |
|---|---|---|---|---|---|---|---|---|---|---|
| B5401 | deleterious | AGPQN (SEQ ID NO:859) | | | | | G | RHKQN (SEQ ID NO:860) | DE | |
| | preferred | FWY | 1° Anchor P | FWYL IVM (SEQ ID NO:861) | | LIVM (SEQ ID NO:862) | | ALIVM (SEQ ID NO:863) | FWYAP (SEQ ID NO:864) | 1° Anchor ATIVLMFWY (SEQ ID NO:865) |
| | deleterious | GPQNDE (SEQ ID NO:866) | | GDESTC (SEQ ID NO:867) | | RHKDE (SEQ ID NO:868) | DE | QNDGE (SEQ ID NO:869) | DE | |

Italicized residues indicate less preferred or "tolerated" residues. The information in this Table is specific for 9-mers unless otherwise specified.

TABLE V

HLA Peptide Scoring Results—85P1B3-A1, 9-mers

| Rank | Start Position | Subsequence Residue Listing | Score (Estimate of Half Time of Disassociation of a Molecule Containing This Subsequence) | Seq.ID# |
|---|---|---|---|---|
| 1 | 114 | VLEAPFLVG | 4.500 | 1. |
| 2 | 192 | LSEKIAELK | 2.700 | 2. |
| 3 | 87 | LADSVHLAW | 2.500 | 3. |
| 4 | 27 | AIDQASFTT | 2.500 | 4. |
| 5 | 164 | LSSDKMVCY | 1.500 | 5. |
| 6 | 217 | LSEVTPDQS | 1.350 | 6. |
| 7 | 182 | ASEMDIQNV | 1.350 | 7. |
| 8 | 12 | CATPPRGDF | 1.000 | 8. |
| 9 | 122 | GIEGSLKGS | 0.900 | 9. |
| 10 | 196 | IAELKEKIV | 0.900 | 10. |
| 11 | 141 | GIPVGFHLY | 0.500 | 11. |
| 12 | 100 | SLGAVVFSR | 0.500 | 12. |
| 13 | 184 | EMDIQNVPL | 0.500 | 13. |
| 14 | 57 | AEEPAAGPQ | 0.450 | 14. |
| 15 | 36 | SMEWDTQVV | 0.450 | 15. |
| 16 | 46 | GSSPLGPAG | 0.300 | 16. |
| 17 | 138 | GSCGIPVGF | 0.300 | 17. |
| 18 | 13 | ATPPRGDFC | 0.250 | 18. |
| 19 | 221 | TPDQSKPEN | 0.250 | 19. |
| 20 | 23 | GTERAIDQA | 0.225 | 20. |
| 21 | 61 | AAGPQLPSW | 0.200 | 21. |
| 22 | 120 | LVGIEGSLK | 0.200 | 22. |
| 23 | 169 | MVCYLLKTK | 0.200 | 23. |
| 24 | 203 | IVLTHNRLK | 0.200 | 24. |
| 25 | 56 | GAEEPAAGP | 0.180 | 25. |
| 26 | 130 | STYNLLFCG | 0.125 | 26. |
| 27 | 128 | KGSTYNLLF | 0.125 | 27. |
| 28 | 140 | CGIPVGFHL | 0.125 | 28. |
| 29 | 124 | EGSLKGSTY | 0.125 | 29. |
| 30 | 109 | VTNNVVLEA | 0.125 | 30. |
| 31 | 1 | MAAQPLRHR | 0.100 | 31. |
| 32 | 2 | AAQPLRHRS | 0.100 | 32. |
| 33 | 69 | WLQPERCAV | 0.100 | 33. |
| 34 | 154 | ALAALRGHF | 0.100 | 34. |
| 35 | 165 | SSDKMVCYL | 0.075 | 35. |
| 36 | 31 | ASFTTSMEW | 0.075 | 36. |
| 37 | 129 | GSTYNLLFC | 0.075 | 37. |

TABLE V-continued

HLA Peptide Scoring Results—85P1B3—A1, 9-mers

| Rank | Start Position | Subsequence Residue Listing | Score (Estimate of Half Time of Disassociation of a Molecule Containing This Subsequence) | Seq.ID# |
|---|---|---|---|---|
| 38 | 149 | YSTHAALAA | 0.075 | 38. |
| 39 | 66 | LPSWLQPER | 0.050 | 39. |
| 40 | 136 | FCGSCGIPV | 0.050 | 40. |
| 41 | 111 | NNVVLEAPF | 0.050 | 41. |
| 42 | 150 | STHAALAAL | 0.050 | 42. |
| 43 | 167 | DKMVCYLLK | 0.050 | 43. |
| 44 | 49 | PLGPAGLGA | 0.050 | 44. |
| 45 | 204 | VLTHNRLKS | 0.050 | 45. |
| 46 | 163 | CLSSDKMVC | 0.050 | 46. |
| 47 | 38 | EWDTQVVKG | 0.050 | 47. |
| 48 | 152 | HAALAALRG | 0.050 | 48. |
| 49 | 179 | IVNASEMDI | 0.050 | 49. |
| 50 | 181 | NASEMIDQN | 0.050 | 50. |

TABLE VI

HLA Peptide Scoring Results—85P1B3—A1, 10-mers

| Rank | Start Position | Subsequence Residue Listing | Score (Estimate of Half Time of Disassociation of a Molecule Containing This Subsequence) | Seq.ID# |
|---|---|---|---|---|
| 1 | 217 | LSEVTPDQSK | 27.000 | 51. |
| 2 | 36 | SMEWDTQVVK | 18.000 | 52. |
| 3 | 196 | IAELKEKIVL | 4.500 | 53. |
| 4 | 69 | WLQPERCAVF | 2.000 | 54. |
| 5 | 114 | VLEAPFLVGI | 1.800 | 55. |
| 6 | 17 | RGDFCGGTER | 1.250 | 56. |
| 7 | 140 | CGIPVGFHLY | 1.250 | 57. |
| 8 | 13 | ATPPRGDFCG | 1.250 | 58. |
| 9 | 163 | CLSSDKMVCY | 1.000 | 59. |
| 10 | 2 | AAQPLRHRSR | 1.000 | 60. |
| 11 | 56 | GAEEPAAGPQ | 0.900 | 61. |
| 12 | 57 | AEEPAAGPQL | 0.900 | 62. |
| 13 | 122 | GIEGSLKGST | 0.900 | 63. |
| 14 | 99 | RSLGAVVFSR | 0.750 | 64. |
| 15 | 27 | AIDQASFTTS | 0.500 | 65. |
| 16 | 90 | SVHLAWDLSR | 0.500 | 66. |
| 17 | 184 | EMDIQNVPLS | 0.500 | 67. |
| 18 | 150 | STHAALAALR | 0.500 | 68. |
| 19 | 46 | GSSPLGPAGL | 0.300 | 69. |

TABLE VI-continued

HLA Peptide Scoring Results—85P1B3—A1, 10-mers

| Rank | Start Position | Subsequence Residue Listing | Score (Estimate of Half Time of Disassociation of a Molecule Containing This Subsequence) | Seq.ID# |
|---|---|---|---|---|
| 20 | 23 | GTERAIDQAS | 0.225 | 70. |
| 21 | 119 | FLVGIEGSLK | 0.200 | 71. |
| 22 | 202 | KIVLTHNRLK | 0.200 | 72. |
| 23 | 186 | DIQNVPLSEK | 0.200 | 73. |
| 24 | 65 | QLPSWLQPER | 0.200 | 74. |
| 25 | 165 | SSDKMVCYLL | 0.150 | 75. |
| 26 | 182 | ASEMDIQNVP | 0.135 | 76. |
| 27 | 94 | AWDLSRSLGA | 0.125 | 77. |
| 28 | 71 | QPERCAVFQC | 0.113 | 78. |
| 29 | 87 | LADSVHLAWD | 0.100 | 79. |
| 30 | 12 | CATPPRGDFC | 0.100 | 80. |
| 31 | 11 | RCATPPRGDF | 0.100 | 81. |
| 32 | 153 | AALAALRGHF | 0.100 | 82. |
| 33 | 61 | AAGPQLPSWL | 0.100 | 83. |
| 34 | 168 | KMVCYLLKTK | 0.100 | 84. |
| 35 | 129 | GSTYNLLFCG | 0.075 | 85. |
| 36 | 192 | LSEKIAELKE | 0.068 | 86. |
| 37 | 116 | EAPFLVGIEG | 0.050 | 87. |
| 38 | 155 | LAALRGHFCL | 0.050 | 88. |
| 39 | 203 | IVLTHNRLKS | 0.050 | 89. |
| 40 | 112 | NVVLEAPFLV | 0.050 | 90. |
| 41 | 139 | SCGIPVGFHL | 0.050 | 91. |
| 42 | 178 | AIVNASEMDI | 0.050 | 92. |
| 43 | 26 | RAIDQASFTT | 0.050 | 93. |
| 44 | 159 | RGHFCLSSDK | 0.050 | 94. |
| 45 | 110 | TNNVVLEAPF | 0.050 | 95. |
| 46 | 108 | RVTNNVVLEA | 0.050 | 96. |
| 47 | 30 | QASFTTSMEW | 0.050 | 97. |
| 48 | 113 | VVLEAPFLVG | 0.050 | 98. |
| 49 | 120 | LVGIEGSLKG | 0.050 | 99. |
| 50 | 137 | CGSCGIPVGF | 0.050 | 100. |

TABLE VII

HLA Peptide Scoring Results—85P1B3—A2, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 113 | VVLEAPFLV | 910.291 | 101. |
| 2 | 212 | SLMKILSEV | 591.888 | 102. |
| 3 | 172 | YLLKTKAIV | 485.348 | 103. |
| 4 | 69 | WLQPERCAV | 319.939 | 104. |
| 5 | 86 | VLADSVHLA | 79.642 | 105. |
| 6 | 134 | LLFCGSCGI | 65.622 | 106. |
| 7 | 168 | KMVCYLLKT | 43.325 | 107. |
| 8 | 78 | FQCAQCHAV | 32.438 | 108. |
| 9 | 119 | FLVGIEGSL | 12.775 | 109. |
| 10 | 112 | NVVLEAPFL | 10.281 | 110. |
| 11 | 202 | KIVLTHNRL | 10.281 | 111. |
| 12 | 195 | KIAELKEKI | 10.087 | 112. |
| 13 | 162 | FCLSSDKMV | 7.727 | 113. |
| 14 | 85 | AVLADSVHL | 6.916 | 114. |
| 15 | 35 | TSMEWDTQV | 6.887 | 115. |
| 16 | 156 | AALRGHFCL | 6.367 | 116. |
| 17 | 54 | GLGAEEPAA | 4.968 | 117. |
| 18 | 191 | PLSEKIAEL | 4.432 | 118. |
| 19 | 33 | FTTSMEWDT | 3.571 | 119. |
| 20 | 93 | LAWDLSRSL | 3.433 | 120. |
| 21 | 115 | LEAPFLVGI | 3.014 | 121. |
| 22 | 27 | AIDQASFTT | 2.377 | 122. |
| 23 | 26 | RAIDQASFT | 2.334 | 123. |
| 24 | 147 | HLYSTHAAL | 2.324 | 124. |
| 25 | 136 | FCGSCGIPV | 2.088 | 125. |
| 26 | 163 | CLSSDKMVC | 2.037 | 126. |
| 27 | 42 | QVVKGSSPL | 1.869 | 127. |
| 28 | 96 | DLSRSLGAV | 1.560 | 128. |
| 29 | 179 | IVNASEMDI | 1.552 | 129. |
| 30 | 101 | LGAVVFSRV | 1.466 | 130. |
| 31 | 36 | SMEWDTQVV | 1.318 | 131. |
| 32 | 205 | LTHNRLKSL | 1.160 | 132. |
| 33 | 140 | CGIPVGFHL | 0.809 | 133. |
| 34 | 62 | AGPQLPSWL | 0.767 | 134. |
| 35 | 126 | SLKGSTYNL | 0.748 | 135. |
| 36 | 165 | SSDKMVCYL | 0.706 | 136. |
| 37 | 209 | RLKSLMKIL | 0.705 | 137. |

TABLE VII-continued

HLA Peptide Scoring Results—85P1B3—A2, 9-mers

| Rank | Start Position | Subsequence Residue Listing | Score (Estimate of Half Time of Disassociation of a Molecule Containing This Subsequence) | Seq.ID# |
|---|---|---|---|---|
| 38 | 150 | STHAALAAL | 0.682 | 138. |
| 39 | 155 | LAALRGHFC | 0.645 | 139. |
| 40 | 197 | AELKEKIVL | 0.630 | 140. |
| 41 | 184 | EMDIQNVPL | 0.463 | 141. |
| 42 | 129 | GSTYNLLFC | 0.410 | 142. |
| 43 | 133 | NLLFCGSCG | 0.276 | 143. |
| 44 | 132 | YNLLFCGSC | 0.273 | 144. |
| 45 | 109 | VTNNVVLEA | 0.270 | 145. |
| 46 | 177 | KAIVNASEM | 0.242 | 146. |
| 47 | 100 | SLGAVVFSR | 0.199 | 147. |
| 48 | 13 | ATPPRGDFC | 0.186 | 148. |
| 49 | 198 | ELKEKIVLT | 0.184 | 149. |
| 50 | 189 | NVPLSEKIA | 0.178 | 150. |

TABLE VIII

HLA Peptide Scoring Results—85P1B3—A2, 10-mers

| Rank | Start Position | Subsequence Residue Listing | Score (Estimate of Half Time of Disassociation of a Molecule Containing This Subsequence) | Seq.ID# |
|---|---|---|---|---|
| 1 | 100 | SLGAVVFSRV | 132.149 | 151. |
| 2 | 204 | VLTHNRLKSL | 83.527 | 152. |
| 3 | 195 | KIAELKEKIV | 56.266 | 153. |
| 4 | 133 | NLLFCGSCGI | 38.601 | 154. |
| 5 | 104 | VVFSRVTNNV | 38.280 | 155. |
| 6 | 112 | NVVLEAPFLV | 35.298 | 156. |
| 7 | 154 | ALAALRGHFC | 27.324 | 157. |
| 8 | 211 | KSLMKILSEV | 13.523 | 158. |
| 9 | 164 | LSSDKMVCYL | 12.295 | 159. |
| 10 | 114 | VLEAPFLVGI | 9.921 | 160. |
| 11 | 181 | NASEMDIQNV | 9.109 | 161. |
| 12 | 183 | SEMDIQNVPL | 6.301 | 162. |
| 13 | 212 | SLMKILSEVT | 5.539 | 163. |
| 14 | 78 | FQCAQCHAVL | 4.085 | 164. |
| 15 | 85 | AVLADSVHLA | 3.699 | 165. |
| 16 | 155 | LAALRGHFCL | 2.925 | 166. |
| 17 | 35 | TSMEWDTQVV | 2.824 | 167. |
| 18 | 26 | RAIDQASFTT | 2.461 | 168. |
| 19 | 41 | TQVVKGSSPL | 2.166 | 169. |

TABLE VIII-continued

HLA Peptide Scoring Results—85P1B3–A2, 10-mers

| Rank | Start Position | Subsequence Residue Listing | Score (Estimate of Half Time of Disassociation of a Molecule Containing This Subsequence) | Seq.ID# |
|---|---|---|---|---|
| 20 | 96 | DLSRSLGAVV | 2.139 | 170. |
| 21 | 190 | VPLSEKIAEL | 2.017 | 171. |
| 22 | 61 | AAGPQLPSWL | 1.632 | 172. |
| 23 | 76 | AVFQCAQCHA | 1.608 | 173. |
| 24 | 149 | YSTHAALAAL | 1.475 | 174. |
| 25 | 128 | KGSTYNLLFC | 1.436 | 175. |
| 26 | 178 | AIVNASEMDI | 1.435 | 176. |
| 27 | 197 | AELKEKIVLT | 1.233 | 177. |
| 28 | 126 | SLKGSTYNLL | 1.122 | 178. |
| 29 | 108 | RVTNNVVLEA | 1.000 | 179. |
| 30 | 34 | TTSMEWDTQV | 0.966 | 180. |
| 31 | 187 | IQNVPLSEKI | 0.881 | 181. |
| 32 | 139 | SCGIPVGFHL | 0.809 | 182. |
| 33 | 111 | NNVVLEAPFL | 0.767 | 183. |
| 34 | 169 | MVCYLLKTKA | 0.739 | 184. |
| 35 | 173 | LLKTKAIVNA | 0.680 | 185. |
| 36 | 147 | HLYSTHAALA | 0.541 | 186. |
| 37 | 172 | YLLKTKAIVN | 0.520 | 187. |
| 38 | 86 | VLADSVHLAW | 0.519 | 188. |
| 39 | 125 | GSLKGSTYNL | 0.516 | 189. |
| 40 | 3 | AQPLRHRSRC | 0.504 | 190. |
| 41 | 95 | WDLSRSLGAV | 0.492 | 191. |
| 42 | 170 | VCYLLKTKAI | 0.370 | 192. |
| 43 | 216 | ILSEVTPDQS | 0.255 | 193. |
| 44 | 146 | FHLYSTHAAL | 0.252 | 194. |
| 45 | 162 | FCLSSDKMVC | 0.226 | 195. |
| 46 | 88 | ADSVHLAWDL | 0.223 | 196. |
| 47 | 82 | QCHAVLADSV | 0.222 | 197. |
| 48 | 141 | GIPVGFHLYS | 0.214 | 198. |
| 49 | 144 | VGFHLYSTHA | 0.204 | 199. |
| 50 | 37 | MEWDTQVVKG | 0.193 | 200. |

TABLE IX

HLA Peptide Scoring Results - 85P1B3 - A3, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 100 | SLGAVVFSR | 54.000 | 201. |
| 2 | 168 | KMVCYLLKT | 4.050 | 202. |
| 3 | 141 | GIPVGFHLY | 3.600 | 203. |
| 4 | 147 | HLYSTHAAL | 3.000 | 204. |
| 5 | 134 | LLFCGSCGI | 3.000 | 205. |
| 6 | 126 | SLKGSTYNL | 2.700 | 206. |
| 7 | 120 | LVGIEGSLK | 2.000 | 207. |
| 8 | 169 | MVCYLLKTK | 1.500 | 208. |
| 9 | 187 | IQNVPLSEK | 1.350 | 209. |
| 10 | 212 | SLMKILSEV | 0.675 | 210. |
| 11 | 119 | FLVGIEGSL | 0.608 | 211. |
| 12 | 54 | GLGAEEPAA | 0.600 | 212. |
| 13 | 154 | ALAALRGHF | 0.600 | 213. |
| 14 | 86 | VLADSVHLA | 0.600 | 214. |
| 15 | 209 | RLKSLMKIL | 0.450 | 215. |
| 16 | 163 | CLSSDKMVC | 0.400 | 216. |
| 17 | 160 | GHFCLSSDK | 0.300 | 217. |
| 18 | 69 | WLQPERCAV | 0.300 | 218. |
| 19 | 172 | YLLKTKAIV | 0.300 | 219. |
| 20 | 37 | MEWDTQVVK | 0.300 | 220. |
| 21 | 203 | IVLTHNRLK | 0.300 | 221. |
| 22 | 202 | KIVLTHNRL | 0.270 | 222. |
| 23 | 195 | KIAELKEKI | 0.270 | 223. |
| 24 | 36 | SMEWDTQVV | 0.200 | 224. |
| 25 | 184 | EMDIQNVPL | 0.180 | 225. |
| 26 | 157 | ALRGHFCLS | 0.180 | 226. |
| 27 | 114 | VLEAPFLVG | 0.180 | 227. |
| 28 | 192 | LSEKIAELK | 0.150 | 228. |
| 29 | 191 | PLSEKIAEL | 0.135 | 229. |
| 30 | 113 | VVLEAPFLV | 0.135 | 230. |
| 31 | 218 | SEVTPDQSK | 0.135 | 231. |
| 32 | 179 | IVNASEMDI | 0.120 | 232. |
| 33 | 76 | AVFQCAQCH | 0.100 | 233. |
| 34 | 213 | LMKILSEVT | 0.100 | 234. |
| 35 | 70 | LQPERCAVF | 0.090 | 235. |
| 36 | 65 | QLPSWLQPE | 0.090 | 236. |
| 37 | 85 | AVLADSVHL | 0.090 | 237. |

TABLE IX-continued

HLA Peptide Scoring Results - 85P1B3 - A3, 9-mers

| Rank | Start Position | Subsequence Residue Listing | Score (Estimate of Half Time of Disassociation of a Molecule Containing This Subsequence) | Seq. ID# |
|---|---|---|---|---|
| 38 | 42 | QVVKGSSPL | 0.090 | 238. |
| 39 | 112 | NVVLEAPFL | 0.090 | 239. |
| 40 | 109 | VTNNVVLEA | 0.090 | 240. |
| 41 | 207 | HNRLKSLMK | 0.080 | 241. |
| 42 | 204 | VLTHNRLKS | 0.080 | 242. |
| 43 | 138 | GSCGIPVGF | 0.068 | 243. |
| 44 | 198 | ELKEKIVLT | 0.068 | 244. |
| 45 | 18 | GDFCGGTER | 0.060 | 245. |
| 46 | 92 | HLAWDLSRS | 0.060 | 246. |
| 47 | 49 | PLGPAGLGA | 0.060 | 247. |
| 48 | 216 | ILSEVTPDQ | 0.045 | 248. |
| 49 | 23 | GTERAIDQA | 0.045 | 249. |
| 50 | 150 | STHAALAAL | 0.045 | 250. |

TABLE X

HLA Peptide Scoring Results - 85P1B3 - A3, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 168 | KMVCYLLKTK | 67.500 | 251. |
| 2 | 119 | FLVGIEGSLK | 45.000 | 252. |
| 3 | 36 | SMEWDTQVVK | 20.000 | 253. |
| 4 | 163 | CLSSDKMVCY | 6.000 | 254. |
| 5 | 191 | PLSEKIAELK | 4.500 | 255. |
| 6 | 65 | QLPSWLQPER | 4.000 | 256. |
| 7 | 69 | WLQPERCAVF | 3.000 | 257. |
| 8 | 114 | VLEAPFLVGI | 2.700 | 258. |
| 9 | 90 | SVHLAWDLSR | 2.400 | 259. |
| 10 | 186 | DIQNVPLSEK | 1.350 | 260. |
| 11 | 147 | HLYSTHAALA | 1.000 | 261. |
| 12 | 100 | SLGAVVFSRV | 0.900 | 262. |
| 13 | 202 | KIVLTHNRLK | 0.900 | 263. |
| 14 | 126 | SLKGSTYNLL | 0.900 | 264. |
| 15 | 133 | NLLFCGSCGI | 0.900 | 265. |
| 16 | 198 | ELKEKIVLTH | 0.810 | 266. |
| 17 | 99 | RSLGAVVFSR | 0.608 | 267. |
| 18 | 86 | VLADSVHLAW | 0.600 | 268. |
| 19 | 204 | VLTHNRLKSL | 0.450 | 269. |
| 20 | 157 | ALRGHFCLSS | 0.360 | 270. |

TABLE X-continued

HLA Peptide Scoring Results - 85P1B3 - A3, 10-mers

| Rank | Start Position | Subsequence Residue Listing | Score (Estimate of Half Time of Disassociation of a Molecule Containing This Subsequence) | Seq. ID# |
|---|---|---|---|---|
| 21 | 173 | LLKTKAIVNA | 0.300 | 271. |
| 22 | 154 | ALAALRGHFC | 0.200 | 272. |
| 23 | 150 | STHAALAALR | 0.200 | 273. |
| 24 | 108 | RVTNNVVLEA | 0.180 | 274. |
| 25 | 178 | AIVNASEMDI | 0.180 | 275. |
| 26 | 104 | VVFSRVTNNV | 0.150 | 276. |
| 27 | 212 | SLMKILSEVT | 0.150 | 277. |
| 28 | 217 | LSEVTPDQSK | 0.150 | 278. |
| 29 | 76 | AVFQCAQCHA | 0.100 | 279. |
| 30 | 85 | AVLADSVHLA | 0.090 | 280. |
| 31 | 112 | NVVLEAPFLV | 0.090 | 281. |
| 32 | 209 | RLKSLMKILS | 0.080 | 282. |
| 33 | 141 | GIPVGFHLYS | 0.072 | 283. |
| 34 | 172 | YLLKTKAIVN | 0.060 | 284. |
| 35 | 96 | DLSRSLGAVV | 0.060 | 285. |
| 36 | 54 | GLGAEEPAAG | 0.060 | 286. |
| 37 | 92 | HLAWDLSRSL | 0.060 | 287. |
| 38 | 216 | ILSEVTPDQS | 0.060 | 288. |
| 39 | 195 | KIAELKEKIV | 0.045 | 289. |
| 40 | 193 | SEKIAELKEK | 0.045 | 290. |
| 41 | 113 | VVLEAPFLVG | 0.041 | 291. |
| 42 | 125 | GSLKGSTYNL | 0.041 | 292. |
| 43 | 166 | SDKMVCYLLK | 0.040 | 293. |
| 44 | 206 | THNRLKSLMK | 0.040 | 294. |
| 45 | 184 | EMDIQNVPLS | 0.036 | 295. |
| 46 | 200 | KEKIVLTHNR | 0.036 | 296. |
| 47 | 134 | LLFCGSCGIP | 0.030 | 297. |
| 48 | 34 | TTSMEWDTQV | 0.030 | 298. |
| 49 | 130 | STYNLLFCGS | 0.030 | 299. |
| 50 | 41 | TQVVKGSSPL | 0.027 | 300. |

TABLE XI

HLA Peptide Scoring Results - 85P1B3 - A11, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 120 | LVGIEGSLK | 2.000 | 301. |
| 2 | 169 | MVCYLLKTK | 1.000 | 302. |

TABLE XI-continued

HLA Peptide Scoring Results - 85P1B3 - A11, 9-mers

| Rank | Start Position | Subsequence Residue Listing | Score (Estimate of Half Time of Disassociation of a Molecule Containing This Subsequence) | Seq. ID# |
|---|---|---|---|---|
| 3 | 187 | IQNVPLSEK | 0.600 | 303. |
| 4 | 203 | IVLTHNRLK | 0.300 | 304. |
| 5 | 100 | SLGAVVFSR | 0.240 | 305. |
| 6 | 160 | GHFCLSSDK | 0.120 | 306. |
| 7 | 37 | MEWDTQVVK | 0.120 | 307. |
| 8 | 113 | VVLEAPFLV | 0.090 | 308. |
| 9 | 218 | SEVTPDQSK | 0.090 | 309. |
| 10 | 207 | HNRLKSLMK | 0.080 | 310. |
| 11 | 76 | AVFQCAQCH | 0.040 | 311. |
| 12 | 66 | LPSWLQPER | 0.040 | 312. |
| 13 | 179 | IVNASEMDI | 0.040 | 313. |
| 14 | 85 | AVLADSVHL | 0.030 | 314. |
| 15 | 112 | NVVLEAPFL | 0.030 | 315. |
| 16 | 42 | QVVKGSSPL | 0.030 | 316. |
| 17 | 23 | GTERAIDQA | 0.030 | 317. |
| 18 | 18 | GDFCGGTER | 0.024 | 318. |
| 19 | 167 | DKMVCYLLK | 0.024 | 319. |
| 20 | 109 | VTNNVVLEA | 0.020 | 320. |
| 21 | 192 | LSEKIAELK | 0.020 | 321. |
| 22 | 202 | KIVLTHNRL | 0.018 | 322. |
| 23 | 9 | RSRCATPPR | 0.012 | 323. |
| 24 | 91 | VHLAWDLSR | 0.012 | 324. |
| 25 | 3 | AQPLRHRSR | 0.012 | 325. |
| 26 | 54 | GLGAEEPAA | 0.012 | 326. |
| 27 | 141 | GIPVGFHLY | 0.012 | 327. |
| 28 | 195 | KIAELKEKI | 0.012 | 328. |
| 29 | 189 | NVPLSEKIA | 0.010 | 329. |
| 30 | 150 | STHAALAAL | 0.010 | 330. |
| 31 | 156 | AALRGHFCL | 0.009 | 331. |
| 32 | 177 | KAIVNASEM | 0.009 | 332. |
| 33 | 212 | SLMKILSEV | 0.008 | 333 |
| 34 | 126 | SLKGSTYNL | 0.008 | 334. |
| 35 | 147 | HLYSTHAAL | 0.008 | 335. |
| 36 | 134 | LLFCGSCGI | 0.008 | 336. |
| 37 | 172 | YLLKTKAIV | 0.006 | 337. |
| 38 | 145 | GFHLYSTHA | 0.006 | 338. |
| 39 | 70 | LQPERCAVF | 0.006 | 339. |

TABLE XI-continued

HLA Peptide Scoring Results - 85P1B3 - A11, 9-mers

| Rank | Start Position | Subsequence Residue Listing | Score (Estimate of Half Time of Disassociation of a Molecule Containing This Subsequence) | Seq. ID# |
|---|---|---|---|---|
| 40 | 130 | STYNLLFCG | 0.006 | 340. |
| 41 | 108 | RVTNNVVLE | 0.006 | 341. |
| 42 | 78 | FQCAQCHAV | 0.006 | 342. |
| 43 | 209 | RLKSLMKIL | 0.006 | 343. |
| 44 | 119 | FLVGIEGSL | 0.006 | 344. |
| 45 | 205 | LTHNRLKSL | 0.005 | 345. |
| 46 | 194 | EKIAELKEK | 0.005 | 346. |
| 47 | 87 | LADSVHLAW | 0.004 | 347. |
| 48 | 1 | MAAQPLRHR | 0.004 | 348. |
| 49 | 154 | ALAALRGHF | 0.004 | 349. |
| 50 | 151 | THAALAALR | 0.004 | 350. |

TABLE XII

HLA Peptide Scoring Results - 85P1B3 - A1, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 168 | KMVCYLLKTK | 0.900 | 351. |
| 2 | 90 | SVHLAWDLSR | 0.800 | 352. |
| 3 | 119 | FLVGIEGSLK | 0.060 | 353. |
| 4 | 36 | SMEWDTQVVK | 0.400 | 354. |
| 5 | 150 | STHAALAALR | 0.200 | 355. |
| 6 | 202 | KIVLTHNRLK | 0.180 | 356. |
| 7 | 186 | DIQNVPLSEK | 0.120 | 357. |
| 8 | 108 | RVTNNVVLEA | 0.120 | 358. |
| 9 | 112 | NVVLEAPFLV | 0.090 | 359. |
| 10 | 65 | QLPSWLQPER | 0.080 | 360. |
| 11 | 159 | RGHFCLSSDK | 0.060 | 361. |
| 12 | 99 | RSLGAVVFSR | 0.054 | 362. |
| 13 | 166 | SDKMVCYLLK | 0.040 | 363. |
| 14 | 76 | AVFQCAQCHA | 0.040 | 364. |
| 15 | 191 | PLSEKIAELK | 0.040 | 365. |
| 16 | 104 | VVFSRVTNNV | 0.040 | 366. |
| 17 | 206 | THNRLKSLMK | 0.040 | 367. |
| 18 | 200 | KEKIVLTHNR | 0.036 | 368. |
| 19 | 85 | AVLADSVHLA | 0.030 | 369. |
| 20 | 193 | SEKIAELKEK | 0.030 | 370. |
| 21 | 217 | LSEVTPDQSK | 0.020 | 371. |

TABLE XII-continued

HLA Peptide Scoring Results - 85P1B3 - A1, 10-mers

| Rank | Start Position | Subsequence Residue Listing | Score (Estimate of Half Time of Disassociation of a Molecule Containing This Subsequence) | Seq. ID# |
|---|---|---|---|---|
| 22 | 169 | MVCYLLKTKA | 0.020 | 372. |
| 23 | 17 | RGDFCGGTER | 0.012 | 373. |
| 24 | 178 | AIVNASEMDI | 0.012 | 374. |
| 25 | 205 | LTHNRLKSLM | 0.010 | 375. |
| 26 | 34 | TTSMEWDTQV | 0.010 | 376. |
| 27 | 41 | TQVVKGSSPL | 0.009 | 377. |
| 28 | 86 | VLADSVHLAW | 0.008 | 378. |
| 29 | 147 | HLYSTHAALA | 0.008 | 379. |
| 30 | 148 | LYSTHAALAA | 0.008 | 380. |
| 31 | 133 | NLLFCGSCGI | 0.006 | 381. |
| 32 | 203 | IVLTHNRLKS | 0.006 | 382. |
| 33 | 78 | FQCAQCHAVL | 0.006 | 383. |
| 34 | 187 | IQNVPLSEKI | 0.006 | 384. |
| 35 | 145 | GFHLYSTHAA | 0.006 | 385. |
| 36 | 48 | SPLGPAGLGA | 0.006 | 386. |
| 37 | 155 | LAALRGHFCL | 0.006 | 387. |
| 38 | 11 | RCATPPRGDF | 0.006 | 388. |
| 39 | 113 | VVLEAPFLVG | 0.006 | 389. |
| 40 | 139 | SCGIPVGFHL | 0.006 | 390. |
| 41 | 195 | KIAELKEKIV | 0.006 | 391. |
| 42 | 171 | CYLLKTKAIV | 0.006 | 392. |
| 43 | 43 | VVKGSSPLGP | 0.004 | 393. |
| 44 | 163 | CLSSDKMVCY | 0.004 | 394. |
| 45 | 100 | SLGAVVFSRV | 0.004 | 395. |
| 46 | 135 | LFCGSCGIPV | 0.004 | 396. |
| 47 | 196 | IAELKEKIVL | 0.004 | 397. |
| 48 | 8 | HRSRCATPPR | 0.004 | 398. |
| 49 | 189 | NVPLSEKIAE | 0.004 | 399. |
| 50 | 126 | SLKGSTYNLL | 0.004 | 400. |

TABLE XIII

HLA Peptide Scoring Results - 85P1B3 - A24, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 171 | CYLLKTKAI | 75.000 | 401. |
| 2 | 202 | KIVLTHNRL | 14.400 | 402. |
| 3 | 131 | TYNLLFCGS | 10.800 | 403. |

TABLE XIII-continued

HLA Peptide Scoring Results - 85P1B3 - A24, 9-mers

| Rank | Start Position | Subsequence Residue Listing | Score (Estimate of Half Time of Disassociation of a Molecule Containing This Subsequence) | Seq. ID# |
|---|---|---|---|---|
| 4 | 140 | CGIPVGFHL | 10.080 | 404. |
| 5 | 209 | RLKSLMKIL | 9.600 | 405. |
| 6 | 119 | FLVGIEGSL | 8.400 | 406. |
| 7 | 62 | AGPQLPSWL | 7.200 | 407. |
| 8 | 89 | DSVHLAWDL | 7.200 | 408. |
| 9 | 112 | NVVLEAPFL | 6.000 | 409. |
| 10 | 42 | QVVKGSSPL | 6.000 | 410. |
| 11 | 47 | SSPLGPAGL | 6.000 | 411. |
| 12 | 85 | AVLADSVHL | 6.000 | 412. |
| 13 | 156 | AALRGHFCL | 6.000 | 413. |
| 14 | 93 | LAWDLSRSL | 5.760 | 414. |
| 15 | 148 | LYSTHAALA | 5.000 | 415. |
| 16 | 126 | SLKGSTYNL | 4.000 | 416. |
| 17 | 184 | EMDIQNVPL | 4.000 | 417. |
| 18 | 147 | HLYSTHAAL | 4.000 | 418. |
| 19 | 79 | QCAQCHAVL | 4.000 | 419. |
| 20 | 165 | SSDKMVCYL | 4.000 | 420. |
| 21 | 205 | LTHNRLKSL | 4.000 | 421. |
| 22 | 150 | STHAALAAL | 4.000 | 422. |
| 23 | 128 | KGSTYNLLF | 4.000 | 423. |
| 24 | 70 | LQPERCAVF | 3.600 | 424. |
| 25 | 111 | NNVVLEAPF | 3.600 | 425. |
| 26 | 195 | KIAELKEKI | 3.168 | 426. |
| 27 | 138 | GSCGIPVGF | 2.800 | 427. |
| 28 | 161 | HFCLSSDKM | 2.750 | 428. |
| 29 | 12 | CATPPRGDF | 2.400 | 429. |
| 30 | 154 | ALAALRGHF | 2.400 | 430. |
| 31 | 188 | QNVPLSEKI | 2.376 | 431. |
| 32 | 177 | KAIVNASEM | 1.650 | 432. |
| 33 | 179 | IVNASEMDI | 1.500 | 433. |
| 34 | 134 | LLFCGSCGI | 1.000 | 434. |
| 35 | 20 | FCGGTERAI | 1.000 | 435. |
| 36 | 105 | VFSRVTNNV | 0.840 | 436. |
| 37 | 77 | VFQCAQCHA | 0.750 | 437. |
| 38 | 197 | AELKEKIVL | 0.600 | 438. |
| 39 | 107 | SRVTNNVVL | 0.600 | 439. |
| 40 | 58 | EEPAAGPQL | 0.600 | 440. |

TABLE XIII-continued

HLA Peptide Scoring Results - 85P1B3 - A24, 9-mers

| Rank | Start Position | Subsequence Residue Listing | Score (Estimate of Half Time of Disassociation of a Molecule Containing This Subsequence) | Seq. ID# |
|---|---|---|---|---|
| 41 | 166 | SDKMVCYLL | 0.560 | 441. |
| 42 | 191 | PLSEKIAEL | 0.528 | 442. |
| 43 | 29 | DQASFTTSM | 0.500 | 443. |
| 44 | 145 | GFHLYSTHA | 0.500 | 444. |
| 45 | 19 | DFCGGTERA | 0.500 | 445. |
| 46 | 127 | LKGSTYNLL | 0.480 | 446. |
| 47 | 26 | RAIDQASFT | 0.360 | 447. |
| 48 | 175 | KTKAIVNAS | 0.336 | 448. |
| 49 | 168 | KMVCYLLKT | 0.330 | 449. |
| 50 | 99 | RSLGAVVFS | 0.300 | 450. |

TABLE XIV

HLA Peptide Scoring Results-85P1B3-A24, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 171 | CYLLKTKAIV | 7.500 | 451. |
| 2 | 131 | TYNLLFCGSC | 7.500 | 452. |
| 3 | 190 | VPLSEKIAEL | 6.600 | 453. |
| 4 | 196 | IAELKEKIVL | 6.000 | 454. |
| 5 | 41 | TQVVKGSSPL | 6.000 | 455. |
| 6 | 125 | GSLKGSTYNL | 6.000 | 456. |
| 7 | 111 | NNVVLEAPFL | 6.000 | 457. |
| 8 | 84 | HAVLADSVHL | 6.000 | 458. |
| 9 | 61 | AAGPQLPSWL | 5.760 | 459. |
| 10 | 139 | SCGIPVGFHL | 5.600 | 460. |
| 11 | 165 | SSDKMVCYLL | 5.600 | 461. |
| 12 | 148 | LYSTHAALAA | 5.000 | 462. |
| 13 | 19 | DFCGGTERAI | 5.000 | 463. |
| 14 | 46 | GSSPLGPAGL | 4.800 | 464. |
| 15 | 92 | HLAWDLSRSL | 4.800 | 465. |
| 16 | 126 | SLKGSTYNLL | 4.800 | 466. |
| 17 | 164 | LSSDKMVCYL | 4.800 | 467. |
| 18 | 118 | PFLVGIEGSL | 4.200 | 468. |
| 19 | 155 | LAALRGHFCL | 4.000 | 469. |
| 20 | 11 | RCATPPRGDF | 4.000 | 470. |
| 21 | 78 | FQCAQCHAVL | 4.000 | 471. |
| 22 | 149 | YSTHAALAAL | 4.000 | 472. |

TABLE XIV-continued

HLA Peptide Scoring Results-85P1B3-A24, 10-mers

| Rank | Start Position | Subsequence Residue Listing | Score (Estimate of Half Time of Disassociation of a Molecule Containing This Subsequence) | Seq. ID# |
|---|---|---|---|---|
| 23 | 106 | FSRVTNNVVL | 4.000 | 473. |
| 24 | 204 | VLTHNRLKSL | 4.000 | 474. |
| 25 | 110 | TNNVVLEAPF | 3.600 | 475. |
| 26 | 69 | WLQPERCAVF | 3.600 | 476. |
| 27 | 153 | AALAALRGHF | 3.600 | 477. |
| 28 | 137 | CGSCGIPVGF | 2.800 | 478. |
| 29 | 97 | LSRSLGAVVF | 2.000 | 479. |
| 30 | 187 | IQNVPLSEKI | 1.980 | 480. |
| 31 | 178 | AIVNASEMDI | 1.500 | 481. |
| 32 | 114 | VLEAPFLVGI | 1.500 | 482. |
| 33 | 133 | NLLFCGSCGI | 1.500 | 483. |
| 34 | 207 | HNRLKSLMKI | 1.100 | 484. |
| 35 | 170 | VCYLLKTKAI | 1.000 | 485. |
| 36 | 77 | VFQCAQCHAV | 0.750 | 486. |
| 37 | 183 | SEMDIQNVPL | 0.720 | 487. |
| 38 | 208 | NRLKSLMKIL | 0.720 | 488. |
| 39 | 201 | EKIVLTHNRL | 0.720 | 489. |
| 40 | 57 | AEEPAAGPQL | 0.720 | 490. |
| 41 | 146 | FHLYSTHAAL | 0.600 | 491. |
| 42 | 105 | VFSRVTNNVV | 0.600 | 492. |
| 43 | 205 | LTHNRLKSLM | 0.600 | 493. |
| 44 | 135 | LFCGSCGIPV | 0.500 | 494. |
| 45 | 161 | HFCLSSDKMV | 0.500 | 495. |
| 46 | 145 | GFHLYSTHAA | 0.500 | 496. |
| 47 | 32 | SFTTSMEWDT | 0.500 | 497. |
| 48 | 88 | ADSVHLAWDL | 0.480 | 498. |
| 49 | 211 | KSLMKILSEV | 0.462 | 499. |
| 50 | 26 | RAIDQASFTT | 0.360 | 500. |

TABLE XV

HLA Peptide Scoring Results-SSPIB3-B7, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 85 | AVLADSVHL | 60.000 | 501. |
| 2 | 156 | AALRGHFCL | 36.000 | 502. |
| 3 | 112 | NVVLEAPFL | 20.000 | 503. |
| 4 | 42 | QVVKGSSPL | 20.000 | 504. |

TABLE XV-continued

HLA Peptide Scoring Results-SSPIB3-B7, 9-mers

| Rank | Start Position | Subsequence Residue Listing | Score (Estimate of Half Time of Disassociation of a Molecule Containing This Subsequence) | Seq. ID# |
|---|---|---|---|---|
| 5 | 62 | AGPQLPSWL | 12.000 | 505. |
| 6 | 93 | LAWDLSRSL | 12.000 | 506. |
| 7 | 150 | STHAALAAL | 4.000 | 507. |
| 8 | 89 | DSVHLAWDL | 4.000 | 508. |
| 9 | 202 | KIVLTHNRL | 4.000 | 509. |
| 10 | 147 | HLYSTHAAL | 4.000 | 510. |
| 11 | 126 | SLKGSTYNL | 4.000 | 511. |
| 12 | 79 | QCAQCHAVL | 4.000 | 512. |
| 13 | 205 | LTHNRLKSL | 4.000 | 513. |
| 14 | 140 | CGIPVGFHL | 4.000 | 514. |
| 15 | 119 | FLVGIEGSL | 4.000 | 515. |
| 16 | 47 | SSPLGPAGL | 4.000 | 516. |
| 17 | 209 | RLKSLMKIL | 4.000 | 517. |
| 18 | 177 | KAIVNASEM | 3.000 | 518. |
| 19 | 4 | QPLRHRSRC | 3.000 | 519. |
| 20 | 179 | IVNASEMDI | 2.000 | 520. |
| 21 | 97 | LSRSLGAVV | 2.000 | 521. |
| 22 | 106 | FSRVTNNVV | 2.000 | 522. |
| 23 | 184 | EMDIQNVPL | 1.200 | 523. |
| 24 | 165 | SSDKMVCYL | 1.200 | 524. |
| 25 | 197 | AELKEKIVL | 1.200 | 525. |
| 26 | 113 | VVLEAPFLV | 1.000 | 526. |
| 27 | 29 | DQASFTTSM | 1.000 | 527. |
| 28 | 35 | TSMEWDTQV | 0.600 | 528. |
| 29 | 117 | APFLVGIEG | 0.600 | 529. |
| 30 | 212 | SLMKILSEV | 0.600 | 530. |
| 31 | 157 | ALRGHFCLS | 0.600 | 531. |
| 32 | 189 | NVPLSEKIA | 0.500 | 532. |
| 33 | 103 | AVVFSRVTN | 0.450 | 533. |
| 34 | 20 | FCGGTERAI | 0.400 | 534. |
| 35 | 134 | LLFCGSCGI | 0.400 | 535. |
| 36 | 107 | SRVTNNVVL | 0.400 | 536. |
| 37 | 188 | QNVPLSEKI | 0.400 | 537. |
| 38 | 127 | LKGSTYNLL | 0.400 | 538. |
| 39 | 191 | PLSEKIAEL | 0.400 | 539. |
| 40 | 166 | SDKMVCYLL | 0.400 | 540. |
| 41 | 58 | EEPAAGPQL | 0.400 | 541. |

TABLE XV-continued

HLA Peptide Scoring Results-SSPIB3-B7, 9-mers

| Rank | Start Position | Subsequence Residue Listing | Score (Estimate of Half Time of Disassociation of a Molecule Containing This Subsequence) | Seq. ID# |
|---|---|---|---|---|
| 42 | 142 | IPVGFHLYS | 0.400 | 542. |
| 43 | 195 | KIAELKEKI | 0.400 | 543. |
| 44 | 75 | CAVFQCAQC | 0.300 | 544. |
| 45 | 155 | LAALRGHFC | 0.300 | 545. |
| 46 | 48 | SPLGPAGLG | 0.300 | 546. |
| 47 | 53 | AGLGAEEPA | 0.300 | 547. |
| 48 | 69 | WLQPERCAV | 0.300 | 548. |
| 49 | 80 | CAQCHAVLA | 0.300 | 549. |
| 50 | 26 | RAIDQASFT | 0.300 | 550. |

TABLE XVI

HLA Peptide Scoring Results-85P1B3-B7, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 190 | VPLSEKIAEL | 80.000 | 551. |
| 2 | 106 | FSRVTNNVVL | 40.000 | 552. |
| 3 | 61 | AAGPQLPSWL | 36.000 | 553. |
| 4 | 84 | HAVLADSVHL | 12.000 | 554. |
| 5 | 155 | LAALRGHFCL | 12.000 | 555. |
| 6 | 46 | GSSPLGPAGL | 4.000 | 556. |
| 7 | 111 | NNVVLEAPFL | 4.000 | 557. |
| 8 | 92 | HLAWDLSRSL | 4.000 | 558. |
| 9 | 78 | FQCAQCHAVL | 4.000 | 559. |
| 10 | 204 | VLTHNRLKSL | 4.000 | 560. |
| 11 | 139 | SCGIPVGFHL | 4.000 | 561. |
| 12 | 149 | YSTHAALAAL | 4.000 | 562. |
| 13 | 126 | SLKGSTYNLL | 4.000 | 563. |
| 14 | 164 | LSSDKMVCYL | 4.000 | 564. |
| 15 | 41 | TQVVKGSSPL | 4.000 | 565. |
| 16 | 207 | HNRLKSLMKI | 4.000 | 566. |
| 17 | 125 | GSLKGSTYNL | 4.000 | 567. |
| 18 | 196 | IAELKEKIVL | 3.600 | 568. |
| 19 | 15 | PPRGDFCGGT | 2.000 | 569. |
| 20 | 48 | SPLGPAGLGA | 2.000 | 570. |
| 21 | 4 | QPLRHRSRCA | 2.000 | 571. |
| 22 | 142 | IPVGFHLYST | 2.000 | 572. |
| 23 | 66 | LPSWLQPERC | 2.000 | 573. |

TABLE XVI-continued

HLA Peptide Scoring Results-85P1B3-B7, 10-mers

| Rank | Start Position | Subsequence Residue Listing | Score (Estimate of Half Time of Disassociation of a Molecule Containing This Subsequence) | Seq. ID# |
|---|---|---|---|---|
| 24 | 85 | AVLADSVHLA | 1.500 | 574. |
| 25 | 76 | AVFQCAQCHA | 1.500 | 575. |
| 26 | 165 | SSDKMVCYLL | 1.200 | 576. |
| 27 | 117 | APFLVGIEGS | 1.200 | 577. |
| 28 | 88 | ADSVHLAWDL | 1.200 | 578. |
| 29 | 183 | SEMDIQNVPL | 1.200 | 579. |
| 30 | 178 | AIVNASEMDI | 1.200 | 580. |
| 31 | 112 | NVVLEAPFLV | 1.000 | 581. |
| 32 | 205 | LTHNRLKSLM | 1.000 | 582. |
| 33 | 104 | VVFSRVTNNV | 1.000 | 583. |
| 34 | 71 | QPERCAVFQC | 0.600 | 584. |
| 35 | 157 | ALRGHFCLSS | 0.600 | 585. |
| 36 | 181 | NASEMDIQNV | 0.600 | 586. |
| 37 | 35 | TSMEWDTQVV | 0.600 | 587. |
| 38 | 59 | EPAAGPQLPS | 0.600 | 588. |
| 39 | 169 | MVCYLLKTKA | 0.500 | 589. |
| 40 | 108 | RVTNNVVLEA | 0.500 | 590. |
| 41 | 3 | AQPLRHRSRC | 0.450 | 591. |
| 42 | 201 | EKIVLTHNRL | 0.400 | 592. |
| 43 | 170 | VCYLLKTKAI | 0.400 | 593. |
| 44 | 146 | FHLYSTHAAL | 0.400 | 594. |
| 45 | 133 | NLLFCGSCGI | 0.400 | 595. |
| 46 | 187 | IQNVPLSEKI | 0.400 | 596. |
| 47 | 208 | NRLKSLMKIL | 0.400 | 597. |
| 48 | 57 | AEEPAAGPQL | 0.360 | 598. |
| 49 | 53 | AGLGAEEPAA | 0.300 | 599. |
| 50 | 154 | ALAALRGHFC | 0.300 | 600. |

TABLE XVII

HLA Peptide Scoring Results-85P1B3-B35, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 164 | LSSDKMVCY | 20.000 | 601. |
| 2 | 177 | KAIVNASEM | 12.000 | 602. |
| 3 | 209 | RLKSLMKIL | 6.000 | 603. |
| 4 | 93 | LAWDLSRSL | 6.000 | 604. |
| 5 | 89 | DSVHLAWDL | 5.000 | 605. |

TABLE XVII-continued

HLA Peptide Scoring Results-85P1B3-B35, 9-mers

| Rank | Start Position | Subsequence Residue Listing | Score (Estimate of Half Time of Disassociation of a Molecule Containing This Subsequence) | Seq. ID# |
|---|---|---|---|---|
| 6 | 138 | GSCGIPVGF | 5.000 | 606. |
| 7 | 47 | SSPLGPAGL | 5.000 | 607. |
| 8 | 126 | SLKGSTYNL | 3.000 | 608. |
| 9 | 12 | CATPPRGDF | 3.000 | 609. |
| 10 | 156 | AALRGHFCL | 3.000 | 610. |
| 11 | 106 | FSRVTMNVV | 3.000 | 611. |
| 12 | 97 | LSRSLGAVV | 3.000 | 612. |
| 13 | 31 | ASFTTSMEW | 2.500 | 613. |
| 14 | 141 | GIPVGFHLY | 2.000 | 614. |
| 15 | 128 | KGSTYNLLF | 2.000 | 615. |
| 16 | 142 | IPVGFHLYS | 2.000 | 616. |
| 17 | 35 | TSMEWDTQV | 2.000 | 617. |
| 18 | 4 | QPLRHRSRC | 2.000 | 618. |
| 19 | 70 | LQPERCAVF | 2.000 | 619. |
| 20 | 202 | KIVLTHNRL | 2.000 | 620. |
| 21 | 29 | DQASFTTSM | 2.000 | 621. |
| 22 | 124 | EGSLKGSTY | 2.000 | 622. |
| 23 | 195 | KIAELKEKI | 1.600 | 623. |
| 24 | 165 | SSDKMVCYL | 1.500 | 624. |
| 25 | 85 | AVLADSVHL | 1.500 | 625. |
| 26 | 112 | NVVLEAPFL | 1.500 | 626. |
| 27 | 61 | AAGPQLPSW | 1.500 | 627. |
| 28 | 26 | RAIDQASFT | 1.200 | 628. |
| 29 | 62 | AGPQLPSWL | 1.000 | 629. |
| 30 | 119 | FLVGIEGSL | 1.000 | 630. |
| 31 | 140 | CGIPVGFHL | 1.000 | 631. |
| 32 | 154 | ALAALRGHF | 1.000 | 632. |
| 33 | 42 | QVVKGSSPL | 1.000 | 633. |
| 34 | 150 | STHAALAAL | 1.000 | 634. |
| 35 | 205 | LTHNRLKSL | 1.000 | 635. |
| 36 | 99 | RSLGAVVFS | 1.000 | 636. |
| 37 | 79 | QCAQCHAVL | 1.000 | 637. |
| 38 | 147 | HLYSTHAAL | 1.000 | 638. |
| 39 | 111 | NNVVLEAPF | 1.000 | 639. |
| 40 | 221 | TPDQSKPEN | 0.600 | 640. |
| 41 | 198 | ELKEKIVLT | 0.600 | 641. |
| 42 | 181 | NASEMDIQN | 0.600 | 642. |

TABLE XVII-continued

HLA Peptide Scoring Results-85P1B3-B35, 9-mers

| Rank | Start Position | Subsequence Residue Listing | Score (Estimate of Half Time of Disassociation of a Molecule Containing This Subsequence) | Seq. ID# |
|---|---|---|---|---|
| 43 | 175 | KTKAIVNAS | 0.600 | 643. |
| 44 | 125 | GSLKGSTYN | 0.500 | 644. |
| 45 | 129 | GSTYNLLFC | 0.500 | 645. |
| 46 | 149 | YSTHAALAA | 0.500 | 646. |
| 47 | 182 | ASEMDIQNV | 0.450 | 647. |
| 48 | 87 | LADSVHLAW | 0.450 | 648. |
| 49 | 113 | VVLEAPFLV | 0.400 | 649. |
| 50 | 20 | FCGGTERAI | 0.400 | 650. |

TABLE XVIII

HLA Peptide Scoring Results-85P1B3-B35, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 190 | VPLSEKIAEL | 20.000 | 651. |
| 2 | 106 | FSRVTNNVVL | 15.000 | 652. |
| 3 | 97 | LSRSLGAVVF | 15.000 | 653. |
| 4 | 164 | LSSDKMVCYL | 10.000 | 654. |
| 5 | 46 | GSSPLGPAGL | 5.000 | 655. |
| 6 | 149 | YSTHAALAAL | 5.000 | 656. |
| 7 | 125 | GSLKGSTYNL | 5.000 | 657. |
| 8 | 84 | HAVLADSVHL | 4.500 | 658. |
| 9 | 153 | AALAALRGHF | 3.000 | 659. |
| 10 | 61 | AAGPQLPSWL | 3.000 | 660. |
| 11 | 35 | TSMEWDTQVV | 3.000 | 661. |
| 12 | 155 | LAALRGHFCL | 3.000 | 662. |
| 13 | 126 | SLKGSTYNLL | 3.000 | 663. |
| 14 | 117 | APFLVGIEGS | 2.000 | 664. |
| 15 | 140 | CGIPVGFHLY | 2.000 | 665. |
| 16 | 59 | EPAAGPQLPS | 2.000 | 666. |
| 17 | 205 | LTHNRLKSLM | 2.000 | 667. |
| 18 | 4 | QPLRHRSRCA | 2.000 | 668. |
| 19 | 66 | LPSWLQPERC | 2.000 | 669. |
| 20 | 142 | IPVGFHLYST | 2.000 | 670. |
| 21 | 163 | CLSSDKMVCY | 2.000 | 671. |
| 22 | 211 | KSLMKILSEV | 2.000 | 672. |
| 23 | 11 | RCATPPRGDF | 2.000 | 673. |
| 24 | 48 | SPLGPAGLGA | 2.000 | 674. |

TABLE XVIII-continued

HLA Peptide Scoring Results-85P1B3-B35, 10-mers

| Rank | Start Position | Subsequence Residue Listing | Score (Estimate of Half Time of Disassociation of a Molecule Containing This Subsequence) | Seq. ID# |
|---|---|---|---|---|
| 25 | 181 | NASEMDIQNV | 1.800 | 675. |
| 26 | 30 | QASFTTSMEW | 1.500 | 676. |
| 27 | 165 | SSDKMVCYLL | 1.500 | 677. |
| 28 | 111 | NNVVLEAPFL | 1.500 | 678. |
| 29 | 196 | IAELKEKIVL | 1.350 | 679. |
| 30 | 26 | RAIDQASFTT | 1.200 | 680. |
| 31 | 207 | HNRLKSLMKI | 1.200 | 681. |
| 32 | 204 | VLTHNRLKSL | 1.000 | 682. |
| 33 | 137 | CGSCGIPVGF | 1.000 | 683. |
| 34 | 86 | VLADSVHLAW | 1.000 | 684. |
| 35 | 41 | TQVVKGSSPL | 1.000 | 685. |
| 36 | 139 | SCGIPVGFHL | 1.000 | 686. |
| 37 | 92 | HLAWDLSRSL | 1.000 | 687. |
| 38 | 69 | WLQPERCAVF | 1.000 | 688. |
| 39 | 78 | FQCAQCHAVL | 1.000 | 689. |
| 40 | 110 | TNNVVLEAPF | 1.000 | 690. |
| 41 | 195 | KIAELKEKIV | 0.800 | 691. |
| 42 | 209 | RLKSLMKILS | 0.600 | 692. |
| 43 | 15 | PPRGDFCGGT | 0.600 | 693. |
| 44 | 71 | QPERCAVFQC | 0.600 | 694. |
| 45 | 89 | DSVHLAWDLS | 0.500 | 695. |
| 46 | 24 | TERAIDQASF | 0.450 | 696. |
| 47 | 170 | VCYLLKTKAI | 0.400 | 697. |
| 48 | 178 | AIVNASEMDI | 0.400 | 698. |
| 49 | 133 | NLLFCGSCGI | 0.400 | 699. |
| 50 | 187 | IQNVPLSEKI | 0.400 | 700. |

TABLE XIX

Motifs and Post-translational modifications

N-glycosylation site

181–184 NASE (SEQ ID NO: 735)

Protein kinase C phosphorylation site
Number of matches: 4

1  24–26 TER
2 126–128 SLK
3 166–168 SDK
4 193–195 SEK

TABLE XIX-continued

Motifs and Post-translational modifications

Casein kinase II phosphorylation site
Number of matches: 3

1  35–38 TSME (SEQ ID NO: 736)
2 183–186 SEMD (SEQ ID NO: 737)
3 225–228 SKPE (SEQ ID NO: 738)

N-myristoylation site
Number of matches: 5

1  23–28 GTERAI (SEQ ID NO: 739)
2 122–127 GIEGSL (SEQ ID NO: 740)
3 125–130 GSLKGS (SEQ ID NO: 741)
4 129–134 GSTYNL (SEQ ID NO: 742)
5 141–146 GIPVGF (SEQ ID NO: 743)

TABLE XIX-continued

Motifs and Post-translational modifications

RGD Cell attachment sequence

17–19 RGD

Cytochrome c family heme-binding site signature

80–85 CAQCHA

TABLE XX

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome b N | 68% | Cytochrome b(N-terminal)/b6/petB | membrane bound oxidase, generate superoxide |
| ig | 19% | Immunoglobuline domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |

TABLE XX-continued

Frequently Occurring Motifs

| Name | avrg. % identity | Description | Potential Function |
|---|---|---|---|
| EGF | 34% | EGF-like domain | 30–40 amino-acid long found in the extracellular domain of membrane-bound proteins or in secreted proteins |
| rvt | 49% | Reverse transcriptase (RNA-dependent DNA polymerase) | |
| ank | 25% | Ank repeat | Cytoplasmic protein, associates integral membrane proteins to the cytoskeleton |
| oxidored ql | 32% | NADH-Ubiquinone/plastoquinone (complex I), various chains | membrane associated. Involved in proton translocation across the membrane |
| efhand | 24% | EF hand | calcium-binding domain, consists of a12 residue loop flanked on both sides by a 12 residue alpha-helical domain |
| rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| fn3 | 20% | Fibronectin type III domain | Located in the extracellular ligand-binding region of receptors and is about 200 amino acid residues long with two pairs of cysteines involved in disulfide bonds |

TABLE XX-continued

Frequently Occurring Motifs

| Name | avrg. % identity | Description | Potential Function |
|---|---|---|---|
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE XXV

Protein Properties

| | Bioinformatic Program | URL | Outcome |
|---|---|---|---|
| ORF | ORF Finder | http://www.ncbi.nlm.gov/gorf | 13–702 (includes stop) |
| Protein Length | | | 229 amino acids |
| Transmembrane region | TM Pred | http://www.ch.embnet.org/ | one TM at aa 129–149 |
| | HMMTop | http://www.enzim.hu/hmmtop/ | one TM at aa 134–158 |
| | Sosui | http://www.genome.ad.jp/SOSui/ | indicates no TM, soluble protein |
| | TMHMM | http://www.cbs.dtu.dk/services/TMHMM | indicates no TM |
| Signal Peptide | Signal P | http://www.cbs.dtu.dk/services/SignalP/ | indicates no signal |
| pI | pI/MW tool | http://www.expasy.ch/tools/ | pI 7.02 |
| Molecular weight | pI/MW tool | http://www.expasy.ch/tools/ | 24.69 kDa |
| Localization | PSORT | http://psort.nibb.ac.jp/ | Cytoplasmic 65% Mitochondrial 10% |
| | PSORT II | http://psort.nibb.ac.jp/ | Mitochondrial 60.9% Cytoplamic 21.7% |
| Motifs | Pfam | http://www.sanger.ac.uk/Pfam/ | no motif detected |
| | Prints | http://www.biochem.ucl.ac.uk/ | no significant motif |
| | Blocks | http://www.blocks.fhcrc.org/ | soybean trypsin inhibitor protease family, Cytochrome c |
| | Prosite | http://www.genome.ad.jp/ | Cytochrome c family, heme binding signature |

The invention claimed is:

1. An isolated monoclonal antibody or fragment thereof that specifically binds to a protein comprising the amino acid sequence of SEQ ID NO: 728, wherein the antibody or fragment thereof is conjugated to a diagnostic agent or a cytotoxic agent.

2. The antibody or fragment thereof of claim 1, wherein the antibody is a human antibody, a humanized antibody or a chimeric antibody.

3. The antibody or fragment thereof of claim 1, wherein the fragment is an Fab, F(ab')2, Fv or sFv fragment.

4. The antibody or fragment thereof of claim 1, wherein the cytotoxic agent is selected from the group consisting of radioactive isotopes, chemotherapeutic agents and toxins.

5. The antibody or fragment thereof of claim 4, wherein the radioactive isotope is selected from the group consisting of $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

6. The antibody or fragment thereof of claim 4, wherein the chemotherapeutic agent is selected from the group consisting of actinomycin, mitomycin, etoposide, tenoposide, vincristine, vinblastine, colchicine, gelonin, and calicheamicin.

7. The antibody or fragment thereof of claim 4, wherein the toxin is selected from the group consisting of diphtheria toxin, enomycin, phenomycin, *Pseudomonas* exotoxin (PE) A, PE40, abrin, abrin A chain, mitogellin, modeccin A chain, and alpha-sarcin.

8. The antibody or fragment thereof of claim 1, wherein the antibody or fragment thereof further comprises a pharmaceutically acceptable carrier.

* * * * *

```
                            SEQUENCE LISTING

<160> NUMBER OF SEQ ID NOS: 879

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 1

Val Leu Glu Ala Pro Phe Leu Val Gly
  1               5

<210> SEQ ID NO 2
<211> LENGTH: 9
<212> TYPE: PRT
<213> ORGANISM: Artificial Sequence
```

```
<220> FEATURE:
<223> OTHER INFORMATION: Description of Artificial Sequence: Peptide
      motif

<400> SEQUENCE: 2

Leu Ser Glu Lys Ile Ala Glu Leu Lys
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 3

Leu Ala Asp Ser Val His Leu Ala Trp
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 4

Ala Ile Asp Gln Ala Ser Phe Thr Thr
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 5

Leu Ser Ser Asp Lys Met Val Cys Tyr
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 6

Leu Ser Glu Val Thr Pro Asp Gln Ser
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 7

Ala Ser Glu Met Asp Ile Gln Asn Val
 1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 8

Cys Ala Thr Pro Pro Arg Gly Asp Phe
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 9

Gly Ile Glu Gly Ser Leu Lys Gly Ser
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 10

Ile Ala Glu Leu Lys Glu Lys Ile Val
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 11

Gly Ile Pro Val Gly Phe His Leu Tyr
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 12

Ser Leu Gly Ala Val Val Phe Ser Arg
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 13

Glu Met Asp Ile Gln Asn Val Pro Leu
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 14

Ala Glu Glu Pro Ala Ala Gly Pro Gln
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 15

Ser Met Glu Trp Asp Thr Gln Val Val
  1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 16

Gly Ser Ser Pro Leu Gly Pro Ala Gly
  1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 17

Gly Ser Cys Gly Ile Pro Val Gly Phe
  1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 18

Ala Thr Pro Pro Arg Gly Asp Phe Cys
  1               5

<210> SEQ ID NO 19
<211> LENGTH: 9
<212> TYPE: PRT
```

```
<213> ORGANISM: Artificial Sequence
<220> FEATURE:
<223> OTHER INFORMATION: Description of Artificial Sequence: Peptide
      motif

<400> SEQUENCE: 19

Thr Pro Asp Gln Ser Lys Pro Glu Asn
  1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 20

Gly Thr Glu Arg Ala Ile Asp Gln Ala
  1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 21

Ala Ala Gly Pro Gln Leu Pro Ser Trp
  1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 22

Leu Val Gly Ile Glu Gly Ser Leu Lys
  1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 23

Met Val Cys Tyr Leu Leu Lys Thr Lys
  1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 24

Ile Val Leu Thr His Asn Arg Leu Lys
  1               5
```

-continued

```
<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 25

Gly Ala Glu Glu Pro Ala Ala Gly Pro
 1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 26

Ser Thr Tyr Asn Leu Leu Phe Cys Gly
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 27

Lys Gly Ser Thr Tyr Asn Leu Leu Phe
 1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 28

Cys Gly Ile Pro Val Gly Phe His Leu
 1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 29

Glu Gly Ser Leu Lys Gly Ser Thr Tyr
 1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 30

Val Thr Asn Asn Val Val Leu Glu Ala
 1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 31

Met Ala Ala Gln Pro Leu Arg His Arg
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 32

Ala Ala Gln Pro Leu Arg His Arg Ser
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 33

Trp Leu Gln Pro Glu Arg Cys Ala Val
 1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 34

Ala Leu Ala Ala Leu Arg Gly His Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 35

Ser Ser Asp Lys Met Val Cys Tyr Leu
 1               5

<210> SEQ ID NO 36
<211> LENGTH: 9
```

```
<212> TYPE: PRT
<213> ORGANISM: Artificial Sequence
<220> FEATURE:
<223> OTHER INFORMATION: Description of Artificial Sequence: Peptide
      motif

<400> SEQUENCE: 36

Ala Ser Phe Thr Thr Ser Met Glu Trp
 1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 37

Gly Ser Thr Tyr Asn Leu Leu Phe Cys
 1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 38

Tyr Ser Thr His Ala Ala Leu Ala Ala
 1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 39

Leu Pro Ser Trp Leu Gln Pro Glu Arg
 1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 40

Phe Cys Gly Ser Cys Gly Ile Pro Val
 1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 41

Asn Asn Val Val Leu Glu Ala Pro Phe
```

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 42

Ser Thr His Ala Ala Leu Ala Ala Leu
 1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 43

Asp Lys Met Val Cys Tyr Leu Leu Lys
 1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 44

Pro Leu Gly Pro Ala Gly Leu Gly Ala
 1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 45

Val Leu Thr His Asn Arg Leu Lys Ser
 1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 46

Cys Leu Ser Ser Asp Lys Met Val Cys
 1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Peptide

```
                               motif

<400> SEQUENCE: 47

Glu Trp Asp Thr Gln Val Val Lys Gly
  1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 48

His Ala Ala Leu Ala Ala Leu Arg Gly
  1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 49

Ile Val Asn Ala Ser Glu Met Asp Ile
  1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 50

Asn Ala Ser Glu Met Asp Ile Gln Asn
  1               5

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 51

Leu Ser Glu Val Thr Pro Asp Gln Ser Lys
  1               5                  10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 52

Ser Met Glu Trp Asp Thr Gln Val Val Lys
  1               5                  10

<210> SEQ ID NO 53
```

```
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 53

Ile Ala Glu Leu Lys Glu Lys Ile Val Leu
  1               5                  10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 54

Trp Leu Gln Pro Glu Arg Cys Ala Val Phe
  1               5                  10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 55

Val Leu Glu Ala Pro Phe Leu Val Gly Ile
  1               5                  10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 56

Arg Gly Asp Phe Cys Gly Gly Thr Glu Arg
  1               5                  10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 57

Cys Gly Ile Pro Val Gly Phe His Leu Tyr
  1               5                  10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 58
```

-continued

```
Ala Thr Pro Pro Arg Gly Asp Phe Cys Gly
 1               5                  10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 59

Cys Leu Ser Ser Asp Lys Met Val Cys Tyr
 1               5                  10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 60

Ala Ala Gln Pro Leu Arg His Arg Ser Arg
 1               5                  10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 61

Gly Ala Glu Glu Pro Ala Ala Gly Pro Gln
 1               5                  10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 62

Ala Glu Glu Pro Ala Ala Gly Pro Gln Leu
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 63

Gly Ile Glu Gly Ser Leu Lys Gly Ser Thr
 1               5                  10

<210> SEQ ID NO 64
<211> LENGTH: 10
<212> TYPE: PRT
<213> ORGANISM: Artificial Sequence
<220> FEATURE:
```

```
<223> OTHER INFORMATION: Description of Artificial Sequence: Peptide
      motif

<400> SEQUENCE: 64

Arg Ser Leu Gly Ala Val Val Phe Ser Arg
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 65

Ala Ile Asp Gln Ala Ser Phe Thr Thr Ser
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 66

Ser Val His Leu Ala Trp Asp Leu Ser Arg
 1               5                  10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 67

Glu Met Asp Ile Gln Asn Val Pro Leu Ser
 1               5                  10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 68

Ser Thr His Ala Ala Leu Ala Ala Leu Arg
 1               5                  10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 69

Gly Ser Ser Pro Leu Gly Pro Ala Gly Leu
 1               5                  10
```

```
<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 70

Gly Thr Glu Arg Ala Ile Asp Gln Ala Ser
 1               5                  10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 71

Phe Leu Val Gly Ile Glu Gly Ser Leu Lys
 1               5                  10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 72

Lys Ile Val Leu Thr His Asn Arg Leu Lys
 1               5                  10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 73

Asp Ile Gln Asn Val Pro Leu Ser Glu Lys
 1               5                  10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 74

Gln Leu Pro Ser Trp Leu Gln Pro Glu Arg
 1               5                  10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 75
```

```
Ser Ser Asp Lys Met Val Cys Tyr Leu Leu
1               5                   10
```

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 76

```
Ala Ser Glu Met Asp Ile Gln Asn Val Pro
1               5                   10
```

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 77

```
Ala Trp Asp Leu Ser Arg Ser Leu Gly Ala
1               5                   10
```

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 78

```
Gln Pro Glu Arg Cys Ala Val Phe Gln Cys
1               5                   10
```

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 79

```
Leu Ala Asp Ser Val His Leu Ala Trp Asp
1               5                   10
```

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 80

```
Cys Ala Thr Pro Pro Arg Gly Asp Phe Cys
1               5                   10
```

<210> SEQ ID NO 81
<211> LENGTH: 10
<212> TYPE: PRT
<213> ORGANISM: Artificial Sequence

```
<220> FEATURE:
<223> OTHER INFORMATION: Description of Artificial Sequence: Peptide
      motif

<400> SEQUENCE: 81

Arg Cys Ala Thr Pro Pro Arg Gly Asp Phe
  1               5                  10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 82

Ala Ala Leu Ala Ala Leu Arg Gly His Phe
  1               5                  10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 83

Ala Ala Gly Pro Gln Leu Pro Ser Trp Leu
  1               5                  10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 84

Lys Met Val Cys Tyr Leu Leu Lys Thr Lys
  1               5                  10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 85

Gly Ser Thr Tyr Asn Leu Leu Phe Cys Gly
  1               5                  10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 86

Leu Ser Glu Lys Ile Ala Glu Leu Lys Glu
  1               5                  10
```

```
<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 87

Glu Ala Pro Phe Leu Val Gly Ile Glu Gly
 1               5                  10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 88

Leu Ala Ala Leu Arg Gly His Phe Cys Leu
 1               5                  10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 89

Ile Val Leu Thr His Asn Arg Leu Lys Ser
 1               5                  10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 90

Asn Val Val Leu Glu Ala Pro Phe Leu Val
 1               5                  10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 91

Ser Cys Gly Ile Pro Val Gly Phe His Leu
 1               5                  10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 92

Ala Ile Val Asn Ala Ser Glu Met Asp Ile
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 93

Arg Ala Ile Asp Gln Ala Ser Phe Thr Thr
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 94

Arg Gly His Phe Cys Leu Ser Ser Asp Lys
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 95

Thr Asn Asn Val Val Leu Glu Ala Pro Phe
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 96

Arg Val Thr Asn Asn Val Val Leu Glu Ala
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 97

Gln Ala Ser Phe Thr Thr Ser Met Glu Trp
1               5                   10

<210> SEQ ID NO 98
<211> LENGTH: 10
<212> TYPE: PRT
```

```
<213> ORGANISM: Artificial Sequence
<220> FEATURE:
<223> OTHER INFORMATION: Description of Artificial Sequence: Peptide
      motif

<400> SEQUENCE: 98

Val Val Leu Glu Ala Pro Phe Leu Val Gly
 1               5                  10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 99

Leu Val Gly Ile Glu Gly Ser Leu Lys Gly
 1               5                  10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 100

Cys Gly Ser Cys Gly Ile Pro Val Gly Phe
 1               5                  10

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 101

Val Val Leu Glu Ala Pro Phe Leu Val
 1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 102

Ser Leu Met Lys Ile Leu Ser Glu Val
 1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 103

Tyr Leu Leu Lys Thr Lys Ala Ile Val
 1               5
```

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 104

Trp Leu Gln Pro Glu Arg Cys Ala Val
 1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 105

Val Leu Ala Asp Ser Val His Leu Ala
 1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 106

Leu Leu Phe Cys Gly Ser Cys Gly Ile
 1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 107

Lys Met Val Cys Tyr Leu Leu Lys Thr
 1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 108

Phe Gln Cys Ala Gln Cys His Ala Val
 1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Peptide
      motif

```
<400> SEQUENCE: 109

Phe Leu Val Gly Ile Glu Gly Ser Leu
 1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 110

Asn Val Val Leu Glu Ala Pro Phe Leu
 1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 111

Lys Ile Val Leu Thr His Asn Arg Leu
 1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 112

Lys Ile Ala Glu Leu Lys Glu Lys Ile
 1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 113

Phe Cys Leu Ser Ser Asp Lys Met Val
 1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 114

Ala Val Leu Ala Asp Ser Val His Leu
 1               5

<210> SEQ ID NO 115
<211> LENGTH: 9
```

```
<212> TYPE: PRT
<213> ORGANISM: Artificial Sequence
<220> FEATURE:
<223> OTHER INFORMATION: Description of Artificial Sequence: Peptide
      motif

<400> SEQUENCE: 115

Thr Ser Met Glu Trp Asp Thr Gln Val
 1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 116

Ala Ala Leu Arg Gly His Phe Cys Leu
 1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 117

Gly Leu Gly Ala Glu Glu Pro Ala Ala
 1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 118

Pro Leu Ser Glu Lys Ile Ala Glu Leu
 1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 119

Phe Thr Thr Ser Met Glu Trp Asp Thr
 1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 120

Leu Ala Trp Asp Leu Ser Arg Ser Leu
```

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 121

Leu Glu Ala Pro Phe Leu Val Gly Ile
 1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 122

Ala Ile Asp Gln Ala Ser Phe Thr Thr
 1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 123

Arg Ala Ile Asp Gln Ala Ser Phe Thr
 1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 124

His Leu Tyr Ser Thr His Ala Ala Leu
 1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 125

Phe Cys Gly Ser Cys Gly Ile Pro Val
 1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Peptide -continued motif

<400> SEQUENCE: 126

Cys Leu Ser Ser Asp Lys Met Val Cys
  1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 127

Gln Val Val Lys Gly Ser Ser Pro Leu
  1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 128

Asp Leu Ser Arg Ser Leu Gly Ala Val
  1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 129

Ile Val Asn Ala Ser Glu Met Asp Ile
  1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 130

Leu Gly Ala Val Val Phe Ser Arg Val
  1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 131

Ser Met Glu Trp Asp Thr Gln Val Val
  1               5

<210> SEQ ID NO 132

```
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 132

Leu Thr His Asn Arg Leu Lys Ser Leu
 1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 133

Cys Gly Ile Pro Val Gly Phe His Leu
 1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 134

Ala Gly Pro Gln Leu Pro Ser Trp Leu
 1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 135

Ser Leu Lys Gly Ser Thr Tyr Asn Leu
 1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 136

Ser Ser Asp Lys Met Val Cys Tyr Leu
 1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 137
```

```
Arg Leu Lys Ser Leu Met Lys Ile Leu
 1               5
```

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 138

```
Ser Thr His Ala Ala Leu Ala Ala Leu
 1               5
```

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 139

```
Leu Ala Ala Leu Arg Gly His Phe Cys
 1               5
```

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 140

```
Ala Glu Leu Lys Glu Lys Ile Val Leu
 1               5
```

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 141

```
Glu Met Asp Ile Gln Asn Val Pro Leu
 1               5
```

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 142

```
Gly Ser Thr Tyr Asn Leu Leu Phe Cys
 1               5
```

<210> SEQ ID NO 143
<211> LENGTH: 9
<212> TYPE: PRT
<213> ORGANISM: Artificial Sequence
<220> FEATURE:

```
<223> OTHER INFORMATION: Description of Artificial Sequence: Peptide
      motif

<400> SEQUENCE: 143

Asn Leu Leu Phe Cys Gly Ser Cys Gly
  1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 144

Tyr Asn Leu Leu Phe Cys Gly Ser Cys
  1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 145

Val Thr Asn Asn Val Val Leu Glu Ala
  1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 146

Lys Ala Ile Val Asn Ala Ser Glu Met
  1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 147

Ser Leu Gly Ala Val Val Phe Ser Arg
  1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 148

Ala Thr Pro Pro Arg Gly Asp Phe Cys
  1               5
```

```
<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 149

Glu Leu Lys Glu Lys Ile Val Leu Thr
 1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 150

Asn Val Pro Leu Ser Glu Lys Ile Ala
 1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 151

Ser Leu Gly Ala Val Val Phe Ser Arg Val
 1               5                  10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 152

Val Leu Thr His Asn Arg Leu Lys Ser Leu
 1               5                  10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 153

Lys Ile Ala Glu Leu Lys Glu Lys Ile Val
 1               5                  10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 154
```

```
Asn Leu Leu Phe Cys Gly Ser Cys Gly Ile
 1               5                  10

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 155

Val Val Phe Ser Arg Val Thr Asn Asn Val
 1               5                  10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 156

Asn Val Val Leu Glu Ala Pro Phe Leu Val
 1               5                  10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 157

Ala Leu Ala Ala Leu Arg Gly His Phe Cys
 1               5                  10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 158

Lys Ser Leu Met Lys Ile Leu Ser Glu Val
 1               5                  10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 159

Leu Ser Ser Asp Lys Met Val Cys Tyr Leu
 1               5                  10

<210> SEQ ID NO 160
<211> LENGTH: 10
<212> TYPE: PRT
<213> ORGANISM: Artificial Sequence
```

```
<220> FEATURE:
<223> OTHER INFORMATION: Description of Artificial Sequence: Peptide
      motif

<400> SEQUENCE: 160

Val Leu Glu Ala Pro Phe Leu Val Gly Ile
 1               5                  10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 161

Asn Ala Ser Glu Met Asp Ile Gln Asn Val
 1               5                  10

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 162

Ser Glu Met Asp Ile Gln Asn Val Pro Leu
 1               5                  10

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 163

Ser Leu Met Lys Ile Leu Ser Glu Val Thr
 1               5                  10

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 164

Phe Gln Cys Ala Gln Cys His Ala Val Leu
 1               5                  10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 165

Ala Val Leu Ala Asp Ser Val His Leu Ala
 1               5                  10
```

```
<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 166

Leu Ala Ala Leu Arg Gly His Phe Cys Leu
 1               5                  10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 167

Thr Ser Met Glu Trp Asp Thr Gln Val Val
 1               5                  10

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 168

Arg Ala Ile Asp Gln Ala Ser Phe Thr Thr
 1               5                  10

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 169

Thr Gln Val Val Lys Gly Ser Ser Pro Leu
 1               5                  10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 170

Asp Leu Ser Arg Ser Leu Gly Ala Val Val
 1               5                  10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 171

Val Pro Leu Ser Glu Lys Ile Ala Glu Leu
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 172

Ala Ala Gly Pro Gln Leu Pro Ser Trp Leu
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 173

Ala Val Phe Gln Cys Ala Gln Cys His Ala
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 174

Tyr Ser Thr His Ala Ala Leu Ala Ala Leu
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 175

Lys Gly Ser Thr Tyr Asn Leu Leu Phe Cys
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 176

Ala Ile Val Asn Ala Ser Glu Met Asp Ile
1               5                   10

<210> SEQ ID NO 177
<211> LENGTH: 10
<212> TYPE: PRT
```

```
<213> ORGANISM: Artificial Sequence
<220> FEATURE:
<223> OTHER INFORMATION: Description of Artificial Sequence: Peptide
      motif

<400> SEQUENCE: 177

Ala Glu Leu Lys Glu Lys Ile Val Leu Thr
 1               5                  10

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 178

Ser Leu Lys Gly Ser Thr Tyr Asn Leu Leu
 1               5                  10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 179

Arg Val Thr Asn Asn Val Val Leu Glu Ala
 1               5                  10

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 180

Thr Thr Ser Met Glu Trp Asp Thr Gln Val
 1               5                  10

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 181

Ile Gln Asn Val Pro Leu Ser Glu Lys Ile
 1               5                  10

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 182

Ser Cys Gly Ile Pro Val Gly Phe His Leu
 1               5                  10
```

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 183

Asn Asn Val Val Leu Glu Ala Pro Phe Leu
 1               5                  10

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 184

Met Val Cys Tyr Leu Leu Lys Thr Lys Ala
 1               5                  10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 185

Leu Leu Lys Thr Lys Ala Ile Val Asn Ala
 1               5                  10

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 186

His Leu Tyr Ser Thr His Ala Ala Leu Ala
 1               5                  10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 187

Tyr Leu Leu Lys Thr Lys Ala Ile Val Asn
 1               5                  10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Peptide
      motif -continued

```
<400> SEQUENCE: 188

Val Leu Ala Asp Ser Val His Leu Ala Trp
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 189

Gly Ser Leu Lys Gly Ser Thr Tyr Asn Leu
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 190

Ala Gln Pro Leu Arg His Arg Ser Arg Cys
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 191

Trp Asp Leu Ser Arg Ser Leu Gly Ala Val
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 192

Val Cys Tyr Leu Leu Lys Thr Lys Ala Ile
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 193

Ile Leu Ser Glu Val Thr Pro Asp Gln Ser
1               5                   10

<210> SEQ ID NO 194
<211> LENGTH: 10
```

```
<212> TYPE: PRT
<213> ORGANISM: Artificial Sequence
<220> FEATURE:
<223> OTHER INFORMATION: Description of Artificial Sequence: Peptide
      motif

<400> SEQUENCE: 194

Phe His Leu Tyr Ser Thr His Ala Ala Leu
  1               5                  10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 195

Phe Cys Leu Ser Ser Asp Lys Met Val Cys
  1               5                  10

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 196

Ala Asp Ser Val His Leu Ala Trp Asp Leu
  1               5                  10

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 197

Gln Cys His Ala Val Leu Ala Asp Ser Val
  1               5                  10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 198

Gly Ile Pro Val Gly Phe His Leu Tyr Ser
  1               5                  10

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 199

Val Gly Phe His Leu Tyr Ser Thr His Ala
```

-continued

```
<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 200

Met Glu Trp Asp Thr Gln Val Val Lys Gly
 1               5                  10

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 201

Ser Leu Gly Ala Val Val Phe Ser Arg
 1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 202

Lys Met Val Cys Tyr Leu Leu Lys Thr
 1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 203

Gly Ile Pro Val Gly Phe His Leu Tyr
 1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 204

His Leu Tyr Ser Thr His Ala Ala Leu
 1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Peptide
```

```
      motif

<400> SEQUENCE: 205

Leu Leu Phe Cys Gly Ser Cys Gly Ile
 1               5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 206

Ser Leu Lys Gly Ser Thr Tyr Asn Leu
 1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 207

Leu Val Gly Ile Glu Gly Ser Leu Lys
 1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 208

Met Val Cys Tyr Leu Leu Lys Thr Lys
 1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 209

Ile Gln Asn Val Pro Leu Ser Glu Lys
 1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 210

Ser Leu Met Lys Ile Leu Ser Glu Val
 1               5

<210> SEQ ID NO 211
```

```
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 211

Phe Leu Val Gly Ile Glu Gly Ser Leu
 1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 212

Gly Leu Gly Ala Glu Glu Pro Ala Ala
 1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 213

Ala Leu Ala Ala Leu Arg Gly His Phe
 1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 214

Val Leu Ala Asp Ser Val His Leu Ala
 1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 215

Arg Leu Lys Ser Leu Met Lys Ile Leu
 1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 216
```

```
Cys Leu Ser Ser Asp Lys Met Val Cys
  1               5
```

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 217

```
Gly His Phe Cys Leu Ser Ser Asp Lys
  1               5
```

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 218

```
Trp Leu Gln Pro Glu Arg Cys Ala Val
  1               5
```

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 219

```
Tyr Leu Leu Lys Thr Lys Ala Ile Val
  1               5
```

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 220

```
Met Glu Trp Asp Thr Gln Val Val Lys
  1               5
```

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 221

```
Ile Val Leu Thr His Asn Arg Leu Lys
  1               5
```

<210> SEQ ID NO 222
<211> LENGTH: 9
<212> TYPE: PRT
<213> ORGANISM: Artificial Sequence
<220> FEATURE:

```
<223> OTHER INFORMATION: Description of Artificial Sequence: Peptide
      motif

<400> SEQUENCE: 222

Lys Ile Val Leu Thr His Asn Arg Leu
 1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 223

Lys Ile Ala Glu Leu Lys Glu Lys Ile
 1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 224

Ser Met Glu Trp Asp Thr Gln Val Val
 1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 225

Glu Met Asp Ile Gln Asn Val Pro Leu
 1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 226

Ala Leu Arg Gly His Phe Cys Leu Ser
 1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 227

Val Leu Glu Ala Pro Phe Leu Val Gly
 1               5
```

```
<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 228

Leu Ser Glu Lys Ile Ala Glu Leu Lys
 1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 229

Pro Leu Ser Glu Lys Ile Ala Glu Leu
 1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 230

Val Val Leu Glu Ala Pro Phe Leu Val
 1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 231

Ser Glu Val Thr Pro Asp Gln Ser Lys
 1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 232

Ile Val Asn Ala Ser Glu Met Asp Ile
 1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 233
```

Ala Val Phe Gln Cys Ala Gln Cys His
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 234

Leu Met Lys Ile Leu Ser Glu Val Thr
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 235

Leu Gln Pro Glu Arg Cys Ala Val Phe
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 236

Gln Leu Pro Ser Trp Leu Gln Pro Glu
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 237

Ala Val Leu Ala Asp Ser Val His Leu
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 238

Gln Val Val Lys Gly Ser Ser Pro Leu
1               5

<210> SEQ ID NO 239
<211> LENGTH: 9
<212> TYPE: PRT
<213> ORGANISM: Artificial Sequence

```
<220> FEATURE:
<223> OTHER INFORMATION: Description of Artificial Sequence: Peptide
      motif

<400> SEQUENCE: 239

Asn Val Val Leu Glu Ala Pro Phe Leu
 1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 240

Val Thr Asn Asn Val Val Leu Glu Ala
 1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 241

His Asn Arg Leu Lys Ser Leu Met Lys
 1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 242

Val Leu Thr His Asn Arg Leu Lys Ser
 1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 243

Gly Ser Cys Gly Ile Pro Val Gly Phe
 1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 244

Glu Leu Lys Glu Lys Ile Val Leu Thr
 1               5
```

```
<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 245

Gly Asp Phe Cys Gly Gly Thr Glu Arg
  1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 246

His Leu Ala Trp Asp Leu Ser Arg Ser
  1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 247

Pro Leu Gly Pro Ala Gly Leu Gly Ala
  1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 248

Ile Leu Ser Glu Val Thr Pro Asp Gln
  1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 249

Gly Thr Glu Arg Ala Ile Asp Gln Ala
  1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 250

Ser Thr His Ala Ala Leu Ala Ala Leu
 1               5

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 251

Lys Met Val Cys Tyr Leu Leu Lys Thr Lys
 1               5                  10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 252

Phe Leu Val Gly Ile Glu Gly Ser Leu Lys
 1               5                  10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 253

Ser Met Glu Trp Asp Thr Gln Val Val Lys
 1               5                  10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 254

Cys Leu Ser Ser Asp Lys Met Val Cys Tyr
 1               5                  10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 255

Pro Leu Ser Glu Lys Ile Ala Glu Leu Lys
 1               5                  10

<210> SEQ ID NO 256
<211> LENGTH: 10
<212> TYPE: PRT
```

```
<213> ORGANISM: Artificial Sequence
<220> FEATURE:
<223> OTHER INFORMATION: Description of Artificial Sequence: Peptide
      motif

<400> SEQUENCE: 256

Gln Leu Pro Ser Trp Leu Gln Pro Glu Arg
 1               5                  10

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 257

Trp Leu Gln Pro Glu Arg Cys Ala Val Phe
 1               5                  10

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 258

Val Leu Glu Ala Pro Phe Leu Val Gly Ile
 1               5                  10

<210> SEQ ID NO 259
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 259

Ser Val His Leu Ala Trp Asp Leu Ser Arg
 1               5                  10

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 260

Asp Ile Gln Asn Val Pro Leu Ser Glu Lys
 1               5                  10

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 261

His Leu Tyr Ser Thr His Ala Ala Leu Ala
 1               5                  10
```

```
<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 262

Ser Leu Gly Ala Val Val Phe Ser Arg Val
 1               5                  10

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 263

Lys Ile Val Leu Thr His Asn Arg Leu Lys
 1               5                  10

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 264

Ser Leu Lys Gly Ser Thr Tyr Asn Leu Leu
 1               5                  10

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 265

Asn Leu Leu Phe Cys Gly Ser Cys Gly Ile
 1               5                  10

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 266

Glu Leu Lys Glu Lys Ile Val Leu Thr His
 1               5                  10

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 267

Arg Ser Leu Gly Ala Val Val Phe Ser Arg
 1               5                  10

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 268

Val Leu Ala Asp Ser Val His Leu Ala Trp
 1               5                  10

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 269

Val Leu Thr His Asn Arg Leu Lys Ser Leu
 1               5                  10

<210> SEQ ID NO 270
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 270

Ala Leu Arg Gly His Phe Cys Leu Ser Ser
 1               5                  10

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 271

Leu Leu Lys Thr Lys Ala Ile Val Asn Ala
 1               5                  10

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 272

Ala Leu Ala Ala Leu Arg Gly His Phe Cys
 1               5                  10

<210> SEQ ID NO 273
<211> LENGTH: 10
```

```
<212> TYPE: PRT
<213> ORGANISM: Artificial Sequence
<220> FEATURE:
<223> OTHER INFORMATION: Description of Artificial Sequence: Peptide
      motif

<400> SEQUENCE: 273

Ser Thr His Ala Ala Leu Ala Ala Leu Arg
 1               5                  10

<210> SEQ ID NO 274
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 274

Arg Val Thr Asn Asn Val Val Leu Glu Ala
 1               5                  10

<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 275

Ala Ile Val Asn Ala Ser Glu Met Asp Ile
 1               5                  10

<210> SEQ ID NO 276
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 276

Val Val Phe Ser Arg Val Thr Asn Asn Val
 1               5                  10

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 277

Ser Leu Met Lys Ile Leu Ser Glu Val Thr
 1               5                  10

<210> SEQ ID NO 278
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 278

Leu Ser Glu Val Thr Pro Asp Gln Ser Lys
```

```
<210> SEQ ID NO 279
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 279

Ala Val Phe Gln Cys Ala Gln Cys His Ala
 1               5                  10

<210> SEQ ID NO 280
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 280

Ala Val Leu Ala Asp Ser Val His Leu Ala
 1               5                  10

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 281

Asn Val Val Leu Glu Ala Pro Phe Leu Val
 1               5                  10

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 282

Arg Leu Lys Ser Leu Met Lys Ile Leu Ser
 1               5                  10

<210> SEQ ID NO 283
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 283

Gly Ile Pro Val Gly Phe His Leu Tyr Ser
 1               5                  10

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence: Peptide
```

-continued motif

<400> SEQUENCE: 284

Tyr Leu Leu Lys Thr Lys Ala Ile Val Asn
 1               5                  10

<210> SEQ ID NO 285
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 285

Asp Leu Ser Arg Ser Leu Gly Ala Val Val
 1               5                  10

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 286

Gly Leu Gly Ala Glu Glu Pro Ala Ala Gly
 1               5                  10

<210> SEQ ID NO 287
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 287

His Leu Ala Trp Asp Leu Ser Arg Ser Leu
 1               5                  10

<210> SEQ ID NO 288
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 288

Ile Leu Ser Glu Val Thr Pro Asp Gln Ser
 1               5                  10

<210> SEQ ID NO 289
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 289

Lys Ile Ala Glu Leu Lys Glu Lys Ile Val
 1               5                  10

<210> SEQ ID NO 290

```
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 290

Ser Glu Lys Ile Ala Glu Leu Lys Glu Lys
 1               5                  10

<210> SEQ ID NO 291
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 291

Val Val Leu Glu Ala Pro Phe Leu Val Gly
 1               5                  10

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 292

Gly Ser Leu Lys Gly Ser Thr Tyr Asn Leu
 1               5                  10

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 293

Ser Asp Lys Met Val Cys Tyr Leu Leu Lys
 1               5                  10

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 294

Thr His Asn Arg Leu Lys Ser Leu Met Lys
 1               5                  10

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 295
```

-continued

```
Glu Met Asp Ile Gln Asn Val Pro Leu Ser
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 296

Lys Glu Lys Ile Val Leu Thr His Asn Arg
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 297

Leu Leu Phe Cys Gly Ser Cys Gly Ile Pro
1               5                   10

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 298

Thr Thr Ser Met Glu Trp Asp Thr Gln Val
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 299

Ser Thr Tyr Asn Leu Leu Phe Cys Gly Ser
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 300

Thr Gln Val Val Lys Gly Ser Ser Pro Leu
1               5                   10

<210> SEQ ID NO 301
<211> LENGTH: 9
<212> TYPE: PRT
<213> ORGANISM: Artificial Sequence
<220> FEATURE:
```

```
<223> OTHER INFORMATION: Description of Artificial Sequence: Peptide
      motif

<400> SEQUENCE: 301

Leu Val Gly Ile Glu Gly Ser Leu Lys
  1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 302

Met Val Cys Tyr Leu Leu Lys Thr Lys
  1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 303

Ile Gln Asn Val Pro Leu Ser Glu Lys
  1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 304

Ile Val Leu Thr His Asn Arg Leu Lys
  1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 305

Ser Leu Gly Ala Val Val Phe Ser Arg
  1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 306

Gly His Phe Cys Leu Ser Ser Asp Lys
  1               5
```

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 307

Met Glu Trp Asp Thr Gln Val Val Lys
 1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 308

Val Val Leu Glu Ala Pro Phe Leu Val
 1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 309

Ser Glu Val Thr Pro Asp Gln Ser Lys
 1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 310

His Asn Arg Leu Lys Ser Leu Met Lys
 1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 311

Ala Val Phe Gln Cys Ala Gln Cys His
 1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 312

```
Leu Pro Ser Trp Leu Gln Pro Glu Arg
  1               5

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 313

Ile Val Asn Ala Ser Glu Met Asp Ile
  1               5

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 314

Ala Val Leu Ala Asp Ser Val His Leu
  1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 315

Asn Val Val Leu Glu Ala Pro Phe Leu
  1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 316

Gln Val Val Lys Gly Ser Ser Pro Leu
  1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 317

Gly Thr Glu Arg Ala Ile Asp Gln Ala
  1               5

<210> SEQ ID NO 318
<211> LENGTH: 9
<212> TYPE: PRT
<213> ORGANISM: Artificial Sequence
```

```
<220> FEATURE:
<223> OTHER INFORMATION: Description of Artificial Sequence: Peptide
      motif

<400> SEQUENCE: 318

Gly Asp Phe Cys Gly Gly Thr Glu Arg
  1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 319

Asp Lys Met Val Cys Tyr Leu Leu Lys
  1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 320

Val Thr Asn Asn Val Val Leu Glu Ala
  1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 321

Leu Ser Glu Lys Ile Ala Glu Leu Lys
  1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 322

Lys Ile Val Leu Thr His Asn Arg Leu
  1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 323

Arg Ser Arg Cys Ala Thr Pro Pro Arg
  1               5
```

```
<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 324

Val His Leu Ala Trp Asp Leu Ser Arg
 1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 325

Ala Gln Pro Leu Arg His Arg Ser Arg
 1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 326

Gly Leu Gly Ala Glu Glu Pro Ala Ala
 1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 327

Gly Ile Pro Val Gly Phe His Leu Tyr
 1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 328

Lys Ile Ala Glu Leu Lys Glu Lys Ile
 1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Peptide
      motif
```

-continued

```
<400> SEQUENCE: 329

Asn Val Pro Leu Ser Glu Lys Ile Ala
 1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 330

Ser Thr His Ala Ala Leu Ala Ala Leu
 1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 331

Ala Ala Leu Arg Gly His Phe Cys Leu
 1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 332

Lys Ala Ile Val Asn Ala Ser Glu Met
 1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 333

Ser Leu Met Lys Ile Leu Ser Glu Val
 1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 334

Ser Leu Lys Gly Ser Thr Tyr Asn Leu
 1               5

<210> SEQ ID NO 335
<211> LENGTH: 9
<212> TYPE: PRT
```

```
<213> ORGANISM: Artificial Sequence
<220> FEATURE:
<223> OTHER INFORMATION: Description of Artificial Sequence: Peptide
      motif

<400> SEQUENCE: 335

His Leu Tyr Ser Thr His Ala Ala Leu
 1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 336

Leu Leu Phe Cys Gly Ser Cys Gly Ile
 1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 337

Tyr Leu Leu Lys Thr Lys Ala Ile Val
 1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 338

Gly Phe His Leu Tyr Ser Thr His Ala
 1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 339

Leu Gln Pro Glu Arg Cys Ala Val Phe
 1               5

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 340

Ser Thr Tyr Asn Leu Leu Phe Cys Gly
 1               5
```

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 341

Arg Val Thr Asn Asn Val Val Leu Glu
 1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 342

Phe Gln Cys Ala Gln Cys His Ala Val
 1               5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 343

Arg Leu Lys Ser Leu Met Lys Ile Leu
 1               5

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 344

Phe Leu Val Gly Ile Glu Gly Ser Leu
 1               5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 345

Leu Thr His Asn Arg Leu Lys Ser Leu
 1               5

<210> SEQ ID NO 346
<211> LENGTH: 9
<212> TYPE: PRT
<213> ORGANISM: Artificial Sequence
<220> FEATURE:
<223> OTHER INFORMATION: Description of Artificial Sequence: Peptide
      motif

```
<400> SEQUENCE: 346

Glu Lys Ile Ala Glu Leu Lys Glu Lys
 1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 347

Leu Ala Asp Ser Val His Leu Ala Trp
 1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 348

Met Ala Ala Gln Pro Leu Arg His Arg
 1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 349

Ala Leu Ala Ala Leu Arg Gly His Phe
 1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 350

Thr His Ala Ala Leu Ala Ala Leu Arg
 1               5

<210> SEQ ID NO 351
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 351

Lys Met Val Cys Tyr Leu Leu Lys Thr Lys
 1               5                  10

<210> SEQ ID NO 352
<211> LENGTH: 10
```

-continued

```
<212> TYPE: PRT
<213> ORGANISM: Artificial Sequence
<220> FEATURE:
<223> OTHER INFORMATION: Description of Artificial Sequence: Peptide
      motif

<400> SEQUENCE: 352

Ser Val His Leu Ala Trp Asp Leu Ser Arg
 1               5                  10

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 353

Phe Leu Val Gly Ile Glu Gly Ser Leu Lys
 1               5                  10

<210> SEQ ID NO 354
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 354

Ser Met Glu Trp Asp Thr Gln Val Val Lys
 1               5                  10

<210> SEQ ID NO 355
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 355

Ser Thr His Ala Ala Leu Ala Ala Leu Arg
 1               5                  10

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 356

Lys Ile Val Leu Thr His Asn Arg Leu Lys
 1               5                  10

<210> SEQ ID NO 357
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 357

Asp Ile Gln Asn Val Pro Leu Ser Glu Lys
```

-continued

<210> SEQ ID NO 358
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 358

Arg Val Thr Asn Asn Val Val Leu Glu Ala
 1               5                  10

<210> SEQ ID NO 359
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 359

Asn Val Val Leu Glu Ala Pro Phe Leu Val
 1               5                  10

<210> SEQ ID NO 360
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 360

Gln Leu Pro Ser Trp Leu Gln Pro Glu Arg
 1               5                  10

<210> SEQ ID NO 361
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 361

Arg Gly His Phe Cys Leu Ser Ser Asp Lys
 1               5                  10

<210> SEQ ID NO 362
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 362

Arg Ser Leu Gly Ala Val Val Phe Ser Arg
 1               5                  10

<210> SEQ ID NO 363
<211> LENGTH: 10
<212> TYPE: PRT
<213> ORGANISM: Artificial Sequence
<220> FEATURE:
<223> OTHER INFORMATION: Description of Artificial Sequence: Peptide

```
                       motif

<400> SEQUENCE: 363

Ser Asp Lys Met Val Cys Tyr Leu Leu Lys
  1               5                  10

<210> SEQ ID NO 364
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 364

Ala Val Phe Gln Cys Ala Gln Cys His Ala
  1               5                  10

<210> SEQ ID NO 365
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 365

Pro Leu Ser Glu Lys Ile Ala Glu Leu Lys
  1               5                  10

<210> SEQ ID NO 366
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 366

Val Val Phe Ser Arg Val Thr Asn Asn Val
  1               5                  10

<210> SEQ ID NO 367
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 367

Thr His Asn Arg Leu Lys Ser Leu Met Lys
  1               5                  10

<210> SEQ ID NO 368
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 368

Lys Glu Lys Ile Val Leu Thr His Asn Arg
  1               5                  10

<210> SEQ ID NO 369
```

```
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 369

Ala Val Leu Ala Asp Ser Val His Leu Ala
 1               5                  10

<210> SEQ ID NO 370
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 370

Ser Glu Lys Ile Ala Glu Leu Lys Glu Lys
 1               5                  10

<210> SEQ ID NO 371
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 371

Leu Ser Glu Val Thr Pro Asp Gln Ser Lys
 1               5                  10

<210> SEQ ID NO 372
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 372

Met Val Cys Tyr Leu Leu Lys Thr Lys Ala
 1               5                  10

<210> SEQ ID NO 373
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 373

Arg Gly Asp Phe Cys Gly Gly Thr Glu Arg
 1               5                  10

<210> SEQ ID NO 374
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 374
```

```
Ala Ile Val Asn Ala Ser Glu Met Asp Ile
 1               5                  10

<210> SEQ ID NO 375
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 375

Leu Thr His Asn Arg Leu Lys Ser Leu Met
 1               5                  10

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 376

Thr Thr Ser Met Glu Trp Asp Thr Gln Val
 1               5                  10

<210> SEQ ID NO 377
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 377

Thr Gln Val Val Lys Gly Ser Ser Pro Leu
 1               5                  10

<210> SEQ ID NO 378
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 378

Val Leu Ala Asp Ser Val His Leu Ala Trp
 1               5                  10

<210> SEQ ID NO 379
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 379

His Leu Tyr Ser Thr His Ala Ala Leu Ala
 1               5                  10

<210> SEQ ID NO 380
<211> LENGTH: 10
<212> TYPE: PRT
<213> ORGANISM: Artificial Sequence
<220> FEATURE:
```

<223> OTHER INFORMATION: Description of Artificial Sequence: Peptide
      motif

<400> SEQUENCE: 380

Leu Tyr Ser Thr His Ala Ala Leu Ala Ala
 1               5                  10

<210> SEQ ID NO 381
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 381

Asn Leu Leu Phe Cys Gly Ser Cys Gly Ile
 1               5                  10

<210> SEQ ID NO 382
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 382

Ile Val Leu Thr His Asn Arg Leu Lys Ser
 1               5                  10

<210> SEQ ID NO 383
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 383

Phe Gln Cys Ala Gln Cys His Ala Val Leu
 1               5                  10

<210> SEQ ID NO 384
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 384

Ile Gln Asn Val Pro Leu Ser Glu Lys Ile
 1               5                  10

<210> SEQ ID NO 385
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 385

Gly Phe His Leu Tyr Ser Thr His Ala Ala
 1               5                  10

```
<210> SEQ ID NO 386
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 386

Ser Pro Leu Gly Pro Ala Gly Leu Gly Ala
 1               5                  10

<210> SEQ ID NO 387
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 387

Leu Ala Ala Leu Arg Gly His Phe Cys Leu
 1               5                  10

<210> SEQ ID NO 388
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 388

Arg Cys Ala Thr Pro Pro Arg Gly Asp Phe
 1               5                  10

<210> SEQ ID NO 389
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 389

Val Val Leu Glu Ala Pro Phe Leu Val Gly
 1               5                  10

<210> SEQ ID NO 390
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 390

Ser Cys Gly Ile Pro Val Gly Phe His Leu
 1               5                  10

<210> SEQ ID NO 391
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 391
```

Lys Ile Ala Glu Leu Lys Glu Lys Ile Val
1               5                   10

<210> SEQ ID NO 392
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 392

Cys Tyr Leu Leu Lys Thr Lys Ala Ile Val
1               5                   10

<210> SEQ ID NO 393
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 393

Val Val Lys Gly Ser Ser Pro Leu Gly Pro
1               5                   10

<210> SEQ ID NO 394
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 394

Cys Leu Ser Ser Asp Lys Met Val Cys Tyr
1               5                   10

<210> SEQ ID NO 395
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 395

Ser Leu Gly Ala Val Val Phe Ser Arg Val
1               5                   10

<210> SEQ ID NO 396
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 396

Leu Phe Cys Gly Ser Cys Gly Ile Pro Val
1               5                   10

<210> SEQ ID NO 397
<211> LENGTH: 10
<212> TYPE: PRT
<213> ORGANISM: Artificial Sequence

```
<220> FEATURE:
<223> OTHER INFORMATION: Description of Artificial Sequence: Peptide
      motif

<400> SEQUENCE: 397

Ile Ala Glu Leu Lys Glu Lys Ile Val Leu
 1               5                  10

<210> SEQ ID NO 398
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 398

His Arg Ser Arg Cys Ala Thr Pro Pro Arg
 1               5                  10

<210> SEQ ID NO 399
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 399

Asn Val Pro Leu Ser Glu Lys Ile Ala Glu
 1               5                  10

<210> SEQ ID NO 400
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 400

Ser Leu Lys Gly Ser Thr Tyr Asn Leu Leu
 1               5                  10

<210> SEQ ID NO 401
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 401

Cys Tyr Leu Leu Lys Thr Lys Ala Ile
 1               5

<210> SEQ ID NO 402
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 402

Lys Ile Val Leu Thr His Asn Arg Leu
 1               5
```

```
<210> SEQ ID NO 403
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 403

Thr Tyr Asn Leu Leu Phe Cys Gly Ser
 1               5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 404

Cys Gly Ile Pro Val Gly Phe His Leu
 1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 405

Arg Leu Lys Ser Leu Met Lys Ile Leu
 1               5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 406

Phe Leu Val Gly Ile Glu Gly Ser Leu
 1               5

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 407

Ala Gly Pro Gln Leu Pro Ser Trp Leu
 1               5

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 408

Asp Ser Val His Leu Ala Trp Asp Leu
 1               5

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 409

Asn Val Val Leu Glu Ala Pro Phe Leu
 1               5

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 410

Gln Val Val Lys Gly Ser Ser Pro Leu
 1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 411

Ser Ser Pro Leu Gly Pro Ala Gly Leu
 1               5

<210> SEQ ID NO 412
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 412

Ala Val Leu Ala Asp Ser Val His Leu
 1               5

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 413

Ala Ala Leu Arg Gly His Phe Cys Leu
 1               5

<210> SEQ ID NO 414
<211> LENGTH: 9
<212> TYPE: PRT
```

```
<213> ORGANISM: Artificial Sequence
<220> FEATURE:
<223> OTHER INFORMATION: Description of Artificial Sequence: Peptide
      motif

<400> SEQUENCE: 414

Leu Ala Trp Asp Leu Ser Arg Ser Leu
 1               5

<210> SEQ ID NO 415
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 415

Leu Tyr Ser Thr His Ala Ala Leu Ala
 1               5

<210> SEQ ID NO 416
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 416

Ser Leu Lys Gly Ser Thr Tyr Asn Leu
 1               5

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 417

Glu Met Asp Ile Gln Asn Val Pro Leu
 1               5

<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 418

His Leu Tyr Ser Thr His Ala Ala Leu
 1               5

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 419

Gln Cys Ala Gln Cys His Ala Val Leu
 1               5
```

<210> SEQ ID NO 420
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 420

Ser Ser Asp Lys Met Val Cys Tyr Leu
 1               5

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 421

Leu Thr His Asn Arg Leu Lys Ser Leu
 1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 422

Ser Thr His Ala Ala Leu Ala Ala Leu
 1               5

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 423

Lys Gly Ser Thr Tyr Asn Leu Leu Phe
 1               5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 424

Leu Gln Pro Glu Arg Cys Ala Val Phe
 1               5

<210> SEQ ID NO 425
<211> LENGTH: 9
<212> TYPE: PRT
<213> ORGANISM: Artificial Sequence
<220> FEATURE:
<223> OTHER INFORMATION: Description of Artificial Sequence: Peptide
      motif -continued

```
<400> SEQUENCE: 425

Asn Asn Val Val Leu Glu Ala Pro Phe
  1               5

<210> SEQ ID NO 426
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 426

Lys Ile Ala Glu Leu Lys Glu Lys Ile
  1               5

<210> SEQ ID NO 427
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 427

Gly Ser Cys Gly Ile Pro Val Gly Phe
  1               5

<210> SEQ ID NO 428
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 428

His Phe Cys Leu Ser Ser Asp Lys Met
  1               5

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 429

Cys Ala Thr Pro Pro Arg Gly Asp Phe
  1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 430

Ala Leu Ala Ala Leu Arg Gly His Phe
  1               5

<210> SEQ ID NO 431
<211> LENGTH: 9
```

-continued

<212> TYPE: PRT
<213> ORGANISM: Artificial Sequence
<220> FEATURE:
<223> OTHER INFORMATION: Description of Artificial Sequence: Peptide
      motif

<400> SEQUENCE: 431

Gln Asn Val Pro Leu Ser Glu Lys Ile
 1               5

<210> SEQ ID NO 432
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 432

Lys Ala Ile Val Asn Ala Ser Glu Met
 1               5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 433

Ile Val Asn Ala Ser Glu Met Asp Ile
 1               5

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 434

Leu Leu Phe Cys Gly Ser Cys Gly Ile
 1               5

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 435

Phe Cys Gly Gly Thr Glu Arg Ala Ile
 1               5

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 436

Val Phe Ser Arg Val Thr Asn Asn Val

-continued

```
<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 437

Val Phe Gln Cys Ala Gln Cys His Ala
 1               5

<210> SEQ ID NO 438
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 438

Ala Glu Leu Lys Glu Lys Ile Val Leu
 1               5

<210> SEQ ID NO 439
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 439

Ser Arg Val Thr Asn Asn Val Val Leu
 1               5

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 440

Glu Glu Pro Ala Ala Gly Pro Gln Leu
 1               5

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 441

Ser Asp Lys Met Val Cys Tyr Leu Leu
 1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Peptide
``` motif

<400> SEQUENCE: 442

Pro Leu Ser Glu Lys Ile Ala Glu Leu
 1               5

<210> SEQ ID NO 443
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 443

Asp Gln Ala Ser Phe Thr Thr Ser Met
 1               5

<210> SEQ ID NO 444
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 444

Gly Phe His Leu Tyr Ser Thr His Ala
 1               5

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 445

Asp Phe Cys Gly Gly Thr Glu Arg Ala
 1               5

<210> SEQ ID NO 446
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 446

Leu Lys Gly Ser Thr Tyr Asn Leu Leu
 1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 447

Arg Ala Ile Asp Gln Ala Ser Phe Thr
 1               5

<210> SEQ ID NO 448

```
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 448

Lys Thr Lys Ala Ile Val Asn Ala Ser
  1               5

<210> SEQ ID NO 449
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 449

Lys Met Val Cys Tyr Leu Leu Lys Thr
  1               5

<210> SEQ ID NO 450
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 450

Arg Ser Leu Gly Ala Val Val Phe Ser
  1               5

<210> SEQ ID NO 451
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 451

Cys Tyr Leu Leu Lys Thr Lys Ala Ile Val
  1               5                  10

<210> SEQ ID NO 452
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 452

Thr Tyr Asn Leu Leu Phe Cys Gly Ser Cys
  1               5                  10

<210> SEQ ID NO 453
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 453
```

-continued

```
Val Pro Leu Ser Glu Lys Ile Ala Glu Leu
1               5                   10

<210> SEQ ID NO 454
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 454

Ile Ala Glu Leu Lys Glu Lys Ile Val Leu
1               5                   10

<210> SEQ ID NO 455
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 455

Thr Gln Val Val Lys Gly Ser Ser Pro Leu
1               5                   10

<210> SEQ ID NO 456
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 456

Gly Ser Leu Lys Gly Ser Thr Tyr Asn Leu
1               5                   10

<210> SEQ ID NO 457
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 457

Asn Asn Val Val Leu Glu Ala Pro Phe Leu
1               5                   10

<210> SEQ ID NO 458
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 458

His Ala Val Leu Ala Asp Ser Val His Leu
1               5                   10

<210> SEQ ID NO 459
<211> LENGTH: 10
<212> TYPE: PRT
<213> ORGANISM: Artificial Sequence
<220> FEATURE:
```

-continued

```
<223> OTHER INFORMATION: Description of Artificial Sequence: Peptide
      motif

<400> SEQUENCE: 459

Ala Ala Gly Pro Gln Leu Pro Ser Trp Leu
 1               5                  10

<210> SEQ ID NO 460
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 460

Ser Cys Gly Ile Pro Val Gly Phe His Leu
 1               5                  10

<210> SEQ ID NO 461
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 461

Ser Ser Asp Lys Met Val Cys Tyr Leu Leu
 1               5                  10

<210> SEQ ID NO 462
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 462

Leu Tyr Ser Thr His Ala Ala Leu Ala Ala
 1               5                  10

<210> SEQ ID NO 463
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 463

Asp Phe Cys Gly Gly Thr Glu Arg Ala Ile
 1               5                  10

<210> SEQ ID NO 464
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 464

Gly Ser Ser Pro Leu Gly Pro Ala Gly Leu
 1               5                  10
```

```
<210> SEQ ID NO 465
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 465

His Leu Ala Trp Asp Leu Ser Arg Ser Leu
 1               5                  10

<210> SEQ ID NO 466
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 466

Ser Leu Lys Gly Ser Thr Tyr Asn Leu Leu
 1               5                  10

<210> SEQ ID NO 467
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 467

Leu Ser Ser Asp Lys Met Val Cys Tyr Leu
 1               5                  10

<210> SEQ ID NO 468
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 468

Pro Phe Leu Val Gly Ile Glu Gly Ser Leu
 1               5                  10

<210> SEQ ID NO 469
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 469

Leu Ala Ala Leu Arg Gly His Phe Cys Leu
 1               5                  10

<210> SEQ ID NO 470
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 470
```

```
Arg Cys Ala Thr Pro Pro Arg Gly Asp Phe
 1               5                  10
```

<210> SEQ ID NO 471
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 471

```
Phe Gln Cys Ala Gln Cys His Ala Val Leu
 1               5                  10
```

<210> SEQ ID NO 472
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 472

```
Tyr Ser Thr His Ala Ala Leu Ala Ala Leu
 1               5                  10
```

<210> SEQ ID NO 473
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 473

```
Phe Ser Arg Val Thr Asn Asn Val Val Leu
 1               5                  10
```

<210> SEQ ID NO 474
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 474

```
Val Leu Thr His Asn Arg Leu Lys Ser Leu
 1               5                  10
```

<210> SEQ ID NO 475
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 475

```
Thr Asn Asn Val Val Leu Glu Ala Pro Phe
 1               5                  10
```

<210> SEQ ID NO 476
<211> LENGTH: 10
<212> TYPE: PRT
<213> ORGANISM: Artificial Sequence

```
<220> FEATURE:
<223> OTHER INFORMATION: Description of Artificial Sequence: Peptide
      motif

<400> SEQUENCE: 476

Trp Leu Gln Pro Glu Arg Cys Ala Val Phe
 1               5                  10

<210> SEQ ID NO 477
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 477

Ala Ala Leu Ala Ala Leu Arg Gly His Phe
 1               5                  10

<210> SEQ ID NO 478
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 478

Cys Gly Ser Cys Gly Ile Pro Val Gly Phe
 1               5                  10

<210> SEQ ID NO 479
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 479

Leu Ser Arg Ser Leu Gly Ala Val Val Phe
 1               5                  10

<210> SEQ ID NO 480
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 480

Ile Gln Asn Val Pro Leu Ser Glu Lys Ile
 1               5                  10

<210> SEQ ID NO 481
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 481

Ala Ile Val Asn Ala Ser Glu Met Asp Ile
 1               5                  10
```

```
<210> SEQ ID NO 482
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 482

Val Leu Glu Ala Pro Phe Leu Val Gly Ile
 1               5                  10

<210> SEQ ID NO 483
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 483

Asn Leu Leu Phe Cys Gly Ser Cys Gly Ile
 1               5                  10

<210> SEQ ID NO 484
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 484

His Asn Arg Leu Lys Ser Leu Met Lys Ile
 1               5                  10

<210> SEQ ID NO 485
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 485

Val Cys Tyr Leu Leu Lys Thr Lys Ala Ile
 1               5                  10

<210> SEQ ID NO 486
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 486

Val Phe Gln Cys Ala Gln Cys His Ala Val
 1               5                  10

<210> SEQ ID NO 487
<211> LENGTH: 10
<212> TYPE: PRT
<213> ORGANISM: Artificial Sequence
<220> FEATURE:
<223> OTHER INFORMATION: Description of Artificial Sequence: Peptide
      motif
```

-continued

```
<400> SEQUENCE: 487

Ser Glu Met Asp Ile Gln Asn Val Pro Leu
 1               5                  10

<210> SEQ ID NO 488
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 488

Asn Arg Leu Lys Ser Leu Met Lys Ile Leu
 1               5                  10

<210> SEQ ID NO 489
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 489

Glu Lys Ile Val Leu Thr His Asn Arg Leu
 1               5                  10

<210> SEQ ID NO 490
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 490

Ala Glu Glu Pro Ala Ala Gly Pro Gln Leu
 1               5                  10

<210> SEQ ID NO 491
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 491

Phe His Leu Tyr Ser Thr His Ala Ala Leu
 1               5                  10

<210> SEQ ID NO 492
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 492

Val Phe Ser Arg Val Thr Asn Asn Val Val
 1               5                  10

<210> SEQ ID NO 493
<211> LENGTH: 10
<212> TYPE: PRT
```

```
<213> ORGANISM: Artificial Sequence
<220> FEATURE:
<223> OTHER INFORMATION: Description of Artificial Sequence: Peptide
      motif

<400> SEQUENCE: 493

Leu Thr His Asn Arg Leu Lys Ser Leu Met
 1               5                  10

<210> SEQ ID NO 494
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 494

Leu Phe Cys Gly Ser Cys Gly Ile Pro Val
 1               5                  10

<210> SEQ ID NO 495
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 495

His Phe Cys Leu Ser Ser Asp Lys Met Val
 1               5                  10

<210> SEQ ID NO 496
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 496

Gly Phe His Leu Tyr Ser Thr His Ala Ala
 1               5                  10

<210> SEQ ID NO 497
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 497

Ser Phe Thr Thr Ser Met Glu Trp Asp Thr
 1               5                  10

<210> SEQ ID NO 498
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 498

Ala Asp Ser Val His Leu Ala Trp Asp Leu
 1               5                  10
```

```
<210> SEQ ID NO 499
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 499

Lys Ser Leu Met Lys Ile Leu Ser Glu Val
 1               5                  10

<210> SEQ ID NO 500
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 500

Arg Ala Ile Asp Gln Ala Ser Phe Thr Thr
 1               5                  10

<210> SEQ ID NO 501
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 501

Ala Val Leu Ala Asp Ser Val His Leu
 1               5

<210> SEQ ID NO 502
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 502

Ala Ala Leu Arg Gly His Phe Cys Leu
 1               5

<210> SEQ ID NO 503
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 503

Asn Val Val Leu Glu Ala Pro Phe Leu
 1               5

<210> SEQ ID NO 504
<211> LENGTH: 9
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 504

Gln Val Val Lys Gly Ser Ser Pro Leu
  1               5

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 505

Ala Gly Pro Gln Leu Pro Ser Trp Leu
  1               5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 506

Leu Ala Trp Asp Leu Ser Arg Ser Leu
  1               5

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 507

Ser Thr His Ala Ala Leu Ala Ala Leu
  1               5

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 508

Asp Ser Val His Leu Ala Trp Asp Leu
  1               5

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 509

Lys Ile Val Leu Thr His Asn Arg Leu
  1               5

<210> SEQ ID NO 510
<211> LENGTH: 9
```

-continued

```
<212> TYPE: PRT
<213> ORGANISM: Artificial Sequence
<220> FEATURE:
<223> OTHER INFORMATION: Description of Artificial Sequence: Peptide
      motif

<400> SEQUENCE: 510

His Leu Tyr Ser Thr His Ala Ala Leu
 1               5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 511

Ser Leu Lys Gly Ser Thr Tyr Asn Leu
 1               5

<210> SEQ ID NO 512
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 512

Gln Cys Ala Gln Cys His Ala Val Leu
 1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 513

Leu Thr His Asn Arg Leu Lys Ser Leu
 1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 514

Cys Gly Ile Pro Val Gly Phe His Leu
 1               5

<210> SEQ ID NO 515
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 515

Phe Leu Val Gly Ile Glu Gly Ser Leu
```

-continued

```
<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 516

Ser Ser Pro Leu Gly Pro Ala Gly Leu
 1               5

<210> SEQ ID NO 517
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 517

Arg Leu Lys Ser Leu Met Lys Ile Leu
 1               5

<210> SEQ ID NO 518
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 518

Lys Ala Ile Val Asn Ala Ser Glu Met
 1               5

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 519

Gln Pro Leu Arg His Arg Ser Arg Cys
 1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 520

Ile Val Asn Ala Ser Glu Met Asp Ile
 1               5

<210> SEQ ID NO 521
<211> LENGTH: 9
<212> TYPE: PRT
<213> ORGANISM: Artificial Sequence
<220> FEATURE:
<223> OTHER INFORMATION: Description of Artificial Sequence: Peptide
```

-continued motif

<400> SEQUENCE: 521

Leu Ser Arg Ser Leu Gly Ala Val Val
 1               5

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 522

Phe Ser Arg Val Thr Asn Asn Val Val
 1               5

<210> SEQ ID NO 523
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 523

Glu Met Asp Ile Gln Asn Val Pro Leu
 1               5

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 524

Ser Ser Asp Lys Met Val Cys Tyr Leu
 1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 525

Ala Glu Leu Lys Glu Lys Ile Val Leu
 1               5

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 526

Val Val Leu Glu Ala Pro Phe Leu Val
 1               5

<210> SEQ ID NO 527

```
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 527

Asp Gln Ala Ser Phe Thr Thr Ser Met
 1               5

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 528

Thr Ser Met Glu Trp Asp Thr Gln Val
 1               5

<210> SEQ ID NO 529
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 529

Ala Pro Phe Leu Val Gly Ile Glu Gly
 1               5

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 530

Ser Leu Met Lys Ile Leu Ser Glu Val
 1               5

<210> SEQ ID NO 531
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 531

Ala Leu Arg Gly His Phe Cys Leu Ser
 1               5

<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 532
```

Asn Val Pro Leu Ser Glu Lys Ile Ala
1               5

<210> SEQ ID NO 533
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 533

Ala Val Val Phe Ser Arg Val Thr Asn
1               5

<210> SEQ ID NO 534
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 534

Phe Cys Gly Gly Thr Glu Arg Ala Ile
1               5

<210> SEQ ID NO 535
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 535

Leu Leu Phe Cys Gly Ser Cys Gly Ile
1               5

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 536

Ser Arg Val Thr Asn Asn Val Val Leu
1               5

<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 537

Gln Asn Val Pro Leu Ser Glu Lys Ile
1               5

<210> SEQ ID NO 538
<211> LENGTH: 9
<212> TYPE: PRT
<213> ORGANISM: Artificial Sequence
<220> FEATURE:

```
<223> OTHER INFORMATION: Description of Artificial Sequence: Peptide
      motif

<400> SEQUENCE: 538

Leu Lys Gly Ser Thr Tyr Asn Leu Leu
 1               5

<210> SEQ ID NO 539
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 539

Pro Leu Ser Glu Lys Ile Ala Glu Leu
 1               5

<210> SEQ ID NO 540
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 540

Ser Asp Lys Met Val Cys Tyr Leu Leu
 1               5

<210> SEQ ID NO 541
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 541

Glu Glu Pro Ala Ala Gly Pro Gln Leu
 1               5

<210> SEQ ID NO 542
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 542

Ile Pro Val Gly Phe His Leu Tyr Ser
 1               5

<210> SEQ ID NO 543
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 543

Lys Ile Ala Glu Leu Lys Glu Lys Ile
 1               5
```

```
<210> SEQ ID NO 544
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 544

Cys Ala Val Phe Gln Cys Ala Gln Cys
  1               5

<210> SEQ ID NO 545
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 545

Leu Ala Ala Leu Arg Gly His Phe Cys
  1               5

<210> SEQ ID NO 546
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 546

Ser Pro Leu Gly Pro Ala Gly Leu Gly
  1               5

<210> SEQ ID NO 547
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 547

Ala Gly Leu Gly Ala Glu Glu Pro Ala
  1               5

<210> SEQ ID NO 548
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 548

Trp Leu Gln Pro Glu Arg Cys Ala Val
  1               5

<210> SEQ ID NO 549
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 549
```

```
Cys Ala Gln Cys His Ala Val Leu Ala
 1               5
```

<210> SEQ ID NO 550
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 550

```
Arg Ala Ile Asp Gln Ala Ser Phe Thr
 1               5
```

<210> SEQ ID NO 551
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 551

```
Val Pro Leu Ser Glu Lys Ile Ala Glu Leu
 1               5                  10
```

<210> SEQ ID NO 552
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 552

```
Phe Ser Arg Val Thr Asn Asn Val Val Leu
 1               5                  10
```

<210> SEQ ID NO 553
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 553

```
Ala Ala Gly Pro Gln Leu Pro Ser Trp Leu
 1               5                  10
```

<210> SEQ ID NO 554
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 554

```
His Ala Val Leu Ala Asp Ser Val His Leu
 1               5                  10
```

<210> SEQ ID NO 555
<211> LENGTH: 10
<212> TYPE: PRT
<213> ORGANISM: Artificial Sequence

```
<220> FEATURE:
<223> OTHER INFORMATION: Description of Artificial Sequence: Peptide
      motif

<400> SEQUENCE: 555

Leu Ala Ala Leu Arg Gly His Phe Cys Leu
 1               5                  10

<210> SEQ ID NO 556
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 556

Gly Ser Ser Pro Leu Gly Pro Ala Gly Leu
 1               5                  10

<210> SEQ ID NO 557
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 557

Asn Asn Val Val Leu Glu Ala Pro Phe Leu
 1               5                  10

<210> SEQ ID NO 558
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 558

His Leu Ala Trp Asp Leu Ser Arg Ser Leu
 1               5                  10

<210> SEQ ID NO 559
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 559

Phe Gln Cys Ala Gln Cys His Ala Val Leu
 1               5                  10

<210> SEQ ID NO 560
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 560

Val Leu Thr His Asn Arg Leu Lys Ser Leu
 1               5                  10
```

```
<210> SEQ ID NO 561
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 561

Ser Cys Gly Ile Pro Val Gly Phe His Leu
  1               5                  10

<210> SEQ ID NO 562
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 562

Tyr Ser Thr His Ala Ala Leu Ala Ala Leu
  1               5                  10

<210> SEQ ID NO 563
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 563

Ser Leu Lys Gly Ser Thr Tyr Asn Leu Leu
  1               5                  10

<210> SEQ ID NO 564
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 564

Leu Ser Ser Asp Lys Met Val Cys Tyr Leu
  1               5                  10

<210> SEQ ID NO 565
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 565

Thr Gln Val Val Lys Gly Ser Ser Pro Leu
  1               5                  10

<210> SEQ ID NO 566
<211> LENGTH: 10
<212> TYPE: PRT
<213> ORGANISM: Artificial Sequence
<220> FEATURE:
<223> OTHER INFORMATION: Description of Artificial Sequence: Peptide
      motif
```

```
<400> SEQUENCE: 566

His Asn Arg Leu Lys Ser Leu Met Lys Ile
 1               5                  10

<210> SEQ ID NO 567
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 567

Gly Ser Leu Lys Gly Ser Thr Tyr Asn Leu
 1               5                  10

<210> SEQ ID NO 568
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 568

Ile Ala Glu Leu Lys Glu Lys Ile Val Leu
 1               5                  10

<210> SEQ ID NO 569
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 569

Pro Pro Arg Gly Asp Phe Cys Gly Gly Thr
 1               5                  10

<210> SEQ ID NO 570
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 570

Ser Pro Leu Gly Pro Ala Gly Leu Gly Ala
 1               5                  10

<210> SEQ ID NO 571
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 571

Gln Pro Leu Arg His Arg Ser Arg Cys Ala
 1               5                  10

<210> SEQ ID NO 572
<211> LENGTH: 10
<212> TYPE: PRT
```

```
<213> ORGANISM: Artificial Sequence
<220> FEATURE:
<223> OTHER INFORMATION: Description of Artificial Sequence: Peptide
      motif

<400> SEQUENCE: 572

Ile Pro Val Gly Phe His Leu Tyr Ser Thr
 1               5                  10

<210> SEQ ID NO 573
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 573

Leu Pro Ser Trp Leu Gln Pro Glu Arg Cys
 1               5                  10

<210> SEQ ID NO 574
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 574

Ala Val Leu Ala Asp Ser Val His Leu Ala
 1               5                  10

<210> SEQ ID NO 575
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 575

Ala Val Phe Gln Cys Ala Gln Cys His Ala
 1               5                  10

<210> SEQ ID NO 576
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 576

Ser Ser Asp Lys Met Val Cys Tyr Leu Leu
 1               5                  10

<210> SEQ ID NO 577
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 577

Ala Pro Phe Leu Val Gly Ile Glu Gly Ser
 1               5                  10
```

<210> SEQ ID NO 578
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 578

Ala Asp Ser Val His Leu Ala Trp Asp Leu
  1               5                  10

<210> SEQ ID NO 579
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 579

Ser Glu Met Asp Ile Gln Asn Val Pro Leu
  1               5                  10

<210> SEQ ID NO 580
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 580

Ala Ile Val Asn Ala Ser Glu Met Asp Ile
  1               5                  10

<210> SEQ ID NO 581
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 581

Asn Val Val Leu Glu Ala Pro Phe Leu Val
  1               5                  10

<210> SEQ ID NO 582
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 582

Leu Thr His Asn Arg Leu Lys Ser Leu Met
  1               5                  10

<210> SEQ ID NO 583
<211> LENGTH: 10
<212> TYPE: PRT
<213> ORGANISM: Artificial Sequence
<220> FEATURE:
<223> OTHER INFORMATION: Description of Artificial Sequence: Peptide
      motif

```
<400> SEQUENCE: 583

Val Val Phe Ser Arg Val Thr Asn Asn Val
 1               5                  10

<210> SEQ ID NO 584
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 584

Gln Pro Glu Arg Cys Ala Val Phe Gln Cys
 1               5                  10

<210> SEQ ID NO 585
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 585

Ala Leu Arg Gly His Phe Cys Leu Ser Ser
 1               5                  10

<210> SEQ ID NO 586
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 586

Asn Ala Ser Glu Met Asp Ile Gln Asn Val
 1               5                  10

<210> SEQ ID NO 587
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 587

Thr Ser Met Glu Trp Asp Thr Gln Val Val
 1               5                  10

<210> SEQ ID NO 588
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 588

Glu Pro Ala Ala Gly Pro Gln Leu Pro Ser
 1               5                  10

<210> SEQ ID NO 589
<211> LENGTH: 10
```

```
<212> TYPE: PRT
<213> ORGANISM: Artificial Sequence
<220> FEATURE:
<223> OTHER INFORMATION: Description of Artificial Sequence: Peptide
      motif

<400> SEQUENCE: 589

Met Val Cys Tyr Leu Leu Lys Thr Lys Ala
 1               5                  10

<210> SEQ ID NO 590
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 590

Arg Val Thr Asn Asn Val Val Leu Glu Ala
 1               5                  10

<210> SEQ ID NO 591
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 591

Ala Gln Pro Leu Arg His Arg Ser Arg Cys
 1               5                  10

<210> SEQ ID NO 592
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 592

Glu Lys Ile Val Leu Thr His Asn Arg Leu
 1               5                  10

<210> SEQ ID NO 593
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 593

Val Cys Tyr Leu Leu Lys Thr Lys Ala Ile
 1               5                  10

<210> SEQ ID NO 594
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 594

Phe His Leu Tyr Ser Thr His Ala Ala Leu
```

-continued

<210> SEQ ID NO 595
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 595

Asn Leu Leu Phe Cys Gly Ser Cys Gly Ile
 1               5                  10

<210> SEQ ID NO 596
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 596

Ile Gln Asn Val Pro Leu Ser Glu Lys Ile
 1               5                  10

<210> SEQ ID NO 597
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 597

Asn Arg Leu Lys Ser Leu Met Lys Ile Leu
 1               5                  10

<210> SEQ ID NO 598
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 598

Ala Glu Glu Pro Ala Ala Gly Pro Gln Leu
 1               5                  10

<210> SEQ ID NO 599
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 599

Ala Gly Leu Gly Ala Glu Glu Pro Ala Ala
 1               5                  10

<210> SEQ ID NO 600
<211> LENGTH: 10
<212> TYPE: PRT
<213> ORGANISM: Artificial Sequence
<220> FEATURE:
<223> OTHER INFORMATION: Description of Artificial Sequence: Peptide

```
           motif

<400> SEQUENCE: 600

Ala Leu Ala Ala Leu Arg Gly His Phe Cys
 1               5                  10

<210> SEQ ID NO 601
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 601

Leu Ser Ser Asp Lys Met Val Cys Tyr
 1               5

<210> SEQ ID NO 602
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 602

Lys Ala Ile Val Asn Ala Ser Glu Met
 1               5

<210> SEQ ID NO 603
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 603

Arg Leu Lys Ser Leu Met Lys Ile Leu
 1               5

<210> SEQ ID NO 604
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 604

Leu Ala Trp Asp Leu Ser Arg Ser Leu
 1               5

<210> SEQ ID NO 605
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 605

Asp Ser Val His Leu Ala Trp Asp Leu
 1               5

<210> SEQ ID NO 606
```

-continued

```
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 606

Gly Ser Cys Gly Ile Pro Val Gly Phe
 1               5

<210> SEQ ID NO 607
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 607

Ser Ser Pro Leu Gly Pro Ala Gly Leu
 1               5

<210> SEQ ID NO 608
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 608

Ser Leu Lys Gly Ser Thr Tyr Asn Leu
 1               5

<210> SEQ ID NO 609
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 609

Cys Ala Thr Pro Pro Arg Gly Asp Phe
 1               5

<210> SEQ ID NO 610
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 610

Ala Ala Leu Arg Gly His Phe Cys Leu
 1               5

<210> SEQ ID NO 611
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 611
```

```
Phe Ser Arg Val Thr Asn Asn Val Val
 1               5

<210> SEQ ID NO 612
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 612

Leu Ser Arg Ser Leu Gly Ala Val Val
 1               5

<210> SEQ ID NO 613
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 613

Ala Ser Phe Thr Thr Ser Met Glu Trp
 1               5

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 614

Gly Ile Pro Val Gly Phe His Leu Tyr
 1               5

<210> SEQ ID NO 615
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 615

Lys Gly Ser Thr Tyr Asn Leu Leu Phe
 1               5

<210> SEQ ID NO 616
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 616

Ile Pro Val Gly Phe His Leu Tyr Ser
 1               5

<210> SEQ ID NO 617
<211> LENGTH: 9
<212> TYPE: PRT
<213> ORGANISM: Artificial Sequence
<220> FEATURE:
```

-continued

```
<223> OTHER INFORMATION: Description of Artificial Sequence: Peptide
      motif

<400> SEQUENCE: 617

Thr Ser Met Glu Trp Asp Thr Gln Val
  1               5

<210> SEQ ID NO 618
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 618

Gln Pro Leu Arg His Arg Ser Arg Cys
  1               5

<210> SEQ ID NO 619
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 619

Leu Gln Pro Glu Arg Cys Ala Val Phe
  1               5

<210> SEQ ID NO 620
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 620

Lys Ile Val Leu Thr His Asn Arg Leu
  1               5

<210> SEQ ID NO 621
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 621

Asp Gln Ala Ser Phe Thr Thr Ser Met
  1               5

<210> SEQ ID NO 622
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 622

Glu Gly Ser Leu Lys Gly Ser Thr Tyr
  1               5
```

```
<210> SEQ ID NO 623
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 623

Lys Ile Ala Glu Leu Lys Glu Lys Ile
 1               5

<210> SEQ ID NO 624
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 624

Ser Ser Asp Lys Met Val Cys Tyr Leu
 1               5

<210> SEQ ID NO 625
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 625

Ala Val Leu Ala Asp Ser Val His Leu
 1               5

<210> SEQ ID NO 626
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 626

Asn Val Val Leu Glu Ala Pro Phe Leu
 1               5

<210> SEQ ID NO 627
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 627

Ala Ala Gly Pro Gln Leu Pro Ser Trp
 1               5

<210> SEQ ID NO 628
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 628
```

-continued

```
Arg Ala Ile Asp Gln Ala Ser Phe Thr
  1               5

<210> SEQ ID NO 629
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 629

Ala Gly Pro Gln Leu Pro Ser Trp Leu
  1               5

<210> SEQ ID NO 630
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 630

Phe Leu Val Gly Ile Glu Gly Ser Leu
  1               5

<210> SEQ ID NO 631
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 631

Cys Gly Ile Pro Val Gly Phe His Leu
  1               5

<210> SEQ ID NO 632
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 632

Ala Leu Ala Ala Leu Arg Gly His Phe
  1               5

<210> SEQ ID NO 633
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 633

Gln Val Val Lys Gly Ser Ser Pro Leu
  1               5

<210> SEQ ID NO 634
<211> LENGTH: 9
<212> TYPE: PRT
<213> ORGANISM: Artificial Sequence
```

```
<220> FEATURE:
<223> OTHER INFORMATION: Description of Artificial Sequence: Peptide
      motif

<400> SEQUENCE: 634

Ser Thr His Ala Ala Leu Ala Ala Leu
 1               5

<210> SEQ ID NO 635
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 635

Leu Thr His Asn Arg Leu Lys Ser Leu
 1               5

<210> SEQ ID NO 636
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 636

Arg Ser Leu Gly Ala Val Val Phe Ser
 1               5

<210> SEQ ID NO 637
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 637

Gln Cys Ala Gln Cys His Ala Val Leu
 1               5

<210> SEQ ID NO 638
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 638

His Leu Tyr Ser Thr His Ala Ala Leu
 1               5

<210> SEQ ID NO 639
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 639

Asn Asn Val Val Leu Glu Ala Pro Phe
 1               5
```

```
<210> SEQ ID NO 640
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 640

Thr Pro Asp Gln Ser Lys Pro Glu Asn
  1               5

<210> SEQ ID NO 641
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 641

Glu Leu Lys Glu Lys Ile Val Leu Thr
  1               5

<210> SEQ ID NO 642
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 642

Asn Ala Ser Glu Met Asp Ile Gln Asn
  1               5

<210> SEQ ID NO 643
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 643

Lys Thr Lys Ala Ile Val Asn Ala Ser
  1               5

<210> SEQ ID NO 644
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 644

Gly Ser Leu Lys Gly Ser Thr Tyr Asn
  1               5

<210> SEQ ID NO 645
<211> LENGTH: 9
<212> TYPE: PRT
<213> ORGANISM: Artificial Sequence
<220> FEATURE:
<223> OTHER INFORMATION: Description of Artificial Sequence: Peptide
      motif
```

-continued

```
<400> SEQUENCE: 645

Gly Ser Thr Tyr Asn Leu Leu Phe Cys
 1               5

<210> SEQ ID NO 646
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 646

Tyr Ser Thr His Ala Ala Leu Ala Ala
 1               5

<210> SEQ ID NO 647
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 647

Ala Ser Glu Met Asp Ile Gln Asn Val
 1               5

<210> SEQ ID NO 648
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 648

Leu Ala Asp Ser Val His Leu Ala Trp
 1               5

<210> SEQ ID NO 649
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 649

Val Val Leu Glu Ala Pro Phe Leu Val
 1               5

<210> SEQ ID NO 650
<211> LENGTH: 9
<212> TYPE: PRT
<213> ORGANISM: Artificial Sequence
<220> FEATURE:
<223> OTHER INFORMATION: Description of Artificial Sequence: Peptide
      motif

<400> SEQUENCE: 650

Phe Cys Gly Gly Thr Glu Arg Ala Ile
 1               5

<210> SEQ ID NO 651
<211> LENGTH: 10
<212> TYPE: PRT
```

<213> ORGANISM: Artificial Sequence
<220> FEATURE:
<223> OTHER INFORMATION: Description of Artificial Sequence: Peptide
      motif

<400> SEQUENCE: 651

Val Pro Leu Ser Glu Lys Ile Ala Glu Leu
 1               5                   10

<210> SEQ ID NO 652
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 652

Phe Ser Arg Val Thr Asn Asn Val Val Leu
 1               5                   10

<210> SEQ ID NO 653
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 653

Leu Ser Arg Ser Leu Gly Ala Val Val Phe
 1               5                   10

<210> SEQ ID NO 654
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 654

Leu Ser Ser Asp Lys Met Val Cys Tyr Leu
 1               5                   10

<210> SEQ ID NO 655
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 655

Gly Ser Ser Pro Leu Gly Pro Ala Gly Leu
 1               5                   10

<210> SEQ ID NO 656
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 656

Tyr Ser Thr His Ala Ala Leu Ala Ala Leu
 1               5                   10

<210> SEQ ID NO 657
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 657

Gly Ser Leu Lys Gly Ser Thr Tyr Asn Leu
 1               5                  10

<210> SEQ ID NO 658
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 658

His Ala Val Leu Ala Asp Ser Val His Leu
 1               5                  10

<210> SEQ ID NO 659
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 659

Ala Ala Leu Ala Ala Leu Arg Gly His Phe
 1               5                  10

<210> SEQ ID NO 660
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 660

Ala Ala Gly Pro Gln Leu Pro Ser Trp Leu
 1               5                  10

<210> SEQ ID NO 661
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 661

Thr Ser Met Glu Trp Asp Thr Gln Val Val
 1               5                  10

<210> SEQ ID NO 662
<211> LENGTH: 10
<212> TYPE: PRT
<213> ORGANISM: Artificial Sequence
<220> FEATURE:
<223> OTHER INFORMATION: Description of Artificial Sequence: Peptide
      motif

```
<400> SEQUENCE: 662

Leu Ala Ala Leu Arg Gly His Phe Cys Leu
 1               5                  10

<210> SEQ ID NO 663
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 663

Ser Leu Lys Gly Ser Thr Tyr Asn Leu Leu
 1               5                  10

<210> SEQ ID NO 664
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 664

Ala Pro Phe Leu Val Gly Ile Glu Gly Ser
 1               5                  10

<210> SEQ ID NO 665
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 665

Cys Gly Ile Pro Val Gly Phe His Leu Tyr
 1               5                  10

<210> SEQ ID NO 666
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 666

Glu Pro Ala Ala Gly Pro Gln Leu Pro Ser
 1               5                  10

<210> SEQ ID NO 667
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 667

Leu Thr His Asn Arg Leu Lys Ser Leu Met
 1               5                  10

<210> SEQ ID NO 668
<211> LENGTH: 10
```

-continued

```
<212> TYPE: PRT
<213> ORGANISM: Artificial Sequence
<220> FEATURE:
<223> OTHER INFORMATION: Description of Artificial Sequence: Peptide
      motif

<400> SEQUENCE: 668

Gln Pro Leu Arg His Arg Ser Arg Cys Ala
1               5                   10

<210> SEQ ID NO 669
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 669

Leu Pro Ser Trp Leu Gln Pro Glu Arg Cys
1               5                   10

<210> SEQ ID NO 670
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 670

Ile Pro Val Gly Phe His Leu Tyr Ser Thr
1               5                   10

<210> SEQ ID NO 671
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 671

Cys Leu Ser Ser Asp Lys Met Val Cys Tyr
1               5                   10

<210> SEQ ID NO 672
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 672

Lys Ser Leu Met Lys Ile Leu Ser Glu Val
1               5                   10

<210> SEQ ID NO 673
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 673

Arg Cys Ala Thr Pro Pro Arg Gly Asp Phe
```

-continued

<210> SEQ ID NO 674
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 674

Ser Pro Leu Gly Pro Ala Gly Leu Gly Ala
1               5                   10

<210> SEQ ID NO 675
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 675

Asn Ala Ser Glu Met Asp Ile Gln Asn Val
1               5                   10

<210> SEQ ID NO 676
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 676

Gln Ala Ser Phe Thr Thr Ser Met Glu Trp
1               5                   10

<210> SEQ ID NO 677
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 677

Ser Ser Asp Lys Met Val Cys Tyr Leu Leu
1               5                   10

<210> SEQ ID NO 678
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 678

Asn Asn Val Val Leu Glu Ala Pro Phe Leu
1               5                   10

<210> SEQ ID NO 679
<211> LENGTH: 10
<212> TYPE: PRT
<213> ORGANISM: Artificial Sequence
<220> FEATURE:
<223> OTHER INFORMATION: Description of Artificial Sequence: Peptide motif

<400> SEQUENCE: 679

Ile Ala Glu Leu Lys Glu Lys Ile Val Leu
 1               5                   10

<210> SEQ ID NO 680
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 680

Arg Ala Ile Asp Gln Ala Ser Phe Thr Thr
 1               5                   10

<210> SEQ ID NO 681
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 681

His Asn Arg Leu Lys Ser Leu Met Lys Ile
 1               5                   10

<210> SEQ ID NO 682
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 682

Val Leu Thr His Asn Arg Leu Lys Ser Leu
 1               5                   10

<210> SEQ ID NO 683
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 683

Cys Gly Ser Cys Gly Ile Pro Val Gly Phe
 1               5                   10

<210> SEQ ID NO 684
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 684

Val Leu Ala Asp Ser Val His Leu Ala Trp
 1               5                   10

<210> SEQ ID NO 685

```
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 685

Thr Gln Val Val Lys Gly Ser Ser Pro Leu
 1               5                  10

<210> SEQ ID NO 686
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 686

Ser Cys Gly Ile Pro Val Gly Phe His Leu
 1               5                  10

<210> SEQ ID NO 687
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 687

His Leu Ala Trp Asp Leu Ser Arg Ser Leu
 1               5                  10

<210> SEQ ID NO 688
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 688

Trp Leu Gln Pro Glu Arg Cys Ala Val Phe
 1               5                  10

<210> SEQ ID NO 689
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 689

Phe Gln Cys Ala Gln Cys His Ala Val Leu
 1               5                  10

<210> SEQ ID NO 690
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 690
```

```
Thr Asn Asn Val Val Leu Glu Ala Pro Phe
  1               5                  10
```

<210> SEQ ID NO 691
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 691

```
Lys Ile Ala Glu Leu Lys Glu Lys Ile Val
  1               5                  10
```

<210> SEQ ID NO 692
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 692

```
Arg Leu Lys Ser Leu Met Lys Ile Leu Ser
  1               5                  10
```

<210> SEQ ID NO 693
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 693

```
Pro Pro Arg Gly Asp Phe Cys Gly Gly Thr
  1               5                  10
```

<210> SEQ ID NO 694
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 694

```
Gln Pro Glu Arg Cys Ala Val Phe Gln Cys
  1               5                  10
```

<210> SEQ ID NO 695
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 695

```
Asp Ser Val His Leu Ala Trp Asp Leu Ser
  1               5                  10
```

<210> SEQ ID NO 696
<211> LENGTH: 10
<212> TYPE: PRT
<213> ORGANISM: Artificial Sequence
<220> FEATURE:

```
<223> OTHER INFORMATION: Description of Artificial Sequence: Peptide
      motif

<400> SEQUENCE: 696

Thr Glu Arg Ala Ile Asp Gln Ala Ser Phe
  1               5                  10

<210> SEQ ID NO 697
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 697

Val Cys Tyr Leu Leu Lys Thr Lys Ala Ile
  1               5                  10

<210> SEQ ID NO 698
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 698

Ala Ile Val Asn Ala Ser Glu Met Asp Ile
  1               5                  10

<210> SEQ ID NO 699
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 699

Asn Leu Leu Phe Cys Gly Ser Cys Gly Ile
  1               5                  10

<210> SEQ ID NO 700
<211> LENGTH: 10
<212> TYPE: PRT
<213> ORGANISM: Artificial Sequence
<220> FEATURE:
<223> OTHER INFORMATION: Description of Artificial Sequence: Peptide
      motif

<400> SEQUENCE: 700

Ile Gln Asn Val Pro Leu Ser Glu Lys Ile
  1               5                  10

<210> SEQ ID NO 701
<211> LENGTH: 496
<212> TYPE: DNA
<213> ORGANISM: Unknown Organism
<220> FEATURE:
<223> OTHER INFORMATION: Description of Unknown Organism: Splice variant
      1 nucleotide sequence

<400> SEQUENCE: 701 ttttttttt  cctatctagc  tatctcttaa  aaacaaaagc  catagtaaat  gcatcagaga      60
tggatattca  aaatgttcct  ctatcagaaa  agattgcaga  ggtaaaattt  catgatggtt    120
```

```
gtatgctttt ttaaaataca gacaactctt gataacttct accaatgaac ttggggatga      180
tgaaatggca tgatgctcaa taatcctttt tacttgattt gaccttccct attgaatttg      240
taatgaaaaa caaaatacta aaaccacact gtaaggtata gttcaggaag aaaggaaaag      300
ctgctcaact gctgcactcc tgcattctcc tttgtgctgg gaatggatat catcatcttg      360
ccatagaggt gtcttctttg caaataccct gtaattgctc aactgtctca gacataagag      420
tgatgaaaca gttattaaga attcctggcc gggcgtggtg gctcacgcct gtaatcccag      480
cactttggcc tcgtgc                                                      496

<210> SEQ ID NO 702
<211> LENGTH: 83
<212> TYPE: DNA
<213> ORGANISM: Unknown Organism
<220> FEATURE:
<223> OTHER INFORMATION: Description of Unknown Organism: 85P1B3
      nucleotide sequence

<400> SEQUENCE: 702
gctatctctt aaaacaaaa gccatagtaa atgcatcaga gatggatatt caaaatgttc      60
ctctatcaga aagattgca gag                                               83

<210> SEQ ID NO 703
<211> LENGTH: 83
<212> TYPE: DNA
<213> ORGANISM: Unknown Organism
<220> FEATURE:
<223> OTHER INFORMATION: Description of Unknown Organism: Splice variant
      1 nucleotide sequence

<400> SEQUENCE: 703
gctatctctt aaaacaaaa gccatagtaa atgcatcaga gatggatatt caaaatgttc      60
ctctatcaga aagattgca gag                                               83

<210> SEQ ID NO 704
<211> LENGTH: 29
<212> TYPE: PRT
<213> ORGANISM: Unknown Organism
<220> FEATURE:
<223> OTHER INFORMATION: Description of Unknown Organism: 85P1B3 peptide
      sequence

<400> SEQUENCE: 704

Tyr Leu Leu Lys Thr Lys Ala Ile Val Asn Ala Ser Glu Met Asp Ile
  1               5                  10                  15

Gln Asn Val Pro Leu Ser Glu Lys Ile Ala Glu Leu Lys
             20                  25

<210> SEQ ID NO 705
<211> LENGTH: 165
<212> TYPE: PRT
<213> ORGANISM: Unknown Organism
<220> FEATURE:
<223> OTHER INFORMATION: Description of Unknown Organism: Splice variant
      1 open reading frame 1 peptide sequence
<220> FEATURE:
<221> NAME/KEY: MOD_RES
<222> LOCATION: (10)
<223> OTHER INFORMATION: Unknown amino acid or stop
<220> FEATURE:
<221> NAME/KEY: MOD_RES
<222> LOCATION: (15)..(16)
<223> OTHER INFORMATION: Unknown amino acid or stop
<220> FEATURE:
<221> NAME/KEY: MOD_RES
```

```
<222> LOCATION: (35)
<223> OTHER INFORMATION: Unknown amino acid or stop
<220> FEATURE:
<221> NAME/KEY: MOD_RES
<222> LOCATION: (56)
<223> OTHER INFORMATION: Unknown amino acid or stop
<220> FEATURE:
<221> NAME/KEY: MOD_RES
<222> LOCATION: (60)..(61)
<223> OTHER INFORMATION: Unknown amino acid or stop
<220> FEATURE:
<221> NAME/KEY: MOD_RES
<222> LOCATION: (74)
<223> OTHER INFORMATION: Unknown amino acid or stop
<220> FEATURE:
<221> NAME/KEY: MOD_RES
<222> LOCATION: (81)..(82)
<223> OTHER INFORMATION: Unknown amino acid or stop
<220> FEATURE:
<221> NAME/KEY: MOD_RES
<222> LOCATION: (87)
<223> OTHER INFORMATION: Unknown amino acid or stop
<220> FEATURE:
<221> NAME/KEY: MOD_RES
<222> LOCATION: (122)
<223> OTHER INFORMATION: Unknown amino acid or stop
<220> FEATURE:
<221> NAME/KEY: MOD_RES
<222> LOCATION: (139)
<223> OTHER INFORMATION: Unknown amino acid or stop
<220> FEATURE:
<221> NAME/KEY: MOD_RES
<222> LOCATION: (141)..(142)
<223> OTHER INFORMATION: Unknown amino acid or stop
<220> FEATURE:
<221> NAME/KEY: MOD_RES
<222> LOCATION: (146)
<223> OTHER INFORMATION: Unknown amino acid or stop
<220> FEATURE:
<221> NAME/KEY: MOD_RES
<222> LOCATION: (158)
<223> OTHER INFORMATION: Unknown amino acid or stop

<400> SEQUENCE: 705

Phe Phe Phe Ser Tyr Leu Ala Ile Ser Xaa Lys Gln Lys Pro Xaa Xaa
 1               5                  10                  15

Met His Gln Arg Trp Ile Phe Lys Met Phe Leu Tyr Gln Lys Arg Leu
            20                  25                  30

Gln Arg Xaa Asn Phe Met Met Val Val Cys Phe Phe Lys Ile Gln Thr
        35                  40                  45

Thr Leu Asp Asn Phe Tyr Gln Xaa Thr Trp Gly Xaa Xaa Asn Gly Met
     50                  55                  60

Met Leu Asn Asn Pro Phe Tyr Leu Ile Xaa Pro Ser Leu Leu Asn Leu
 65                  70                  75                  80

Xaa Xaa Lys Thr Lys Tyr Xaa Asn His Thr Val Arg Tyr Ser Ser Gly
                85                  90                  95

Arg Lys Glu Lys Leu Leu Asn Cys Cys Thr Pro Ala Phe Ser Phe Val
            100                 105                 110

Leu Gly Met Asp Ile Ile Ile Leu Pro Xaa Arg Cys Leu Leu Cys Lys
        115                 120                 125

Tyr Leu Val Ile Ala Gln Leu Ser Gln Thr Xaa Glu Xaa Xaa Asn Ser
    130                 135                 140

Tyr Xaa Glu Phe Leu Ala Gly Arg Gly Ser Arg Leu Xaa Ser Gln
145                 150                 155                 160

His Phe Gly Leu Val
            165
```

```
<210> SEQ ID NO 706
<211> LENGTH: 165
<212> TYPE: PRT
<213> ORGANISM: Unknown Organism
<220> FEATURE:
<223> OTHER INFORMATION: Description of Unknown Organism: Splice variant
      1 open reading frame 2 peptide sequence
<220> FEATURE:
<221> NAME/KEY: MOD_RES
<222> LOCATION: (6)
<223> OTHER INFORMATION: Unknown amino acid or stop
<220> FEATURE:
<221> NAME/KEY: MOD_RES
<222> LOCATION: (38)
<223> OTHER INFORMATION: Unknown amino acid or stop
<220> FEATURE:
<221> NAME/KEY: MOD_RES
<222> LOCATION: (64)
<223> OTHER INFORMATION: Unknown amino acid or stop
<220> FEATURE:
<221> NAME/KEY: MOD_RES
<222> LOCATION: (72)
<223> OTHER INFORMATION: Unknown amino acid or stop
<220> FEATURE:
<221> NAME/KEY: MOD_RES
<222> LOCATION: (78)
<223> OTHER INFORMATION: Unknown amino acid or stop
<220> FEATURE:
<221> NAME/KEY: MOD_RES
<222> LOCATION: (91)
<223> OTHER INFORMATION: Unknown amino acid or stop
<220> FEATURE:
<221> NAME/KEY: MOD_RES
<222> LOCATION: (131)
<223> OTHER INFORMATION: Unknown amino acid or stop

<400> SEQUENCE: 706

Phe Phe Phe Pro Ile Xaa Leu Ser Leu Lys Asn Lys Ser His Ser Lys
 1               5                  10                  15

Cys Ile Arg Asp Gly Tyr Ser Lys Cys Ser Ser Ile Arg Lys Asp Cys
                20                  25                  30

Arg Gly Lys Ile Ser Xaa Trp Leu Tyr Ala Phe Leu Lys Tyr Arg Gln
            35                  40                  45

Leu Leu Ile Thr Ser Thr Asn Glu Leu Gly Asp Asp Glu Met Ala Xaa
     50                  55                  60

Cys Ser Ile Ile Leu Phe Thr Xaa Phe Asp Leu Pro Tyr Xaa Ile Cys
 65                  70                  75                  80

Asn Glu Lys Gln Asn Thr Lys Thr Thr Leu Xaa Gly Ile Val Gln Glu
                85                  90                  95

Glu Arg Lys Ser Cys Ser Thr Ala Ala Leu Leu His Ser Pro Leu Cys
            100                 105                 110

Trp Glu Trp Ile Ser Ser Ser Cys His Arg Gly Val Phe Phe Ala Asn
        115                 120                 125

Thr Leu Xaa Leu Leu Asn Cys Leu Arg His Lys Ser Asp Glu Thr Val
    130                 135                 140

Ile Lys Asn Ser Trp Pro Gly Val Val Ala His Ala Cys Asn Pro Ser
145                 150                 155                 160

Thr Leu Ala Ser Cys
                165

<210> SEQ ID NO 707
<211> LENGTH: 164
<212> TYPE: PRT
<213> ORGANISM: Unknown Organism
<220> FEATURE:
<223> OTHER INFORMATION: Description of Unknown Organism: Splice variant
      1 open reading frame 3 peptide sequence
```

```
<220> FEATURE:
<221> NAME/KEY: MOD_RES
<222> LOCATION: (44)
<223> OTHER INFORMATION: Unknown amino acid or stop
<220> FEATURE:
<221> NAME/KEY: MOD_RES
<222> LOCATION: (50)..(51)
<223> OTHER INFORMATION: Unknown amino acid or stop
<220> FEATURE:
<221> NAME/KEY: MOD_RES
<222> LOCATION: (67)
<223> OTHER INFORMATION: Unknown amino acid or stop
<220> FEATURE:
<221> NAME/KEY: MOD_RES
<222> LOCATION: (93)
<223> OTHER INFORMATION: Unknown amino acid or stop

<400> SEQUENCE: 707

Phe Phe Phe Leu Ser Ser Tyr Leu Leu Lys Thr Lys Ala Ile Val Asn
  1               5                  10                  15

Ala Ser Glu Met Asp Ile Gln Asn Val Pro Leu Ser Glu Lys Ile Ala
             20                  25                  30

Glu Val Lys Phe His Asp Gly Cys Met Leu Phe Xaa Asn Thr Asp Asn
         35                  40                  45

Ser Xaa Xaa Leu Leu Pro Met Asn Leu Gly Met Met Lys Trp His Asp
 50                  55                  60

Ala Gln Xaa Ser Phe Leu Leu Asp Leu Thr Phe Pro Ile Glu Phe Val
 65                  70                  75                  80

Met Lys Asn Lys Ile Leu Lys Pro His Cys Lys Val Xaa Phe Arg Lys
             85                  90                  95

Lys Gly Lys Ala Ala Gln Leu Leu His Ser Cys Ile Leu Leu Cys Ala
            100                 105                 110

Gly Asn Gly Tyr His His Leu Ala Ile Glu Val Ser Ser Leu Gln Ile
            115                 120                 125

Pro Cys Asn Cys Ser Thr Val Ser Asp Ile Arg Val Met Lys Gln Leu
        130                 135                 140

Leu Arg Ile Pro Gly Arg Ala Trp Trp Leu Thr Pro Val Ile Pro Ala
145                 150                 155                 160

Leu Trp Pro Arg

<210> SEQ ID NO 708
<211> LENGTH: 4
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 708

Lys Asp Glu Leu
  1

<210> SEQ ID NO 709
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 709

His His His His His His
  1               5
```

<210> SEQ ID NO 710
<211> LENGTH: 14
<212> TYPE: PRT
<213> ORGANISM: Unknown Organism
<220> FEATURE:
<223> OTHER INFORMATION: Description of Unknown Organism: Tetanus toxoid peptide

<400> SEQUENCE: 710

Gln Tyr Ile Lys Ala Asn Ser Lys Phe Ile Gly Ile Thr Glu
 1               5                  10

<210> SEQ ID NO 711
<211> LENGTH: 21
<212> TYPE: PRT
<213> ORGANISM: Plasmodium falciparum

<400> SEQUENCE: 711

Asp Ile Glu Lys Lys Ile Ala Lys Met Glu Lys Ala Ser Ser Val Phe
 1               5                  10                  15

Asn Val Val Asn Ser
            20

<210> SEQ ID NO 712
<211> LENGTH: 16
<212> TYPE: PRT
<213> ORGANISM: Streptococcus sp.

<400> SEQUENCE: 712

Gly Ala Val Asp Ser Ile Leu Gly Gly Val Ala Thr Tyr Gly Ala Ala
 1               5                  10                  15

<210> SEQ ID NO 713
<211> LENGTH: 13
<212> TYPE: PRT
<213> ORGANISM: Artificial Sequence
<220> FEATURE:
<223> OTHER INFORMATION: Description of Artificial Sequence: Formula peptide
<220> FEATURE:
<221> NAME/KEY: MOD_RES
<222> LOCATION: (3)
<223> OTHER INFORMATION: Cyclohexylalanine, Phe or Tyr

<400> SEQUENCE: 713

Ala Lys Xaa Val Ala Ala Trp Thr Leu Lys Ala Ala Ala
 1               5                  10

<210> SEQ ID NO 714
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 714
ttttgatcaa gcttttttttt tttttttttt tttttttttt ttt                43

<210> SEQ ID NO 715
<211> LENGTH: 42
<212> TYPE: DNA
<213> ORGANISM: Artificial Sequence
<220> FEATURE:
<223> OTHER INFORMATION: Description of Artificial Sequence: Synthetic adaptor

<400> SEQUENCE: 715

```
ctaatacgac tcactatagg gctcgagcgg ccgcccgggc ag         42
```

<210> SEQ ID NO 716
<211> LENGTH: 12
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 716

```
gatcctgccc gg                                          12
```

<210> SEQ ID NO 717
<211> LENGTH: 40
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 717

```
gtaatacgac tcactatagg gcagcgtggt cgcggccgag            40
```

<210> SEQ ID NO 718
<211> LENGTH: 10
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 718

```
gatcctcggc                                             10
```

<210> SEQ ID NO 719
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 719

```
ctaatacgac tcactatagg gc                               22
```

<210> SEQ ID NO 720
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 720

```
tcgagcggcc gcccgggcag ga                               22
```

<210> SEQ ID NO 721
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 721

```
agcgtggtcg cggccgagga                                  20
```

<210> SEQ ID NO 722

-continued

```
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 722
atatcgccgc gctcgtcgtc gacaa                                              25

<210> SEQ ID NO 723
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 723
agccacacgc agctcattgt agaagg                                             26

<210> SEQ ID NO 724
<211> LENGTH: 319
<212> TYPE: DNA
<213> ORGANISM: Artificial Sequence
<220> FEATURE:
<223> OTHER INFORMATION: Description of Artificial Sequence: 85P1B3
      nucleotide sequence

<400> SEQUENCE: 724
gatcagagga cacatgggac tctgcatctt aattcctaaa tttacagtca aagacatttt        60
cagagataag tattatgaat tcaataagaa tctaaagtaa gttcttaagg caaatagcta      120
taaaagagaa gaatccttag tctctcatct tctaaaaaca gcttcacaaa taatttggaa      180
aatcagccta aggtaaaata gaaactgcat ttcccctcca ttcttgaagc caatcttttt      240
caagaaatga ctaagcagca cctgttgttg aagacagcaa taaagcctga acctgacact      300
caagctttgg tacaggatc                                                   319

<210> SEQ ID NO 725
<211> LENGTH: 319
<212> TYPE: DNA
<213> ORGANISM: Artificial Sequence
<220> FEATURE:
<223> OTHER INFORMATION: Description of Artificial Sequence: 85P1B3
      nucleotide sequence

<400> SEQUENCE: 725
gatcagagga cacatgggac tctgcatctt aattcctaaa tttacagtca aagacatttt        60
cagagataag tattatgaat tcaataagaa tctaaagtaa gttcttaagg caaatagcta      120
taaaagagaa gaatccttag tctctcatct tctaaaaaca gcttcacaaa taatttggaa      180
aatcagccta aggtaaaata gaaactgcat ttcccctcca ttcttgaagc caatcttttt      240
caagaaatga ctaagcagca cctgttgttg aagacagcaa taaagcctga acctgacact      300
caagctttgg tacaggatc                                                   319

<210> SEQ ID NO 726
<211> LENGTH: 319
<212> TYPE: DNA
<213> ORGANISM: Homo sapiens

<400> SEQUENCE: 726
gatcagagga cacatgggac tctgcatctt aattcctaaa tttacagtca aagacatttt        60
cagagataag tattatgaat tcaataagaa tctaaagtaa gttcttaagg caaatagcta      120
```

```
taaaagagaa gaatccttag tctctcatct tctaaaaaca gcttcacaaa taatttggaa      180
aatcagccta aaggtaaata gaaactgcat ttcccctcca ttcttgaagc caatctttt       240 caagaaatga ctaagcagca cctgttgttg aagacagcaa taaagcctga acctgacact      300
caagctttgg tacaggatc                                                  319
```

```
<210> SEQ ID NO 727
<211> LENGTH: 1262
<212> TYPE: DNA
<213> ORGANISM: Unknown Organism
<220> FEATURE:
<223> OTHER INFORMATION: Description of Unknown Organism: 85P1B3/OIP5
      clone A nucleotide sequence
<220> FEATURE:
<221> NAME/KEY: CDS
<222> LOCATION: (13)..(699)

<400> SEQUENCE: 727
```

```
ggctgcggga ag atg gcg gct cag ccg ctg cgg cat cgc tca cgt tgt gca        51
              Met Ala Ala Gln Pro Leu Arg His Arg Ser Arg Cys Ala
                1               5                  10 acg ccg ccc cgg ggg gac ttt tgt ggt ggc act gag agg gcg att gac          99
Thr Pro Pro Arg Gly Asp Phe Cys Gly Gly Thr Glu Arg Ala Ile Asp
         15                  20                  25 caa gct tct ttt acg acc tcc atg gag tgg gat acg cag gtg gtg aag         147
Gln Ala Ser Phe Thr Thr Ser Met Glu Trp Asp Thr Gln Val Val Lys
 30                  35                  40                  45 ggg tcc tcg ccg ctc ggc ccc gca ggg ctg ggg gct gag gag cca gcc         195
Gly Ser Ser Pro Leu Gly Pro Ala Gly Leu Gly Ala Glu Glu Pro Ala
                 50                  55                  60 gcc ggc ccg cag ctg ccg tct tgg ctg cag cct gag agg tgc gct gtg         243
Ala Gly Pro Gln Leu Pro Ser Trp Leu Gln Pro Glu Arg Cys Ala Val
             65                  70                  75 ttc cag tgc gca cag tgt cac gca gtg ctc gcc gac tcg gtg cac ctc         291
Phe Gln Cys Ala Gln Cys His Ala Val Leu Ala Asp Ser Val His Leu
         80                  85                  90 gcc tgg gac ctg tcg cgg tcc ctc ggg gcc gtg gtc ttc tcc aga gtt         339
Ala Trp Asp Leu Ser Arg Ser Leu Gly Ala Val Val Phe Ser Arg Val
     95                 100                 105 aca aat aac gtc gtt ttg gaa gcg ccc ttc cta gtt ggc att gaa ggt         387
Thr Asn Asn Val Val Leu Glu Ala Pro Phe Leu Val Gly Ile Glu Gly
110                 115                 120                 125 tca ctc aaa ggc agt act tac aac ctt tta ttc tgt ggt tct tgt ggg         435
Ser Leu Lys Gly Ser Thr Tyr Asn Leu Leu Phe Cys Gly Ser Cys Gly
                130                 135                 140 att ccc gtt ggt ttc cat ctg tat tct acc cat gct gcc ctg gct gcc         483
Ile Pro Val Gly Phe His Leu Tyr Ser Thr His Ala Ala Leu Ala Ala
            145                 150                 155 ttg aga ggt cac ttc tgc ctt tcc agt gac aaa atg gtg tgc tat ctc         531
Leu Arg Gly His Phe Cys Leu Ser Ser Asp Lys Met Val Cys Tyr Leu
        160                 165                 170 tta aaa aca aaa gcc ata gta aat gca tca gag atg gat att caa aat         579
Leu Lys Thr Lys Ala Ile Val Asn Ala Ser Glu Met Asp Ile Gln Asn
175                 180                 185 gtt cct cta tca gaa aag att gca gag ctg aaa gag aag ata gtg cta         627
Val Pro Leu Ser Glu Lys Ile Ala Glu Leu Lys Glu Lys Ile Val Leu
190                 195                 200                 205 acg cac aat cgc tta aaa tca cta atg aag att ctg agt gaa gtg act         675
Thr His Asn Arg Leu Lys Ser Leu Met Lys Ile Leu Ser Glu Val Thr
                210                 215                 220
```

```
cct gac cag tcc aag cca gaa aac tgatcctgta ccaaagcttg agtgtcaggt    729
Pro Asp Gln Ser Lys Pro Glu Asn
            225 tcaggcttta ttgctgtctt caacaacagg tgctgcttag tcatttcttg aaaaagattg    789 gcttcaagaa tggagggaa atgcagtttc tatttacctt taggctgatt ttccaaatta    849 tttgtgaagc tgtttttaga agatgagaga ctaaggattc ttctctttta tagctatttg    909 ccttaagaac ttactttaga ttcttattga attcataata cttatctctg aaaatgtctt    969 tgactgtaaa tttaggaatt aagatgcaga gtcccatgtg tcctctgatc taaagttgca   1029 tggttggtct gaaatagag ttgggcttaa tgttgacttc tattactcct gcatggagca   1089 gttgttatga atactaatac atcacttttt aacttctgta aaatacagat cataatattc   1149 tataggtaat gtttaataaa ttgcctgaat aataaaaaaa aaaaaaaaaa aaaaaaaaa   1209 aaaaaaaaaa aaaaaaaaaa aaaaaaaaaa aaaaaaaaa aaaaaaaaaa aaa          1262
```

<210> SEQ ID NO 728
<211> LENGTH: 229
<212> TYPE: PRT
<213> ORGANISM: Unknown Organism
<220> FEATURE:
<223> OTHER INFORMATION: Description of Unknown Organism: 85P1B3/OIP5
      clone A protein

<400> SEQUENCE: 728

```
Met Ala Ala Gln Pro Leu Arg His Arg Ser Arg Cys Ala Thr Pro Pro
 1               5                  10                  15

Arg Gly Asp Phe Cys Gly Gly Thr Glu Arg Ala Ile Asp Gln Ala Ser
             20                  25                  30

Phe Thr Thr Ser Met Glu Trp Asp Thr Gln Val Val Lys Gly Ser Ser
         35                  40                  45

Pro Leu Gly Pro Ala Gly Leu Gly Ala Glu Pro Ala Ala Gly Pro
     50                  55                  60

Gln Leu Pro Ser Trp Leu Gln Pro Glu Arg Cys Ala Val Phe Gln Cys
 65                  70                  75                  80

Ala Gln Cys His Ala Val Leu Ala Asp Ser Val His Leu Ala Trp Asp
                 85                  90                  95

Leu Ser Arg Ser Leu Gly Ala Val Val Phe Ser Arg Val Thr Asn Asn
            100                 105                 110

Val Val Leu Glu Ala Pro Phe Leu Val Gly Ile Glu Gly Ser Leu Lys
        115                 120                 125

Gly Ser Thr Tyr Asn Leu Leu Phe Cys Gly Ser Cys Gly Ile Pro Val
    130                 135                 140

Gly Phe His Leu Tyr Ser Thr His Ala Ala Leu Ala Ala Leu Arg Gly
145                 150                 155                 160

His Phe Cys Leu Ser Ser Asp Lys Met Val Cys Tyr Leu Leu Lys Thr
                165                 170                 175

Lys Ala Ile Val Asn Ala Ser Glu Met Asp Ile Gln Asn Val Pro Leu
            180                 185                 190

Ser Glu Lys Ile Ala Glu Leu Lys Glu Lys Ile Val Leu Thr His Asn
        195                 200                 205

Arg Leu Lys Ser Leu Met Lys Ile Leu Ser Glu Val Thr Pro Asp Gln
    210                 215                 220

Ser Lys Pro Glu Asn
225
```

```
<210> SEQ ID NO 729
<211> LENGTH: 229
<212> TYPE: PRT
<213> ORGANISM: Unknown Organism
<220> FEATURE:
<223> OTHER INFORMATION: Description of Unknown Organism: 85P1B3/OIP5
      protein sequence

<400> SEQUENCE: 729

Met Ala Ala Gln Pro Leu Arg His Arg Ser Arg Cys Ala Thr Pro Pro
  1               5                  10                  15

Arg Gly Asp Phe Cys Gly Gly Thr Glu Arg Ala Ile Asp Gln Ala Ser
             20                  25                  30

Phe Thr Thr Ser Met Glu Trp Asp Thr Gln Val Val Lys Gly Ser Ser
         35                  40                  45

Pro Leu Gly Pro Ala Gly Leu Gly Ala Glu Glu Pro Ala Ala Gly Pro
     50                  55                  60

Gln Leu Pro Ser Trp Leu Gln Pro Glu Arg Cys Ala Val Phe Gln Cys
 65                  70                  75                  80

Ala Gln Cys His Ala Val Leu Ala Asp Ser Val His Leu Ala Trp Asp
                 85                  90                  95

Leu Ser Arg Ser Leu Gly Ala Val Val Phe Ser Arg Val Thr Asn Asn
            100                 105                 110

Val Val Leu Glu Ala Pro Phe Leu Val Gly Ile Glu Gly Ser Leu Lys
        115                 120                 125

Gly Ser Thr Tyr Asn Leu Leu Phe Cys Gly Ser Cys Gly Ile Pro Val
    130                 135                 140

Gly Phe His Leu Tyr Ser Thr His Ala Ala Leu Ala Ala Leu Arg Gly
145                 150                 155                 160

His Phe Cys Leu Ser Ser Asp Lys Met Val Cys Tyr Leu Leu Lys Thr
                165                 170                 175

Lys Ala Ile Val Asn Ala Ser Glu Met Asp Ile Gln Asn Val Pro Leu
            180                 185                 190

Ser Glu Lys Ile Ala Glu Leu Lys Glu Lys Ile Val Leu Thr His Asn
        195                 200                 205

Arg Leu Lys Ser Leu Met Lys Ile Leu Ser Glu Val Thr Pro Asp Gln
    210                 215                 220

Ser Lys Pro Glu Asn
225

<210> SEQ ID NO 730
<211> LENGTH: 229
<212> TYPE: PRT
<213> ORGANISM: Unknown Organism
<220> FEATURE:
<223> OTHER INFORMATION: Description of Unknown Organism: 85P1B3 protein
      sequence

<400> SEQUENCE: 730

Met Ala Ala Gln Pro Leu Arg His Arg Ser Arg Cys Ala Thr Pro Pro
  1               5                  10                  15

Arg Gly Asp Phe Cys Gly Gly Thr Glu Arg Ala Ile Asp Gln Ala Ser
             20                  25                  30

Phe Thr Thr Ser Met Glu Trp Asp Thr Gln Val Val Lys Gly Ser Ser
         35                  40                  45

Pro Leu Gly Pro Ala Gly Leu Gly Ala Glu Glu Pro Ala Ala Gly Pro
     50                  55                  60

Gln Leu Pro Ser Trp Leu Gln Pro Glu Arg Cys Ala Val Phe Gln Cys
```

-continued

```
                65                  70                  75                  80
Ala Gln Cys His Ala Val Leu Ala Asp Ser Val His Leu Ala Trp Asp
                    85                  90                  95
Leu Ser Arg Ser Leu Gly Ala Val Val Phe Ser Arg Val Thr Asn Asn
                100                 105                 110
Val Val Leu Glu Ala Pro Phe Leu Val Gly Ile Glu Gly Ser Leu Lys
                115                 120                 125
Gly Ser Thr Tyr Asn Leu Leu Phe Cys Gly Ser Cys Gly Ile Pro Val
                130                 135                 140
Gly Phe His Leu Tyr Ser Thr His Ala Ala Leu Ala Ala Leu Arg Gly
145                 150                 155                 160
His Phe Cys Leu Ser Ser Asp Lys Met Val Cys Tyr Leu Leu Lys Thr
                165                 170                 175
Lys Ala Ile Val Asn Ala Ser Glu Met Asp Ile Gln Asn Val Pro Leu
                180                 185                 190
Ser Glu Lys Ile Ala Glu Leu Lys Glu Lys Ile Val Leu Thr His Asn
                195                 200                 205
Arg Leu Lys Ser Leu Met Lys Ile Leu Ser Glu Val Thr Pro Asp Gln
210                 215                 220
Ser Lys Pro Glu Asn
225

<210> SEQ ID NO 731
<211> LENGTH: 229
<212> TYPE: PRT
<213> ORGANISM: Homo sapiens

<400> SEQUENCE: 731

Met Ala Ala Gln Pro Leu Arg His Arg Ser Arg Cys Ala Thr Pro Pro
1               5                   10                  15
Arg Gly Asp Phe Cys Gly Gly Thr Glu Arg Ala Ile Asp Gln Ala Ser
                20                  25                  30
Phe Thr Thr Ser Met Glu Trp Asp Thr Gln Val Val Lys Gly Ser Ser
            35                  40                  45
Pro Leu Gly Pro Ala Gly Leu Gly Ala Glu Glu Pro Ala Ala Gly Pro
        50                  55                  60
Gln Leu Pro Ser Trp Leu Gln Pro Glu Arg Cys Ala Val Phe Gln Cys
65                  70                  75                  80
Ala Gln Cys His Ala Val Leu Ala Asp Ser Val His Leu Ala Trp Asp
                    85                  90                  95
Leu Ser Arg Ser Leu Gly Ala Val Val Phe Ser Arg Val Thr Asn Asn
                100                 105                 110
Val Val Leu Glu Ala Pro Phe Leu Val Gly Ile Glu Gly Ser Leu Lys
                115                 120                 125
Gly Ser Thr Tyr Asn Leu Leu Phe Cys Gly Ser Cys Gly Ile Pro Val
                130                 135                 140
Gly Phe His Leu Tyr Ser Thr His Ala Ala Leu Ala Ala Leu Arg Gly
145                 150                 155                 160
His Phe Cys Leu Ser Ser Asp Lys Met Val Cys Tyr Leu Leu Lys Thr
                165                 170                 175
Lys Ala Ile Val Asn Ala Ser Glu Met Asp Ile Gln Asn Val Pro Leu
                180                 185                 190
Ser Glu Lys Ile Ala Glu Leu Lys Glu Lys Ile Val Leu Thr His Asn
                195                 200                 205
```

Arg Leu Lys Ser Leu Met Lys Ile Leu Ser Glu Val Thr Pro Asp Gln
    210                 215                 220

Ser Lys Pro Glu Asn
225

<210> SEQ ID NO 732
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 732
catgggactc tgcatcttaa ttcc                                          24

<210> SEQ ID NO 733
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 733
caggttcagg ctttattgct gtct                                          24

<210> SEQ ID NO 734
<211> LENGTH: 24
<212> TYPE: DNA
<213> ORGANISM: Artificial Sequence
<220> FEATURE:
<223> OTHER INFORMATION: Description of Artificial Sequence: Synthetic
      FLAG tag

<400> SEQUENCE: 734
gattacaagg atgacgacga taag                                          24

<210> SEQ ID NO 735
<211> LENGTH: 4
<212> TYPE: PRT
<213> ORGANISM: Unknown Organism
<220> FEATURE:
<223> OTHER INFORMATION: Description of Unknown Organism:
      N-glycosylation site motif

<400> SEQUENCE: 735

Asn Ala Ser Glu
  1

<210> SEQ ID NO 736
<211> LENGTH: 4
<212> TYPE: PRT
<213> ORGANISM: Unknown Organism
<220> FEATURE:
<223> OTHER INFORMATION: Description of Unknown Organism: casein kinase
      II phosphorylation site motif

<400> SEQUENCE: 736

Thr Ser Met Glu
  1

<210> SEQ ID NO 737
<211> LENGTH: 4
<212> TYPE: PRT
<213> ORGANISM: Unknown Organism
<220> FEATURE:
<223> OTHER INFORMATION: Description of Unknown Organism: casein kinase
      II phosphorylation site motif

```
<400> SEQUENCE: 737

Ser Glu Met Asp
 1

<210> SEQ ID NO 738
<211> LENGTH: 4
<212> TYPE: PRT
<213> ORGANISM: Unknown Organism
<220> FEATURE:
<223> OTHER INFORMATION: Description of Unknown Organism: casein kinase
      II phosphorylation site motif

<400> SEQUENCE: 738

Ser Lys Pro Glu
 1

<210> SEQ ID NO 739
<211> LENGTH: 6
<212> TYPE: PRT
<213> ORGANISM: Unknown Organism
<220> FEATURE:
<223> OTHER INFORMATION: Description of Unknown Organism:
      N-myristoylation site motif

<400> SEQUENCE: 739

Gly Thr Glu Arg Ala Ile
 1               5

<210> SEQ ID NO 740
<211> LENGTH: 6
<212> TYPE: PRT
<213> ORGANISM: Unknown Organism
<220> FEATURE:
<223> OTHER INFORMATION: Description of Unknown Organism:
      N-myristoylation site motif

<400> SEQUENCE: 740

Gly Ile Glu Gly Ser Leu
 1               5

<210> SEQ ID NO 741
<211> LENGTH: 6
<212> TYPE: PRT
<213> ORGANISM: Unknown Organism
<220> FEATURE:
<223> OTHER INFORMATION: Description of Unknown Organism:
      N-myristoylation site motif

<400> SEQUENCE: 741

Gly Ser Leu Lys Gly Ser
 1               5

<210> SEQ ID NO 742
<211> LENGTH: 6
<212> TYPE: PRT
<213> ORGANISM: Unknown Organism
<220> FEATURE:
<223> OTHER INFORMATION: Description of Unknown Organism:
      N-myristoylation site motif

<400> SEQUENCE: 742

Gly Ser Thr Tyr Asn Leu
 1               5

<210> SEQ ID NO 743
<211> LENGTH: 6
```

```
<212> TYPE: PRT
<213> ORGANISM: Unknown Organism
<220> FEATURE:
<223> OTHER INFORMATION: Description of Unknown Organism:
      N-myristoylation site motif

<400> SEQUENCE: 743

Gly Ile Pro Val Gly Phe
 1               5

<210> SEQ ID NO 744
<211> LENGTH: 6
<212> TYPE: PRT
<213> ORGANISM: Unknown Organism
<220> FEATURE:
<223> OTHER INFORMATION: Description of Unknown Organism: cytochrome c
      family heme-binding site motif

<400> SEQUENCE: 744

Cys Ala Gln Cys His Ala
 1               5

<210> SEQ ID NO 745
<211> LENGTH: 29
<212> TYPE: PRT
<213> ORGANISM: Unknown Organism
<220> FEATURE:
<223> OTHER INFORMATION: Description of Unknown Organism: 85P1B3 variant
      peptide sequence

<400> SEQUENCE: 745

Tyr Leu Leu Lys Thr Lys Ala Ile Val Asn Ala Ser Glu Met Asp Ile
 1               5                  10                  15

Gln Asn Val Pro Leu Ser Glu Lys Ile Ala Glu Val Lys

<210> SEQ ID NO 746
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 746
catgggactc tgcatcttaa ttcc                                           24

<210> SEQ ID NO 747
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 747
caggttcagg ctttattgct gtct                                           24

<210> SEQ ID NO 748
<211> LENGTH: 6
<212> TYPE: PRT
<213> ORGANISM: Homo sapiens

<400> SEQUENCE: 748

Thr Ile Leu Val Met Ser
 1               5

<210> SEQ ID NO 749
<211> LENGTH: 7
```

-continued

<212> TYPE: PRT
<213> ORGANISM: Homo sapiens

<400> SEQUENCE: 749

Leu Ile Val Met Ala Thr Gln
 1               5

<210> SEQ ID NO 750
<211> LENGTH: 6
<212> TYPE: PRT
<213> ORGANISM: Homo sapiens

<400> SEQUENCE: 750

Ile Val Met Ala Thr Leu
 1               5

<210> SEQ ID NO 751
<211> LENGTH: 7
<212> TYPE: PRT
<213> ORGANISM: Homo sapiens

<400> SEQUENCE: 751

Val Ser Met Ala Thr Leu Ile
 1               5

<210> SEQ ID NO 752
<211> LENGTH: 8
<212> TYPE: PRT
<213> ORGANISM: Homo sapiens

<400> SEQUENCE: 752

Tyr Phe Trp Ile Val Leu Met Thr
 1               5

<210> SEQ ID NO 753
<211> LENGTH: 6
<212> TYPE: PRT
<213> ORGANISM: Homo sapiens

<400> SEQUENCE: 753

Phe Ile Tyr Trp Leu Met
 1               5

<210> SEQ ID NO 754
<211> LENGTH: 8
<212> TYPE: PRT
<213> ORGANISM: Homo sapiens

<400> SEQUENCE: 754

Val Ile Leu Phe Met Trp Tyr Ala
 1               5

<210> SEQ ID NO 755
<211> LENGTH: 8
<212> TYPE: PRT
<213> ORGANISM: Homo sapiens

<400> SEQUENCE: 755

Phe Tyr Leu Trp Met Ile Val Ala
 1               5

<210> SEQ ID NO 756
<211> LENGTH: 8
<212> TYPE: PRT
<213> ORGANISM: Homo sapiens

```
<400> SEQUENCE: 756

Phe Trp Tyr Leu Ile Met Val Ala
1               5

<210> SEQ ID NO 757
<211> LENGTH: 8
<212> TYPE: PRT
<213> ORGANISM: Homo sapiens

<400> SEQUENCE: 757

Phe Trp Tyr Leu Ile Val Met Ala
1               5

<210> SEQ ID NO 758
<211> LENGTH: 6
<212> TYPE: PRT
<213> ORGANISM: Homo sapiens

<400> SEQUENCE: 758

Gln Leu Ile Val Met Pro
1               5

<210> SEQ ID NO 759
<211> LENGTH: 8
<212> TYPE: PRT
<213> ORGANISM: Homo sapiens

<400> SEQUENCE: 759

Phe Trp Tyr Met Ile Val Leu Ala
1               5

<210> SEQ ID NO 760
<211> LENGTH: 7
<212> TYPE: PRT
<213> ORGANISM: Homo sapiens

<400> SEQUENCE: 760

Leu Met Val Gln Ile Ala Thr
1               5

<210> SEQ ID NO 761
<211> LENGTH: 6
<212> TYPE: PRT
<213> ORGANISM: Homo sapiens

<400> SEQUENCE: 761

Val Leu Ile Met Ala Thr
1               5

<210> SEQ ID NO 762
<211> LENGTH: 11
<212> TYPE: PRT
<213> ORGANISM: Homo sapiens

<400> SEQUENCE: 762

Leu Met Val Ile Ser Ala Thr Phe Cys Gly Asp
1               5                   10

<210> SEQ ID NO 763
<211> LENGTH: 6
<212> TYPE: PRT
<213> ORGANISM: Homo sapiens

<400> SEQUENCE: 763
```

Lys Tyr Arg His Phe Ala
1               5

<210> SEQ ID NO 764
<211> LENGTH: 12
<212> TYPE: PRT
<213> ORGANISM: Homo sapiens

<400> SEQUENCE: 764

Val Thr Met Leu Ile Ser Ala Gly Asn Cys Asp Phe
1               5                   10

<210> SEQ ID NO 765
<211> LENGTH: 4
<212> TYPE: PRT
<213> ORGANISM: Homo sapiens

<400> SEQUENCE: 765

Lys Arg Tyr His
1

<210> SEQ ID NO 766
<211> LENGTH: 4
<212> TYPE: PRT
<213> ORGANISM: Homo sapiens

<400> SEQUENCE: 766

Tyr Phe Trp Met
1

<210> SEQ ID NO 767
<211> LENGTH: 4
<212> TYPE: PRT
<213> ORGANISM: Homo sapiens

<400> SEQUENCE: 767

Phe Leu Ile Trp
1

<210> SEQ ID NO 768
<211> LENGTH: 7
<212> TYPE: PRT
<213> ORGANISM: Homo sapiens

<400> SEQUENCE: 768

Met Val Thr Ala Leu Ile Ser
1               5

<210> SEQ ID NO 769
<211> LENGTH: 8
<212> TYPE: PRT
<213> ORGANISM: Homo sapiens

<400> SEQUENCE: 769

Met Val Ala Leu Phe Ile Ser Thr
1               5

<210> SEQ ID NO 770
<211> LENGTH: 7
<212> TYPE: PRT
<213> ORGANISM: Homo sapiens

<400> SEQUENCE: 770

Ala Val Thr Met Ser Leu Ile

-continued

```
1               5

<210> SEQ ID NO 771
<211> LENGTH: 8
<212> TYPE: PRT
<213> ORGANISM: Homo sapiens

<400> SEQUENCE: 771

Leu Met Phe Trp Tyr Ala Ile Val
1               5

<210> SEQ ID NO 772
<211> LENGTH: 8
<212> TYPE: PRT
<213> ORGANISM: Homo sapiens

<400> SEQUENCE: 772

Leu Met Phe Trp Tyr Ile Val Ala
1               5

<210> SEQ ID NO 773
<211> LENGTH: 8
<212> TYPE: PRT
<213> ORGANISM: Homo sapiens

<400> SEQUENCE: 773

Leu Ile Val Phe Trp Tyr Ala Met
1               5

<210> SEQ ID NO 774
<211> LENGTH: 8
<212> TYPE: PRT
<213> ORGANISM: Homo sapiens

<400> SEQUENCE: 774

Ile Met Phe Trp Tyr Ala Leu Val
1               5

<210> SEQ ID NO 775
<211> LENGTH: 9
<212> TYPE: PRT
<213> ORGANISM: Homo sapiens

<400> SEQUENCE: 775

Ala Thr Ile Val Leu Met Phe Trp Tyr
1               5

<210> SEQ ID NO 776
<211> LENGTH: 7
<212> TYPE: PRT
<213> ORGANISM: Homo sapiens

<400> SEQUENCE: 776

Phe Met Tyr Leu Ile Val Trp
1               5

<210> SEQ ID NO 777
<211> LENGTH: 9
<212> TYPE: PRT
<213> ORGANISM: Homo sapiens

<400> SEQUENCE: 777

Val Ser Thr Cys Pro Ala Leu Ile Met
1               5
```

<210> SEQ ID NO 778
<211> LENGTH: 7
<212> TYPE: PRT
<213> ORGANISM: Homo sapiens

<400> SEQUENCE: 778

Met Phe Leu Ile Val Trp Tyr
 1               5

<210> SEQ ID NO 779
<211> LENGTH: 4
<212> TYPE: PRT
<213> ORGANISM: Homo sapiens

<400> SEQUENCE: 779

Pro Ala Met Gln
 1

<210> SEQ ID NO 780
<211> LENGTH: 9
<212> TYPE: PRT
<213> ORGANISM: Homo sapiens

<400> SEQUENCE: 780

Val Met Ala Thr Ser Pro Leu Ile Cys
 1               5

<210> SEQ ID NO 781
<211> LENGTH: 7
<212> TYPE: PRT
<213> ORGANISM: Homo sapiens

<400> SEQUENCE: 781

Met Phe Leu Ile Val Trp Tyr
 1               5

<210> SEQ ID NO 782
<211> LENGTH: 9
<212> TYPE: PRT
<213> ORGANISM: Homo sapiens

<400> SEQUENCE: 782

Ile Val Met Ser Ala Cys Thr Pro Leu
 1               5

<210> SEQ ID NO 783
<211> LENGTH: 6
<212> TYPE: PRT
<213> ORGANISM: Homo sapiens

<400> SEQUENCE: 783

Leu Ile Val Met Phe Tyr
 1               5

<210> SEQ ID NO 784
<211> LENGTH: 7
<212> TYPE: PRT
<213> ORGANISM: Homo sapiens

<400> SEQUENCE: 784

Leu Ile Val Met Phe Ala Tyr
 1               5

<210> SEQ ID NO 785

```
<211> LENGTH: 6
<212> TYPE: PRT
<213> ORGANISM: Homo sapiens

<400> SEQUENCE: 785

Asp Asn Gln Glu Ser Thr
 1               5

<210> SEQ ID NO 786
<211> LENGTH: 7
<212> TYPE: PRT
<213> ORGANISM: Homo sapiens

<400> SEQUENCE: 786

Met Phe Leu Ile Val Trp Tyr
 1               5

<210> SEQ ID NO 787
<211> LENGTH: 9
<212> TYPE: PRT
<213> ORGANISM: Homo sapiens

<400> SEQUENCE: 787

Val Met Ser Thr Ala Cys Pro Leu Ile
 1               5

<210> SEQ ID NO 788
<211> LENGTH: 6
<212> TYPE: PRT
<213> ORGANISM: Homo sapiens

<400> SEQUENCE: 788

Thr Ile Leu Val Met Ser
 1               5

<210> SEQ ID NO 789
<211> LENGTH: 7
<212> TYPE: PRT
<213> ORGANISM: Homo sapiens

<400> SEQUENCE: 789

Leu Ile Val Met Ala Thr Gln
 1               5

<210> SEQ ID NO 790
<211> LENGTH: 6
<212> TYPE: PRT
<213> ORGANISM: Homo sapiens

<400> SEQUENCE: 790

Leu Ile Val Met Ala Thr
 1               5

<210> SEQ ID NO 791
<211> LENGTH: 7
<212> TYPE: PRT
<213> ORGANISM: Homo sapiens

<400> SEQUENCE: 791

Val Ser Met Ala Thr Leu Ile
 1               5

<210> SEQ ID NO 792
<211> LENGTH: 8
<212> TYPE: PRT
```

<213> ORGANISM: Homo sapiens

<400> SEQUENCE: 792

Tyr Phe Trp Ile Val Leu Met Thr
1               5

<210> SEQ ID NO 793
<211> LENGTH: 6
<212> TYPE: PRT
<213> ORGANISM: Homo sapiens

<400> SEQUENCE: 793

Phe Ile Tyr Trp Leu Met
1               5

<210> SEQ ID NO 794
<211> LENGTH: 4
<212> TYPE: PRT
<213> ORGANISM: Homo sapiens

<400> SEQUENCE: 794

Leu Ile Val Met
1

<210> SEQ ID NO 795
<211> LENGTH: 8
<212> TYPE: PRT
<213> ORGANISM: Homo sapiens

<400> SEQUENCE: 795

Val Ile Leu Phe Met Trp Tyr Ala
1               5

<210> SEQ ID NO 796
<211> LENGTH: 8
<212> TYPE: PRT
<213> ORGANISM: Homo sapiens

<400> SEQUENCE: 796

Phe Tyr Leu Trp Met Ile Val Ala
1               5

<210> SEQ ID NO 797
<211> LENGTH: 8
<212> TYPE: PRT
<213> ORGANISM: Homo sapiens

<400> SEQUENCE: 797

Phe Trp Tyr Leu Ile Met Val Ala
1               5

<210> SEQ ID NO 798
<211> LENGTH: 8
<212> TYPE: PRT
<213> ORGANISM: Homo sapiens

<400> SEQUENCE: 798

Phe Trp Tyr Leu Ile Val Met Ala
1               5

<210> SEQ ID NO 799
<211> LENGTH: 6
<212> TYPE: PRT
<213> ORGANISM: Homo sapiens -continued

```
<400> SEQUENCE: 799

Gln Leu Ile Val Met Pro
 1               5

<210> SEQ ID NO 800
<211> LENGTH: 8
<212> TYPE: PRT
<213> ORGANISM: Homo sapiens

<400> SEQUENCE: 800

Phe Trp Tyr Met Ile Val Leu Ala
 1               5

<210> SEQ ID NO 801
<211> LENGTH: 4
<212> TYPE: PRT
<213> ORGANISM: Homo sapiens

<400> SEQUENCE: 801

Gly Phe Tyr Trp
 1

<210> SEQ ID NO 802
<211> LENGTH: 4
<212> TYPE: PRT
<213> ORGANISM: Homo sapiens

<400> SEQUENCE: 802

Asp Glu Gln Asn
 1

<210> SEQ ID NO 803
<211> LENGTH: 8
<212> TYPE: PRT
<213> ORGANISM: Homo sapiens

<400> SEQUENCE: 803

Arg His Lys Leu Ile Val Met Pro
 1               5

<210> SEQ ID NO 804
<211> LENGTH: 4
<212> TYPE: PRT
<213> ORGANISM: Homo sapiens

<400> SEQUENCE: 804

Gly Arg His Lys
 1

<210> SEQ ID NO 805
<211> LENGTH: 8
<212> TYPE: PRT
<213> ORGANISM: Homo sapiens

<400> SEQUENCE: 805

Ala Ser Thr Cys Leu Ile Val Met
 1               5

<210> SEQ ID NO 806
<211> LENGTH: 4
<212> TYPE: PRT
<213> ORGANISM: Homo sapiens

<400> SEQUENCE: 806
```

Asp Glu Ala Ser
1

<210> SEQ ID NO 807
<211> LENGTH: 4
<212> TYPE: PRT
<213> ORGANISM: Homo sapiens

<400> SEQUENCE: 807

Gly Ser Thr Cys
1

<210> SEQ ID NO 808
<211> LENGTH: 4
<212> TYPE: PRT
<213> ORGANISM: Homo sapiens

<400> SEQUENCE: 808

Ala Ser Thr Cys
1

<210> SEQ ID NO 809
<211> LENGTH: 4
<212> TYPE: PRT
<213> ORGANISM: Homo sapiens

<400> SEQUENCE: 809

Leu Ile Val Met
1

<210> SEQ ID NO 810
<211> LENGTH: 9
<212> TYPE: PRT
<213> ORGANISM: Homo sapiens

<400> SEQUENCE: 810

Arg His Lys Asp Glu Pro Tyr Phe Trp
1               5

<210> SEQ ID NO 811
<211> LENGTH: 8
<212> TYPE: PRT
<213> ORGANISM: Homo sapiens

<400> SEQUENCE: 811

Ser Thr Met Asp Glu Ala Gln Asn
1               5

<210> SEQ ID NO 812
<211> LENGTH: 5
<212> TYPE: PRT
<213> ORGANISM: Homo sapiens

<400> SEQUENCE: 812

Tyr Phe Trp Gln Asn
1               5

<210> SEQ ID NO 813
<211> LENGTH: 5
<212> TYPE: PRT
<213> ORGANISM: Homo sapiens

<400> SEQUENCE: 813

Pro Ala Ser Thr Cys
1               5

```
<210> SEQ ID NO 814
<211> LENGTH: 8
<212> TYPE: PRT
<213> ORGANISM: Homo sapiens

<400> SEQUENCE: 814

Arg His Lys Gly Leu Ile Val Met
 1               5

<210> SEQ ID NO 815
<211> LENGTH: 6
<212> TYPE: PRT
<213> ORGANISM: Homo sapiens

<400> SEQUENCE: 815

Arg His Lys Tyr Phe Trp
 1               5

<210> SEQ ID NO 816
<211> LENGTH: 10
<212> TYPE: PRT
<213> ORGANISM: Homo sapiens

<400> SEQUENCE: 816

Tyr Phe Trp Ser Thr Cys Leu Ile Val Met
 1               5                  10

<210> SEQ ID NO 817
<211> LENGTH: 4
<212> TYPE: PRT
<213> ORGANISM: Homo sapiens

<400> SEQUENCE: 817

Asp Glu Ala Ser
 1

<210> SEQ ID NO 818
<211> LENGTH: 9
<212> TYPE: PRT
<213> ORGANISM: Homo sapiens

<400> SEQUENCE: 818

Arg His Lys Asp Glu Pro Tyr Phe Trp
 1               5

<210> SEQ ID NO 819
<211> LENGTH: 4
<212> TYPE: PRT
<213> ORGANISM: Homo sapiens

<400> SEQUENCE: 819

Pro Arg His Lys
 1

<210> SEQ ID NO 820
<211> LENGTH: 7
<212> TYPE: PRT
<213> ORGANISM: Homo sapiens

<400> SEQUENCE: 820

Leu Met Ile Val Gln Ala Thr
 1               5
```

<210> SEQ ID NO 821
<211> LENGTH: 6
<212> TYPE: PRT
<213> ORGANISM: Homo sapiens

<400> SEQUENCE: 821

Val Leu Ile Met Ala Thr
1               5

<210> SEQ ID NO 822
<211> LENGTH: 5
<212> TYPE: PRT
<213> ORGANISM: Homo sapiens

<400> SEQUENCE: 822

Asp Glu Arg Lys His
1               5

<210> SEQ ID NO 823
<211> LENGTH: 5
<212> TYPE: PRT
<213> ORGANISM: Homo sapiens

<400> SEQUENCE: 823

Asp Glu Arg Lys His
1               5

<210> SEQ ID NO 824
<211> LENGTH: 7
<212> TYPE: PRT
<213> ORGANISM: Homo sapiens

<400> SEQUENCE: 824

Leu Met Ile Val Gln Ala Thr
1               5

<210> SEQ ID NO 825
<211> LENGTH: 4
<212> TYPE: PRT
<213> ORGANISM: Homo sapiens

<400> SEQUENCE: 825

Leu Val Ile Met
1

<210> SEQ ID NO 826
<211> LENGTH: 7
<212> TYPE: PRT
<213> ORGANISM: Homo sapiens

<400> SEQUENCE: 826

Phe Tyr Trp Leu Val Ile Met
1               5

<210> SEQ ID NO 827
<211> LENGTH: 6
<212> TYPE: PRT
<213> ORGANISM: Homo sapiens

<400> SEQUENCE: 827

Val Leu Ile Met Ala Thr
1               5

<210> SEQ ID NO 828
<211> LENGTH: 4

<212> TYPE: PRT
<213> ORGANISM: Homo sapiens

<400> SEQUENCE: 828

Arg Lys His Ala
 1

<210> SEQ ID NO 829
<211> LENGTH: 5
<212> TYPE: PRT
<213> ORGANISM: Homo sapiens

<400> SEQUENCE: 829

Asp Glu Arg Lys His
 1               5

<210> SEQ ID NO 830
<211> LENGTH: 11
<212> TYPE: PRT
<213> ORGANISM: Homo sapiens

<400> SEQUENCE: 830

Leu Met Val Ile Ser Ala Thr Phe Cys Gly Asp
 1               5                  10

<210> SEQ ID NO 831
<211> LENGTH: 7
<212> TYPE: PRT
<213> ORGANISM: Homo sapiens

<400> SEQUENCE: 831

Pro Arg His Lys Tyr Phe Trp
 1               5

<210> SEQ ID NO 832
<211> LENGTH: 6
<212> TYPE: PRT
<213> ORGANISM: Homo sapiens

<400> SEQUENCE: 832

Lys Tyr Arg His Phe Ala
 1               5

<210> SEQ ID NO 833
<211> LENGTH: 12
<212> TYPE: PRT
<213> ORGANISM: Homo sapiens

<400> SEQUENCE: 833

Val Thr Leu Met Ile Ser Ala Gly Asn Cys Asp Phe
 1               5                  10

<210> SEQ ID NO 834
<211> LENGTH: 4
<212> TYPE: PRT
<213> ORGANISM: Homo sapiens

<400> SEQUENCE: 834

Lys Arg Tyr His
 1

<210> SEQ ID NO 835
<211> LENGTH: 6
<212> TYPE: PRT
<213> ORGANISM: Homo sapiens

```
<400> SEQUENCE: 835

Tyr Phe Trp Arg His Lys
1               5

<210> SEQ ID NO 836
<211> LENGTH: 4
<212> TYPE: PRT
<213> ORGANISM: Homo sapiens

<400> SEQUENCE: 836

Tyr Phe Trp Met
1

<210> SEQ ID NO 837
<211> LENGTH: 4
<212> TYPE: PRT
<213> ORGANISM: Homo sapiens

<400> SEQUENCE: 837

Phe Leu Ile Trp
1

<210> SEQ ID NO 838
<211> LENGTH: 5
<212> TYPE: PRT
<213> ORGANISM: Homo sapiens

<400> SEQUENCE: 838

Asp Glu Arg His Lys
1               5

<210> SEQ ID NO 839
<211> LENGTH: 4
<212> TYPE: PRT
<213> ORGANISM: Homo sapiens

<400> SEQUENCE: 839

Tyr Phe Trp Met
1

<210> SEQ ID NO 840
<211> LENGTH: 4
<212> TYPE: PRT
<213> ORGANISM: Homo sapiens

<400> SEQUENCE: 840

Tyr Phe Trp Pro
1

<210> SEQ ID NO 841
<211> LENGTH: 4
<212> TYPE: PRT
<213> ORGANISM: Homo sapiens

<400> SEQUENCE: 841

Phe Leu Ile Trp
1

<210> SEQ ID NO 842
<211> LENGTH: 7
<212> TYPE: PRT
<213> ORGANISM: Homo sapiens

<400> SEQUENCE: 842
```

Met Val Thr Ala Leu Ile Ser
1               5

<210> SEQ ID NO 843
<211> LENGTH: 8
<212> TYPE: PRT
<213> ORGANISM: Homo sapiens

<400> SEQUENCE: 843

Met Val Ala Leu Phe Ile Ser Thr
1               5

<210> SEQ ID NO 844
<211> LENGTH: 4
<212> TYPE: PRT
<213> ORGANISM: Homo sapiens

<400> SEQUENCE: 844

Ala Tyr Phe Trp
1

<210> SEQ ID NO 845
<211> LENGTH: 6
<212> TYPE: PRT
<213> ORGANISM: Homo sapiens

<400> SEQUENCE: 845

Tyr Phe Trp Ser Thr Cys
1               5

<210> SEQ ID NO 846
<211> LENGTH: 7
<212> TYPE: PRT
<213> ORGANISM: Homo sapiens

<400> SEQUENCE: 846

Ala Val Thr Met Ser Leu Ile
1               5

<210> SEQ ID NO 847
<211> LENGTH: 7
<212> TYPE: PRT
<213> ORGANISM: Homo sapiens

<400> SEQUENCE: 847

Tyr Phe Trp Leu Ile Val Met
1               5

<210> SEQ ID NO 848
<211> LENGTH: 6
<212> TYPE: PRT
<213> ORGANISM: Homo sapiens

<400> SEQUENCE: 848

Arg His Lys Phe Trp Tyr
1               5

<210> SEQ ID NO 849
<211> LENGTH: 8
<212> TYPE: PRT
<213> ORGANISM: Homo sapiens

<400> SEQUENCE: 849

Leu Met Phe Trp Tyr Ala Ile Val

```
                1               5

<210> SEQ ID NO 850
<211> LENGTH: 5
<212> TYPE: PRT
<213> ORGANISM: Homo sapiens

<400> SEQUENCE: 850

Asp Glu Gln Asn Pro
1               5

<210> SEQ ID NO 851
<211> LENGTH: 7
<212> TYPE: PRT
<213> ORGANISM: Homo sapiens

<400> SEQUENCE: 851

Phe Trp Tyr Leu Ile Val Met
1               5

<210> SEQ ID NO 852
<211> LENGTH: 8
<212> TYPE: PRT
<213> ORGANISM: Homo sapiens

<400> SEQUENCE: 852

Leu Met Phe Trp Tyr Ile Val Ala
1               5

<210> SEQ ID NO 853
<211> LENGTH: 8
<212> TYPE: PRT
<213> ORGANISM: Homo sapiens

<400> SEQUENCE: 853

Leu Ile Val Phe Trp Tyr Ala Met
1               5

<210> SEQ ID NO 854
<211> LENGTH: 11
<212> TYPE: PRT
<213> ORGANISM: Homo sapiens

<400> SEQUENCE: 854

Ala Gly Pro Asp Glu Arg His Lys Ser Thr Cys
1               5                   10

<210> SEQ ID NO 855
<211> LENGTH: 4
<212> TYPE: PRT
<213> ORGANISM: Homo sapiens

<400> SEQUENCE: 855

Asp Glu Gln Asn
1

<210> SEQ ID NO 856
<211> LENGTH: 7
<212> TYPE: PRT
<213> ORGANISM: Homo sapiens

<400> SEQUENCE: 856

Leu Ile Val Met Phe Trp Tyr
1               5
```

```
<210> SEQ ID NO 857
<211> LENGTH: 7
<212> TYPE: PRT
<213> ORGANISM: Homo sapiens

<400> SEQUENCE: 857

Leu Ile Val Met Phe Trp Tyr
 1               5

<210> SEQ ID NO 858
<211> LENGTH: 8
<212> TYPE: PRT
<213> ORGANISM: Homo sapiens

<400> SEQUENCE: 858

Ile Met Phe Trp Tyr Ala Leu Val
 1               5

<210> SEQ ID NO 859
<211> LENGTH: 5
<212> TYPE: PRT
<213> ORGANISM: Homo sapiens

<400> SEQUENCE: 859

Ala Gly Pro Gln Asn
 1               5

<210> SEQ ID NO 860
<211> LENGTH: 5
<212> TYPE: PRT
<213> ORGANISM: Homo sapiens

<400> SEQUENCE: 860

Arg His Lys Gln Asn
 1               5

<210> SEQ ID NO 861
<211> LENGTH: 8
<212> TYPE: PRT
<213> ORGANISM: Homo sapiens

<400> SEQUENCE: 861

Pro Phe Trp Tyr Leu Ile Val Met
 1               5

<210> SEQ ID NO 862
<211> LENGTH: 4
<212> TYPE: PRT
<213> ORGANISM: Homo sapiens

<400> SEQUENCE: 862

Leu Ile Val Met
 1

<210> SEQ ID NO 863
<211> LENGTH: 5
<212> TYPE: PRT
<213> ORGANISM: Homo sapiens

<400> SEQUENCE: 863

Ala Leu Ile Val Met
 1               5

<210> SEQ ID NO 864
```

```
<211> LENGTH: 5
<212> TYPE: PRT
<213> ORGANISM: Homo sapiens

<400> SEQUENCE: 864

Phe Trp Tyr Ala Pro
 1               5

<210> SEQ ID NO 865
<211> LENGTH: 9
<212> TYPE: PRT
<213> ORGANISM: Homo sapiens

<400> SEQUENCE: 865

Ala Thr Ile Val Leu Met Phe Trp Tyr
 1               5

<210> SEQ ID NO 866
<211> LENGTH: 6
<212> TYPE: PRT
<213> ORGANISM: Homo sapiens

<400> SEQUENCE: 866

Gly Pro Gln Asn Asp Glu
 1               5

<210> SEQ ID NO 867
<211> LENGTH: 6
<212> TYPE: PRT
<213> ORGANISM: Homo sapiens

<400> SEQUENCE: 867

Gly Asp Glu Ser Thr Cys
 1               5

<210> SEQ ID NO 868
<211> LENGTH: 5
<212> TYPE: PRT
<213> ORGANISM: Homo sapiens

<400> SEQUENCE: 868

Arg His Lys Asp Glu
 1               5

<210> SEQ ID NO 869
<211> LENGTH: 5
<212> TYPE: PRT
<213> ORGANISM: Homo sapiens

<400> SEQUENCE: 869

Gln Asn Asp Gly Glu
 1               5

<210> SEQ ID NO 870
<211> LENGTH: 4
<212> TYPE: PRT
<213> ORGANISM: Homo sapiens

<400> SEQUENCE: 870

Asn Ala Ser Glu
 1

<210> SEQ ID NO 871
<211> LENGTH: 4
<212> TYPE: PRT
```

<213> ORGANISM: Homo sapiens

<400> SEQUENCE: 871

Thr Ser Met Glu
1

<210> SEQ ID NO 872
<211> LENGTH: 4
<212> TYPE: PRT
<213> ORGANISM: Homo sapiens

<400> SEQUENCE: 872

Ser Glu Met Asp
1

<210> SEQ ID NO 873
<211> LENGTH: 4
<212> TYPE: PRT
<213> ORGANISM: Homo sapiens

<400> SEQUENCE: 873

Ser Lys Pro Glu
1

<210> SEQ ID NO 874
<211> LENGTH: 6
<212> TYPE: PRT
<213> ORGANISM: Homo sapiens

<400> SEQUENCE: 874

Gly Thr Glu Arg Ala Ile
1               5

<210> SEQ ID NO 875
<211> LENGTH: 6
<212> TYPE: PRT
<213> ORGANISM: Homo sapiens

<400> SEQUENCE: 875

Gly Ile Glu Gly Ser Leu
1               5

<210> SEQ ID NO 876
<211> LENGTH: 6
<212> TYPE: PRT
<213> ORGANISM: Homo sapiens

<400> SEQUENCE: 876

Gly Ser Leu Lys Gly Ser
1               5

<210> SEQ ID NO 877
<211> LENGTH: 6
<212> TYPE: PRT
<213> ORGANISM: Homo sapiens

<400> SEQUENCE: 877

Gly Ser Thr Tyr Asn Leu
1               5

<210> SEQ ID NO 878
<211> LENGTH: 6
<212> TYPE: PRT
<213> ORGANISM: Homo sapiens

```
<400> SEQUENCE: 878

Gly Ile Pro Val Gly Phe
 1               5

<210> SEQ ID NO 879
<211> LENGTH: 6
<212> TYPE: PRT
<213> ORGANISM: Homo sapiens

<400> SEQUENCE: 879

Cys Ala Gln Cys His Ala
 1               5
```